US011278668B2

(12) United States Patent
Gupta et al.

(10) Patent No.: US 11,278,668 B2
(45) Date of Patent: Mar. 22, 2022

(54) ANALYTE SENSOR AND MEDICANT DELIVERY DATA EVALUATION AND ERROR REDUCTION APPARATUS AND METHODS

(71) Applicant: GlySens Incorporated, San Diego, CA (US)

(72) Inventors: Piyush Gupta, San Diego, CA (US); Joseph Lucisano, San Diego, CA (US)

(73) Assignee: GlySens Incorporated, San Diego, CA (US)

( * ) Notice: Subject to any disclaimer, the term of this patent is extended or adjusted under 35 U.S.C. 154(b) by 848 days.

(21) Appl. No.: 15/853,574

(22) Filed: Dec. 22, 2017

(65) Prior Publication Data

US 2019/0192768 A1 Jun. 27, 2019

(51) Int. Cl.
*A61M 5/142* (2006.01)
*A61B 5/145* (2006.01)
(Continued)

(52) U.S. Cl.
CPC ....... *A61M 5/14276* (2013.01); *A61B 5/0004* (2013.01); *A61B 5/1468* (2013.01);
(Continued)

(58) Field of Classification Search
CPC ............ A61M 5/14276; A61M 5/1726; A61M 5/1723; A61B 5/0004; A61B 5/14532;
(Continued)

(56) References Cited

U.S. PATENT DOCUMENTS 2,508,523 A 5/1950 Krebs
2,563,062 A 8/1951 Perley
(Continued)

FOREIGN PATENT DOCUMENTS

AU 2012286753 A1 2/2014
AU 2016382976 A1 8/2018
(Continued)

OTHER PUBLICATIONS

Alvarez-Icaza M., et al., "Mass Production of Biosensors," Analytical Chemistry, 1993, vol. 65 (11), pp. 525-533.
Anderson J.M., "Biological Responses to Materials." Annual Review of Materials Research, 2001, vol. 31, pp. 81-110.
Armour J.C., et al., "Application of a Chronic Intravascular Blood Glucose Sensor in Dogs," Diabetes, 1990, vol. 39 (12), pp. 1519-1526.
Bard A.J., et al., "Electrochemical Methods: Fundamentals and Applications," 2nd Edition, 2000.
(Continued)

*Primary Examiner* — Tiffany Legette
(74) *Attorney, Agent, or Firm* — Gazdzinski & Associates, PC

(57) ABSTRACT

Apparatus and methods for error modeling and correction in one or both of (i) a partially or fully implanted or non-implanted medicant delivery mechanism (such as a pump), and (ii) implanted physiologic parameter sensor. In one exemplary embodiment, the apparatus and methods employ a training mode of operation, whereby the apparatus conducts "machine learning" to model one or more errors (e.g., unmodeled variable system errors) associated with the medicant dose calculation process, and (ii) generation of a medicant delivery operational model (based at least in part on data collected/received in the training mode), which is applied to correct or compensate for the errors during normal operation of the sensor and pump system. This enhances accuracy of medicant delivery, such as over the lifetime of an implanted pump at a single implantation site, or during multiple relocations of a transcutaneously implanted pump), and enables "personalization" of the pump to each user.

31 Claims, 50 Drawing Sheets

(51) Int. Cl.
   *A61B 5/00*     (2006.01)
   *A61B 5/1468*   (2006.01)
   *G16H 50/00*    (2018.01)
   *A61M 5/172*    (2006.01)

(52) U.S. Cl.
   CPC ........ *A61B 5/14532* (2013.01); *A61B 5/4839* (2013.01); *A61M 5/1723* (2013.01); *G16H 50/00* (2018.01); *A61B 5/7264* (2013.01); *A61B 2560/0247* (2013.01)

(58) Field of Classification Search
   CPC ... A61B 5/7264; A61B 5/1468; A61B 6/4839; A61B 6/0004; A61B 6/14532; A61B 6/1468; A61B 6/7264; A61B 256/0247; A61B 256/72; A61B 256/7271; A61B 256/7275; A61B 256/7282; A61B 256/746; A61B 256/7267; G61H 10/60; G61H 20/17; G61H 40/63; G61H 50/20; G61H 50/50; G06N 7/00
   See application file for complete search history.

(56) References Cited

U.S. PATENT DOCUMENTS

| | | |
|---|---|---|
| 2,805,191 A | 9/1957 | Hersch |
| 2,864,750 A | 12/1958 | Hughes Jr. et al. |
| 2,998,371 A | 8/1961 | Sabins |
| 3,099,575 A | 7/1963 | Hill |
| 3,246,235 A | 4/1966 | Allsopp |
| 3,249,250 A | 5/1966 | McKee |
| 3,300,345 A | 1/1967 | Lyons, Jr. |
| 3,308,046 A | 3/1967 | Suleski |
| 3,458,421 A | 7/1969 | Harald |
| 3,505,195 A | 4/1970 | Borge et al. |
| 3,542,662 A | 11/1970 | Hicks et al. |
| 3,616,412 A | 10/1971 | Gnage |
| 3,957,613 A | 5/1976 | Macur |
| 4,036,716 A | 7/1977 | Hulthe |
| 4,088,550 A | 5/1978 | Malkin |
| 4,240,438 A | 12/1980 | Shults et al. |
| 4,306,952 A | 12/1981 | Jansen |
| 4,340,457 A | 7/1982 | Kater |
| 4,361,153 A | 11/1982 | Slocum et al. |
| 4,366,033 A | 12/1982 | Richter et al. |
| 4,431,004 A | 2/1984 | Bessman et al. |
| 4,458,686 A | 7/1984 | Clark, Jr. |
| 4,484,987 A | 11/1984 | Gough |
| 4,494,950 A | 1/1985 | Fischell |
| 4,541,431 A | 9/1985 | Ibrahim et al. |
| 4,550,732 A | 11/1985 | Batty, Jr. et al. |
| 4,553,547 A | 11/1985 | Keimel |
| 4,571,589 A | 2/1986 | Slocum et al. |
| 4,637,861 A | 1/1987 | Krull et al. |
| 4,650,547 A | 3/1987 | Gough |
| 4,671,288 A | 6/1987 | Gough |
| 4,703,756 A | 11/1987 | Gough et al. |
| 4,746,218 A | 5/1988 | Lord, III |
| 4,748,562 A | 5/1988 | Miller et al. |
| 4,759,828 A | 7/1988 | Young et al. |
| 4,781,798 A | 11/1988 | Gough |
| 4,830,713 A | 5/1989 | Gagescu |
| 4,890,620 A | 1/1990 | Gough |
| 5,042,902 A | 8/1991 | Huebscher et al. |
| 5,046,242 A | 9/1991 | Kuzma |
| 5,077,476 A | 12/1991 | Rosenthal |
| 5,105,811 A | 4/1992 | Kuzma |
| 5,112,455 A | 5/1992 | Cozzette et al. |
| 5,150,516 A | 9/1992 | Boero et al. |
| 5,165,406 A | 11/1992 | Wong |
| 5,189,717 A | 2/1993 | Larson et al. |
| 5,264,103 A | 11/1993 | Yoshioka et al. |
| 5,272,283 A | 12/1993 | Kuzma |
| 5,273,203 A | 12/1993 | Webster |
| 5,283,104 A | 2/1994 | Aoude et al. |
| 5,283,204 A | 2/1994 | Rhodes et al. |
| 5,284,140 A | 2/1994 | Allen et al. |
| 5,322,063 A | 6/1994 | Allen et al. |
| 5,337,475 A | 8/1994 | Aoude et al. |
| 5,395,504 A | 3/1995 | Saurer et al. |
| 5,431,160 A | 7/1995 | Wilkins |
| 5,487,855 A | 1/1996 | Moeggenborg et al. |
| 5,497,772 A | 3/1996 | Schulman et al. |
| 5,560,098 A | 10/1996 | Robins |
| 5,660,163 A | 8/1997 | Schulman et al. |
| 5,692,299 A | 12/1997 | Daems et al. |
| 5,695,623 A | 12/1997 | Michel et al. |
| 5,711,861 A | 1/1998 | Ward et al. |
| 5,727,283 A | 3/1998 | Webster |
| 5,741,330 A | 4/1998 | Brauker et al. |
| 5,750,926 A | 5/1998 | Schulman et al. |
| 5,776,324 A | 7/1998 | Usala |
| 5,777,060 A | 7/1998 | Van Antwerp |
| 5,782,755 A | 7/1998 | Chance et al. |
| 5,782,891 A | 7/1998 | Hassler et al. |
| 5,791,344 A | 8/1998 | Schulman et al. |
| 5,804,048 A | 9/1998 | Wong et al. |
| 5,821,011 A | 10/1998 | Taylor et al. |
| 5,842,983 A | 12/1998 | Abel et al. |
| 5,855,995 A | 1/1999 | Haq et al. |
| 5,864,088 A | 1/1999 | Sato et al. |
| 5,882,494 A | 3/1999 | Van Antwerp |
| 5,887,240 A | 3/1999 | Fournier et al. |
| 5,932,175 A | 8/1999 | Knute et al. |
| 5,942,842 A | 8/1999 | Fogle, Jr. |
| 5,964,993 A | 10/1999 | Blubaugh, Jr. et al. |
| 5,985,129 A | 11/1999 | Gough et al. |
| 6,001,067 A | 12/1999 | Shults et al. |
| 6,027,479 A | 2/2000 | Alei et al. |
| 6,041,496 A | 3/2000 | Haq et al. |
| 6,081,736 A | 6/2000 | Colvin et al. |
| 6,090,503 A | 7/2000 | Taylor et al. |
| 6,096,066 A | 8/2000 | Chen et al. |
| 6,107,083 A | 8/2000 | Collins et al. |
| 6,119,208 A | 9/2000 | White et al. |
| 6,175,752 B1 | 1/2001 | Say et al. |
| 6,193,421 B1 | 2/2001 | Tamekuni et al. |
| 6,200,772 B1 | 3/2001 | Vadgama et al. |
| 6,212,416 B1 | 4/2001 | Ward et al. |
| 6,221,513 B1 | 4/2001 | Lasater |
| 6,403,944 B1 | 6/2002 | MacKenzie et al. |
| 6,466,810 B1 | 10/2002 | Ward et al. |
| 6,516,808 B2 | 2/2003 | Schulman |
| 6,551,252 B2 | 4/2003 | Sackner et al. |
| 6,558,321 B1 | 5/2003 | Burd et al. |
| 6,642,015 B2 | 11/2003 | Vachon et al. |
| 6,721,587 B2 | 4/2004 | Gough |
| 6,741,877 B1 | 5/2004 | Shults et al. |
| 6,809,607 B2 | 10/2004 | Nagasaka |
| 6,812,404 B1 | 11/2004 | Martinez |
| 6,832,114 B1 | 12/2004 | Whitehurst et al. |
| 6,843,107 B2 | 1/2005 | Newman et al. |
| 6,931,268 B1 | 8/2005 | Kiani-Azarbayjany et al. |
| 7,005,796 B2 | 2/2006 | Kolluri et al. |
| 7,079,881 B2 | 7/2006 | Schulman et al. |
| 7,106,939 B2 | 9/2006 | Labrake et al. |
| 7,110,803 B2 | 9/2006 | Shults et al. |
| 7,134,999 B2 | 11/2006 | Brauker et al. |
| 7,136,689 B2 | 11/2006 | Shults et al. |
| 7,140,787 B2 | 11/2006 | Yamauchi et al. |
| 7,146,203 B2 | 12/2006 | Botvinick et al. |
| 7,161,727 B2 | 1/2007 | Callies et al. |
| 7,189,341 B2 | 3/2007 | Li et al. |
| 7,192,450 B2 | 3/2007 | Brauker et al. |
| 7,226,978 B2 | 6/2007 | Tapsak et al. |
| 7,248,912 B2 | 7/2007 | Gough et al. |
| 7,323,142 B2 | 1/2008 | Pendo et al. |
| 7,336,984 B2 | 2/2008 | Gough et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,480,988 B2 | 1/2009 | Ok et al. |
| 7,497,827 B2 | 3/2009 | Brister et al. |

(56) References Cited

U.S. PATENT DOCUMENTS

| | | |
|---|---|---|
| 7,514,791 B2 | 4/2009 | Shah et al. |
| 7,525,298 B2 | 4/2009 | Morgan et al. |
| 7,761,130 B2 | 7/2010 | Simpson et al. |
| 7,857,760 B2 | 12/2010 | Brister et al. |
| 7,871,456 B2 | 1/2011 | Gough et al. |
| 7,875,293 B2 | 1/2011 | Shults et al. |
| 7,881,763 B2 | 2/2011 | Brauker et al. |
| 7,894,870 B1 | 2/2011 | Lucisano et al. |
| 8,133,178 B2 | 3/2012 | Brauker et al. |
| 8,270,661 B2 | 9/2012 | Sorensen et al. |
| 8,357,107 B2 | 1/2013 | Draudt et al. |
| 8,690,820 B2 | 4/2014 | Cinar et al. |
| 8,763,245 B1 | 7/2014 | Lucisano et al. |
| 8,763,246 B2 | 7/2014 | Nishioka et al. |
| 9,002,711 B2 | 4/2015 | Morinaka et al. |
| 9,119,528 B2 | 9/2015 | Cobelli et al. |
| 9,247,901 B2 | 2/2016 | Kamath et al. |
| 9,325,060 B2 | 4/2016 | Kalistaja et al. |
| 9,362,776 B2 | 6/2016 | Low et al. |
| 9,444,027 B2 | 9/2016 | Dibra et al. |
| 9,451,908 B2 | 9/2016 | Kamath et al. |
| 9,782,111 B2 | 10/2017 | Lucisano et al. |
| 10,041,897 B2 | 8/2018 | Lucisano et al. |
| 10,182,336 B1 | 1/2019 | Stockton et al. |
| 10,638,979 B2 | 5/2020 | Gupta et al. |
| 10,660,550 B2 | 5/2020 | Lucisano et al. |
| 10,736,553 B2 | 8/2020 | Lucisano et al. |
| 2002/0013613 A1 | 1/2002 | Haller et al. |
| 2002/0026108 A1 | 2/2002 | Colvin et al. |
| 2002/0042561 A1 | 4/2002 | Schulman et al. |
| 2002/0123087 A1 | 9/2002 | Vachon et al. |
| 2002/0156355 A1 | 10/2002 | Gough |
| 2002/0161286 A1 | 10/2002 | Gerber et al. |
| 2002/0193671 A1 | 12/2002 | Ciurczak et al. |
| 2003/0048621 A1 | 3/2003 | Blood et al. |
| 2003/0049166 A1 | 3/2003 | Pendo et al. |
| 2003/0053784 A1 | 3/2003 | Labrake et al. |
| 2003/0126593 A1 | 7/2003 | Mault |
| 2003/0179167 A1 | 9/2003 | Kolluri et al. |
| 2003/0181794 A1 | 9/2003 | Rini et al. |
| 2003/0187338 A1 | 10/2003 | Say et al. |
| 2003/0217966 A1 | 11/2003 | Tapsak et al. |
| 2003/0228681 A1 | 12/2003 | Ritts et al. |
| 2004/0011671 A1 | 1/2004 | Shults et al. |
| 2004/0012935 A1 | 1/2004 | Tagi et al. |
| 2004/0057043 A1 | 3/2004 | Newman et al. |
| 2004/0064133 A1 | 4/2004 | Miller et al. |
| 2004/0106857 A1 | 6/2004 | Gough et al. |
| 2004/0158194 A1 | 8/2004 | Wolff et al. |
| 2004/0167080 A1 | 8/2004 | Dodge et al. |
| 2004/0176669 A1 | 9/2004 | Colvin et al. |
| 2004/0190111 A1 | 9/2004 | Callies et al. |
| 2004/0199059 A1 | 10/2004 | Brauker et al. |
| 2004/0211260 A1 | 10/2004 | Girmonsky |
| 2004/0220459 A1 | 11/2004 | Schlegel et al. |
| 2005/0027175 A1 | 2/2005 | Yang |
| 2005/0027463 A1 | 2/2005 | Goode, Jr. et al. |
| 2005/0031689 A1 | 2/2005 | Shults et al. |
| 2005/0033132 A1 | 2/2005 | Shults et al. |
| 2005/0052858 A1 | 3/2005 | Shima et al. |
| 2005/0059871 A1 | 3/2005 | Gough et al. |
| 2005/0107677 A1 | 5/2005 | Ward et al. |
| 2005/0124873 A1 | 6/2005 | Shults et al. |
| 2005/0143635 A1 | 6/2005 | Kamath et al. |
| 2005/0154271 A1 | 7/2005 | Rasdal et al. |
| 2005/0177036 A1 | 8/2005 | Shults et al. |
| 2005/0196322 A1 | 9/2005 | Truex et al. |
| 2005/0245799 A1 | 11/2005 | Brauker et al. |
| 2005/0245971 A1 | 11/2005 | Brockway et al. |
| 2005/0251083 A1 | 11/2005 | Carr-Brendel et al. |
| 2005/0272989 A1 | 12/2005 | Shah et al. |
| 2006/0020186 A1 | 1/2006 | Brister et al. |
| 2006/0074338 A1 | 4/2006 | Greenwald et al. |
| 2006/0085137 A1 | 4/2006 | Bartkowiak et al. |
| 2006/0086624 A1 | 4/2006 | Tapsak et al. |
| 2006/0195029 A1 | 8/2006 | Shults et al. |
| 2006/0200044 A1 | 9/2006 | Freeman et al. |
| 2006/0204536 A1 | 9/2006 | Shults et al. |
| 2006/0247736 A1 | 11/2006 | Roberts |
| 2006/0257995 A1 | 11/2006 | Simpson et al. |
| 2006/0257996 A1 | 11/2006 | Simpson et al. |
| 2006/0263763 A1 | 11/2006 | Simpson et al. |
| 2007/0151868 A1 | 7/2007 | Staib et al. |
| 2007/0173761 A1 | 7/2007 | Kanderian et al. |
| 2008/0033269 A1 | 2/2008 | Zhang |
| 2008/0033272 A1 | 2/2008 | Gough et al. |
| 2008/0034972 A1 | 2/2008 | Gough et al. |
| 2008/0039702 A1 | 2/2008 | Hayter et al. |
| 2008/0086042 A1 | 4/2008 | Brister et al. |
| 2008/0132974 A1 | 6/2008 | Strother et al. |
| 2008/0197024 A1 | 8/2008 | Simpson et al. |
| 2008/0200791 A1 | 8/2008 | Simpson et al. |
| 2008/0317276 A1 | 12/2008 | Sorensen et al. |
| 2009/0055149 A1 | 2/2009 | Hayter et al. |
| 2009/0102678 A1* | 4/2009 | Mazza ............... A61B 5/1473 340/693.9 |
| 2009/0131176 A1 | 5/2009 | Simpson et al. |
| 2009/0131776 A1 | 5/2009 | Simpson et al. |
| 2009/0182388 A1 | 7/2009 | Von Arx et al. |
| 2009/0221890 A1 | 9/2009 | Saffer |
| 2009/0240120 A1 | 9/2009 | Mensinger et al. |
| 2009/0242425 A1 | 10/2009 | Kamath et al. |
| 2009/0281399 A1 | 11/2009 | Keel et al. |
| 2010/0041971 A1 | 2/2010 | Goode, Jr. et al. |
| 2010/0094110 A1 | 4/2010 | Heller et al. |
| 2010/0145317 A1 | 6/2010 | Laster et al. |
| 2010/0149042 A1 | 6/2010 | Utsi et al. |
| 2010/0222847 A1 | 9/2010 | Goetz |
| 2010/0249558 A1 | 9/2010 | Yodfat et al. |
| 2011/0022025 A1 | 1/2011 | Savoie et al. |
| 2011/0137142 A1 | 6/2011 | Lucisano et al. |
| 2011/0221590 A1 | 9/2011 | Baker et al. |
| 2011/0319734 A1 | 12/2011 | Gottlieb et al. |
| 2012/0262298 A1 | 10/2012 | Bohm et al. |
| 2012/0283960 A1 | 11/2012 | Budiman |
| 2012/0323100 A1 | 12/2012 | Kamath et al. |
| 2013/0016573 A1 | 1/2013 | Goel et al. |
| 2013/0030273 A1 | 1/2013 | Tapsak et al. |
| 2013/0132416 A1 | 5/2013 | Hayter et al. |
| 2013/0165819 A1 | 6/2013 | Tieu |
| 2013/0172692 A1 | 7/2013 | Choi et al. |
| 2013/0178727 A1 | 7/2013 | Hayter et al. |
| 2013/0197332 A1 | 8/2013 | Lucisano et al. |
| 2014/0005505 A1 | 1/2014 | Peyser et al. |
| 2014/0046148 A1 | 2/2014 | Simpson et al. |
| 2014/0121989 A1 | 5/2014 | Kamath et al. |
| 2014/0309510 A1 | 10/2014 | Lucisano et al. |
| 2014/0323960 A1 | 10/2014 | Sloan |
| 2014/0350652 A1 | 11/2014 | Suwito |
| 2015/0163602 A1 | 6/2015 | Pedersen et al. |
| 2015/0250429 A1 | 9/2015 | Hampapuram et al. |
| 2015/0289823 A1 | 10/2015 | Rack-Gomer et al. |
| 2015/0306304 A1 | 10/2015 | Schabbach et al. |
| 2015/0335285 A1 | 11/2015 | Poon et al. |
| 2016/0022180 A1 | 1/2016 | Joseph et al. |
| 2016/0029966 A1 | 2/2016 | Salas-Boni et al. |
| 2016/0033340 A1 | 2/2016 | Todd et al. |
| 2016/0073964 A1 | 3/2016 | Cobelli et al. |
| 2016/0134980 A1 | 5/2016 | Abolfathi |
| 2016/0163174 A1 | 6/2016 | Zhang et al. |
| 2016/0235300 A1 | 8/2016 | Goodnow et al. |
| 2016/0310027 A1 | 10/2016 | Han |
| 2016/0317744 A1 | 11/2016 | Rule et al. |
| 2017/0074757 A1 | 3/2017 | Garcia et al. |
| 2017/0173262 A1 | 6/2017 | Veltz |
| 2017/0181628 A1 | 6/2017 | Burnette et al. |
| 2017/0181630 A1 | 6/2017 | Mahalingam et al. |
| 2017/0181674 A1 | 6/2017 | Lucisano et al. |
| 2017/0325725 A1 | 11/2017 | Shah et al. |
| 2017/0347932 A1 | 12/2017 | Lucisano et al. |
| 2017/0357776 A1 | 12/2017 | Baker et al. |
| 2018/0000395 A1 | 1/2018 | Lucisano et al. |
| 2018/0140239 A1 | 5/2018 | Lucisano et al. |
| 2018/0153450 A1 | 6/2018 | Routh et al. |

(56) References Cited

U.S. PATENT DOCUMENTS

| | | | |
|---|---|---|---|
| 2018/0279911 | A1 | 10/2018 | Lucisano et al. |
| 2018/0348154 | A1 | 12/2018 | Lucisano et al. |
| 2019/0020439 | A1 | 1/2019 | Fawaz et al. |
| 2019/0150805 | A1 | 5/2019 | Routh et al. |
| 2019/0212323 | A1 | 7/2019 | Gupta et al. |
| 2019/0246957 | A1 | 8/2019 | Lucisano et al. |
| 2019/0380628 | A1 | 12/2019 | Routh et al. |
| 2020/0000386 | A1 | 1/2020 | Gupta et al. |
| 2020/0037932 | A1 | 2/2020 | Lucisano et al. |
| 2020/0330043 | A1 | 10/2020 | Gupta et al. |
| 2020/0337619 | A1 | 10/2020 | Lucisano et al. |
| 2020/0352480 | A1 | 11/2020 | Lucisano et al. |
| 2021/0022652 | A1 | 1/2021 | Lucisano et al. |

FOREIGN PATENT DOCUMENTS

| | | |
|---|---|---|
| AU | 2017201943 B2 | 10/2018 |
| AU | 2020201630 A1 | 3/2020 |
| CA | 2843008 A1 | 1/2013 |
| CA | 3009489 A1 | 7/2017 |
| CN | 1355670 A | 6/2002 |
| CN | 1592570 A | 3/2005 |
| CN | 101006374 A | 7/2007 |
| CN | 201207090 Y | 3/2009 |
| CN | 103826528 A | 5/2014 |
| EP | 0206531 A1 | 12/1986 |
| EP | 0852414 B1 | 11/2004 |
| EP | 2312782 A1 | 4/2011 |
| EP | 2736404 A1 | 6/2014 |
| EP | 3463059 A1 | 4/2019 |
| EP | 3478171 A1 | 5/2019 |
| EP | 3544491 A1 | 10/2019 |
| EP | 3547905 A1 | 10/2019 |
| EP | 3652547 A1 | 5/2020 |
| EP | 3906842 | 10/2021 |
| EP | 39068421 | 11/2021 |
| JP | H11295556 A | 10/1999 |
| JP | 2000121863 A | 4/2000 |
| JP | 2005308982 A | 11/2005 |
| JP | 2007121886 A | 5/2007 |
| JP | 6321540 B2 | 5/2018 |
| KR | 20140082642 A | 7/2014 |
| WO | WO-9207525 A1 | 5/1992 |
| WO | WO-9213271 A1 | 8/1992 |
| WO | WO-2008013881 A2 | 1/2008 |
| WO | WO-2010002502 A2 | 1/2010 |
| WO | WO-2011018407 A1 | 2/2011 |
| WO | WO-2011120014 A1 | 9/2011 |
| WO | WO-2013016573 A1 | 1/2013 |
| WO | WO-2014035672 A2 | 3/2014 |
| WO | WO-2016014987 A2 | 1/2016 |
| WO | WO-2017117283 A1 | 7/2017 |
| WO | WO-2017210110 A1 | 12/2017 |
| WO | WO-2018005773 A1 | 1/2018 |
| WO | WO-2018097885 A1 | 5/2018 |
| WO | WO-2018102011 A1 | 6/2018 |
| WO | WO-2018183345 A1 | 10/2018 |
| WO | WO-2019013936 A1 | 1/2019 |
| WO | WO-2019126795 A1 | 6/2019 |
| WO | WO-2019135988 A1 | 7/2019 |
| WO | WO-2019246133 A1 | 12/2019 |
| WO | WO-2020006307 A1 | 1/2020 |

OTHER PUBLICATIONS

Bilitewski U., et al., "Glucose Biosensors Based on Thick Film Technology," Biosensors and Bioelectronics, 1991, vol. 6, pp. 369-373.

Bremer T.M., et al., "Benchmark Data from the Literature for Evaluation of New Glucose Sensing Technologies," Diabetes Technology and therapeutics, 2001, vol. 3 (3), pp. 409-418.

Cha, C.S., et al., "Electrochemical Behaviour of Microfabricated Thick-film Electrodes," Sensors and Actuators B., 1990, vol. 2, pp. 277-281.

Choleau, et al., "Calibration of a Subcutaneous Amperometric Glucose Sensor Implanted for 7 Days in Diabetic Patients Part 2. Superiority of the One-point Calibration Method," Biosensors and Bioelectronics, 2002, vol. 17, pp. 641-646.

Choleau, et al., "Calibration of a Subcutaneous Amperometric Glucose Sensor Part 1. Effect of Measurement Uncertainties on the Determination of Sensor Sensitivity and Background Current.," Biosensors and Bioelectronics, 2002, vol. 17, pp. 647-654.

Conway M.J., et al., "Radio Telemetry of Blood Po2 in Vivo," Biomedical Engineering, 1973, vol. 8 (10), pp. 428-430.

Data Sheet—Platinum Oxygen Sensor Materials, Component Metallizations, OS1/OS2/OS3, Heraeus.

Data Sheet Cermet Platinum Conductor data sheet, 5542 Print GD, 5542 Pouring GD, Electro-Science Laboratories,Inc.

Data Sheet—4082 and 3804 Platinum Conductors, MEMS Sensor Materials, Ferro Electronic Materials.

Dhakar L., "Skin Based Flexible Triboelectric Nanogenerators with Motion Sensing Capability," Micro Electro Mechanical Systems (MEMS), 2015 28th IEEE International Conference on, 2015, IEEE, pp. 106-109.

Dutronc, P., et al., "Influence of the Nature of the Screen-printed Electrode Metal on the Transport and Detection Properties of Thick-film Semiconductor Gas Sensors," Sensors and Actuators B, 1992, vol. 6, pp. 279-284.

ELISA Kit Manual Human C3a #550499.

ELISA Kit Manual Human C4a #5550947.

Fischer U., et al., "A Membrane Combination for Implantable Glucose Sensors. Measurements in Undiluted Biological Fluids," Transactions—American Society for Artificial Internal Organs. 1982, vol. 28, pp. 245-248.

Golonka L.J., et al., "The influence of the Electrode Material on the Sensitivity of an $Sno_2$ Thick-film Gas Sensor," Sensors and Actuators B, 1994, vol. 18-19, pp. 453-456.

Gough D.A., et al., "A Novel Rotated Disc Electrode and Time Lag Method for Characterizing Mass Transport in Liquid-membrane Systems," Journal of the American Institute of Chemical Engineers, 1980, vol. 26, pp. 1013.

Gough D.A., et al., "Membrane-covered, Rotated Disc Electrode," Analytical Chemistry, 1979, vol. 51, pp. 439-444.

Gough D.A., et al., "Two-Dimensional Enzyme Electrode Sensor for Glucose," Analytical Chemistry, 1985, vol. 57 (12), pp. 2351-2357.

Gough, et al., "Function of an Implanted Tissue Glucose Sensor for More than 1 Year in Animals", Science Translational Medicine, Jul. 28, 2010, vol. 2 (42), pp. 42ra53.

Holc J., et al., "Interaction Between Thick-film Platinum Electrodes and Yttria-stabilized $Zro_2$ Ceramic," Journal of Materials Science Letters, 1989, vol. 8, pp. 635-637.

Holmes, et al., Handbook of Thick Film Technology, Electrochemical Publications Ltd (Glasgow: Bell and Bain Ltd., 1976).

Jablecki M., et al., "Simulations of the Frequency Response of Implantable Glucose Sensors," Analytical Chemistry, 2000, vol. 72 (8), pp. 1853-1859.

Kovatchev B.P., et al., "Graphical and Numerical Evaluation of Continuous Glucose Sensing Time Lag," Diabetes Technology Therapeutics, 2009, vol. 11 (3), pp. 139-143.

Kroschwitz J., "Concise encyclopedia of polymer science and engineering," John Wiley, 1990, pp. 599-1341.

Lemey S., et al., "Wearable Flexible Lightweight Modular RFID Tag With Integrated Energy Harvester," IEEE Transactions on Microwave Theory and Techniques, 2016, vol. 64.7, pp. 2304-2314.

Leypoldt J.K., et al., "Diffusion and the Limiting Substrate in Two-substrate Immobilized Enzyme Systems," Biotechnology and Bioengineering, 1982, vol. 24 (12), pp. 2705-2719.

Leypoldt J.K., et al., "Model of a Two-substrate Enzyme Electrode for Glucose," Analytical Chemistry, 1984, vol. 56 (14), pp. 2896-2904.

Lucisano, et al., "In Vitro Stability of an Oxygen Sensor," Analytical Chemistry, 1987, vol. 59 (5), pp. 736-739.

(56) References Cited

OTHER PUBLICATIONS

Lucisano, Ph.D. Dissertation, Univ. of Calif. (San Diego), pp. xv-xvi, 8-10, 26-30, 34-36, 96-97 (made available to the public on Dec. 15, 1988)—Call No. "T3.6.L821987".

Ma, et al., "A Biocompatible and Biodegradable Protein Hydrogel with Green and Red Autofluorescence: Preparation, Characterization and In Vivo Biodegradation Tracking and Modeling," Scientific Reports (Nature.com) published Jan. 27, 2016.

Makale M.T., et al., "Tissue Window Chamber System for Validation of Implanted Oxygen Sensors," American Journal of Physiology. Heart and Circulatory Physiology, 2003, vol. 284 (6), pp. 2288-2294.

Mckean B.D., et al., "A Telemetry-instrumentation System for Chronically Implanted Glucose and Oxygen Sensors," IEEE Transactions on Biomedical Engineering, 1988, vol. 35 (7), pp. 526-532.

Mcnaught A.D., et al., "The Compendium of Chemical Terminology," The Gold Book, Second Edition, Blackwell Science,1997.

Rich A., "Shielding and Guarding," Analog Dialogue, 1983, vol. 17 (1), pp. 8-13.

Sargent B.J., et al., "Design and Validation of the Transparent Oxygen Sensor Array," Biomedical Engineering, IEEE Transactions On, 1991, vol. 38 (5), pp. 476-482.

Schultz J.S., et al., "Optical Fiber Affinity Sensors," Methods in Enzymology, K. Mosbach, Ed., Academic Press, 1988, vol. 137, pp. 349-366.

Takei K., et al., "Design for a 400-MHz Passive RFID Prototype System for Long Range Applications," to be published in Proc. IEEE Int. Symp. Antennas Propag. 2007.

West, Electrodeposition and Corrosion Processes, 1971.

Wong CM., et al., "Glucose Oxidase: Natural Occurrence, Function, Properties and Industrial Applications," Applied Microbiology and Biotechnology, 2008, vol. 78 (6), pp. 927-938.

Morris C.G., Definition of "Machine Learning", Academic Press Dictionary of Science and Technology (4th ed.), 1992, Oxford, UK: Elsevier Science & Technology. Retrieved from https://search.credoreference.com/content/entry/apdst/machine_learning/0?institutionId=743.

Heraeus Technical Data Sheet,Thick Film Materials, Product CL11-5100, retrieved from the Internet on Jun. 14, 2019.

Heraeus Technical Data Sheet,Thick Film Materials, Product CL11-5349, retrieved from the Internet on Jun. 14, 2019.

Heraeus Technical Data Sheet,Thick Film Materials, Product CL11-6109, retrieved from the Internet on Jun. 14, 2019.

Heraeus Technical Data Sheet,Thick Film Materials, Product LP11-4493, retrieved from the Internet on Jun. 14, 2019.

Bluetooth Specifications "Multi-Channel Adaptation Protocol" published (revised) Jan. 24, 2007, 58 pages.

Bluetooth Compliance Requirements, Bluetooth Specification, Version 5.0, Part B, Dec. 6, 2016, 14 pages.

Continuous Glucose Monitoring Profile, Bluetooth® Profile Specification, Nov. 2014, revision V1.0.0, Group Prepared By MEG WG, 52 pages.

IEEE 802.11 standard, 1997, URL: http://www.ieeexplore.ieee.org/documenU654779, 459 pages.

Wi-Fi Direct (including inter alia, "Wi-Fi Peer-to-Peer (P2P) Specification"), Version 1.5, 2014, Wi-Fi Alliance, 90 pages.

* cited by examiner

| Starting Glucose Level (mg/dl) | Insulin Dose (Units) | Expected Glucose-Lowering Magnitude (mg/dl) | Expected Nadir Glucose Range (mg/dl) |
|---|---|---|---|
| 500 | 8 | 380 – 420 | 80 – 120 |
| 400 | 6 | 280 - 320 | 80 – 120 |
| 300 | 4 | 180 – 220 | 80 – 120 |
| 200 | 2 | 80 – 120 | 80 – 120 |

FIG. 14C

ANALYTE SENSOR AND MEDICANT DELIVERY DATA EVALUATION AND ERROR REDUCTION APPARATUS AND METHODS

RELATED APPLICATIONS

This application is related to co-owned U.S. patent application Ser. No. 13/559,475 filed Jul. 26, 2012 entitled "Tissue Implantable Sensor With Hermetically Sealed Housing," Ser. No. 14/982,346 filed Dec. 29, 2015 and entitled "Implantable Sensor Apparatus and Methods", Ser. No. 15/170,571 filed Jun. 1, 2016 and entitled "Biocompatible Implantable Sensor Apparatus and Methods", Ser. No. 15/197,104 filed Jun. 29, 2016 and entitled "Bio-adaptable Implantable Sensor Apparatus and Methods", Ser. No. 15/359,406 filed Nov. 22, 2016 and entitled "Heterogeneous Analyte Sensor Apparatus and Methods", Ser. No. 15/368,436 filed Dec. 2, 2016 and entitled "Analyte Sensor Receiver Apparatus and Methods", Ser. No. 15/472,091 filed Mar. 28, 2017 and entitled "Analyte Sensor User Interface Apparatus and Methods," and Ser. No. 15/645,913 filed Jul. 10, 2017 and entitled "Analyte Sensor Data Evaluation and Error Reduction Apparatus and Methods," each of the foregoing incorporated herein by reference in its entirety.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

TECHNICAL FIELD

The disclosure relates generally to the field of data analysis and processing, including for sensors, therapy devices, implants and other devices (such as those which can be used consistent with human beings or other living entities for in vivo detection and measurement or delivery of various solutes such as e.g., medicant), and in one exemplary aspect to methods and apparatus enabling the use of such sensors, measurement/delivery devices, and/or other electronic devices for, e.g. monitoring of one or more physiological parameters, including through use of error identification, analysis, and/or correction routines or computer programs to enhance the accuracy and reliability of such physiological parameter measurements, as well as the delivery of solutes based on such measurements.

DESCRIPTION OF RELATED TECHNOLOGY

Implantable electronics is a rapidly expanding discipline within the medical arts. Owing in part to significant advances in electronics and wireless technology integration, miniaturization, performance, and material biocompatibility, sensors or other types of electronics which once were beyond the realm of reasonable use within a living subject (i.e., in vivo) can now be surgically implanted within such subjects with minimal effect on the recipient subject, and in fact convey many inherent benefits.

One particular area of note relates to blood analyte monitoring for subjects, such as for example glucose monitoring for those with so-called "type 1" or "type 2" diabetes.

As is well known, regulation of blood glucose is impaired in people with diabetes by: (1) the inability of the pancreas to adequately produce the glucose-regulating hormone insulin; (2) the insensitivity of various tissues that use insulin to take up glucose; or (3) a combination of both of these phenomena. Safe and effective correction of this dysregulation requires blood glucose monitoring.

Currently, glucose monitoring in the diabetic population is based largely on collecting blood by "fingersticking" and determining its glucose concentration by conventional assay. This procedure has several disadvantages, including: (1) the discomfort associated with the procedure, which should be performed repeatedly each day; (2) the near impossibility of sufficiently frequent sampling (some blood glucose excursions require sampling every 20 minutes, or more frequently, to accurately treat); and (3) the requirement that the user initiate blood collection, which precludes warning strategies that rely on automatic early detection. Using the extant fingersticking procedure, the frequent sampling regimen that would be most medically beneficial cannot be realistically expected of even the most committed patients, and automatic sampling, which would be especially useful during periods of sleep, is not available.

Implantable glucose sensors (e.g., continuous glucose monitoring (CGM) sensors) have long been considered as an alternative to intermittent monitoring of blood glucose levels by the fingerstick method of sample collection. These devices may be fully implanted, where all components of the sensor system reside within the body and there are no through-the-skin (i.e. percutaneous) elements, or they may be partially implanted, where certain components reside within the body but are physically connected to additional components external to the body via one or more percutaneous elements, or they may be of a hybrid nature, where one element of the sensor system is fully implanted, but another element required for operation (e.g. a power source for the implanted element) must be worn in close proximity to the implanted element, but outside of the body on the skin at all times that the system is intended to operate. Further, such devices provide users a great deal of freedom from potentially painful intermittent sampling methods such as "fingersticking." as well as having to remember and obtain self-administered blood analyte readings.

The accuracy of blood analyte detection and measurement is an important consideration for implanted analyte sensors, especially in the context of current blood glucose monitoring systems (such as e.g., fully implanted blood glucose sensor systems), and even the future development of implantable blood glucose monitoring systems (such as e.g., in support of the development of an artificial pancreas). Hence, ensuring accurate measurement for extended periods of time (and minimizing the need for any other confirmatory or similar analyses) is of great significance. In conventional sensors, accuracy can be adversely affected by a myriad of factors such as e.g., random noise, foreign body response (FBR), other tissue responses, anoxia or hypoxia in the region of the analyte sensor, blood analyte tissue dynamics, mechanical jarring, migration, and/or other variables.

Sensor error due to such factors can be expressed by the mean absolute relative difference (MARD) between the sensor output and a set of comparison measurements (i.e., a reference measurement), or by the frequency of outliers in the comparison. In one example, the relationship between a measured blood analyte level and a reference blood analyte level (taken at a corresponding point in time) can be expressed by Equation (1) below:

$$BA_{ref} = BA_{cal} - BA_{s\_error} - e \qquad \text{Eqn. (1)}$$

The term "BA" is used herein to indicate blood analyte in general, and in Equation (1), "$BA_{ref}$" is a blood analyte level measured using an external source, "$BA_{cal}$" is a blood analyte level measured by a calibrated implanted sensor, "$BA_{s\_error}$" is systematic sensor error due to unmodeled (and possibly user-specific) system variables, while "e" is error due to random noise, including that of sensor components.

Many known sensor systems include mechanisms and/or programming for signal processing to reduce signal error due to random noise. For example, random noise error is primarily caused by random fluctuations in electrical signals received and/or produced by the sensor components, which can be modeled and/or approximated prior to implantation. Thus, random noise can be reduced via application of one or more standardized signal filters (such as e.g., finite impulse response (FIR), infinite impulse response (IIF), Kalman, Bayesian, and/or other signal processing filters) to the raw or calculated signal data. Accordingly, conventional sensor systems are often pre-programmed for application of random noise signal filters which are implemented during operation (i.e., analyte detection and reporting) of the implanted sensor system. FIG. 1 shows a typical method 100 (generalized) for operation of a conventional implantable analyte sensor. See e.g., U.S. patent application Ser. No. 13/742,694 entitled "Systems and Methods for Providing Sensitive and Specific Alarms."

However, "unmodeled" system variables (e.g., variables which are user and/or context-dependent, and hence may behave differently in each individual and/or context of measurement) present a particularly difficult challenge in determining and maintaining the accuracy of blood analyte measurements in an implanted sensor system. For instance, some analyte detection variables may be user-specific or context-specific based on factors such as, inter alia, disease presentation, anatomy, physiology, metabolism or metabolic rate, medications, diet, activities, habits, climate or geographic region of residence, altitude, lifestyle of the user and/or errors introduced via an imperfect calibration of the sensor. As the foregoing unmodeled system variables primarily affect analyte detection by implanted sensor systems in vivo (and may be highly variable or dynamic in nature), it is nearly impossible to pre-program or adapt a conventional sensor system with standardized mechanisms to account for such variables prior to implantation. While algorithms exist that are utilized for predicting a future blood glucose measurement, assuming the current measurements to be accurate, in order to predict the likelihood of hypoglycemia/hyperglycemia (see e.g., U.S. patent application Ser. No. 14/659,500 entitled "Glycemic Urgency Assessment and Alerts Interface," and Ser. No. 14/720,668 entitled "Systems And Methods For Dynamically And Intelligently Monitoring A Host's Glycemic Condition After an Alert is Triggered"), these approaches in no way seek to (or actually) improve the accuracy of blood glucose measurements in real-time.

Specifically, although conventional implantable sensor systems provide logic or programming to reduce error due to random noise, such blood analyte detection systems do not allow for correction of error due to unmodeled variables of the type previously described (i.e., user- and/or context-specific variables), which is highly desirable in that disease presentation, physiology, lifestyle, etc. may be different for each user, and may also dynamically change as a function of time or in response to a specific event occurring to or within the user.

Moreover, the impact of the foregoing unmodeled system variables (as well as error resulting from such variables) may be compounded when the implanted sensor system is used in combination with other semi-implantable, implantable, and/or non-implantable medical devices, such as medicant delivery devices (e.g., pumps).

As but one example, a CGM sensor system can be used in combination with a partially implanted (i.e., transcutaneous) pump for subcutaneous delivery of medicant, such as rapid-acting insulin. Specifically, analyte data (e.g., BA level, BA rate of change (ROC), etc.) from the CGM sensor system may be utilized for regulating or calculating a volume or rate of dispense of insulin to the patient via the partially implanted pump.

Precise insulin dosages can be programmed and/or calculated based on the analyte data, and automatically administered by the pump. In some use cases, the CGM data are reported to a user or medical professional (such as via an external user interface or display), and the partially implanted pump is then programmed by the user or medical professional to automatically dispense medicant at a specific volume and/or rate, based on an analysis of the CGM data. In other examples, the partially implanted pump receives analyte data from the CGM system via data communication with a separate intermediary control device (and/or direct communication with the pump which has control apparatus integrated therein). Thus, an appropriate dose of medicant can be automatically calculated and dispensed by the partially implanted pump based on the analyte data reported by the CGM system to a processor device (and associated calculation algorithm) in data communication with the pump.

Partially implanted insulin pumps are thereby configured to provide basal insulin around the clock, which is delivered at constant programmable rates or selectively tailored to the patient's real-time glucose profile. The partially implanted pumps further enable delivery of insulin boluses, which are administered during meal times to correct for high blood glucose levels associated with ingestion of food. For the pump (or an associated processing device) to accurately calculate bolus insulin amounts or rates, additional information input by the user is typically required, such as the estimated carbohydrate content of a meal.

Insulin pumps are intended to mimic certain aspects of normal pancreatic function and thereby provide basal-bolus insulin delivery that is improved over periodic insulin injections. Insulin pumps are reported to convey a myriad of advantages to the user, such as: (i) increased flexibility in daily living with regard to mealtimes, travel, work schedule, etc.; (ii) closer match of insulin delivery to physiological needs; (iii) automatic delivery of medicant during periods of rest (e.g., during sleep); (iv) reduced glycemic variability and improved glycemic control; (v) minimization of insulin peak and absorption-related variability; (vi) decreased risk of severe hypoglycemia and need for emergency medical attention; (vii) reduced hospitalization and associated costs of care; and (viii) reduced pain associated with multiple daily insulin injections, collectively resulting in an overall improved quality of life. See e.g., McAdams and Rizvi, "*An Overview of Insulin Pumps and Glucose Sensors for the Generalist*" J Clin Med. 2016 Jan.; 5(1):5, which is herein incorporated by reference in its entirety.

Exemplary transcutaneous pumps which can be used in combination with CGM sensors include tethered pumps, such as the Medtronic MiniMed® 670G Insulin Pump and the Tandem® t:slim X2™ Insulin Pump, and tubeless patch pumps, such as the OmniPod® Insulin Pump. For detailed descriptions of the foregoing exemplary pumps, see MiniMed® 670G System User Guide© 2016 Medtronic MiniMed, Inc., t:slim X2™ Insulin Pump User Guide© 2016 Tandem Diabetes Care, Inc., and UST400 User Guide Insulin Management System © 2014, 2015 Insulet Corporation, each of which is herein incorporated by reference in its entirety. See also U.S. Pat. No. 6,960,192, entitled "Transcutaneous Fluid Delivery System" and issued on Nov. 1, 2005; U.S. Pat. No. 7,267,665, entitled "Closed Loop System for Controlling Insulin Infusion" and issued on Sep. 11, 2007; and U.S. Pat. No. 7,819,843, entitled "External Infusion Device with Remote Programming, Bolus Estimator and/or Vibration Alarm Capabilities" and issued on Oct. 26, 2010, each of which is herein incorporated by reference in its entirety.

Tethered pumps are characterized by a tube or catheter which fluidly couples a medicant reservoir to an adhesive infusion set. The infusion set includes a cannula for insertion through the user's skin. A control device, which houses the medicant reservoir, a pump actuator, and a battery, is carried (e.g., held in a pocket) or worn (e.g., attached to a belt) by the user.

The tubeless patch pumps include a medicant reservoir, a pump actuator, and a battery, and an adhesive infusion set which are, as a unit, attached directly to the user's skin. After enablement and subcutaneous insertion of a cannula within the insertion set, the patch pump wirelessly communicates with a separate controlling device (e.g., a dedicated control device or a user's personal mobile device) for insulin delivery.

Each of the foregoing transcutaneous pumps requires relocation of the infusion set periodically (e.g., every two to three days), as the implanted cannula is subject to occlusion and insertion site infection, which can deleteriously affect medicant delivery (e.g., under-infusion of insulin). Thus, the transcutaneous pump user must undergo introduction of a new cannula at least every few days. As the cannula is continuously relocated, insulin absorption kinetics can unpredictably vary from one site to another (e.g., insulin absorption may vary at the front of the abdomen vs. the outer thigh) during use of the transcutaneous pump. Further, as the transcutaneous pump system is only semi-implanted, the exposed portions are subject mechanical jarring during use, which may also have unpredictable effects on insulin delivery.

Although not commercially available in the United States, CGM sensor systems can alternatively be used in combination with fully implanted pumps, such as a pump implanted in the intraperitoneal cavity of a user. Exemplary fully implantable pumps are described in U.S. Pat. No. 6,974,437, entitled "Microprocessor Controlled Ambulatory Medical Apparatus with Hand Held Communication Device" and issued on Dec. 13, 2005; and U.S. Pat. No. 4,871,351, entitled "Implantable Medication Infusion System" and issued on Oct. 3, 1989, each of which is herein incorporated by reference in its entirety. See also Lee, Joon Bok; Dassau, Eyal; Gondhalekar, Ravi et al. (2016) "*Enhanced Model Predictive Control (eMPC) Strategy for Automated Glucose Control*" Ind Eng Chem Res 55:11857-11868, which is herein incorporated by reference in its entirety.

Similar to partially implanted pumps, insulin dosages are programmed and/or calculated based on the analyte data (e.g., BA level, BA rate of change (ROC), etc.), and automatically administered. In some examples, the CGM data are reported to a user or medical professional, and the implanted pump is then programmed by the user or medical professional to automatically dispense medicant at specific rates based on an analysis of the CGM data. Additionally or alternatively, an appropriate dose of medicant can be automatically calculated and dispensed by the implanted pump based on the analyte data reported by the CGM system to a processor device in data communication with the pump. A user can provide additional information (e.g., the estimated carbohydrate content of a meal) and instruction to the implanted pump for delivery of insulin boluses during meal times.

In addition to the above described advantages of partially implanted pumps, fully implanted pumps enable, inter alia, (i) additional user freedom from repeated cannula relocation and insertion; (ii) delivery of insulin directly into the peritoneal cavity, which is believed to route insulin more quickly to the liver and reduce a concentration of insulin in the peripheral bloodstream; (iii) rapid glucose and insulin response dynamics within the body; (iv) decreased potential for accidental jarring of the pump due to e.g., "bumping"; and (v) increased mimic of normal pancreatic function and physiologic insulin action.

Fully implanted pumps generally include a catheter and a biocompatible housing which encloses a reservoir, a pump actuator, and a battery. A first end of the catheter is fluidly coupled to the reservoir and an opposing open end which is configured to be free within body tissues after implantation in the peritoneal cavity of a user. The reservoir is refillable via a subcutaneous port and requires refill by a medical professional at approximately three-month cycles. An additional port is located at the catheter attachment point of the housing, and can be flushed by a medical professional to clear occlusions or blockages from the catheter.

Like conventional implanted sensors, accuracy of fully implantable pumps can be adversely affected by factors associated with long term implantation such as e.g., FBR and protein deposits (which may cause occlusion or blockage of the catheter), other tissue responses, blood and tissue dynamics at the implantation site, mechanical jarring, and/or other variables.

Alternative to use of partially or fully implantable medicant pumps, non-implantable pumps may be used for subcutaneous medicant delivery based received on CGM sensor system data. Specifically, analyte data (e.g., BA level, BA rate of change (ROC), etc.) from the CGM sensor system may be utilized for calculating a volume and/or a time at which to dispense medicant (e.g., insulin) via an injection operation carried out by the user (e.g., positioning of the pump at an injection site, and subsequent manual actuation).

Similar to the implantable pumps, precise insulin dosages can be calculated based on the analyte data. However, as discussed supra, medicant delivery is carried out via positioning (i.e., transient subcutaneous placement of a needle) and manual actuation of the pump. In some examples, the non-implantable pump (or a processing device associated therewith) can send an alert to the user to communicate an appropriate time for medicant delivery, and, in response to the notification, the user carries out the medicant delivery procedure. Thus, an appropriate dose of medicant can be automatically calculated and/or scheduled based on the analyte data reported by the CGM system to a processor device (and associated calculation algorithm) in data communication with the non-implantable pump.

Exemplary non-implantable pumps which can be used in combination with CGM sensors include "smart" insulin pens, such as the Gluco Duo (from Tone Product Design) and the InPen®. For detailed description of the latter exemplary non-implantable pump, see INPEN® REUSABLE PEN INJECTOR User Manual © 2015 Companion Medical, Inc.

Further, exemplary non-implantable pumps are described in U.S. Patent Publication Nos. 2016/0012205, entitled "Medicine Administering System Including Injection Pen and Companion Device and published on Jan. 14, 2016, and 2017/0068799, entitled "System for Administering a Medicament" and published on Mar. 9, 2017, each of which is herein incorporated by reference in its entirety.

In yet another alternative to use of partially or fully implantable, or even non-implantable medicant pumps, other manual delivery mechanisms such as e.g., ocular, oral, subcutaneous, suppository, and/or transcutaneous mechanisms may be used for medicant delivery based on received CGM sensor system data. Thus, analyte data (e.g., BA level, BA rate of change (ROC), etc.) from the CGM sensor system may be utilized for calculating a volume and/or a time at which to manually dispense medicant (e.g., insulin) via manual delivery operation carried out by the user (e.g., injection with a hypodermic needle and syringe, jet injector, or the like).

Accordingly, medicant delivery which is guided, at least in part, by sensor BA readings and accomplished via either partially implanted or fully implanted pumps (or even non-implantable pumps or other manual/semi-manual delivery mechanisms) is subject to unmodeled system variables which affect the sensor ($BA_{s\_error}$), as well as any unmodeled system variables which affect the delivery device or pump ($BA_{p\_error}$).

In addition to those unmodeled system variables that can affect sensor accuracy, unmodeled system variables present a challenge in determining and maintaining the accuracy of medicant delivery via a partially implanted, fully implanted, or non-implanted pump or even non-pump delivery mechanisms (used in combination with an implanted sensor system). For instance, medicant absorption rates may be user-specific or context-specific based on factors such as, inter alia, location of cannula insertion, time elapsed since cannula insertion, medicant stability, medicant sensitivity of the user, disease presentation, anatomy, physiology, metabolism or metabolic rate either of the user as a whole or local to the cannula insertion site, other ingested medications, diet, activities, habits, climate or geographic region of residence, altitude, lifestyle of the user and/or errors introduced via an imperfect calibration of the pump.

Additionally, mechanical pump components are subject to normal "wear and tear" over the lifetime of the pump, as well as potentially being susceptible to external environmental influences (e.g., altitude, strong external magnetic fields, shock and vibration) which may also affect accuracy for at least periods of time. Further, implanted pump components are subject to FBR and other wound healing processes which can affect flow of medicant from the pump, such as by partial occlusion of the cannula or catheter or other infusion site issues.

The effect of pump error due to such factors can be characterized by the mean absolute relative difference (MARD) between a set of blood analyte reference measurements taken at given points in medicant treatment (e.g., prior to dispensing medicant, at the time of medicant dispensement, at incremental periods after dispensing medicant, etc.), and an expected blood analyte level or range at the given points of medicant treatment, or by the frequency of outliers in the comparison. In one example, the relationship between a measured reference blood analyte level and a target blood analyte level (corresponding to a point in treatment for the measured reference blood analyte level) can be expressed by Equation (2) below:

$$BA_{ref} = BA_{target} - BA_{p\_error} - e \qquad \text{Eqn. (2)}$$

In Equation (2), "$BA_{ref}$" is a blood analyte level measured using an external source, "$BA_{target}$" is a pre-determined blood analyte level which is desired or expected at a specific point of treatment, and "$BA_{p\_error}$" is systematic error in pump effect (i.e. the extent to which the effect of the delivered medicant differs from an anticipated effect) or "pump error" due to unmodeled (and possibly user-specific) system variables, and "e" is error due to random noise, including random noise related to the pump components.

Many known pump systems include mechanisms and/or programming for detecting pump errors due to complete or partial occlusion or other mechanical and/or processing issues, depletion of the medicant reservoir, determination that a bolus input received from a user does not match an expected bolus input, over or under delivery based on detected stroke volume of the pump, over- or under-delivery due to processing errors, etc., each of which may be addressed via a notification to the user and/or suspension of insulin delivery.

Further, random noise error may be caused by random fluctuations in electrical signals received and/or produced by the pump components, which can in some cases be at least partially modeled and/or approximated prior to implantation. Thus, random noise can in some cases be reduced via application of one or more standardized signal filters, such as those described above, to the raw or calculated signal data. However, "unmodeled" system variables (e.g., variables which are user and/or context-dependent, and hence may behave differently in each individual and/or context of measurement) present a particularly difficult challenge in determining and maintaining the accuracy of effective medicant delivery in a partially or fully implanted pump system. FIG. 9 shows a typical prior art method 900 (generalized) for operation of a conventional partially or fully implantable pump system.

Although conventional partially implantable, fully implantable, and non-implantable pump systems used in combination with CGM provide logic or programming to reduce error due to the foregoing detectable pump errors, such systems do not enable correction of error due to unmodeled variables of the type previously described (i.e., user- and/or context-specific variables), which is highly desirable in that disease presentation, physiology, lifestyle, etc. may be different for each user, and may also dynamically change as a function of time or in response to a specific event occurring to or within the user. As the foregoing unmodeled system variables primarily affect analyte detection and medicant delivery by implanted sensor and associated pump systems in vivo (and may be highly variable or dynamic in nature), it is nearly impossible to pre-program or adapt a conventional sensor and pump system with standardized mechanisms to account for such variables prior to implantation (or partial implantation) and/or activation and use.

The Assignee hereof has recently developed improved methods and apparatus for implanting and measuring blood analytes such as glucose; see, inter alia, U.S. patent application Ser. Nos. 13/559,475, 14/982,346, 15/170,571, 15/197,104, 15/359,406, 15/368,436, 15/472,091, and 15/645,913, previously incorporated herein. However, the Assignee has further recognized that areas of potential improvement over the prior art relate to, inter alia, providing an implanted analyte sensor system configured for improved accuracy of blood analyte level detection and reporting used in combination with partially implanted or fully implanted delivery devices (e.g., pumps) such as via in vivo adaptation to and/or modeling of the aforementioned unmodeled sensor and pump system variables.

Accordingly, there is a salient need for more user-specific (and user-adaptive) methods and apparatus for in vivo determination of error due to unmodeled system variables, and resulting (i) improved accuracy of blood analyte data measurement and calculation, as well as (ii) improved accuracy and/or efficacy of dispense of medicant based on the calculated analyte data.

SUMMARY

The present disclosure satisfies the foregoing needs by providing, inter alia, improved apparatus (including an implanted sensor used in combination with partially implanted and fully implanted pumps, as well as associated logic) and methods, for accurately providing information relating to sensed analyte data and dispensing medicant based on the sensed analyte data, including for example accounting or correcting for one or more sensor signal errors and one or more pump errors due to one or more unmodeled variables within a living subject.

In a first aspect, an apparatus for use an implantable pump apparatus is disclosed. In one embodiment, the apparatus includes a first data processing apparatus configured for data communication with the pump apparatus and a second data processing apparatus associated with an analyte sensor apparatus; and a storage apparatus in data communication with the processing apparatus. In one variant, the storage apparatus comprises a computer program which, when executed, causes the data processing apparatus to: (i) receive corrected blood analyte data from the blood analyte sensor while operated in a detection mode, the detection mode comprising application of an error correction operational model on blood analyte signal data generated by the sensor apparatus so as to correct or compensate for one or more sensor error sources; (ii) cause operation of the pump apparatus in an initial pump training mode, the initial pump training mode comprising at least utilization of the corrected blood analyte data; (iii) based at least in part on the operation of the pump apparatus in the initial pump training mode, cause generation of a pump error correction operational model; and (iv) subsequent to generation of the pump error correction operational model, cause operation of the pump apparatus in an auto-dispense mode, the auto-dispense mode comprising application of the pump error correction operational model on medicant data generated by the pump apparatus so as to correct or compensate for one or more pump error sources.

In varying implementations, the first data processing apparatus is disposed (i) on an external receiver apparatus with a partially implanted pump apparatus integrated therewith; (ii) on an external receiver apparatus which is non-integral to a partially implanted pump apparatus; or (iii) on a receiver apparatus disposed external to a user within which the pump apparatus is fully implanted, and the causation of generation of the pump error correction operational model comprises receipt of corrected blood analyte data from the sensor apparatus during the pump training mode via a data communication interface of the first processing apparatus, the first processor apparatus configured to perform the generation of the model via utilization of the corrected blood analyte data, stored target blood analyte data, and pump dispense data. In some implementations, the pump dispense data are received via the data communication interface from a non-integrated partially implanted or fully implanted pump apparatus.

In one variant, the implanted analyte sensor includes a glucose sensor (part of a so-called "continuous glucose monitor" or CGM), and the corrected blood analyte data are corrected blood glucose concentration data and/or corrected blood glucose rate of change (ROC) data. In one implementation, the glucose sensor is an oxygen-based glucose sensor. In another implementation, the glucose sensor is a hydrogen peroxide-based glucose sensor. In yet another implementation, the glucose sensor includes both a hydrogen peroxide-based sensor and oxygen-based glucose sensor.

In one variant, the pump apparatus includes a reservoir fluidly coupled to a catheter and one or more pump actuators for dispensement of insulin to a user, and the corrected medicant data comprises a corrected volume or rate for dispensement of insulin from the reservoir.

In another variant, the operation of the first processing apparatus in the initial pump training mode includes: (i) receipt of time-stamped corrected blood analyte data from the second processing apparatus in data communication with the sensor apparatus; (ii) collection of time-stamped pump dispense data; and (iii) accessing stored target blood analyte data based on volume or rate of medicant dispensement and duration of time lapsed post-dispensement. The initial pump training mode optionally further comprises collection of time-stamped data derived from one or more ancillary sensors.

In another implementation, the operation of the first processing apparatus in the initial pump training mode includes a determination that a training data collection threshold has been met; and in response to the determination, termination of the pump training mode operation. For example, the training data collection threshold may comprise a pre-determined number of data points, and/or a pre-determined duration of time.

In yet another variant of the apparatus, the generation of the pump error correction operational model includes: (i) generation of pump error data via calculation of a blood analyte error value at each of a plurality of corresponding time points from the stored target blood analyte data and the time-stamped corrected blood analyte data (received from the sensor); (ii) application of one or more mathematical models on at least the pump error data and data related to one or more other parameters; (iii) identification of at least one of the one or more other parameters which has a high correlation to the pump error data; and (iv) utilization of the identified at least one of the one or more other parameters, at least one of the one or more mathematical models, and the pump error data to generate the pump error correction operational model.

In one implementation, the data related to one or more other parameters includes data related to: (i) one or more times of day, and/or (ii) one or more ranges of blood analyte concentration.

In another implementation, the data related to one or more other parameters includes data related to: (i) a location of infusion set insertion, and/or (ii) a duration of time lapsed after infusion set insertion.

In yet another implementation, the data related to one or more other parameters includes data contemporaneously collected from one or more other sensors such as e.g., a pressure sensor and/or a temperature sensor. In another example, the one or more other sensors comprise at least a different blood analyte sensor, such as for detection of another blood analyte, and the data related to one or more other parameters comprises data related to blood concentration of the other analyte.

In yet another variant of the first processing apparatus, the operation of the pump apparatus in the corrected auto-dispense further includes: (i) receipt of the current corrected blood analyte data from the second processing apparatus; (ii) processing of the corrected blood analyte signal data via the application of the pump error correction operational model; (iii) generation of corrected medicant volume and/or rate data based at least on the processed corrected blood analyte level; and (iv) causation of the pump to dispense medicant according to the corrected medicant volume and/or rate data.

In yet another variant of the first processing apparatus, the computer program is further configured to, when executed, cause the first data processing apparatus to determine that one or more subsequent training mode criteria are met. In one implementation, the determination includes a determination that current error data are greater than a pre-determined error threshold, and/or that a time elapsed after the initial training mode is greater than a pre-determined time threshold.

In yet another variant of the first processing apparatus, the computer program is further configured to, when executed, cause the first data processing apparatus to determine that the current error data are less than an occlusion threshold. In one implementation, the computer program is further configured to, when executed, based at least in part that the error data are less the occlusion threshold, generate and cause transmission of a notification to the user to flush the pump catheter or move the location of the infusion site.

In another aspect, an apparatus for use with an implantable pump apparatus is disclosed. In one embodiment, the apparatus includes a data processing apparatus configured for data communication with the pump apparatus; and a storage apparatus in data communication with the processing apparatus. In one variant, the storage apparatus comprises a computer program which, when executed, causes the data processing apparatus to: (i) receive reference blood analyte data from an external source; (ii) cause operation of the pump apparatus in an initial pump training mode, the initial pump training mode comprising at least utilization of the reference blood analyte data; (iii) based at least in part on the operation of the pump apparatus in the initial pump training mode, cause generation of a pump error correction operational model; and (iv) subsequent to generation of the pump error correction operational model, cause operation of the pump apparatus in an auto-dispense mode, the auto-dispense mode comprising application of the pump error correction operational model on medicant data generated by the pump apparatus so as to correct or compensate for one or more pump error sources.

In one variant, the reference blood analyte data from an external source comprises user entered reference blood analyte data.

In yet another embodiment, the apparatus includes a first data processing apparatus configured for data communication with the pump apparatus and an analyte sensor apparatus; and a storage apparatus in data communication with the processing apparatus. In one variant, the storage apparatus comprises a computer program which, when executed, causes the data processing apparatus to: (i) cause operation of the blood analyte sensor apparatus in an initial training mode; (ii) based at least in part on the operation of the sensor apparatus in the initial training mode, cause generation of a sensor error correction operational model; (iii) subsequent to generation of the sensor error correction operational model, cause operation of the analyte sensor apparatus in a detection mode, the detection mode comprising application of the error correction operational model on blood analyte signal data generated by the sensor apparatus so as to correct or compensate for one or more error sources and produce corrected blood analyte data; (iv) cause operation of the pump apparatus in an initial pump training mode, the pump training mode at least in part comprising utilization of the corrected blood analyte data; (iii) based at least in part on the operation of the pump apparatus in the initial pump training mode, cause generation of a pump error correction operational model; and (iv) subsequent to generation of the pump error correction operational model, cause operation of the pump apparatus in an auto-dispense mode, the auto-dispense mode comprising application of the pump error correction operational model on medicant data generated by the pump apparatus so as to correct or compensate for one or more pump error sources.

In another aspect of the disclosure, a method of automatically dispensing medicant via a pump apparatus based on the blood analyte level is disclosed. In one embodiment, the method includes: (i) receiving corrected blood analyte data from a processor apparatus associated with a blood analyte sensing apparatus operating in a detection mode, the operating in the detection mode including applying the sensor error correction operational model on at least a portion of current blood analyte signal data; (ii) operating the pump apparatus in an initial training mode utilizing the corrected blood analyte data; (iii) based at least in part on the operating of the pump apparatus in the initial training mode, generating a pump error correction operational model; and (iv) subsequent to generating the pump error correction operational model, operating the pump apparatus in an auto-dispense mode, the operating in the auto-dispense mode including applying the pump error correction operational model on at least a portion of current blood analyte signal data.

In another embodiment, the method includes: (i) receiving reference blood analyte data from an external source; (ii) operating the pump apparatus in an initial training mode utilizing the reference blood analyte data; (iii) based at least in part on the operating of the pump apparatus in the initial training mode, generating a pump error correction operational model; and (iv) subsequent to generating the pump error correction operational model, operating the pump apparatus in an auto-dispense mode, the operating in the auto-dispense mode including applying the pump error correction operational model on at least a portion of current blood analyte signal data.

In yet another aspect of the disclosure, a method of monitoring a blood analyte level of a living being using a blood analyte sensing apparatus and automatically dispensing medicant via a pump apparatus based on the blood analyte level is disclosed. In one embodiment, the method includes: (i) operating the blood analyte sensing apparatus in an initial training mode; (ii) based at least in part on the operating of the sensor apparatus in the initial training mode, generating a sensor error correction operational model; (iii) subsequent to generating the sensor error correction operational model, operating the blood analyte sensing apparatus in a detection mode to generate corrected blood analyte data, the operating in the detection mode including applying the sensor error correction operational model on at least a portion of current blood analyte signal data; (iv) operating the pump apparatus in an initial training mode utilizing the corrected blood analyte data; (v) based at least in part on the operating of the pump apparatus in the initial training mode, generating a pump error correction operational model; and (vi) subsequent to generating the pump error correction operational model, operating the pump apparatus in an auto-dispense mode, the operating in the auto-dispense mode including applying the pump error correction operational model on at least a portion of current blood analyte signal data.

In another aspect, a computer readable apparatus is disclosed. In one embodiment, the computer readable apparatus comprises a storage medium (e.g., magnetic, solid state, optical, or other storage medium) having at least one computer program disposed thereon and readable by a computerized apparatus. The at least one computer program includes, in one variant, a plurality of instructions which, when executed on the computerized apparatus, cause operation of one or more medicant dispensing apparatus in a training mode, prior to operating the one or more apparatus in a detection mode. Operation in the training mode enables generation of one or more user-specific operational models (via e.g., "machine learning"), which can be used to at least partially correct for systemic or other errors during analyte detection and medicant delivery in subsequent modes.

In another aspect, a method of operating an implanted medicant pump is disclosed. In one embodiment, the implanted medicant pump is subject to one or more sources of systematic error, and the method includes: obtaining corrected blood analyte data from a blood analyte sensor system operated in a detection mode according to a sensor error correction operational model; obtaining first medicant dose data from an implanted pump apparatus, the obtained medicant dose data subject to the one or more sources of error; obtaining reference data for targeted medicant response of a user at least in part corresponding to the first medicant dose data; evaluating the obtained corrected blood analyte data, first medicant dose data, and the reference data using one or more machine learning algorithms; generating a pump operational error correction model based at least on the evaluating; and applying the generated pump operational model to second medicant dose data to correct for at least one of the one or more sources of error associated with the implanted pump.

In one variant, the method does not require identification or human understanding of one or more physical or physiologic mechanisms causing the at least one of the one or more sources of error associated with the implanted pump.

In another aspect, a method of monitoring a blood analyte level of a living being using a blood analyte sensing apparatus and automatically calculating a medicant dose for a non-implantable pump apparatus based on the blood analyte level is disclosed.

In yet another aspect, a method of compensating for or correcting errors caused at least in part by unknown or poorly understood mechanisms or sources associated with an implanted pump is disclosed.

In yet another aspect, a method of compensating for or correcting errors caused at least in part by unknown or poorly understood mechanisms associated with medicant reactivity and/or absorption within a patient is disclosed.

In yet another aspect of the disclosure, a computerized network apparatus is disclosed. In one embodiment, the network apparatus includes a cloud-based server apparatus configured to store, and optionally analyze, blood analyte data and medicant delivery data for a population of users (e.g., persons with at least partly implanted blood analyte sensors and at least partly implanted pumps, and/or their caregivers).

In still another aspect of the disclosure, a portable electronic apparatus is disclosed. In one embodiment, the portable electronic apparatus includes a portable receiver device configured to train an implanted medicant pump via, inter alia, wireless data communication therewith.

Other features and advantages of the present disclosure will immediately be recognized by persons of ordinary skill in the art with reference to the attached drawings and detailed description of exemplary embodiments as given below.

In another aspect of the present disclosure, a medicant dosing apparatus for use with a medicant delivery device is disclosed. In one embodiment, the medicant dosing apparatus includes: a storage apparatus in data communication with data processing apparatus, the storage apparatus including a computer program which is configured to, when executed by the data processing apparatus, cause the medicant dosing apparatus to: (i) cause operation of the medicant delivery device in a training mode; (ii) based at least in part on the operation of the medicant delivery device in the training mode, cause generation of an error correction operational model; and (iii) subsequent to generation of the error correction operational model, cause operation of the medicant delivery device in an operational mode.

In one variant, the operational mode includes: receipt of physiologic parameter signal data generated by the physiologic parameter sensor apparatus; and utilization of the physiologic parameter signal data and the error correction operational model so as to generate a prediction of one or more error sources associated with medicant delivery, and to correct or compensate for the predicted one or more error sources.

In another embodiment, the medicant dosing apparatus includes: a storage apparatus in data communication with processing apparatus, the storage apparatus including instructions configured to, when executed by the processing apparatus, cause the medicant dosing apparatus to: (i) receive data relating to operation of the medicant delivery device in a training mode; (ii) cause generation of an error correction operational model based at least in part on the received data; (iii) cause receipt of sensor data generated by the sensor apparatus; and (iv) utilize the sensor data and the error correction operation model to estimate one or more unmodeled errors associated with delivery of the medicant, and produce at least one compensation for the estimated one or more unmodeled errors.

In another aspect of the present disclosure, a medicant dosing apparatus for use with a medicant delivery device and a sensor apparatus is disclosed. In one embodiment, the medicant dosing apparatus includes: a storage apparatus in data communication with processing apparatus, the storage apparatus including at least one computer program having a plurality of instructions configured to, when executed by the processing apparatus, cause the medicant dosing apparatus to at least: (i) generate data relating to an error correction operational model, the generation of the data based at least in part on operation of the medicant delivery device in a training mode; (ii) cause operation of the sensor apparatus in a sensor training mode; (iii) based at least in part on the operation of the sensor apparatus in the sensor training mode, cause generation of a sensor error correction operational model; and (iv) cause application of the error correction operational model to at least a portion of current sensor signal data.

BRIEF DESCRIPTION OF THE DRAWINGS

FIG. 14C is a representation of tabular data corresponding to exemplary expected blood glucose response to insulin for various starting glucose levels.

FIGS. 1-9 and 11A-14C ©Copyright 2016-2017 GlySens Incorporated. All rights reserved. All other figures ©copyright of their respective copyright holders.

DETAILED DESCRIPTION

Figure 1:
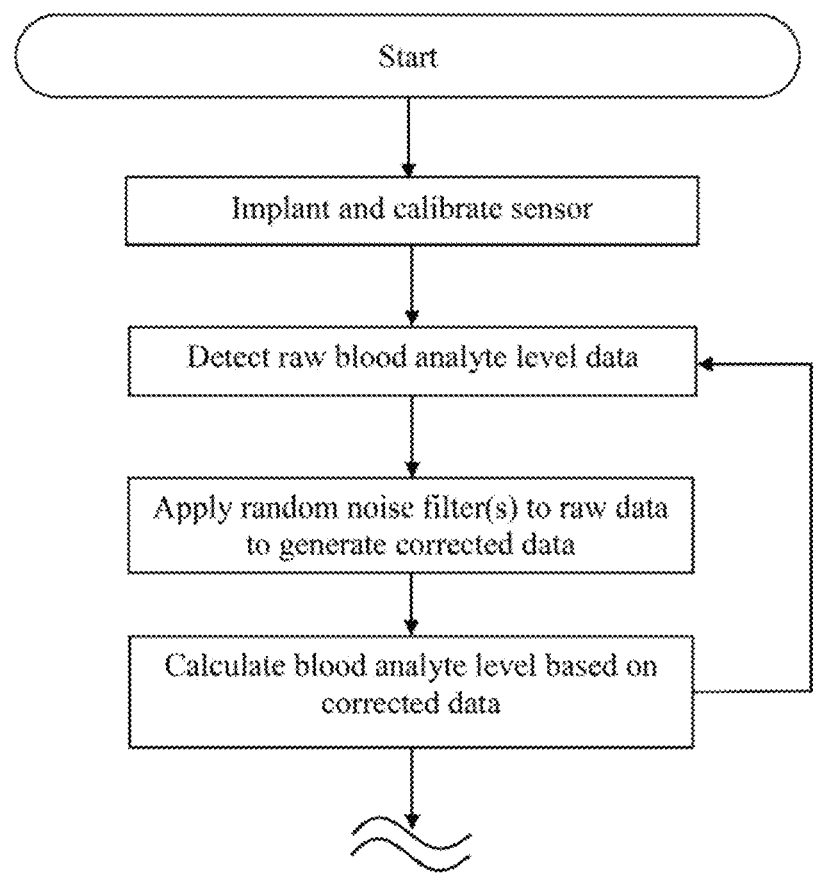
FIG. 1 is a logical flow diagram illustrating a typical prior art method for operating an at least partly implantable blood analyte monitoring system.

Reference is now made to the drawings, wherein like numerals refer to like parts throughout.

Overview

One aspect of the present disclosure leverages Assignee's recognition that many of the above-described disabilities of the prior art in providing accurate blood analyte data and automatically calculating an appropriate amount, time, and/or rate for medicant delivery based on blood analyte data are due to a lack of an ability to account or correct for otherwise "unmodeled" variable errors in calculation of blood analyte data and medicant dosing data which occur when implanted sensors and associated implanted or non-implanted medicant pumps (or even non-pump medicant delivery mechanisms) are utilized in vivo. Further, the Assignee hereof recognizes that error in blood analyte sensor data and medicant dosing data due to such unmodeled variables is often user-specific and/or only determinable after implantation of the sensor and/or pump. Such disabilities of the prior art can be mitigated or even completely eliminated via (i) personalized and dynamic detection of blood analyte level and compensation for associated errors when the sensor is implanted within the user, and (ii) personalized and dynamic calculation of medicant dosage and/or compensation for associated errors when the pump is activated and utilized (whether partially implanted, fully implanted, or non-implanted) by the specific user.

Accordingly, the apparatus and methods of the present disclosure, in one exemplary embodiment, employ receipt of accurate blood analyte data (e.g., corrected sensor data from a processing apparatus associated with an implanted sensor or reference blood analyte data from an external source, such as blood analyte levels obtained by fingersticking) at a processing apparatus which controls the pump. The aforementioned corrected sensor data may be generated by the apparatus and methods described in U.S. patent application Ser. No. 15/645,913, previously incorporated herein. The received corrected sensor data and/or reference blood analyte data are utilized by the pump during a training mode of operation, whereby the processing apparatus associated with the pump (or processing logic associated therewith, whether on-board or off-board) conducts "machine learning" to model one or more unmodeled variable system errors associated with the medicant dispensement data calculation, and generation of a pump error correction operational model (based at least in part on data collected/received in the training mode), which is applied to correct or compensate for the errors during an auto-dispense mode operation of implanted pumps or an auto-calculate mode operation of non-implanted pumps or other manual medicant delivery mechanisms.

In another exemplary embodiment, the apparatus and methods of the present disclosure employ a training mode of operation of a sensor and pump system, whereby the processing apparatus conducts machine learning to model one or more unmodeled variable system errors associated with the blood analyte measurement process, and generation of a sensor operational model (based at least in part on data collected/received in the sensor training mode), which is applied to correct or compensate for the errors during normal operation of the sensor for collection of blood analyte data. Further, the processing apparatus additionally communicates with the pump for operation of the sensor and pump system in a pump training mode, whereby the processing apparatus conducts machine learning to model one or more unmodeled variable system errors associated with the medicant dosing calculation process, and generation of a pump operational model (based at least in part on data collected/received in the pump training mode), which is applied to correct or compensate for the errors during normal operation of the pump for calculation of medicant dosage data. In one variant, the training mode operation of the sensor precedes the training mode operation of the pump, and the corrected sensor data are utilized during training mode operation of the pump. In another variant, the training mode operations of the sensor and the pump are at least partially concurrent, and reference blood analyte data from an external source is used during the training mode operations.

In yet another exemplary embodiment, the foregoing implanted sensor system and sensor operational model can be utilized in generation of a patient-specific medicant dosing model. In some examples, the patient-specific medicant dosing model is applicable to delivery of medicants without use of a pump (i.e., manual medicant delivery via e.g., oral, ocular, subcutaneous, cutaneous, nasal or other mechanisms) and/or manual or semi-manual medicant pump mechanisms. In such examples, unmodeled variables related to user-specific medicant absorption or affect (based on e.g., physiology, lifestyle, and/or disease presentation of a specific individual) can be modeled via operation of the implanted sensor system and monitoring of analyte levels before, during and after medicant delivery to the user. Based on the generated patient-specific medicant dosing model, a processor associated with the sensor system (or a separate processor which receives sensor data) may communicate to the user an appropriate dosage or time for delivery of the medicant via manual administration or semi-manual administration. Thus, the application further contemplates generation of a patient-specific dosing model that can be associated with any type of medicant delivery mechanism.

The methods and apparatus of the present disclosure also, in one embodiment, leverage the only recently-available capability for long-term implantation of blood analyte sensing devices (such as the oxygen-based blood glucose sensing device manufactured by the Assignee hereof), to yet further enhance device signal stability and accuracy over extended periods of implantation, including through "personalization" of the sensor apparatus via the aforementioned training mode and subsequent sensor operational model generation, and/or utilization of the corrected sensor data for operation of the implanted pump in the pump training mode, as well as subsequent pump operational model generation and utilization.

Moreover, exemplary embodiments of the methods and apparatus disclosed herein need not have any fundamental or even basic knowledge of the mechanism(s) underlying the unmodeled variables/errors; rather, the system(s) can advantageously identify, model and compensate for such errors without having to understand how or why the errors occur (such as in the case of a poorly understood or previously unknown physiologic phenomenon occurring within the specific user).

Additionally, the foregoing pump training mode can be repeated (as necessary, on a prescribed schedule, or according to yet other bases), even as disease presentation or other physiological or lifestyle characteristics of the user change over that same time. In one variant, the pump training mode is repeated each time a transcutaneous pump insertion set is relocated to a new insertion site. In another variant, the pump training mode is repeated after each catheter flushing operation and/or medicant refilling operation of a fully implanted sensor to maintain accuracy throughout the implantation lifetime.

Methods of use of the aforementioned blood analyte detection system utilized with (or integral to) a medicant dispensement pump system, as well as other aspects, are also disclosed herein.

It will be appreciated that although reference is made throughout to "blood analyte" and "blood analyte level," that the principles of the invention apply equally to any system that utilizes a medicant delivery device to modulate a measurable physiologic parameter, and is not restricted to systems where the parameter is solely a blood analyte level. To that end, the terms "blood analyte" and "blood analyte level" can be taken as synonymous with "physiologic parameter" and "physiologic parameter level."

Detailed Description of Exemplary Embodiments

Exemplary embodiments of the present disclosure are now described in detail.

While these embodiments are primarily discussed in the context of a fully implantable glucose sensor, such as those exemplary embodiments described herein, and/or those set forth in U.S. Patent Application Publication No. 2013/0197332 filed Jul. 26, 2012 entitled "Tissue Implantable Sensor With Hermetically Sealed Housing;" U.S. Pat. No. 7,894,870 to Lucisano et al. issued Feb. 22, 2011 and entitled "Hermetic Implantable Sensor;" U.S. Patent Application Publication No. 2011/0137142 to Lucisano et al. published Jun. 9, 2011 and entitled "Hermetic Implantable Sensor;" U.S. Pat. No. 8,763,245 to Lucisano et al. issued Jul. 1, 2014 and entitled "Hermetic Feedthrough Assembly for Ceramic Body;" U.S. Patent Application Publication No. 2014/0309510 to Lucisano et al. published Oct. 16, 2014 and entitled "Hermetic Feedthrough Assembly for Ceramic Body;" U.S. Pat. No. 7,248,912 to Gough et al. issued Jul. 24, 2007 and entitled "Tissue Implantable Sensors for Measurement of Blood Solutes;" and U.S. Pat. No. 7,871,456 to Gough et al. issued Jan. 18, 2011 and entitled "Membranes with Controlled Permeability to Polar and Apolar Molecules in Solution and Methods of Making Same;" and U.S. Patent Application Publication No. 2013/0197332 to Lucisano et al. published Aug. 1, 2013 and entitled "Tissue Implantable Sensor with Hermetically Sealed Housing;" PCT Patent Application Publication No. 2013/016573 to Lucisano et al. published Jan. 31, 2013 and entitled "Tissue Implantable Sensor with Hermetically Sealed Housing," each of the foregoing incorporated herein by reference in its entirety, as well as those of U.S. patent application Ser. Nos. 13/559,475, 14/982,346, 15/170,571, and 15/197,104, 15/359,406, 15/368,436, 15/472,091, and 15/645,913 previously incorporated herein, it will be recognized by those of ordinary skill that the present disclosure is not so limited. In fact, the various aspects of the disclosure are useful with, inter alia, other types of implantable sensors, implantable pumps, and/or electronic devices.

Further, while the following embodiments describe specific implementations of e.g., biocompatible oxygen-based multi-sensor element devices for measurement of glucose utilized with biocompatible transcutaneous or fully implanted insulin pump devices having specific configurations, protocols, locations, and orientations for implantation (e.g., sensor implantation proximate the waistline on a human abdomen with the sensor array disposed proximate to fascial tissue; see e.g., U.S. patent application Ser. No. 14/982,346, entitled "Implantable Sensor Apparatus and Methods" and filed Dec. 29, 2015, previously incorporated herein; transcutaneous pump implantation at the front or back of the torso, upper arms, and thighs; see e.g., MiniMed® 670G System User Guide© 2016 Medtronic MiniMed, Inc., previously incorporated herein; and pump implantation within the intraperitoneal cavity; see e.g., Waxman et al., "*Implantable Programmable Insulin Pumps for the Treatment of Diabetes*" Arch Surg. 1992; 127: 10342-1037, which is herein incorporated by reference in its entirety), those of ordinary skill in the related arts will readily appreciate that such descriptions are purely illustrative, and in fact the methods and apparatus described herein can be used consistent with, and without limitation: (i) in living beings other than humans; (ii) other types or configurations of sensors (e.g., other types, enzymes, and/or theories of operation of glucose sensors, sensors other than glucose sensors, such as e.g., sensors for other analytes such as urea, lactate); (iii) other implantation locations and/or techniques (including without limitation transcutaneous or non-implanted devices as applicable); and/or (iv) other devices (e.g., non-sensors and non-substance delivery devices).

As used herein, the term "analyte" refers without limitation to a substance or chemical species that is of interest in an analytical procedure. In general, the analyte itself may or may not be directly measurable, in cases where it is not, a measurement of the analyte (e.g., glucose) can be derived through measurement of chemical constituents, components, or reaction byproducts associated with the analyte (e.g., hydrogen peroxide, oxygen, free electrons, etc.).

As used herein, the terms "delivery device" and "medicant delivery device" refer to a device configured for delivery of solutes, including without limitation one or more mechanical or electro-mechanical pumps, such as partially implanted or fully implanted pumps, as well as other delivery modes such as diffusion (e.g., through a membrane or other barrier), or even dissolution of solids. Exemplary partially implantable pumps include transcutaneous pumps which include an implantable portion (e.g., a cannula, a needle, etc.) coupled to a non-implantable portion (e.g., a housing, a reservoir, a pump actuator, etc.). Exemplary fully implantable pumps include subcutaneous pumps, which are implanted beneath the skin of a user and are in data communication with an external controlling (e.g., processing) apparatus.

As used herein, the terms "detector" and "sensor" refer without limitation to a device having one or more elements (e.g., detector element, sensor element, sensing elements, etc.) that generate, or can be made to generate, a signal indicative of a measured parameter, such as the concentration of an analyte (e.g., glucose) or its associated chemical constituents and/or byproducts (e.g., hydrogen peroxide, oxygen, free electrons, etc.). Such a device may be based on electrochemical, electrical, optical, mechanical, thermal, or other principles as generally known in the art. Such a device may consist of one or more components, including for example, one, two, three, or four electrodes, and may further incorporate immobilized enzymes or other biological or physical components, such as membranes, to provide or enhance sensitivity or specificity for the analyte.

As used herein, the terms "orient," "orientation," and "position" refer, without limitation, to any spatial disposition of a device and/or any of its components relative to another object or being, and in no way connote an absolute frame of reference.

As used herein, the terms "top," "bottom," "side," "up," "down," and the like merely connote, without limitation, a relative position or geometry of one component to another, and in no way connote an absolute frame of reference or any required orientation. For example, a "top" portion of a component may actually reside below a "bottom" portion when the component is mounted to another device (e.g., host sensor).

As used herein the term "parent platform" refers without limitation to any device, group of devices, and/or processes with which a client or peer device (including for example the various embodiments of local receiver described here) may logically and/or physically communicate to transfer or exchange data. Examples of parent platforms can include, without limitation, smartphones, tablet computers, laptops, smart watches, personal computers/desktops, servers (local or remote), gateways, dedicated or proprietary analyte receiver devices, medical diagnostic equipment, and even other local receivers acting in a peer-to-peer or dualistic (e.g., master/slave) modality.

As used herein, the term "application" (or "app") refers generally and without limitation to a unit of executable software that implements a certain functionality or theme. The themes of applications vary broadly across any number of disciplines and functions (such as on-demand content management, e-commerce transactions, brokerage transactions, home entertainment, calculator etc.), and one application may have more than one theme. The unit of executable software generally runs in a predetermined environment; for example, the Java® environment.

As used herein, the term "computer program" or "software" is meant to include any sequence or human or machine cognizable steps which perform a function. Such program may be rendered in virtually any programming language or environment including, for example, C/C++, Fortran, COBOL, PASCAL, assembly language, markup languages (e.g., HTML, SGML, XML, VoXML), and the like, as well as object-oriented environments such as the Common Object Request Broker Architecture (CORBA), Java® (including J2ME, Java Beans, etc.) and the like.

As used herein, the terms "Internet" and "internet" are used interchangeably to refer to inter-networks including, without limitation, the Internet. Other common examples include but are not limited to: a network of external servers, "cloud" entities (such as memory or storage not local to a device, storage generally accessible at any time via a network connection, or cloud-based or distributed processing or other services), service nodes, access points, controller devices, client devices, etc.

As used herein, the term "memory" includes any type of integrated circuit or other storage device adapted for storing digital data including, without limitation, ROM, PROM, EEPROM, DRAM, SDRAM, DDR/2 SDRAM, EDO/FPMS, RLDRAM, SRAM, "flash" memory (e.g., NAND/NOR), 3D memory, and PSRAM.

As used herein, the terms "microprocessor" and "processor" or "digital processor" are meant generally to include all types of digital processing devices including, without limitation, digital signal processors (DSPs), reduced instruction set computers (RISC), general-purpose (CISC) processors, microprocessors, gate arrays (e.g., FPGAs), PLDs, state machines, reconfigurable computer fabrics (RCFs), array processors, secure microprocessors, and application-specific integrated circuits (ASICs). Such digital processors may be contained on a single unitary integrated circuit (IC) die, or distributed across multiple components.

As used herein, the term "network" refers generally to any type of telecommunications or data network including, without limitation, hybrid fiber coax (HFC) networks, satellite networks, telco networks, and data networks (including MANs, WANs, LANs, WLANs, internets, and intranets), cellular networks, as well as so-called "mesh"

networks and "IoTs" (Internet(s) of Things). Such networks or portions thereof may utilize any one or more different topologies (e.g., ring, bus, star, loop, etc.), transmission media (e.g., wired/RF cable, RF wireless, millimeter wave, optical, etc.) and/or communications or networking protocols.

As used herein, the term "interface" refers to any signal or data interface with a component or network including, without limitation, those of the FireWire (e.g., FW400, FW800, etc.), USB (e.g., USB 2.0, 3.0. OTG), Ethernet (e.g., 10/100, 10/100/1000 (Gigabit Ethernet), 10-Gig-E, etc.), MoCA, LTE/LTE-A, Wi-Fi (802.11), WiMAX (802.16), Z-wave, PAN (e.g., 802.15)/Zigbee, CBRS (Citizens Broadband Radio Service), Bluetooth, Bluetooth Low Energy (BLE) or power line carrier (PLC) families.

As used herein, the term "storage" refers to without limitation computer hard drives, memory, RAID devices or arrays, optical media (e.g., CD-ROMs, Laserdiscs, Blu-Ray, etc.), solid state devices (SSDs), flash drives, cloud-hosted storage, or network attached storage (NAS), or any other devices or media capable of storing data or other information.

As used herein, the term "Wi-Fi" refers to, without limitation and as applicable, any of the variants of IEEE-Std. 802.11 or related standards including 802.11 a/b/g/n/s/v/ac/ax or 802.11-2012/2013, as well as Wi-Fi Direct (including inter alia, the "Wi-Fi Peer-to-Peer (P2P) Specification", incorporated herein by reference in its entirety).

As used herein, the term "wireless" means any wireless signal, data, communication, or other interface including without limitation Wi-Fi, Bluetooth (including BLE or "Bluetooth Smart"), 3G (3GPP/3GPP2), HSDPA/HSUPA, TDMA, CDMA (e.g., IS-95A, WCDMA, etc.), FHSS, DSSS, GSM, PAN/802.15, WiMAX (802.16), 802.20, Zigbee®, Z-wave, narrowband/FDMA, OFDM, PCS/DCS, LTE/LTE-A/LTE-U/LTE-LAA, CBRS (Citizens Broadband Radio Service), analog cellular, CDPD, satellite systems, millimeter wave or microwave systems, acoustic, and infrared (i.e., IrDA).

Exemplary Implantable Sensor

Figure 2:
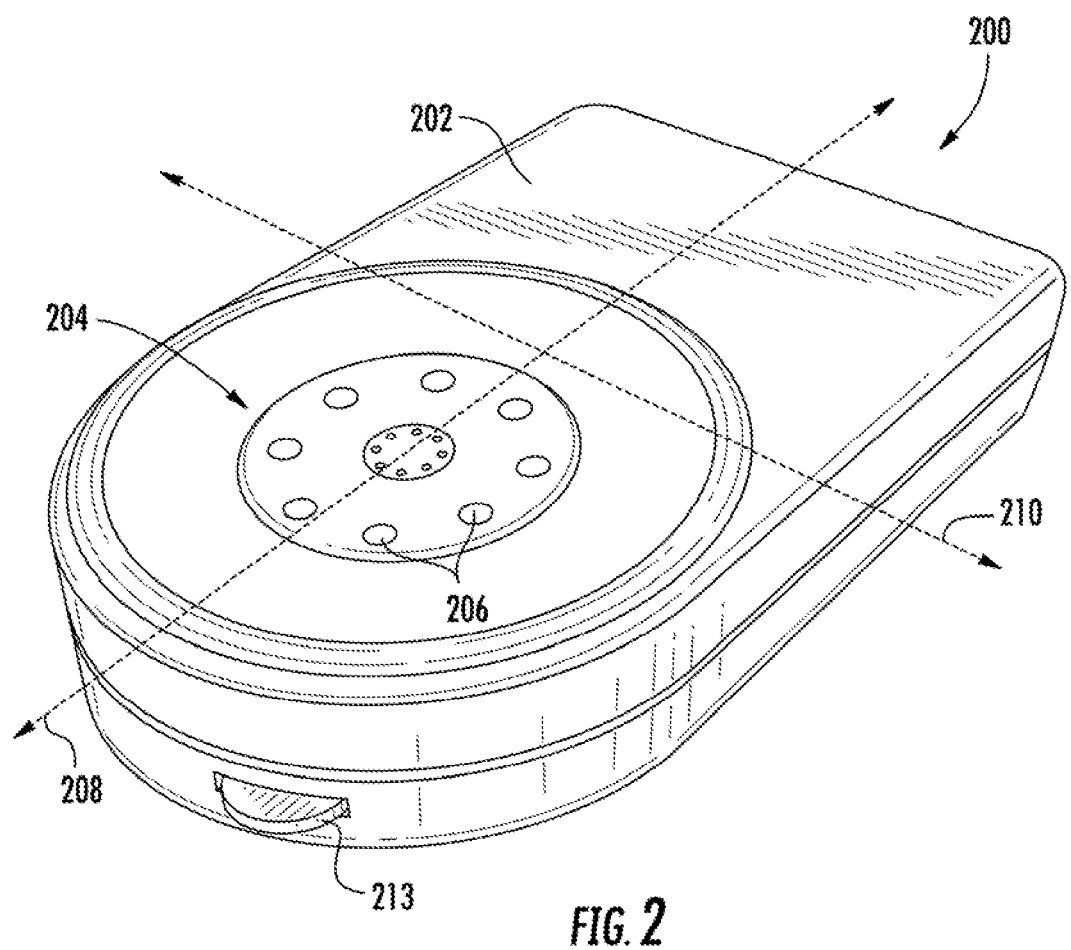
FIG. 2 is a front perspective view of one exemplary embodiment of a fully implantable biocompatible sensor apparatus useful with various aspects of the present disclosure.
Figure 2A:
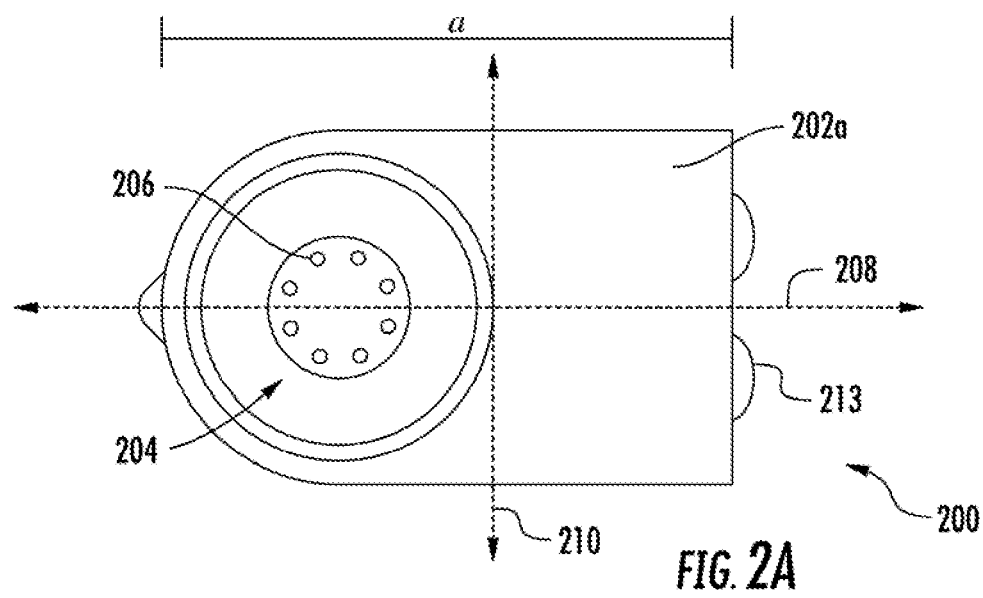
FIGS. 2A-2C are top, bottom, and side elevation views, respectively, of the exemplary sensor apparatus of FIG. 2.
Figure 2B:
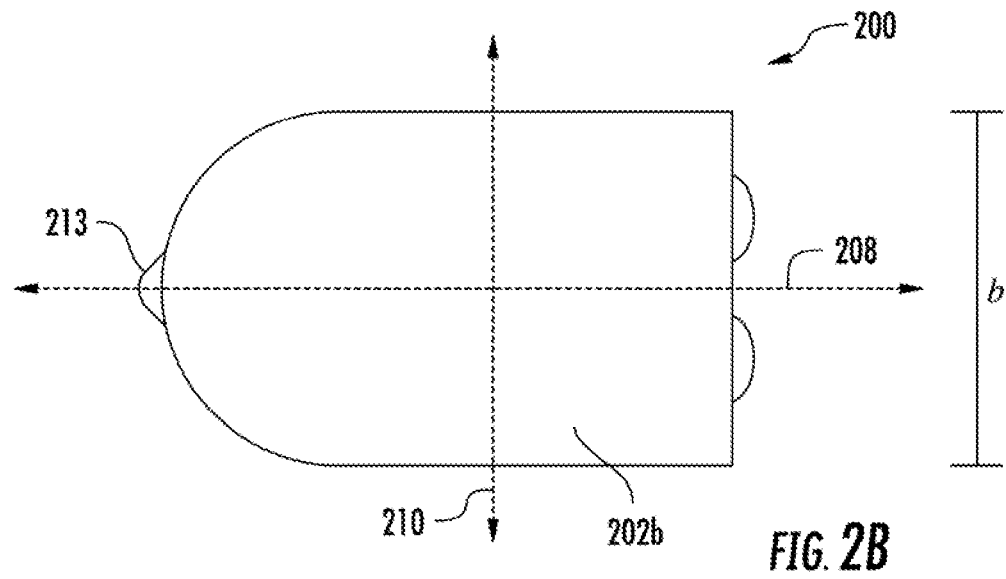
Figure 2C:
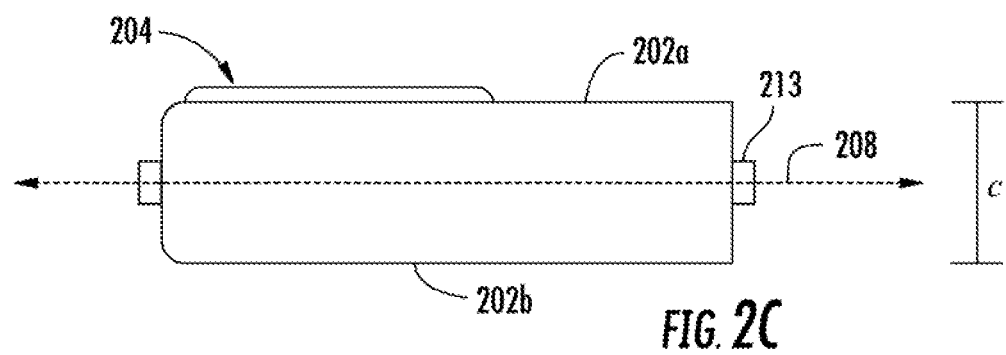

Referring now to FIGS. 2-2C, one exemplary embodiment of a sensor apparatus useful with various aspects of the present disclosure is shown and described.

As shown in FIGS. 2-2C, the exemplary sensor apparatus 200 comprises a somewhat planar housing structure 202 with a sensing region 204 disposed on one side thereof (i.e., a top face 202a). As described in greater detail below with respect to FIGS. 4-5, the exemplary substantially planar shape of the housing 202 provides mechanical stability for the sensor apparatus 200 after implantation, thereby helping to preserve the orientation of the apparatus 200 and mitigate any tissue response induced by movement of the apparatus while implanted. Notwithstanding, the present disclosure contemplates sensor apparatus of shapes and/or sizes other than that of the exemplary apparatus 200.

The sensor apparatus of FIGS. 2-2C further includes a plurality of individual sensor elements 206 with their active surfaces disposed substantially within the sensing region 204 on the top face 202a of the apparatus housing. In the exemplary embodiment (i.e., an oxygen-based glucose sensor), the eight (8) sensing elements 206 are grouped into four pairs, one element of each pair an active or "primary" sensor with enzyme matrix, and the other a reference or "secondary" (oxygen) sensor. Exemplary implementations of the sensing elements and their supporting circuitry and components are described in, inter alia, U.S. Pat. No. 7,248,912, previously incorporated herein. It will be appreciated, however, that the type and operation of the sensor apparatus may vary; i.e., other types of sensor elements/sensor apparatus, configurations, and signal processing techniques thereof may be used consistent with the various aspects of the present disclosure, including, for example, signal processing techniques based on various combinations of signals from individual elements in the otherwise spatially-defined sensing elements pairs.

The illustrated embodiment of FIGS. 2-2C includes a sensing region 204 which facilitates some degree of "interlock" of the surrounding tissue (and any subsequent tissue response generated by the host) so as to ensure direct and sustained contact between the sensing region 204 and the blood vessels of the surrounding tissue during the entire term of implantation (as well as advantageously maintaining contact between the sensing region 204 and the same tissue; i.e., without significant relative motion between the two).

The sensor apparatus 200 also includes in the exemplary embodiment a wireless radio frequency transmitter (or transceiver, depending if signals are intended to be received by the apparatus), not shown. As described in the aforementioned documents incorporated herein, the transmitter/transceiver may be configured to transmit modulated radio frequency signals to an external receiver/transceiver, such as a dedicated receiver device, or alternatively a properly equipped consumer electronic device such as a smartphone or tablet computer. Moreover, the sensor apparatus 200 may be configured to transmit signals to (whether in conjunction with the aforementioned external receiver, or in the alternative) a partially or fully implanted or in vivo receiving device, such as an implanted pump or other medication or substance delivery system (e.g., an insulin pump or dispensing apparatus, such as those shown in FIGS. 10A-10F and discussed infra), embedded "logging" device, or other. It is also appreciated that other forms of wireless communication may be used for such applications, including for example inductive (electromagnetic induction) based systems, or even those based on capacitance or electric fields, or even optical (e.g., infrared) systems where a sufficiently clear path of transmission and reception exists, such as two devices in immediately adjacent disposition, or even ultrasonic systems where the two devices are sufficiently close and connected by sound-conductive media such as body tissues or fluids, or a purposely implanted component.

The sensor apparatus of FIGS. 2-2C also includes a plurality (three in this instance) of tabs or anchor apparatus 213 disposed substantially peripheral on the apparatus housing. These anchor apparatus provide the implanting surgeon with the opportunity to anchor the apparatus to the anatomy of the living subject, so as to frustrate translation and/or rotation of the sensor apparatus 200 within the subject immediately after implantation but before any tissue response (e.g., FBR) of the subject has a chance to immobilize (such as via interlock with the sensing region of the apparatus. See e.g., U.S. patent application Ser. No. 14/982, 346 filed Dec. 29, 2015 and entitled "Implantable Sensor Apparatus and Methods" previously incorporated herein, for additional details and considerations regarding the aforementioned anchor apparatus 213 (which may include, for example features to receive sutures (dissolvable or otherwise), tissue ingrowth structures, and/or the like).

Moreover, another exemplary embodiment of the sensor apparatus 200 described herein may include either or both of: (i) multiple detector elements with respective "staggered" ranges/rates of detection operating in parallel, and/or (ii) multiple detector elements with respective "staggered" ranges/rates of detection that are selectively switched on/off in response to, e.g., the analyte concentration reaching a prescribed upper or lower threshold, as described in the foregoing patent application Ser. No. 15/170,571 previously incorporated herein.

The present disclosure further contemplates that such thresholds or bounds: (i) can be selected independent of one another; and/or (ii) can be set dynamically while the apparatus 200 is implanted. For example, in one scenario, operational detector elements are continuously or periodically monitored to confirm accuracy, and/or detect any degradation of performance (e.g., due to equipment degradation, progressive FBR affecting that detector element, etc.); when such degradation is detected, affecting say a lower limit of analyte concentration that can be detected, that particular detector element can have its lower threshold adjusted upward, such that handoff to another element capable of more accurately monitoring concentrations in that range. Note that these thresholds or bounds are to be distinguished from those associated with the user interface (UI) described subsequently herein, the latter being independent of the data source/capability/configuration associated with the sensor detector elements.

It will be appreciated that the relatively smaller dimensions of the sensor apparatus (as compared to many conventional implant dimensions)—on the order of 40 mm in length (dimension "a" on FIGS. 2A-2C) by 25 mm in width (dimension "b" on FIGS. 2A-2C) by 10 mm in height (dimension "c" on FIGS. 2A-2C)—may reduce the extent of injury (e.g., reduced size of incision, reduced tissue disturbance/removal, etc.) and/or the surface area available for blood/tissue and sensor material interaction, which may in turn reduce intensity and duration of the host wound healing response. It is also envisaged that as circuit integration is increased, and component sizes (e.g., Lithium or other batteries) decrease, and further improvements are made, the sensor may increasingly be appreciably miniaturized, thereby further leveraging this factor.

Sensor System Architectures—

As described elsewhere herein, exemplary embodiments of the present disclosure utilize machine learning algorithms to, inter alia, compensate for systemic errors, whether well modeled, or unmodeled, affecting a blood analyte sensor apparatus, and in certain embodiments, those affecting substance delivery, such as medicant delivery devices (e.g., insulin pumps) and/or manual/semi-manual medicant delivery mechanisms (e.g., subcutaneous insulin injection via a syringe or a computerized insulin injection pen). Notably, such algorithms may be implemented in computerized logic (software, firmware, or even hardware) that is resident in any number of different locations within the system, including: (i) within the implanted sensor apparatus itself; (ii) "off-board" the sensor apparatus, such as in an external receiver apparatus (examples of which are described below); (iii) off-board, in a connected "cloud" entity; and/or combinations of the foregoing (e.g., in a distributed computing architecture). Accordingly, the following embodiments are merely examples of such types of architectures, and the various aspects of the present disclosure are in no way limited thereto.

Figure 3:
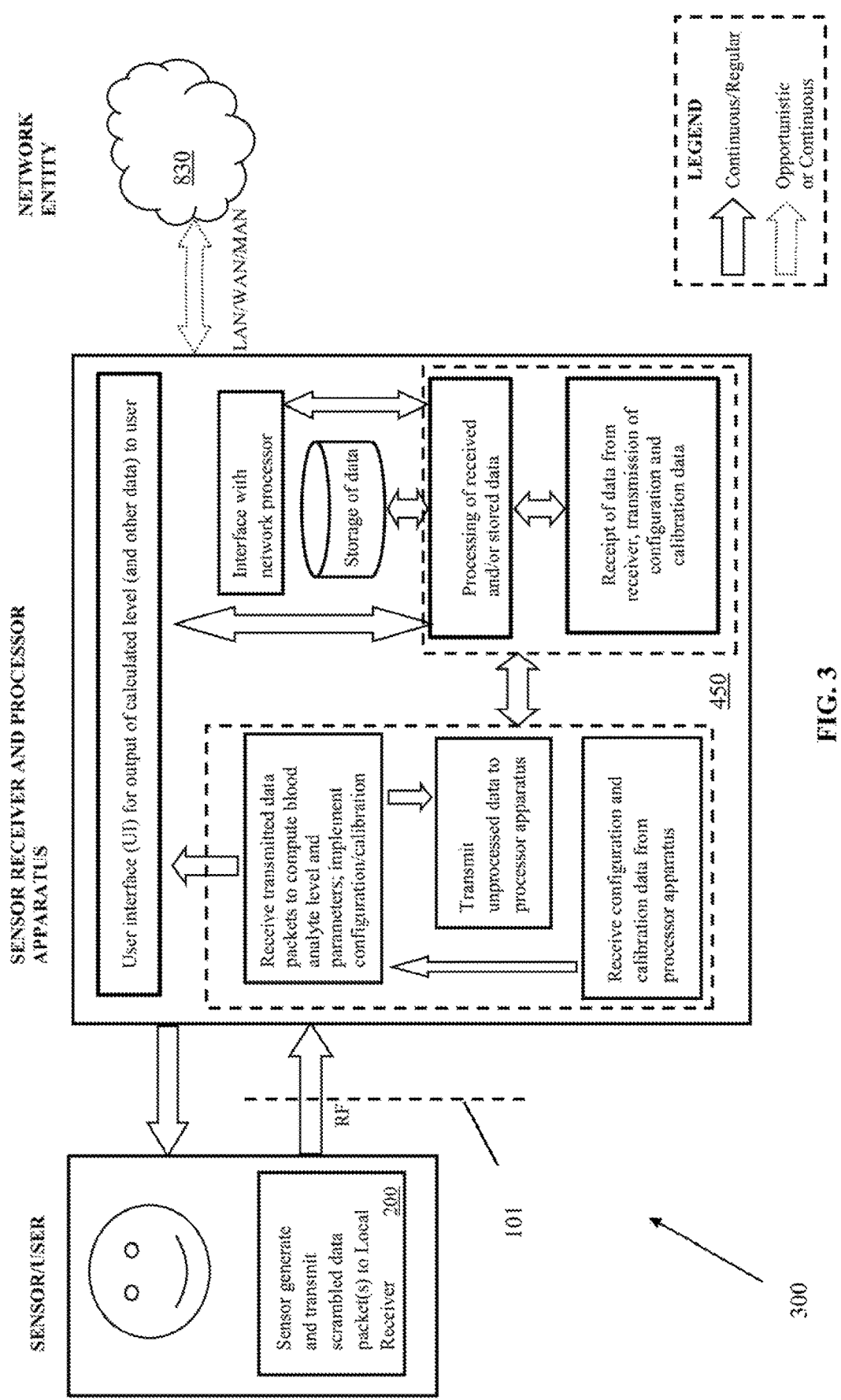
FIG. 3 is a logical block diagram illustrating one embodiment of a system architecture for, inter alia, monitoring blood analyte levels within a user, useful with various aspects of the present disclosure.

Referring now to FIG. 3, one embodiment of a system architecture 300 for, inter alia, monitoring blood analyte levels within a user, useful with the machine learning-based methods and apparatus of present disclosure, is described in detail. As depicted in FIG. 3, the system architecture comprises a sensor apparatus 200 (e.g., that of FIGS. 2-2C discussed above, or yet other types of device) associated with a user, a receiver and processor apparatus 450 and a network entity 830. The sensor apparatus 200 in this embodiment communicates with the receiver and processor apparatus 450 via a wireless interface (described in detail below) through the user's tissue boundary 101. The receiver and processor apparatus 450 may also, if desired, communicate with one or more network entities 800 via a LAN/WLAN, MAN, or other topology, such as for "cloud" data storage, analysis, convenience of access at other locations/synchronization with other user platforms, etc.

Figure 3A:
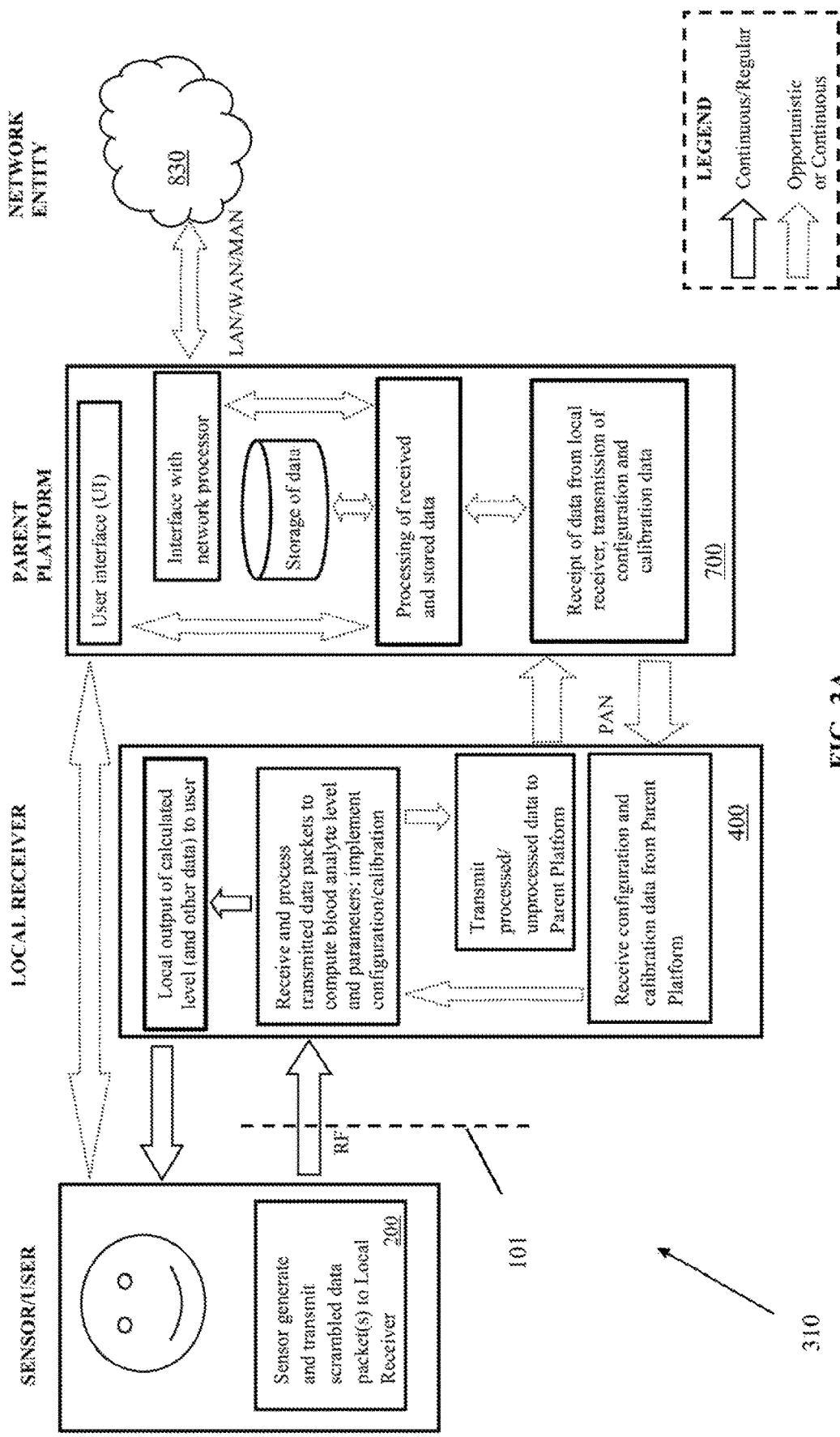
FIG. 3A is a logical block diagram illustrating another embodiment of a system architecture for, inter alia, monitoring blood analyte levels within a user, useful with various aspects of the present disclosure.

As shown in FIG. 3A, another exemplary system architecture 310 comprises a sensor apparatus 200 (e.g., that of FIG. 2 discussed above, or yet other types of device) associated with a user, a local receiver 400, a parent platform 700, and a network entity 830. The sensor apparatus 200 in this embodiment communicates with the local receiver 400 via a wireless interface (described in detail below) through the user's tissue boundary 101. The local receiver 400 communicates (e.g., wirelessly) with the one or more parent platform(s) 600 via a PAN (e.g., Bluetooth or similar) RF interface, as discussed in greater detail below. The parent platform 700 may also, if desired, communicate with one or more network entities 830 via a LAN/WLAN, MAN, or other topology, such as for "cloud" data storage, analysis, convenience of access at other locations/synchronization with other user platforms, etc.

In exemplary system architecture shown in FIG. 3A, the local receiver 400 is a lower profile and/or wearable local receiver apparatus (e.g., small profile wristband, fob, tooth or other implant, skin-adherent patch, ear "bud" or plug, a ring worn in the finger, etc.) as compared to the receiver and processor apparatus 450 shown in FIG. 3. The local receiver apparatus 400 can include a user alert mechanism and/or minimal user interface (UI) such as, e.g., a substantially flat and flexible LED (e.g., graphene-based), AMOLED, or OTFT (organic thin-film transistor) display device, haptic mechanism (e.g., a vibration mechanism), auditory mechanism (e.g., speakers), and/or other user-signaling capabilities and mechanisms (e.g., indicator lights). Various exemplary configurations for the local receiver 400 are shown and described in U.S. patent application Ser. No. 15/368,436 filed Dec. 2, 2016 previously incorporated herein.

As indicated in FIG. 3A, the communications between the sensor 200 and the local receiver 400 are generally continuous and reliable in nature (similar to communication between the sensor 200 and the receiver and processor apparatus 450 of FIG. 3). In contrast, the communication between the local receiver 400 and the parent platform(s) can be either continuous or opportunistic (or any desired combination thereof between the various components of each) in nature. Such opportunistic communication can be a significant advantage of the architecture 300 over the prior art; i.e., the ability for the sensor 200 and a reduced form-factor local receiver 400 to communicate regularly to enable reliable and effectively constant monitoring and user awareness of their blood analyte (e.g., glucose) level, without being "tethered" to larger, bulkier, and perhaps activity-limiting parent devices, including for extended periods of time.

Specifically, in the illustrated architecture 310, the local receiver 400 acts as a reduced- or limited-functionality indicator and monitor for the user that reliably operates for comparatively extended periods of time without external input or calibration, thereby obviating the parent platform during those periods. As described later herein, the reduced form factor advantageously enables the user to further: (i) engage in activities which they could not otherwise engage in if "tethered" to the parent platform, and (ii) effortlessly keep the local receiver with them at all times, and obtain reliable blood analyte data and other useful information (e.g., trend, rate of change (ROC), and other sensor-data derived parameters), in a non-obtrusive (or even covert) manner.

In the example of system architecture 310, when communication between the parent platform 600 and the local receiver does occur, the exemplary architecture 310 enables two-way data transfer, including: (i) transfer of stored data extracted from the sensor wireless transmissions to the local receiver, to the parent platform for archiving, analysis, transfer to a network entity, etc.; (ii) transfer of sensor-specific identification data and/or local receiver-specific data between the local receiver and the parent platform; (iii) transfer of external calibration data (e.g., derived from an independent test method such as a fingerstick or blood glucose monitor and input either automatically or manually to the parent platform) from the parent to the local receiver; and (iv) transfer of local receiver configuration or other data (e.g., software/firmware updates, user-prescribed receiver settings for alarms, warning/buffer values, indication formats or parameters, historical blood analyte levels for the user, results of analysis by the parent 700 or network entity 830 of such data, diagnoses, security or data scrambling/encryption codes or keys, etc.) from the parent 600 to the local receiver 400.

Figure 3B:
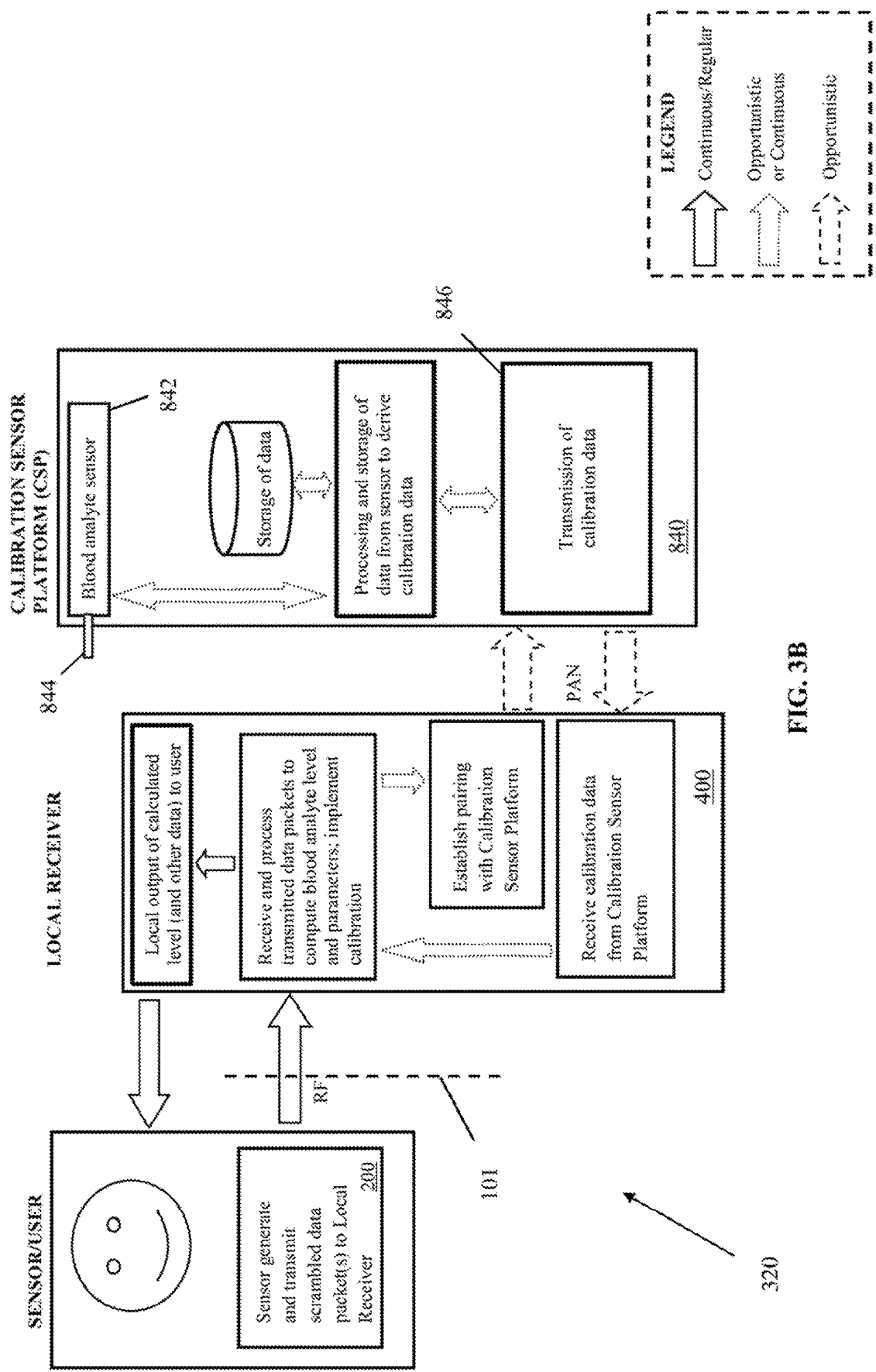
FIG. 3B is a logical block diagram illustrating yet another embodiment of a system architecture for, inter alia, monitoring blood analyte levels within a user, according to the present disclosure.

FIG. 3B shows yet another embodiment of a system architecture 320 for, inter alia, monitoring blood analyte levels within a user, useful with the present disclosure. As shown in FIG. 3B, the architecture 320 comprises a sensor apparatus 200 associated with a user, a local receiver 400, and calibration sensor platform 900. As with the embodiment of FIG. 3A, the sensor apparatus 200 in this embodiment communicates with the local receiver 400 via a wireless interface through the user's tissue boundary 101. The local receiver 400 communicates (e.g., wirelessly) with one or more calibration sensor platform(s) or CSPs 900 via a PAN (e.g., Bluetooth or similar) RF interface, as discussed in greater detail below, or via IR (e.g., IrDA-compliant), optical or other short-range communication modality. As described in greater detail below, the CSP 900 in the illustrated embodiment comprises a calibration data source for the local receiver 400, which may stand in the place of the more fully-functioned parent platform 700 for at least provision of calibration data.

As indicated in FIG. 3B, the communications between the sensor 200 and the local receiver 400 are again generally continuous or regular in nature while the communication between the local receiver 400 and the CSP 840 is purposely opportunistic in nature.

When the opportunistic communication between the CSP 840 and the local receiver does occur, the exemplary architecture 310 enables at least one-way data transfer, including transfer of external calibration data (e.g., derived from an independent test method such as the "fingerstick" or other form of blood analyte sensor 842 of the CSP 840 from the CSP to the local receiver 400. In an exemplary implementation, the CSP 840 comprises a "smart" fingerstick apparatus, including at least (i) sufficient onboard processing capability to generate calibration data useful with the local receiver 400 based on signals or data output from the blood sensor 842, and (ii) a data interface to enable transmission of the data to the local receiver 400. In one configuration, the sensor 842 includes a needle or lancet apparatus 844 which draws a sample of the user's blood for the sensor 842 to analyze. Electronic glucose "fingerstick" apparatus (including those with replaceable single-use lancets) and re-usable electronic components are well known in the relevant arts, and accordingly not described further herein. See e.g., U.S. Pat. No. 8,357,107 to Draudt, et al. issued Jan. 22, 2013 and incorporated herein by reference in its entirety, for one example of such technology. The sensor 842 analyzes the extracted blood obtained via the lancet 844 and (via the onboard processing) produces data indicative of a blood glucose level (or at least generates data from which such level may be derived), such data being provided to the communications interface 846 for transfer to the local receiver 400. The transmitted data are then utilized within the local receiver 400 for calibration of the data generated by the implanted sensor 200.

In one variant, the interface 846 comprises a Bluetooth-compliant interface, such that a corresponding Bluetooth interface of the local receiver can "pair" with the CSP 840 to effect transfer of the calibration data wirelessly. Hence, the user with implanted sensor 200 can simply use a fingerstick-based or other type of external calibration data source to periodically (e.g., once weekly) confirm the accuracy and/or update the calibration of the implanted sensor 200 via opportunistic communication between the local receiver 400 (e.g., small profile wristband, fob, etc.) and CSP 840 when convenient for the user. Advantageously, many persons with diabetes possess such electronic fingerstick-based devices, and wireless communication capability is readily added thereto by the manufacturer at little additional cost.

In another variant, the communications interface comprises an IR or optical "LOS" interface such as one compliant with IrDA technology, such that the user need merely establish a line-of-sight path between the emitter of the CSP 840 and the receptor of the local receiver 400, akin to a television remote control. As yet another alternative, a near-field communication (NFC) antenna may be utilized to transfer data wirelessly between the apparatus 400, 840 when placed in close range (i.e., "swiped"). Yet other communication modalities will be recognized by those of ordinary skill given the present disclosure. Additional functionalities of the local receiver 400 and parent platform 700 are described in U.S. patent application Ser. No. 15/368,436 filed Dec. 2, 2016 and previously incorporated herein.

It will be appreciated that the architectures shown in FIGS. 3-3B are in no way exclusive of one another, and in fact may be used together (such as at different times and/or via different use cases). For example, CSP 840 can be used in combination with receiver and processor apparatus 450 for opportunistic communication of calibration data. Myriad other permutations of use cases involving one or more of the various components 200, 400, 450, 700, 800, 840 are envisaged by the present disclosure. Various system architecture and communication pathways of system components are shown and described in U.S. patent application Ser. No. 15/368,436 filed Dec. 2, 2016 and previously incorporated herein.

Sensor Apparatus—

Figure 4:
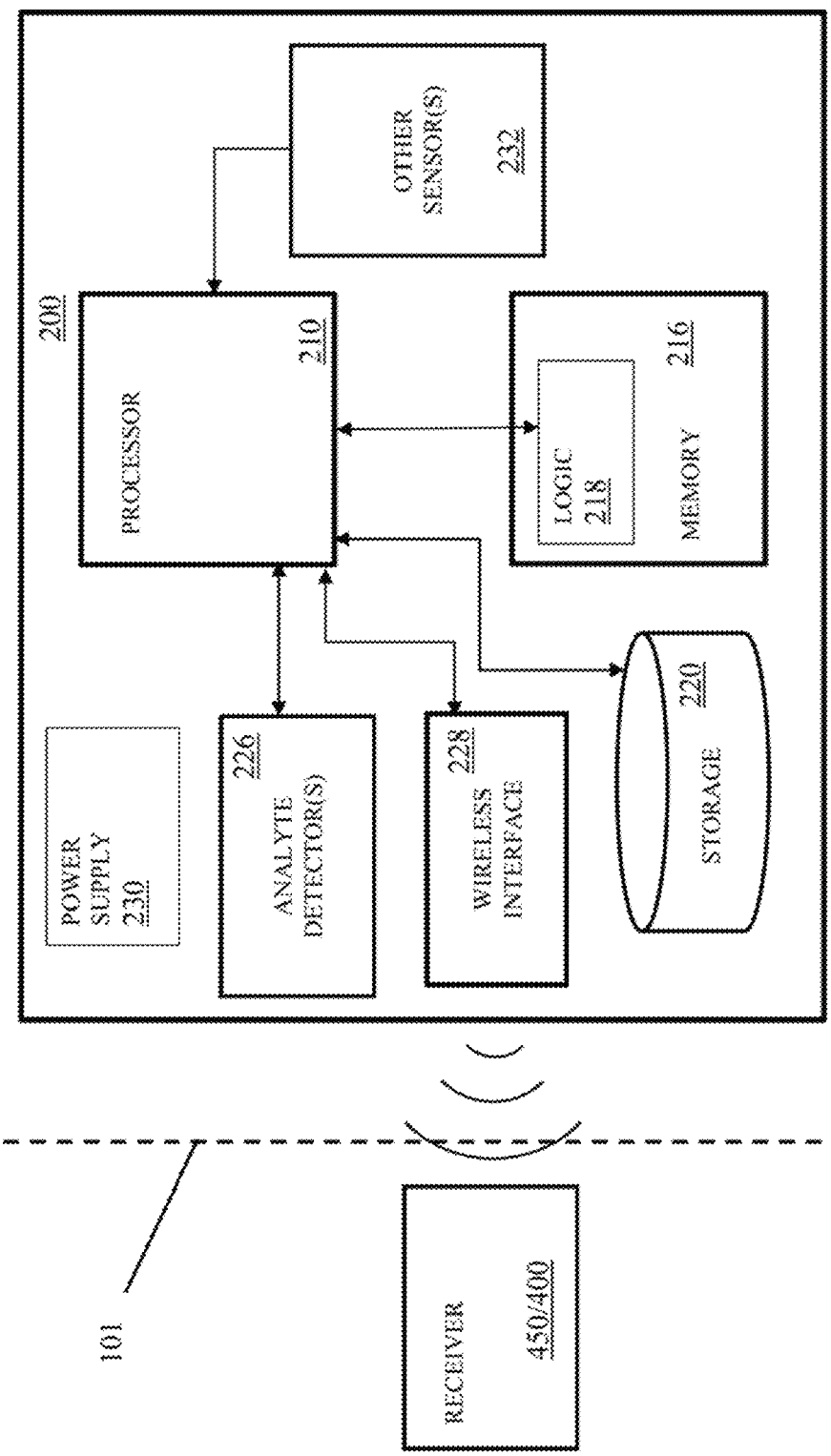
FIG. 4 is a functional block diagram illustrating an exemplary implantable sensor apparatus and local receiver apparatus of FIGS. 3-3B.

FIG. 4 is a functional block diagram illustrating an exemplary implantable sensor apparatus 200 and local receiver and processor apparatus 450 or local receiver apparatus 400 according to one embodiment of the present disclosure. As shown, the sensor apparatus 200 includes a processor 210 (e.g., digital RISC, CISC, and/or DSP device), and/or a microcontroller (not shown), memory 216, software/firmware 218 operative to execute on the processor 210 and stored in e.g., a program memory portion of the processor 210 (not shown), or the memory 216, a mass storage device 220 (e.g., NAND or NOR flash, SSD, etc. to store collected raw or preprocessed data or other data of interest), one or more analyte detectors 226, a wireless interface 228 (e.g., narrowband, PAN such as Bluetooth, or other, described below), a power supply 230 (e.g., a primary Lithium or rechargeable NiMH or Lithium ion battery).

Also depicted in FIG. 4, the sensor apparatus 200 can optionally include one or more additional internal sensors 232. The internal sensor(s) 232 may be any of a temperature sensor, an accelerometer, a pressure sensor, a pulse meter, a conductivity meter, pH (i.e., hydronium ion concentration), electric field sensor, and/or other (non-target) analyte-detection sensors (e.g., other blood analytes). In an alternate embodiment, the one or more internal sensors can be located in a separate implantable apparatus positioned proximate to the sensor 200 during implantation.

As can be appreciated by those of ordinary skill given the present disclosure, any number of different hardware/software/firmware architectures and component arrangements can be utilized for the sensor apparatus 200 of FIG. 4, the foregoing being merely illustrative. For instance, a less-capable (processing, sensing, and/or data storage-wise) or "thinner" configuration may be used (e.g., excluding the one or more additional internal sensors), or additional functionality not shown added (e.g., including additional types of other sensors and/or components).

Sensor Receiver Apparatus—

Figure 4A:
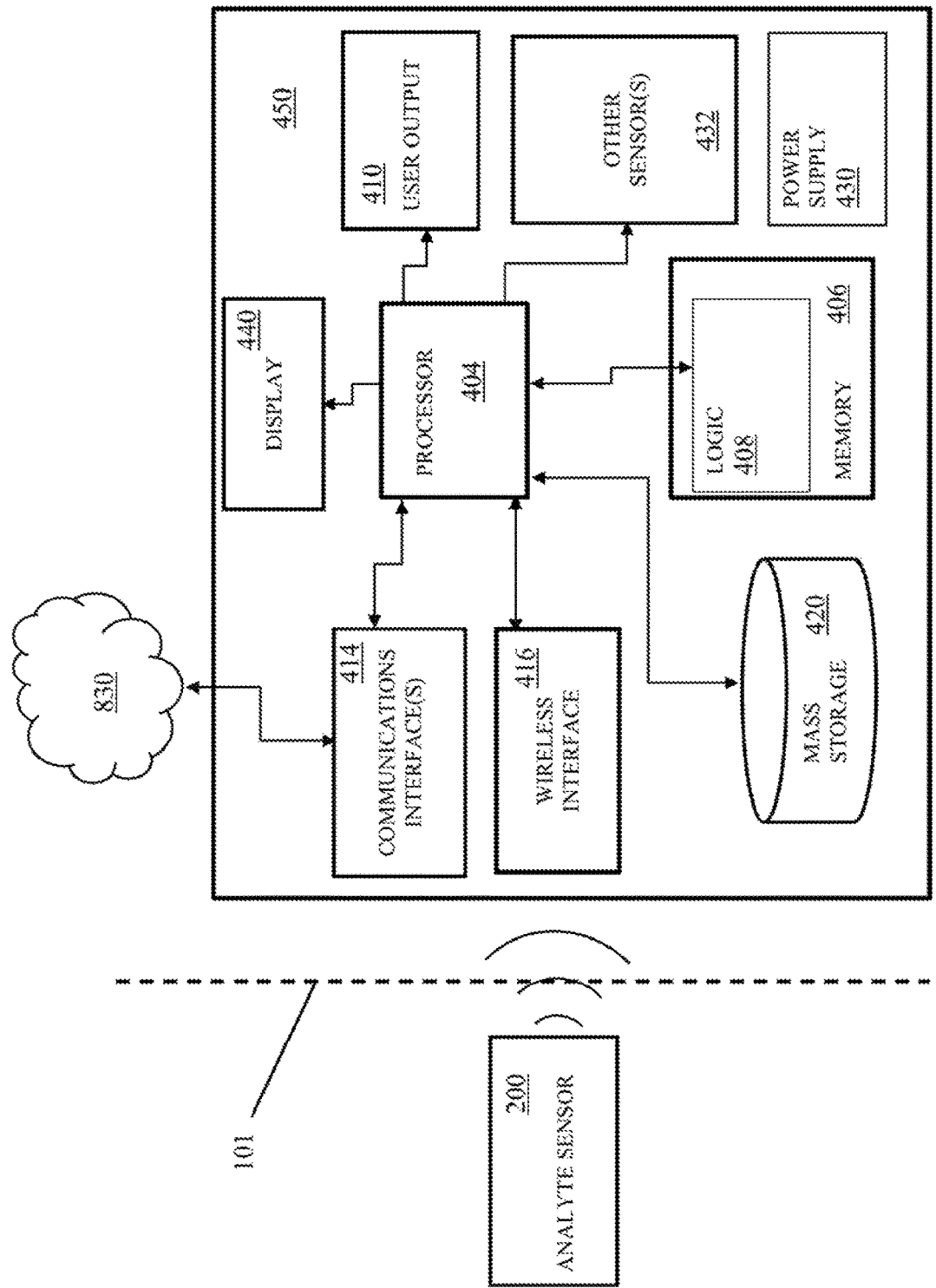
FIG. 4A is a functional block diagram illustrating an exemplary embodiment of the dedicated receiver and processor apparatus of FIG. 3.
Figure 4B:
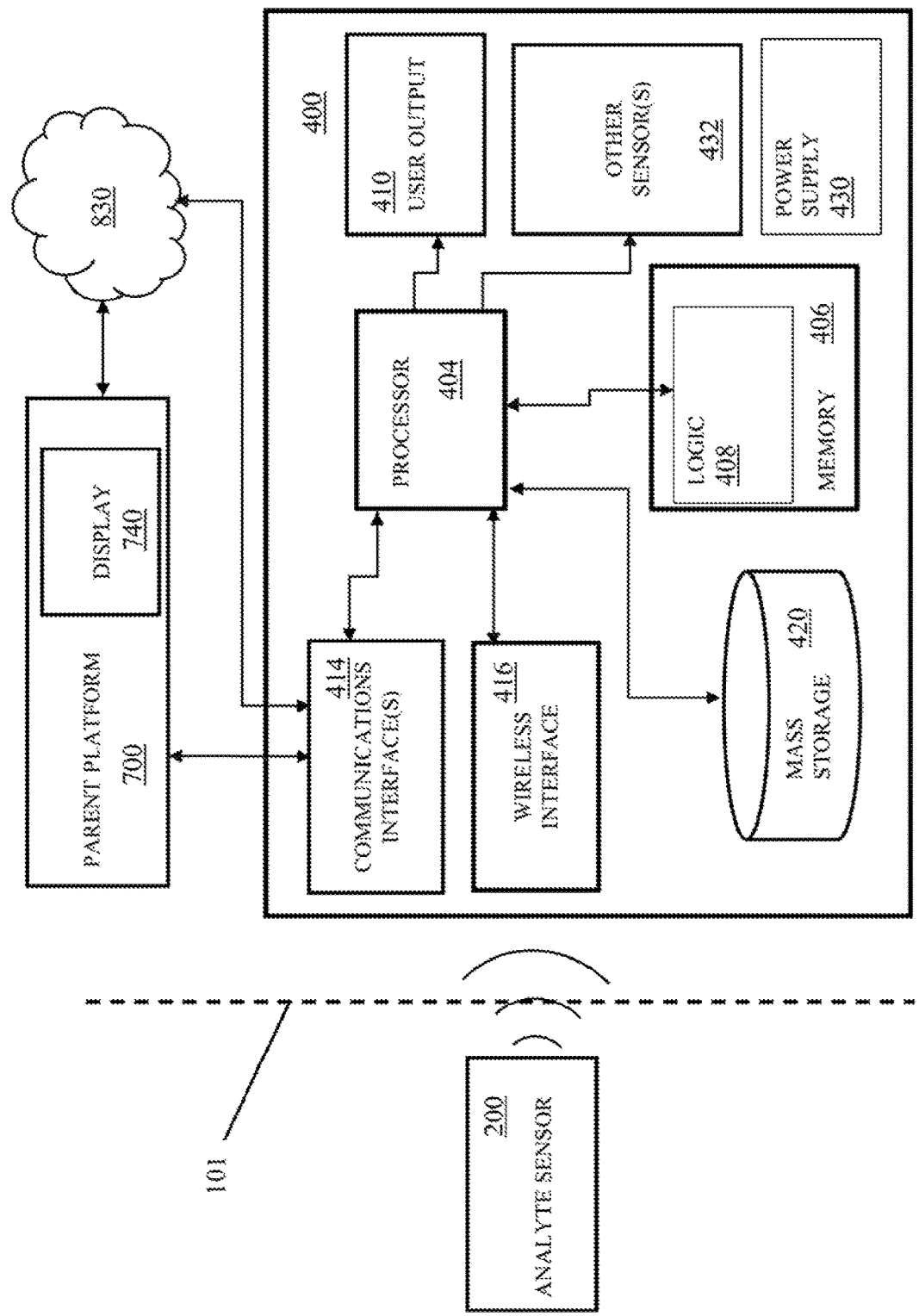
FIG. 4B is a functional block diagram illustrating an exemplary embodiment of local receiver apparatus of FIGS. 3A and 3B.

Referring now to FIGS. 4A-4B, various embodiments of the sensor receiver apparatus 400 and 450 shown in FIGS. 3-3B herein are described in detail.

FIG. 4A depicts a functional block diagram of one embodiment of the receiver and processor apparatus 450 (i.e., a dedicated receiver apparatus), in wireless communication with the analyte sensor 200 of FIG. 3 via the interposed tissue (boundary) 101. As noted previously, the present disclosure contemplates use of partially-implanted (e.g., transcutaneous or percutaneous) or even non-implanted analyte sensor devices, as well as the fully-implanted device (e.g., sensor apparatus 200 of FIGS. 2-2C). As shown in FIG. 4A, the dedicated receiver apparatus 450 includes a processor 404 (e.g., digital RISC, CISC, and/or DSP device), and/or a microcontroller (not shown), memory 406, software/firmware 408 operative to execute on the processor 404 and stored in e.g., a program memory portion of the processor 404 (not shown), or the memory 406, a mass storage device 420 (e.g., NAND or NOR flash, SSD, etc. to store received raw or preprocessed data, post-processed data, or other data of interest), a wireless interface 416 (e.g., narrowband or other, described below) for communication with the sensor apparatus 200, a communications (e.g., wireless) interface 414 for communication with the network entity 830 (if desired), a power supply 430 (e.g., NiMH or Lithium ion battery, or other as described below), and a graphical display device 440. The dedicated receiver apparatus 450 can optionally include one or more output device(s) 410 (i.e., other types of user outputs in addition to the graphical display device 440) for communication of the desired data (e.g., glucose level, rate, trend, battery "low" alerts, etc.) in addition to the display 440. As described in greater detail subsequently herein the output device(s) may include for example visual, audible, and/or tactile (e.g., haptic) modalities or mechanisms, which can be used alone or in concert depending on user context, desired functionality, and receiver and processor apparatus configuration.

Additionally, the apparatus 450 can optionally include one or more additional external sensors 432. The one or more external sensors 432 may be any of a temperature sensor, an accelerometer, a pulse meter, a blood pressure sensor, and/or other types of sensors. In one example, the external sensors 432 of the receiver 450 can be used in place of the one or more internal sensors 232 of the sensor apparatus 200. In another example, the external sensors 432 can be used cooperatively with the internal sensors 232 to, inter alia, generate a duplicate set of data and/or a complimentary set of data collected from the internal sensors of the implanted sensor device.

In one specific implementation, the external sensors 432 can be calibrated to the internal sensors 232 (such as e.g., during "training mode" operation of the sensor system), In such an implementation, subsequent "other sensor" data (i.e., data collected from sensors other than the target blood analyte sensor) can be collected from the external sensors 432 during operation of the sensor system in the "detection mode". Further, the internal sensors can be substantially turned "off", thereby e.g., decreasing power usage and/or processing requirements of the implanted sensor.

FIG. 4B is a functional block diagram showing one embodiment of the local receiver apparatus 400, in wireless communication with the parent platform 700 and the analyte sensor 200 (discussed supra) of FIG. 4 via the interposed tissue (boundary) 101.

Similar to the receiver and processor apparatus 450, the local receiver apparatus 400 includes a processor 404 (e.g., digital RISC, CISC, and/or DSP device), and/or a microcontroller (not shown), memory 406, software/firmware 408 operative to execute on the processor 404 and stored in e.g., a program memory portion of the processor 404 (not shown), or the memory 406, a mass storage device 420 (e.g., NAND or NOR flash, SSD, etc. to store received raw or preprocessed data, post-processed data, or other data of interest), a wireless interface 416 (e.g., narrowband or other, described below) for communication with the sensor apparatus 200, a communications (e.g., wireless) interface 414 for communication with the parent platform 700 and/or the network entity 830 (if desired), and a power supply 430 (e.g., NiMH or Lithium ion battery, or other as described below). The apparatus 400 also includes one or more output device(s) 410 (such as e.g., visual, audible, and/or haptic modalities or alert mechanisms) for communication of the desired data (e.g., glucose level, rate, trend, battery "low" alerts, etc.). Additionally, the apparatus 400 can optionally include one or more external sensors 432, such as those described above with reference to FIG. 4. In an alternate embodiment, the one or more other sensors can be located in a separate implantable apparatus positioned proximate to the sensor 200 during implantation.

Notably, in the embodiment shown in FIG. 4B, the local receiver 400 lacks a full graphical display device (such as the graphical display device 440 shown in FIG. 4A). Exclusion of the foregoing graphical display allows for overall reduced dimensions of the local receiver apparatus 400 making it suitably sized for wear or implantation (such as the exemplary wearable and implantable local receivers discussed supra and described in U.S. patent application Ser. No. 15/368,436 filed Dec. 2, 2016 and previously incorporated herein). Rather, the data from the local receiver apparatus 400 is displayed at a full graphical display device 640 associated with the parent platform 700. In some embodiments, the local receiver 400 includes a reduced or limited graphical display (i.e., small graphical display) as one of the output device(s) 410. For example, a wrist wearable local receiver can include a small LCD, or even a capacitive touch screen for sending alerts and/or other information to the user as well as receiving input from the user. Additional configurations and functionality of the various receiver apparatus are described in U.S. patent application Ser. No. 15/368,436 filed Dec. 2, 2016 and previously incorporated herein.

Sensor System Operational Methods—

Figure 5:
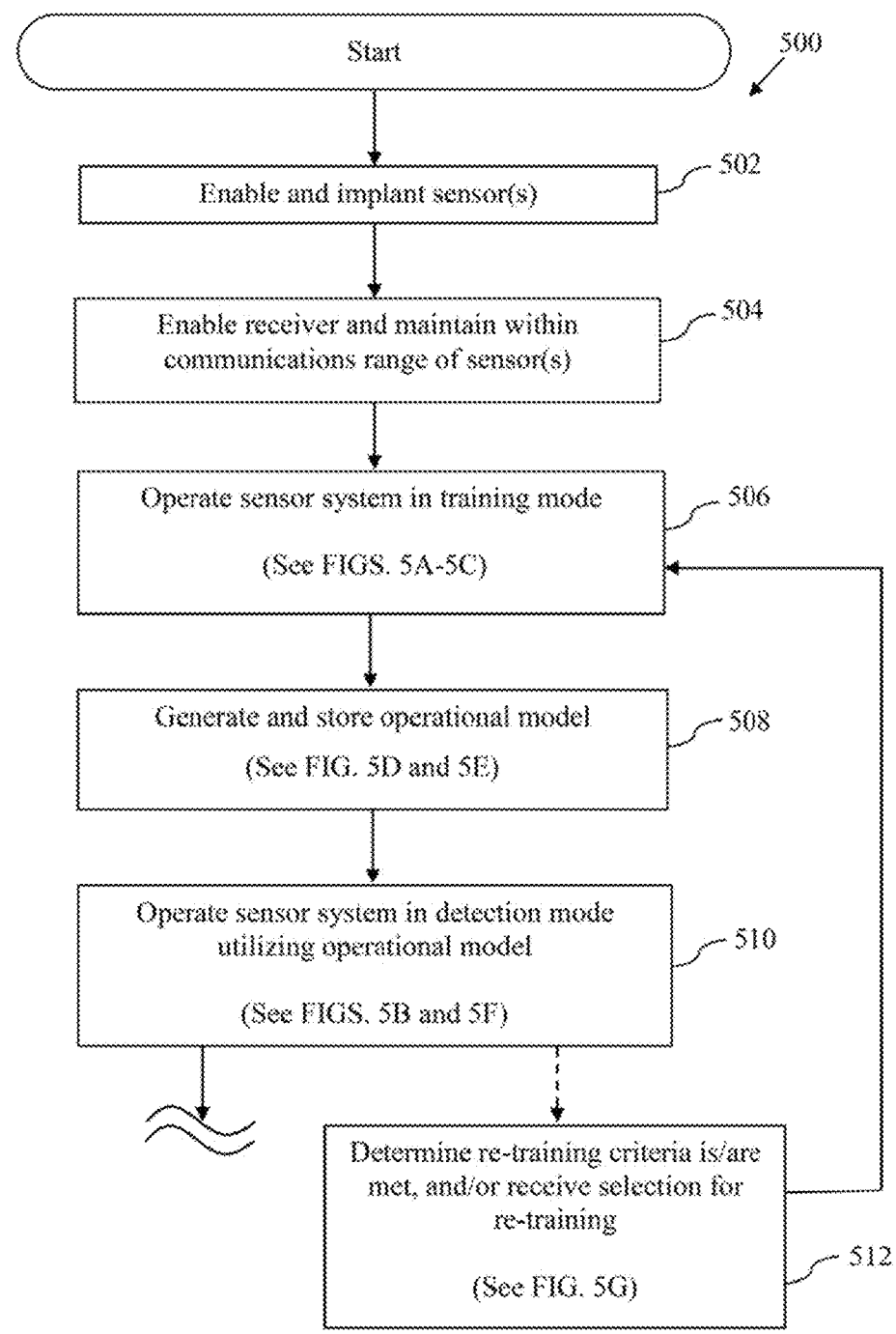
FIG. 5 is a logical flow diagram illustrating one exemplary embodiment of a generalized method of operating the implantable sensor system for blood analyte measurement according to the present disclosure.
Figure 6:
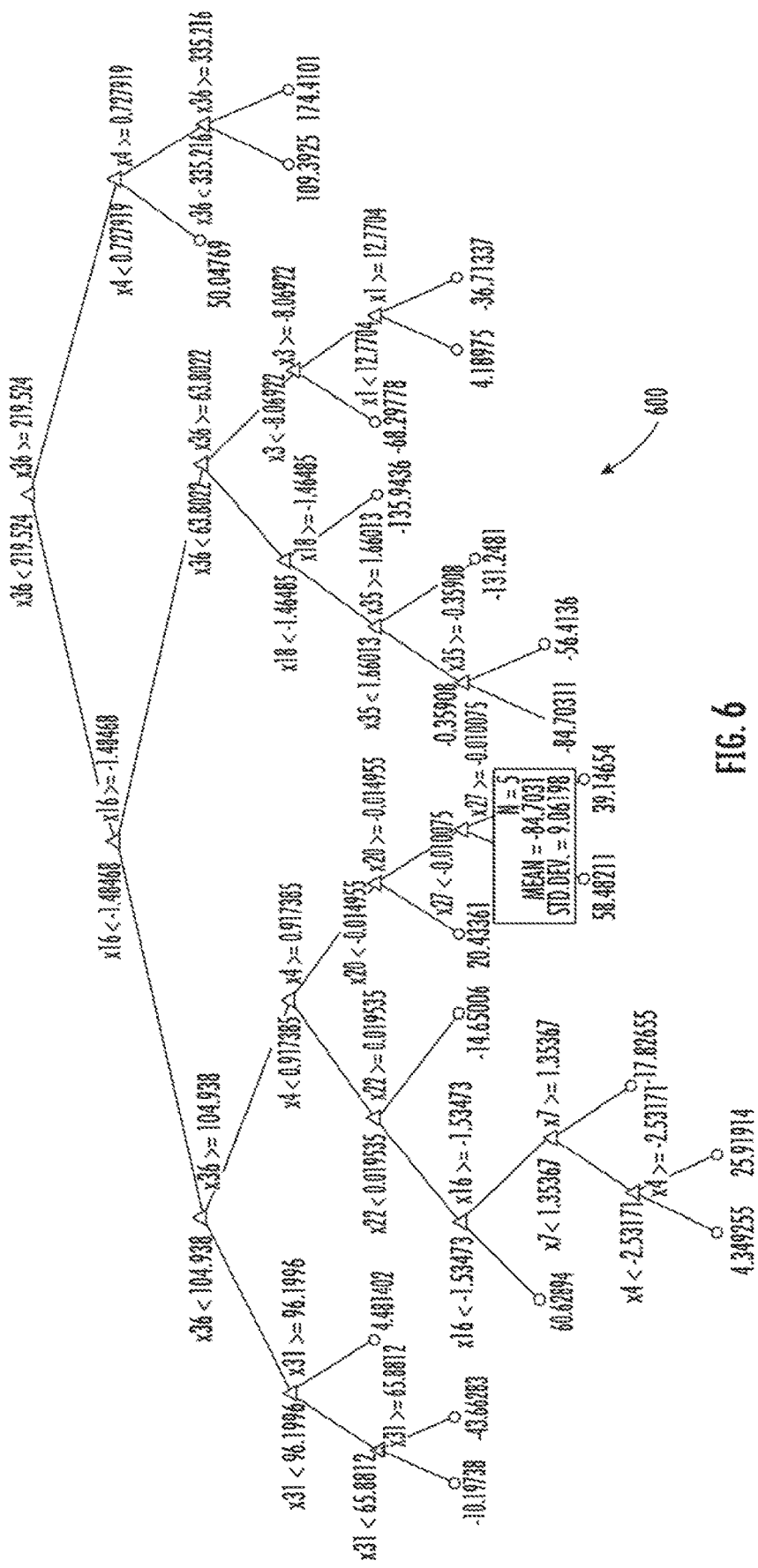
FIG. 6 is a graphical representation of an exemplary decision tree used in model generation according to one embodiment of the present disclosure, wherein each end-node predicts a specific error (or source).

Referring now to FIGS. 5-6, exemplary embodiments of the methods of operating the analyte sensing system (e.g., a system including either or both of the local receiver apparatus 400 and the receiver and processor apparatus 450) are described in detail.

FIG. 5 is a logical flow diagram depicting an exemplary embodiment of a generalized method 500 for operation of the sensor system according to the present disclosure. As shown in FIG. 5, the method 500 includes first enabling and implanting the sensor 200 (or others) per step 502. In the case of the implantable sensor of FIG. 2, the sensor is enabled, implanted in the host (such as via the procedures described in U.S. patent application Ser. No. 14/982,346 filed Dec. 29, 2015 previously incorporated herein), and tested as part of step 502.

Next, the receiver apparatus 400, 450 (e.g., any of those of FIGS. 4-4A herein) is enabled, and maintained within communications range of the sensor apparatus, per step 504. In one variant, the exemplary embodiment of the sensor apparatus 200 uses a 433 MHz narrowband RF transmitter (such frequency having good signal transmission characteristics through human tissue), and hence has a communications range, dependent on transmission power, of at least several feet. Hence, in one implementation of the method step 504, the host/user merely needs to keep the receiver 400, 450 within arm's reach, or somewhere on their body personally. As discussed infra, however, certain embodiments of the disclosure may implement the "machine learning" aspects indigenously on the implanted sensor apparatus 200 itself, thereby effectively obviating the need for communication with the external receiver 400, 450, at least for functions relating to systemic or other error modeling and correction.

Subsequent to enablement and implantation of the sensor (and enablement of the receiver), the sensor system is operated in an initial sensor "training mode" (step 506, and described below in greater detail with respect to FIGS. 5A-5C), wherein the detector elements of the sensor 200 are operational and producing signals, yet the data are not output to the user or other entity, but rather used for "off line" analysis and error model generation.

Data collected and/or received during the sensor training mode operation are then used to generate and store a sensor operational model (such as e.g., a user-specific sensor operational model) (step 508, and described below in greater detail with respect to FIGS. 5D-5E).

Figure 5A:
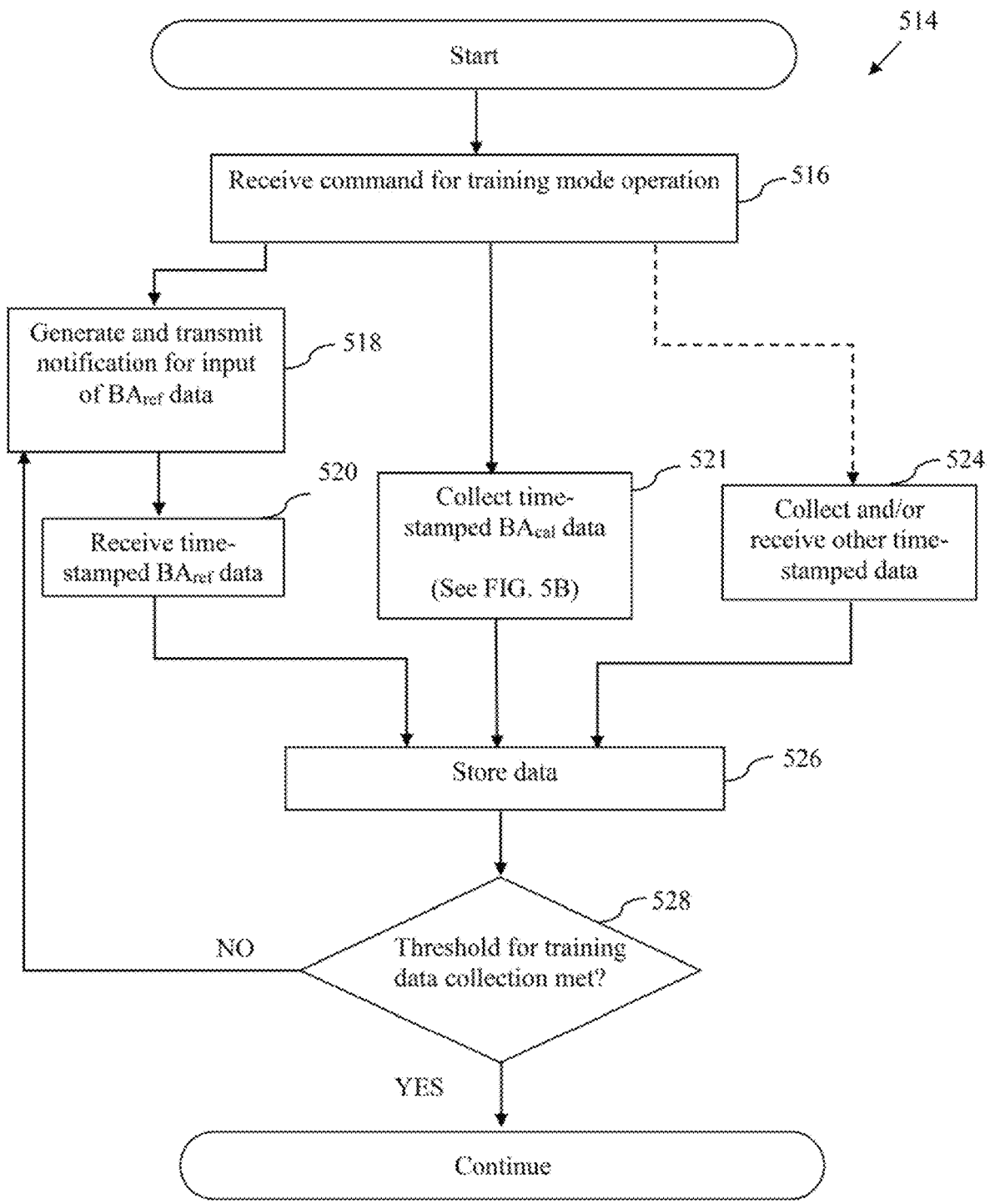
FIG. 5A is a logical flow diagram illustrating one exemplary implementation of the sensor "training mode" operation of the implantable sensor system according to the method of FIG. 5.
Figure 5B:
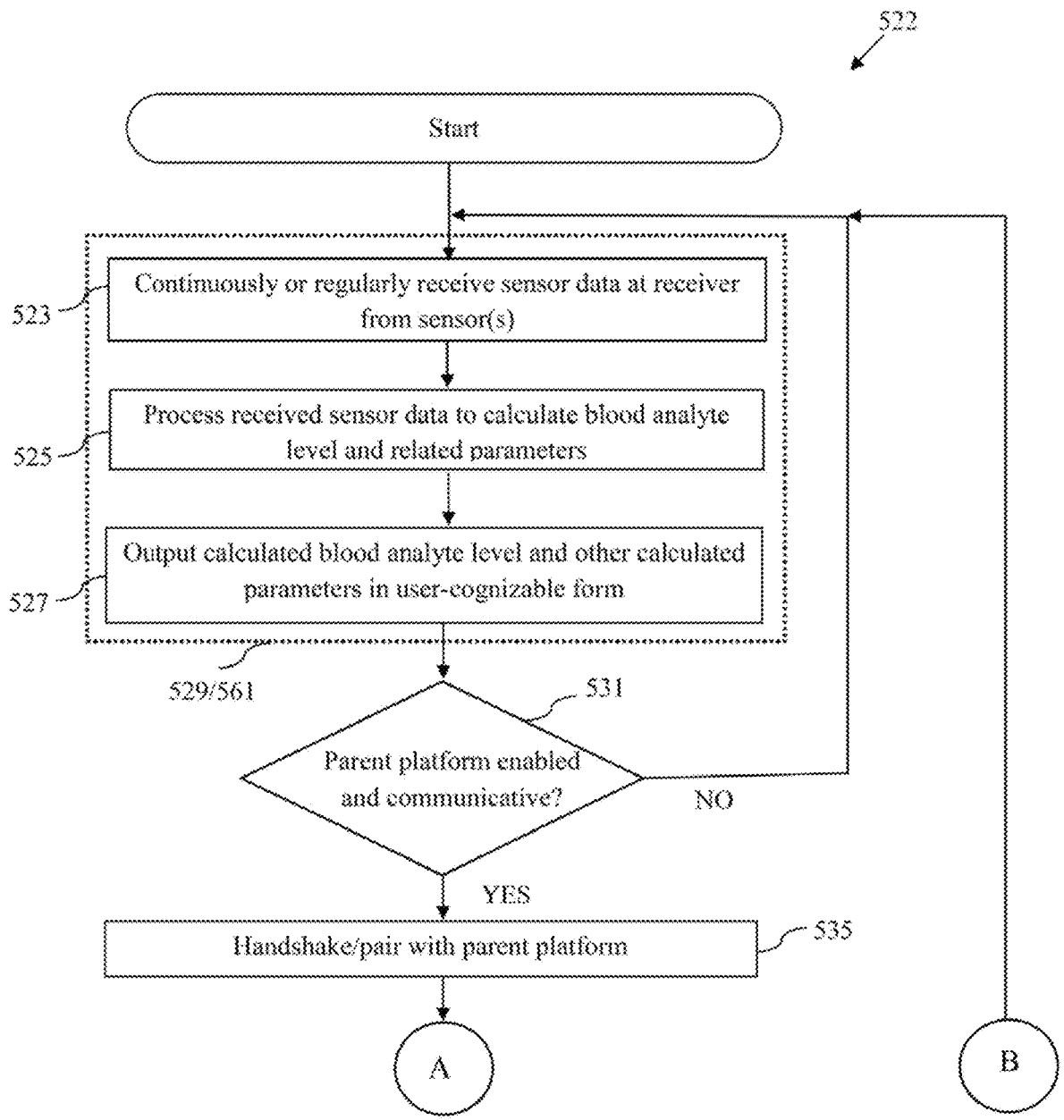
FIG. 5B is a logical flow diagram illustrating one exemplary implementation of the sensor analyte detection and output according to the method of FIG. 5.
Figure 5B:
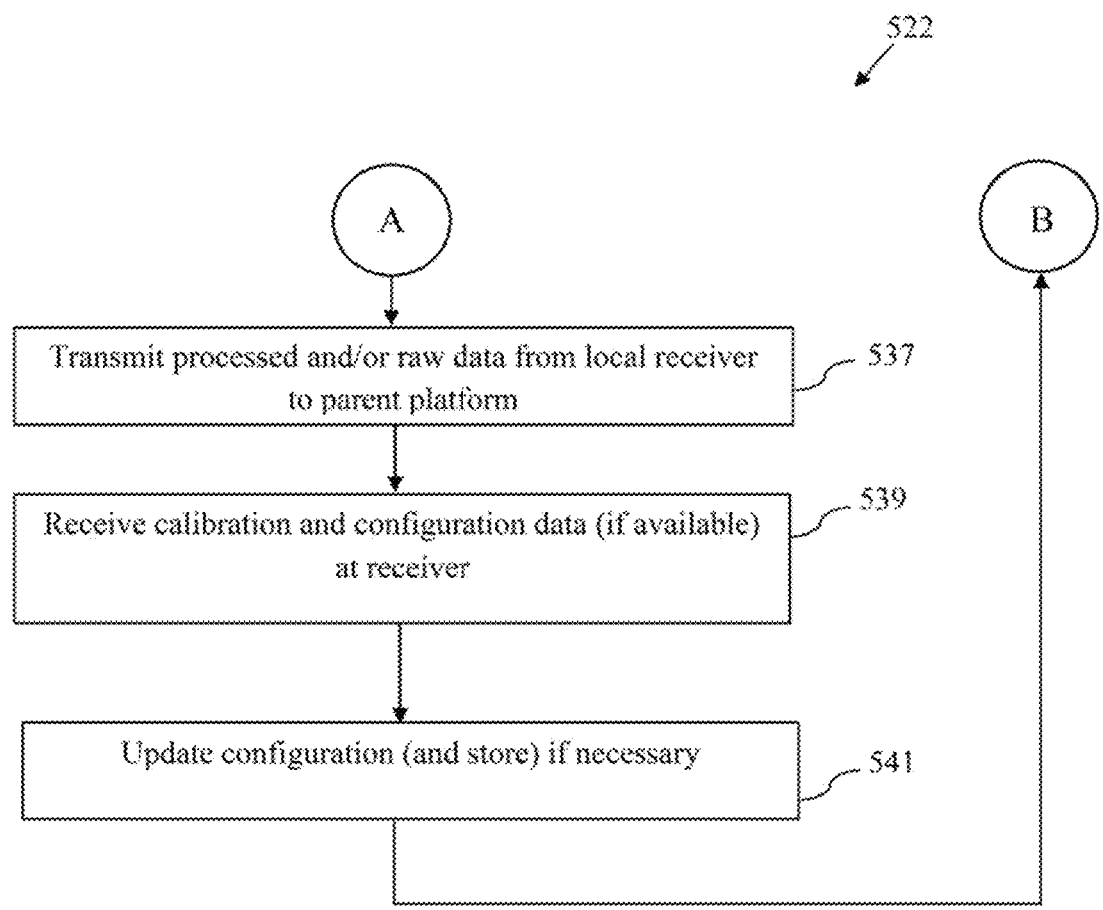
Figure 5C:
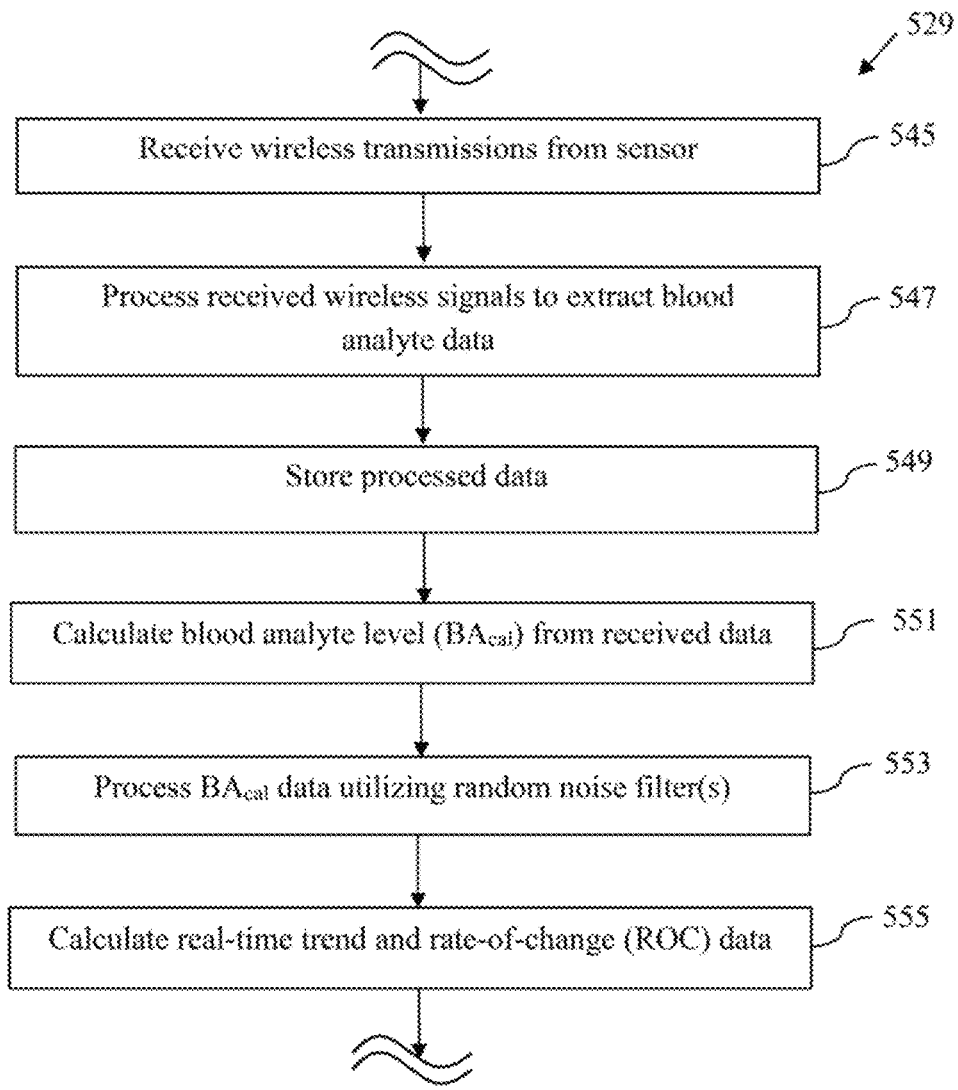
FIG. 5C is a logical flow diagram illustrating one exemplary implementation of the sensor data processing and output during sensor "training mode" operation according to the method of FIG. 5B.
Figure 5D:
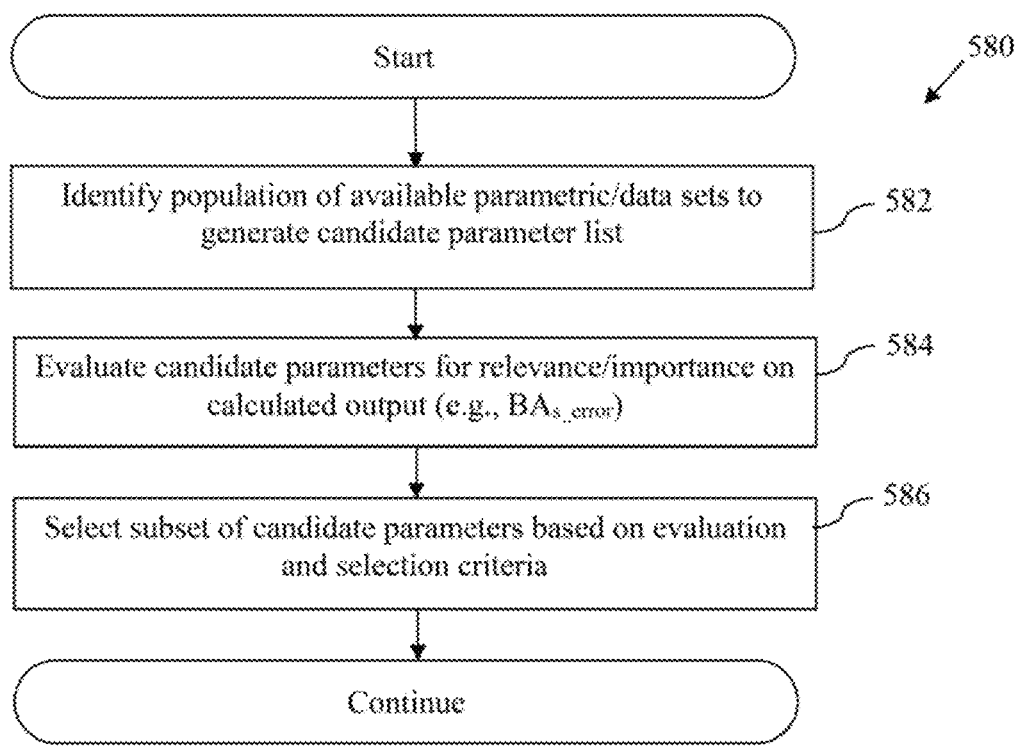
FIG. 5D is a logical flow diagram illustrating one exemplary implementation of sensor operational model parameter selection methodology according to the method of FIG. 5.
Figure 5E:
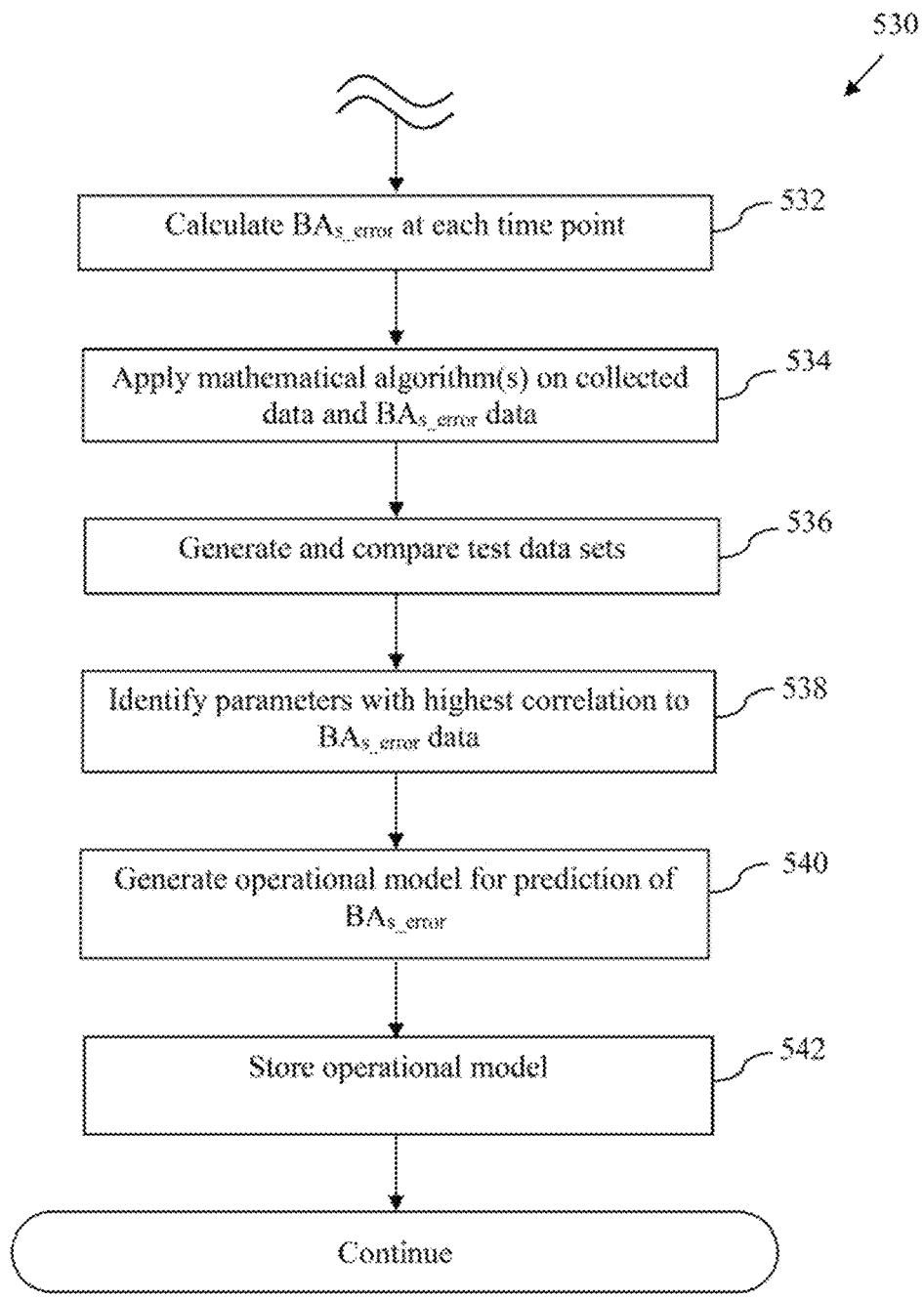
FIG. 5E is a logical flow diagram illustrating one exemplary implementation of sensor operational model generation for the implantable sensor system according to the method of FIG. 5.
Figure 5F:
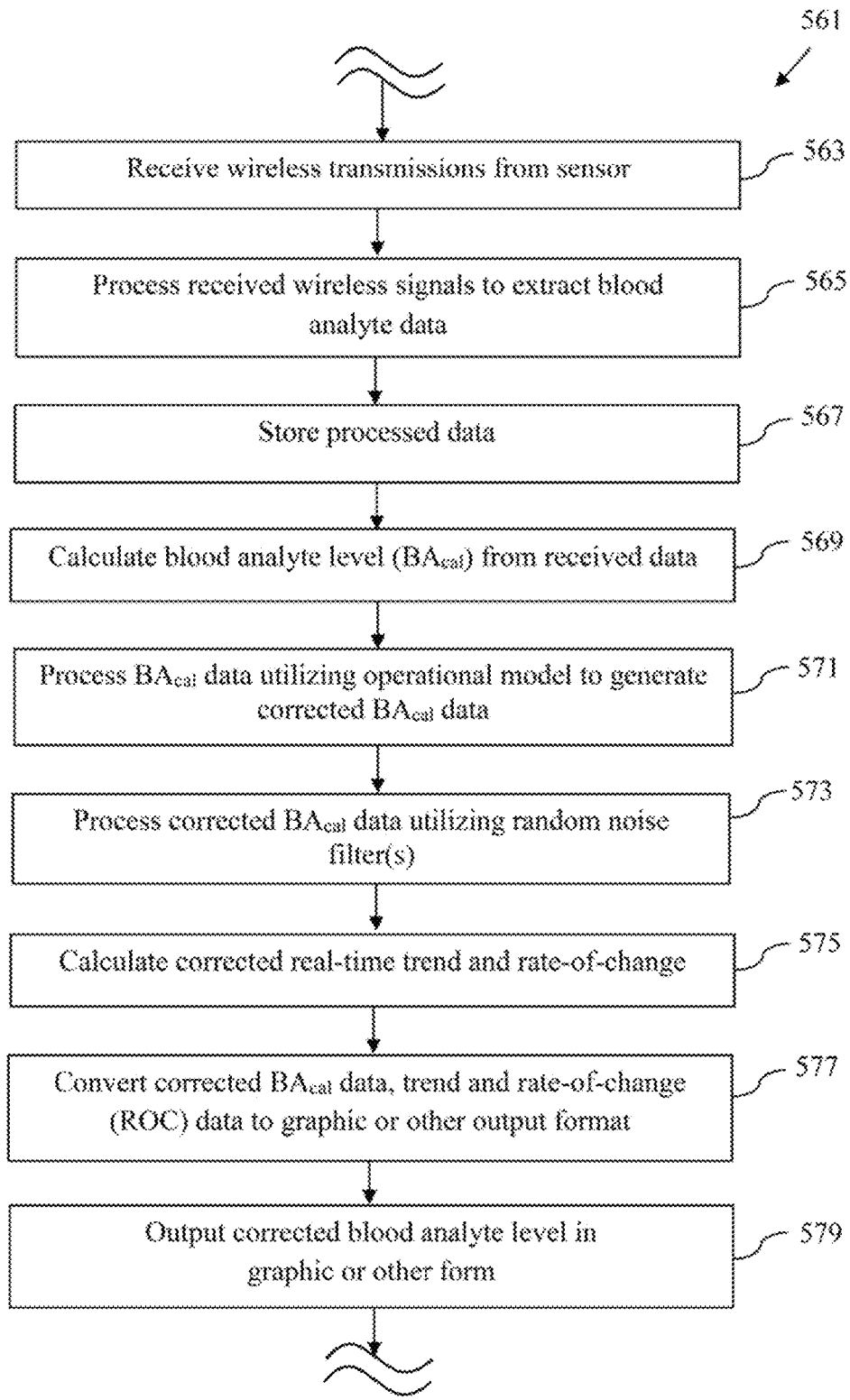
FIG. 5F is a logical flow diagram illustrating one exemplary implementation of the sensor data processing and output during "detection mode" operation according to the method of FIG. 5B.

Next, at step 510, after the sensor model is generated, the sensor system is operated in a detection mode (i.e., a mode whereby data collected from the user are corrected as needed, and output for use by the user or other entity such as a caregiver), based on the sensor operational model (see discussion of FIGS. 5B and 5F provided subsequently herein).

Figure 5G:
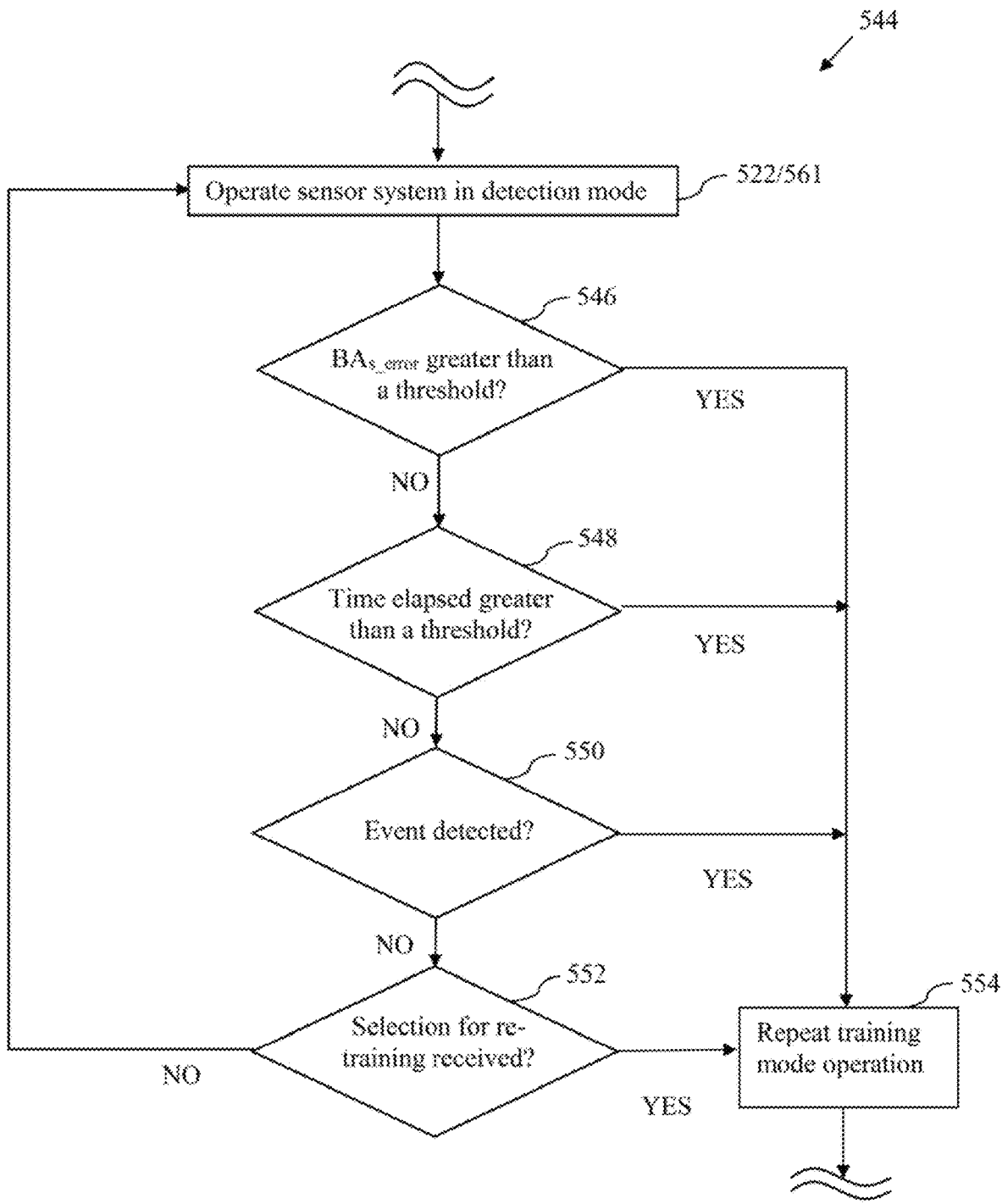
FIG. 5G is a logical flow diagram illustrating one exemplary implementation for determination of whether sensor re-training criteria are met for the implantable sensor system according to the method of FIG. 5.

In some embodiments, operation of the sensor system utilizing the initial sensor operational model is continued until explant of the sensor. Optionally, per step 512, the system can determine that one or more criteria for operation of the system in a subsequent sensor training mode (i.e., sensor "re-training") are met as described in greater detail below, and/or the system can receive a selection from a user or a medical professional/caregiver for sensor re-training (see discussion of FIG. 5G provided below). If such a determination or selection is made, the sensor system returns to step 506 for a repeated operation in the sensor training mode.

It is also appreciated that while the generalized methodology set forth above with respect to FIG. 5 utilizes implant of the sensor 200 as a precondition for training of the machine learning algorithms (so as to ostensibly provide the best training environment for that particular sensor/user combination), this may not always be a requirement. For example, the present disclosure contemplates conditions where the sensor 200 may be "pre-trained" prior to implantation, such as based on data previously acquired for that same individual (e.g., as part of a prior training session and/or prior sensor implantation), or even data derived from one or more similarly situated individuals (e.g., family member, similar physiologic characteristics, similar disease expression, etc.). In such cases, the sensor 200 to be implanted in the individual may for instance be pre-programmed with data representative of a prior sensor operational model using wireless or other data communication with the sensor 200 (such as via its 433 MHz or Bluetooth wireless interface described supra) prior to implantation, such that the sensor model (data) are stored and accessible immediately upon activation of the sensor 200 in vivo.

It is further appreciated that the training of the sensor, and/or application of the derived sensor model (per step 508 of FIG. 5) may be delayed or "phased in" over time. For instance, in one contemplated scenario, the machine learning logic may be programmed to collect data and generate several sensor operational models, including further analysis of the sensor models with respect to one another (and/or other criteria or models, such as those based on purely theoretical or certain a priori assumptions). In one such implementation, two or more successive sensor models are generated via sensor data collected after implantation, and evaluated against one another for factors such as inter-model consistency, and/or rates of change of various attributes of the model (i.e., loosely correlated to an operational "shelf life" of the sensor model(s)).

Similarly, different paradigms for generation of the sensor models can be tested against one another, such as where for example a first sensor model accounting for N factors or systemic error sources is compared against a second sensor model accounting for N-x factors or sources, the latter ostensibly requiring less processing overhead and/or other resources. In effect, there may be diminishing returns to increasingly sophisticated senor modeling approaches, at the cost of additional required sensor inputs, processing, power consumption within the sensor 200, etc., especially when the incremental improvement afforded by the sensor model is within a prescribed allowable error band or tolerance of the system (e.g., when the more complex sensor model generates an improvement in measured blood glucose level accuracy of 0.1 mg/dl, but the system display, data storage, or other requisite accuracy is only 1 mg/dl).

Yet further, the present disclosure contemplates use of two or more sensor models collectively, whether in parallel or in sequence (or based on context or events, such as may be detected by one or more ancillary sensors of the type described supra; e.g., pressure, temperature, acceleration, conductivity, pH, oxygen level, blood flow, electrical impedance, and others). For example, in one such scenario, the corrections or other output generated through application of a given sensor model to operational data may be averaged or otherwise mathematically or statistically combined, or weighted, with similar outputs or corrections generated from other heterogeneous sensor models, so as to avoid any particular model skewing the correction unduly. Likewise, certain sensor models may be best suited or perform best when in a prescribed context or operational setting, and hence the weighting of that model (or even use or non-use of the sensor model in its entirety) may be algorithmically adjusted based on e.g., sensor data input(s). As a simple illustration, consider a user with implanted sensor 200 who is ambulatory (as determined by e.g., accelerometer data resident on the sensor 200 or external receiver 400, 450, and/or yet other sensors such as body temperature). Certain systemic sensor error sources may be more applicable or present themselves to a greater degree in an ambulatory vs. non-ambulatory state, and hence sensor models adapted to such error sources would ostensibly perform better in the ambulatory state as compared to others not so adapted. Hence, upon detection of ambulation, the computerized logic may select (or at least more heavily weight) such ambulation-specific models for application to the generated operational sensor data.

Sensor Training Mode Operation

Turning now to FIG. 5A, a logical flow diagram of an exemplary embodiment of a method 514 for operation of the sensor system in the sensor training mode (step 506 of FIG. 5) is shown and described.

First, at step 516, a command is received to operate the sensor system in the sensor training mode. In one example, after enablement and implantation of the sensor, the user, a medical professional or caregiver enters a selection for operating the sensor system in the training mode via a graphical user interface (GUI) displayed on a display device associated with one or both of the receiver 400, 450 and/or the parent platform 600, such as touch-screen icon selection corresponding to a "calibration" or "learning" function or the like, which causes generation and transmission of a wireless data command to the sensor 200. In an alternate example, the sensor system can be automatically configured to operate in the sensor training mode after implantation e.g., by performing an automatic "boot-up" procedure, such as based on pre-stored firmware in e.g., ROM. In other words, once the sensor is enabled and implanted, and paired (wirelessly) with the receiver 400, 450, the sensor system can automatically enter sensor training mode operation.

In yet another alternate example, the sensor system can be pre-programmed to automatically operate in the sensor training mode after implantation each time that it receives (either based on a user input into the receiver 400, 450 or via direct transmission from a reference meter associated with the user and the sensor system) a new reference analyte value.

In any of the above examples, the command to initiate sensor training mode operation (via e.g., a received wireless command or automatic initiation) can be optionally delayed. In some cases, initiation of the sensor training mode can be set to occur after expiration of a delay period (e.g., a day, a week, a month, etc.). Such a delay period can, depending on the desired functionality, be selected by the user or medical professional, or alternatively the delay period can be pre-programmed. Provision of the delay period can allow the tissue surrounding the implanted sensor to heal and/or adjust to the presence of the sensor prior to collecting "training" data from the implanted sensor (thereby making the physiologic and chemical environment surrounding the implanted sensor 200 ostensibly more stable, including blood vessel perfusion in the immediate locality). Note that this delay is to be contrasted with that described previously; i.e., the latter referencing application of the model(s) to operational data.

After the sensor training mode is initialized, a notification is generated and transmitted to the GUI requesting input of external blood analyte reference data ($BA_{ref}$) per step 518. For example, during sensor training mode operation, the sensor system can periodically transmit notifications to a user to enter a manual blood analyte reading such as e.g., a blood glucose level determined via the aforementioned "fingersticking" method and/or laboratory-type analyzers (e.g., YSI analyzers). For example, notifications may be sent to the user hourly, every two hours, every three hours, daily, weekly, or according to other desired notification schedules. Alternatively, the user may obtain and enter manual blood analyte readings spontaneously (i.e. not in response to any notification); in such a case, if the rate of entry of blood analyte reference data by the user exceeds a programmed threshold, then the need for notifications may be obviated.

Thus, either spontaneously or in response to receipt of the notification, the user obtains and inputs $BA_{ref}$ data (such as e.g., entering data via the GUI) which are received by the sensor system per step 520. The $BA_{ref}$ data either include a time-stamp generated by an external digital blood analyte measurement device or are time-stamped when received by the sensor system. It is noted in passing that in some cases the internal time domains maintained by physically separate devices are not perfectly aligned, and hence a time stamp applied to data transmitted from a device before transmission (e.g., based on collection of the data at actual time t) is different than or misaligned with a time stamp applied by another device to data collected at that same (actual) time t. Hence, the two time stamps indicate different values, even though both actually collected at time t. Accordingly, the present disclosure contemplates using a single, unified time domain (e.g., that of the sensor apparatus 200, or the receiver 400, or even the parent platform 600), for consistency, such as where all data are time-stamped with values associated with the unified domain. It will be appreciated that the time-stamping in such implementations, while conducted based on the unified domain, need not be performed by the device maintaining the unified domain (clock). For example, in one variant, the parent platform 600 periodically transmits clock signals indicative of time in its unified domain (referenced to a known standard or event) to the receiver apparatus 400 and/or sensor apparatus 200, the receiving devices using this data to periodically align their own clock domains as needed. Other schemes for maintaining unified time-stamp data between the various data sets and devices will be appreciated by those of ordinary skill given the present disclosure.

In an alternative example, a user can manually enter a time at which the $BA_{ref}$ data were collected. In another alternative example, the $BA_{ref}$ data can be digitally uploaded to the sensor system without requiring a user to manually input the $BA_{ref}$ reading.

It is also appreciated that user notification and/or input may be obviated in favor of direct communication between the sensor system and the source of $BA_f$, such as where the sensor system generates and transmits a datagram to an API (application programming interface) of the reference data source, requesting the reference data. Upon receiving the datagram, the reference data source generates and transmits a responsive datagram containing the requested reference data and any other appropriate data such as temporal reference, source ID, CRC or other error correction data, etc. The user may also be given confirmatory capability via the GUI if desired (e.g., notification to the user via GUI display that the source has sent a $BA_{ref}$ value to the sensor 200, and requesting assent by the user via the GUI or other input device of the receiver 400, 450 to enter and utilize the value). Alternatively, the reference data source may initiate the data transmission activity, when e.g., new reference data have been generated and are available for transmission to the sensor system.

Contemporaneous with the receipt of $BA_{ref}$ data, the sensor system collects and calculates a measured blood analyte level reading ($BA_{cal}$) per step 521.

Methods for collection and calculation of blood analyte level during sensor training mode operation of the sensor system are discussed with reference to FIGS. 5B and 5C. Specifically, an exemplary embodiment of a method 522 of operating the implanted sensor 200 with the local receiver apparatus 400 and the parent platform 600 and/or the receiver and processor apparatus 450 for collection and calculation of training mode $BA_{cal}$ data, as well as an exemplary method 529 of data processing and output during sensor training mode operation are described in detail infra.

Specifically, as shown in FIG. 5B, the enabled sensor 200 communicates data wirelessly to the receiver apparatus 400, 450, such as on a periodic, event-driven, continuous, or other basis per step 523 of the method 522. Note that the transmission and reception frequencies or schedule need not necessarily coincide completely. For instance, the transmitter of the sensor apparatus 200 may transmit according to a prescribed periodicity or frequency, while the receiver 400, 450 may utilize a less frequent sampling of the transmissions, or the transmissions may be buffered or queued for opportunistic transmission (and/or processing by the receiver 400, 450). Similarly, a polling or similar approach may be used, such as where the receiver 400, 450 polls the sensor 200 when it is ready to receive the data, which may be periodic or aperiodic in nature.

Per step 525, the received sensor data are processed to calculate blood analyte level, and any related parameters or data derived therefrom. Such processing may occur when the data are received, or collectively in one or more aggregations or batches of data (e.g., sensor data collected or received over a prescribed time period, number of iterations, representative of a prescribed duration of in vivo operation, or other).

Optionally, per step 527, the calculated blood analyte level (e.g., glucose concentration in e.g., mg/dL or mmol/L) is output to the user in a cognizable form, such as visually, via haptic apparatus, audibly, and/or yet other means, as described elsewhere herein. Similarly, other information (such as, e.g., trend of the blood glucose level, ROC, and/or alert notifications discussed in detail infra) may be output from the receiver 400, 450 via the same or different cognizable medium. It will be appreciated that output of blood analyte level may also be withheld or suspended during sensor training mode operation, so as to avoid potentially erroneous values being perceived by the user before sensor model generation and application are completed.

With use of the local receiver 400, the method 522 further may include determining whether the parent platform 600 (e.g., the user's more fully-functioned tablet, smartphone, etc.) is "communicative" with the local receiver 400 (per step 531), so as to enable the parent platform to utilize its functionality in supply and/or processing of the obtained data. When communications between the local receiver 400 and the parent platform 600 are enabled (per step 535), the local receiver and parent platform handshake (e.g., pair according to a Bluetooth pairing protocol) and/or an Internet of Things (IoT) protocol, with the local receiver as the slave, and the parent as the master).

It will be appreciated that while the foregoing scenario contemplates use of a local receiver 400 to communicate with the parent platform 600, the present disclosure also contemplates, inter alia, use of direct communication between the sensor apparatus 200 and the parent platform 600, such as via wireless (RF) communications. In one such implementation, the sensor apparatus 200 includes a Bluetooth wireless interface (e.g., BLE variant) which operates at 2.4 GHz and which has been demonstrated by the Assignee hereof to penetrate human tissue with sufficient efficacy so as to maintain a wireless communication channel between e.g., the implanted sensor apparatus 200 and the comparably Bluetooth-equipped parent platform 600, the latter further including an application program or firmware configured to extract data (whether raw or pre-processed on-board the sensor apparatus 200) from one or more messages wirelessly transmitted from the sensor 200. Additional details on one exemplary implementation of the sensor-to-parent platform interface are described in co-pending U.S. application Ser. No. 15/368,436 filed Dec. 2, 2016 and entitled "Analyte Sensor Receiver Apparatus and Methods", previously incorporated herein.

At step 537, processed and/or raw data from the local receiver 400 are transmitted to the parent platform 600. Per step 539, the receiver(s) receive the configuration and/or calibration data (as applicable from the parent platform 600 in an example where a local receiver 400 is utilized), e.g., such as "fingerstick" or blood glucose monitor (BGM) values entered by the user via the GUI. Alternatively, in an example where a receiver and processor apparatus 450 is utilized, a user or a medical professional can enter configuration and/or calibration information via a GUI displayed at the apparatus 450.

Per step 541, the configuration of the receiver (e.g., the alarm setting values, alert logic or hierarchy such as "haptic then visual then audible", etc.) is also optionally updated as needed. Similar to the optional withholding or suspension of output of blood analyte level during sensor training mode operation of the sensor system, receipt of configuration updates may be optionally suspended or withheld during the sensor training mode and later updated when the receiver initiates detection mode operation.

Alternatively, if the parent platform is not "communicative" (e.g., outside range, busy, preempted, etc.) per step 531 of the method, operation of the local receiver 400 is continued (i.e., periodic or continuous receipt and processing of sensor data).

FIG. 5C is a logical flow diagram illustrating one exemplary implementation of the sensor data processing and output methodology 529 for the local receiver 400 and the parent platform 600 (or the receiver and processor apparatus 450) during training mode operation according to the method 522 of FIG. 5B. As shown, the method 529 in one embodiment includes first receiving the wireless data transmissions from the (implanted) sensor 200 per step 545. Next, per step 547, the received wireless signals are processed, and the processed data stored (step 549). Exemplary implementations of sensor data receipt and demodulation/unscrambling methodology for the receivers 400, 450 are described in U.S. patent application Ser. No. 15/368,436 previously incorporated herein.

Next, the calculated blood analyte level ($BA_{cal}$) is determined per step 551. Optionally, one or more random noise signal filters (such as e.g., finite impulse response (FIR), infinite impulse response (IIF), Kalman, Bayesian, and/or other signal processing filters) can be applied to the $BA_{cal}$ reading to correct for error due to random noise (i.e., "e"

defined supra) per step 553. As a brief aside, as will be appreciated by artisans of ordinary skill in the signal processing arts, typical "white" noise or "random" noise is characterized by a constant power spectral density. Colored noise spectra may have non-constant power spectral density; e.g., red tinted noise has less attenuation at longer wavelengths (lower frequencies), whereas blue tinted noise has less attenuation at shorter wavelengths (higher frequencies). Common techniques for removing the effects of random noise include without limitation e.g., time based averaging, statistical sampling, spectrally weighted averaging, and/or any number of other weighted filtering techniques.

Further, other parameters of interest if any (such as real-time trend and/or rate of change) are calculated per step 555.

Returning to FIG. 5A, per step 524, in addition to receiving the $BA_{ref}$ data and collecting/calculating the $BA_{cal}$ data, the sensor system can optionally collect and/or receive other data. In one exemplary implementation, the system can collect data (hereinafter "$OS_{cal}$" data) received from one or more other sensors (such as e.g., internal sensors 232 on the implanted sensor 200, external sensors 432 such as on the receiver or parent platform, or other additional sensors associated with the blood analyte detection system). For example, the one or more internal sensors 232 associated with the implanted sensor 200 (or similar sensors implanted proximate to the sensor 200) can collect/calculate internal $OS_{cal}$ data such as e.g., internal body temperature in the region of the implanted sensor, pulse rate of the user, motion and/or orientation data, pressure, pH, local blood flow/tissue perfusion, electrical impedance of the sensor/tissue interface, blood analyte concentration of other non-target analytes (e.g., oxygen), and/or other internal data. In another example, the one or more external sensors 432 associated with the receiver 400, 450 can collect external $OS_{cal}$ data such as e.g., external body temperature, pulse rate of the user, blood pressure, motion and/or orientation data, and/or other external data, or even pre-processed "state" or other context data; e.g., as to what activity or state the user is currently engaged in (such as ambulatory, sleeping, exercising, eating, etc., so in effect the computerized modeling logic does not have to deduce or derive this information from raw sensor data alone). In another example, the $OS_{cal}$ data can include information that the system calculates using stored data, and may comprise, e.g., the length of time that the sensor has been in operation, the rate of change of sensor signals, etc.

Additionally or alternatively, a user or medical practitioner/caregiver can manually enter other external data such as e.g., body temperature, pulse rate, blood pressure, indicator of exercise, an indicator of intake of medication, an indicator of resting state (e.g., sleep), an indicator of active state (e.g., exercise), an indicator of ingestion of food (e.g., slow-acting carbohydrates, fast-acting carbohydrates, etc.), and/or other manually entered data, such as via a user interface and an application layer program operative to run on the receiver 400, 450, or parent platform 600 (depending on how each is configured). It will be appreciated that manually entered data can be used alone or in combination with data collected via the internal sensors 232 and/or the external sensors 432.

In another implementation, the other data can comprise both internal $OS_{cal}$ data and external $OS_{cal}$ data (and/or manually entered external data). In one such variant, the internal sensor data are generated only periodically, such as during several discrete periods during training phase operation to ensure signal stability, yet minimize electrical power consumption with the sensor 200 so as to, inter alia, enhance battery life. In another variant, the external $OS_{cal}$ data can be calibrated to the internal $OS_{cal}$ data during the training mode operation, such as where internal temperature is registered (by the internal temperature sensor of the analyte sensor 200, or a separately implanted internal sensor) as a first value that is higher than say an externally-sensed temperature produced by a skin temperature sensor on the local receiver 400, thereby requiring application of an offset or calibration factor for data generated by the external sensor to reflect internal body temperature. Thus, in subsequent sensor detection mode operation of the system, the external sensors (e.g., sensors 432 on the receiver) can be utilized, and the internal sensors can be substantially "turned off," thereby decreasing power and processing demands on the implanted sensor 200 (or the other sensors implanted proximate to the sensor 200 if used).

In yet another variant, both the external $OS_{cal}$ data and the internal $OS_{cal}$ data are collected and utilized during the sensor training mode operation and the detection mode operation to improve accuracy via e.g., collating data from multiple sources. In still other variants, external and internal $OS_{cal}$ data can be dynamically selected for use during detection mode operation based on data analyses carried out during the operational model generation (discussed infra).

In each of the above implementations, the other data (i.e., the $OS_{cal}$ data and/or manually entered data) are optionally time stamped such that they can later be temporally correlated with the $BA_{ref}$ data and the $BA_{cal}$ data during data processing.

Per step 526 of FIG. 5A, the data collected and received at steps 520-524 are stored on a storage device associated with the sensor 200, the receiver 400, 450, the parent platform 600, and/or another storage device in data communication with the sensor system. For example, the data can be stored at one or more of the mass storage 420 associated with the receiver 400, 450, the storage 220 associated with the sensor 200, a storage device associated with the parent platform 600 (not shown), or a network ("cloud") storage device accessible via data communication with the network 830. Storage is effected via the software/firmware operative to run on the calculating or receiving platform. For example, in one configuration, the collected data are calculated on-board the sensor 200 using its internal computerized logic alone, and the resulting data stored locally onboard the sensor 200. In another configuration, data calculation is offloaded to the external receiver 400, 450 or even parent platform via the wireless interface of the sensor, and the processed data returned to the sensor 200 for local storage. In another configuration, the data calculation is offloaded to the external receiver 400, 450 or parent platform via the wireless interface of the sensor, and the processed data stored external to the user (i.e., in the receiver 400, 450 or parent or cloud), and a wireless datagram sent to the sensor apparatus 200 indicating to the latter that the values have been calculated, and are accessible at prescribed data storage locations, or via API calls.

Receipt, collection, and storage of data are continued until a threshold of stored data or other criterion is met. Specifically, in the embodiment of method 514, it is determined whether a statistically relevant amount of data has been stored at decision block 528. In one exemplary implementation, the sensor training mode is employed for a predetermined amount of time (e.g., one day, one week, two weeks, etc.). In the foregoing implementation, the threshold for data collection is the pre-determined amount of time for the duration of the sensor training mode operation; therefore, the determination of whether the threshold for data collection has been met includes determining if a time elapsed since the initiation of the sensor training mode is greater than the pre-determined amount of time, such as via a clock function resident on the local receiver logic. This threshold can be made irrespective of actual data collected, or coupled with a prescribed threshold of data collection volume (described infra).

In another implementation, the sensor training mode is implemented until a pre-determined number of data points (i.e., a pre-determined amount of data having corresponding time points) are collected. In this implementation, the threshold for data collection is the pre-determined number of data points; and therefore, the determination of whether the threshold for data collection has been met includes determining if a number of collected data points is greater than the pre-determined number of data points (which may be e.g., on a numerical basis such as an integer number, on an aggregated data size/storage value such as N kb or Mb, on a storage address basis such as a number of row/column addresses in a memory array, or yet other). It will be appreciated that other threshold criteria and/or a combination of threshold criteria may be utilized to determine whether the sensor system has collected sufficient sensor "training mode" data. For instance, the data collection may be controlled based on a subsequent processing of collected data, such as where a prescribed first amount of data is obtained, and subsequent steps of the methodology herein (i.e., model processing/generation) are performed to determine if satisfactory results can be obtained, such as based on statistical criteria. In effect, a trial run on analysis and model generation may be performed using a given amount of collected data, so as to determine statistical or other sufficiency of the data with respect to generation of a useful model. Depending on the sensor model chosen for application during the operational phase or mode (which may in fact be multiple models applied in series or tandem), certain data sets may or may not be sufficient for model generation and application in terms of their size, diversity, etc. Hence, by performing "look ahead" processing (including in an iterative fashion; i.e., wherein a first data set is collected, evaluated, and second heterogeneous or more expansive data set is subsequently collected and evaluated), the data collection threshold may be dynamically specified, as opposed to a predetermined value which, while conservative, may cause undue delay and utilization of sensor processing resources (and hence power consumption).

Per method 514, if the data collection threshold or criterion has not yet been met at decision block 528, data collection is continued. Alternatively, if the threshold or criterion is met, the training mode operation of the sensor system is completed, and the collected and received data are subsequently analyzed and processed for sensor operational model generation as described elsewhere herein.

Although not specifically depicted in FIG. 5A, it will be appreciated that the sensor training mode operation can additionally include a "manual override" or similar function selectable by a user and/or a medical professional. In one example, the manual override function allows the method 514 to stop prior to meeting the data collection threshold/criterion, and proceed to the sensor operational model generation. In another example, the manual override function allows the method 514 to continue (i.e., allows collection of "training data" to continue) after the data collection threshold/criterion is met, prior to sensor operational model generation, so as to permit enrichment of the collected data set, or for other reasons (e.g., to ensure that readings are taken in different ambulatory or other user contexts such that the data are representative in such regards).

Sensor Operational Model Generation

Referring now to FIGS. 5D-5E, exemplary methodologies for model parameter identification and sensor operational model generation are described in detail.

As shown in FIG. 5D, the method of sensor model parameter identification 580 includes first identifying a set of available model parameters per step 582. This set may be identified for example based on the available sensors and/or data accessible in a given hardware/software environment within which the sensor apparatus 200 will be used. For example, the accessible sensor/data set may be as little as (i) the blood analyte sensor(s) on the sensor apparatus 200, and (ii) external blood analyte (e.g., BG) reference data, such as from a fingerstick calibration device. More fully featured/instrumented applications may include more sensors and data sources. In the exemplary context of blood glucose measurement, some of the likely candidate parameters include: (i) reference background pO2 ($O_2$ partial pressure) measured by the CGM sensor; (ii) electrode(s) current measured by the CGM sensor; (ii) rate-of-change of electrode(s) current measured by the CGM sensor; (iv) temperature measured by a temperature sensor (e.g. a thermistor) embedded in the CGM sensor or separate therefrom; (v) accelerations measured by an accelerometer embedded in or external to the CGM; (v) pressure (e.g., via indigenous piezoelectric or other sensor on the implant 200), (vi) pH, and (vii) "state" variable inputs such as user-input data regarding their activities, ambulatory state, items eaten and times, and the like.

Next, per step 584, the candidate sensor model parameters identified in step 582 are evaluated for selection. In one embodiment, the candidate parameters are evaluated using analytical techniques structured to identify relative parameter importance. For example, once candidate parameters and a particular machine learning algorithm (including e.g., Decision Tree, Random Forest, etc.) are defined, those parameters demonstrating utility in reducing a specified error measure (e.g. MARD, MAD, outlier prevalence, etc.) in a training data set are selected by means of a "feature selection" technique. For example, when a Random Forest algorithm is trained using the model parameters and reference-derived $BG_{s\_error}$, an "out-of-bag" or other predictor (parameter) importance can be evaluated, such as by permuting the input parameter values. See e.g., *Out-of-Bag Estimation*, L. Brieman, et al, University of California at Berkley (https://www.stat.berkeley.edu/~breiman/OOBestimation.pdf), incorporated herein by reference in its entirety, as one exemplary approach. In such an analysis, the parameters with higher importance metrics tend to better predict the output variable, $BG_{s\_error}$.

Lastly, per step 586, a final list of parameters can then be selected, such as for example based on a pre-defined threshold of predictor importance. Alternatively, a simple criterion to select a prescribed number (e.g., top 'n') of predictors can be employed.

It will be appreciated that the parameter identification process may be conducted algorithmically (e.g., by an application computer program or other software based on provided data sets, heuristically by a human, or combinations thereof. Moreover, if the relevant sensor model parameters are known a priori, such model identification methodology 580 may be completely obviated.

Turning now to FIG. 5E, an exemplary embodiment of a method 530 for data analysis and generation of a sensor operational model (e.g., a user-specific operational model for an implanted sensor) is shown and described.

Per step 532, blood analyte detection error data ($BA_{s\_error}$ data) is first calculated for the $BA_{cal}$ data, based on the received $BA_{ref}$ data, for each of the $BA_{cal}$: $BA_{ref}$ pair. For example, the $BA_{s\_error}$ data can be calculated as the difference between the calibrated analyte sensor output ($BA_{cal}$ data) and the external analyte reference data ($BA_{ref}$ data), as set forth in Eqn. (3) below:

$$BA_{s\_error} = BA_{cal} - BA_{ref} \quad (3)$$

Alternatively (or in tandem), the $BA_{s\_error}$ data can be calculated as the relative difference (RD) between the $BA_{cal}$ data and the $BA_{ref}$ data, as set forth in Eqn. (4) below:

$$RD = \frac{(BA_{cal} - BA_{ref})}{BA_{cal}} \quad (4)$$

Additionally or alternatively, the $BA_{s\_error}$ data can be calculated utilizing one or more other methods (such as e.g., standard deviation, mean absolute difference, etc.).

After calculation of $BA_{s\_error}$ data, per step 534, one or more "machine learning" algorithms are selected/identified for modeling the $BA_{s\_error}$ data. In one implementation, a single algorithm is pre-selected (e.g., an experimentally pre-determined algorithm) for utilization in model generation prior to implantation of the sensor. Differently stated, the sensor system can be pre-programmed to utilize a single desired algorithm, such as e.g., an algorithm selected for its particular attributes such as robustness, accuracy, etc. In another implementation, a medical practitioner may select (e.g., prescribe) one of multiple algorithms for use in a specific patient (i.e., user) prior to or after implantation of the sensor, ostensibly based on the desirability of that algorithm for use within the particular user based on their particular physiologic attributes, lifestyle, sensor location, etc. For example, in each of the foregoing implementations, the desired algorithm or the prescribed algorithm may be selected based on known algorithm characteristics (e.g., speed, accuracy, required processing power, robustness to errors, etc.), and/or characteristics of the user (e.g., known medications or treatments, known lifestyle characteristics, known disease characteristics, etc.), including based on prior analysis of the algorithms prior to implantation such as via computer analysis on various test or patient-derived data sets.

An exemplary decision tree 600 (i.e., Decision Tree-based algorithm) is shown in FIG. 6, wherein each end-node predicts a specific error (or source). The Decision Tree is generated using an algorithm which recursively splits a node (parent), containing training data, into two child nodes (Left and Right) based on a predictor variable, its threshold value, and an objective error criterion (e.g., mean square error, etc.). The Left node comprises all of the training samples from the parent node that have predictor values less than the threshold whereas the Right node comprises all of the training samples from the parent node that have predictor values greater than or equal to the threshold. The (child) nodes are continued to be split until a termination criterion is met. For example, further splitting of a node can be terminated if the number of training samples in the node is equal to or smaller than a predefined threshold. The nodes that cannot be split further are called leaves (end-nodes). Once a Decision Tree is generated, an error estimation through this decision tree requires traversing the tree nodes utilizing binary decisions based on the respective model parameters and their thresholds. Once an end-node (also called 'leaf') of a tree is reached, the error estimate (e.g., mean value of the error in all of its training samples) associated with the leaf is used for the correction.

In yet another implementation, more than one machine learning algorithm (including e.g., Decision Tree, Random Forest, Naïve Bayes classification, support vector machines (SVM), Gradient Boosting, and AdaBoost) can be utilized to model the training data during sensor operational model generation, and the algorithm that yields the "best" result can be used in the sensor operational model. For example, the sensor system (or external platform such as the receiver 400, 450, or parent 600) can be pre-programmed to analyze the data via e.g., three (3) different machine learning algorithms, thereby generating at least three sets of data (i.e., at least one set of data output from each algorithm). Each of the sets of data can then be compared or otherwise evaluated against performance criteria to identify the "best" algorithm for generation of the sensor operational model. In the foregoing example, the "best" algorithm may be selected based on a desired characteristic such as e.g., speed, accuracy, required processing power, robustness, and/or other desired features. The initial set of three algorithms in this example may be selected by the aforementioned experimental or other analytical evaluation, based on the particular attributes of the user in which the sensor 200 is intended to be implanted. For instance, the data vectors for a given individual (e.g., height/weight, BMI, race/ethnicity, age, stage of disease progression, etc.) can be evaluated to identify a previously determined subset of algorithms which are better suited to those falling within such classes, and their implanted sensor 200 preprogrammed with that subset of algorithms, in effect pre-filtering the algorithms for that individual so that the best algorithm(s) can be more rapidly converged on during sensor model generation.

Further, in each of the foregoing implementations, the one or more machine learning algorithms may be differentially applied to selected portions of the collected data in order to analyze various parameters which may or may not be correlated with error occurring at the implanted sensor (i.e., correlated with the $BA_{s\_error}$ data). In a variant where only the $BA_{cal}$ data are collected from the implanted sensor during sensor training mode operation (i.e., no external data or $OS_{cal}$ data are received/collected), variables or parameters can include the sensor element(s) of origin (e.g., an identification of one of four sensor element pairs 206 shown in FIGS. 2-2A), electrode current at one or more of the sensor elements, rate-of-change (ROC) of electrode current at one or more of the sensor elements, reference (i.e., background) of oxygen concentration measured by one or more of the sensor elements, time of day (e.g., 6 AM, 7 AM, 8 AM, etc.), range of time of day (e.g., early morning, midday, night, etc.), range of blood analyte concentration (e.g., high range, median range, low range, etc.), age of sensor (i.e. length of time the sensor has been operating), impedance among sensor elements (both within the sensor itself and as measured through tissue adjacent to the sensor), and/or other determinable parameters that can be extracted from the sensor data.

In another variant where other data (e.g., internal $OS_{cal}$ data, external $OS_{cal}$ data, or other user input data) are received and/or collected in addition to the $BA_{cal}$ data during training mode operation, variables or parameters can additionally include temperature, acceleration, orientation, pressure, pulse rate, one or more other non-target blood analyte concentrations, intake of medication, intake of food, designated resting period of the user, designated active period the user, and/or other determinable parameters that can be extracted from the other sensor data and/or the user input data such as user state or context data. Per step 586 (FIG. 5D), a final list of one or more parameters is selected based on a predictor importance/relevance criterion.

As a brief aside, machine learning algorithms construct models of behavior from a set of sample inputs (here, e.g., blood glucose calibration data). Such models enable performance of a set of tasks as a function of previous experience, based on optimizing a performance metric as a function of the experience. Machine learning is typically further categorized into supervised, unsupervised and reinforcement based learning based on the types of input/output generated by the system.

So-called "supervised learning" algorithms determine a set of tasks to optimize outputs from a set of inputs; where a supervising entity (e.g., a human trainer) has defined the appropriate inputs and outputs. So-called "unsupervised learning" takes a non-curated data set and attempts to interpolate a series of relationships to identify e.g., inputs and outputs. So-called "reinforcement learning" algorithms are adapted to receive feedback over a plurality of training trials using dynamically generated input.

Various functions of the apparatus or systems described herein may be implemented within various ones of the foregoing categories of machine learning. For example, supervised learning solutions may be useful to quickly adapt the known input $BA_{cal}$ to the expected output $BA_{ref}$. Unsupervised learning may be used to find hidden correlations between the various sensor inputs; for example, unsupervised learning may be able to infer complex interrelationships between e.g., heart rate, oxygenation, and blood glucose which would be otherwise too complex to generically model, or the bases for which are unknown. Reinforcement techniques may be used by doctors, or other trained personnel to fine tune and or further tailor measurements. Still other applications of the foregoing will be readily appreciated by those of ordinary skill in the related arts.

The aforementioned machine learning algorithms are purely illustrative examples of artificial intelligence algorithms that are configured to adapt to changes in data sets. More generally, artisans of ordinary skill in the related arts will appreciate that any logic that is configured to learn or be trained from a set of initial training data, and subsequently predict or provide decisions for physiological parameters (e.g., glucose) may be substituted with equivalent success, given the contents of the present disclosure. For example, another machine learning algorithm referred to as Support Vector Machine (SVM) with a linear or non-linear kernel can be utilized to model the $BA_{s\_error}$ as a function of input model parameters. In the case of a linear kernel SVM, $BA_{s\_error}$ is modeled as a linear function of model parameters by utilizing a training data set and minimizing a pre-defined cost function (J) subject to criteria on residuals and cost function variables. As an example, if background pO2 (pO2) and rate-of-change of background pO2 (roc_pO2) are used as model parameters for estimating $BA_{s\_error}$, a linear SVM model can be generated as:

$$F(x) = A*pO2 + B*roc\_pO2 + C \quad (5)$$

Where F(x) provides an estimate of $BA_{s\_error}$, given the measurement of pO2 and roc_pO2 from the sensor, and A, B, C are model parameters generated using a training data set comprising N training samples, a cost function, and model constraints. Example forms of cost function (J) and model constraints (K) are provided below as equations (6) and (7):

$$J = 0.5*(A*A + B*B) + x\sum_{n=1}^{N}(\varepsilon_n + \varepsilon_n^*) \quad (6)$$

$$K = \bigvee n \begin{cases} BA_{s\_error} - (A*pO2 + B*roc\_pO2 + C) \leq \alpha + \varepsilon_n \\ (A*pO2 + B*roc\_pO2 + C) - BA_{s\_error} \leq \alpha + \varepsilon_n^* \\ \varepsilon_n \geq 0 \end{cases} \quad (7)$$

$$\varepsilon_n^* \geq 0$$

Where α is a predefined residual margin, and ε is a slack variable (soft margin) allowing the model generation to converge.

Per step 540, an operational model is then generated for prediction of $BA_{s\_error}$ during normal operation of the implanted sensor (i.e., detection mode operation) based on the one or more selected/identified parameters and the determined relationship with $BA_{s\_error}$. The model is stored at one or more of the storage devices discussed supra (step 542) for subsequent use during operation of the sensor system in the detection mode (step 510 of FIG. 5).

It will also be appreciated that instead of modeling the blood analyte error (e.g., $BG_{s\_error}$ in the foregoing examples) directly, the apparatus and methods described herein may be adapted to use model parameters including for instance the "calibrated" CGM-generated blood glucose values ($CG_{cal}$), computed by applying a known calibration transform to the raw CGM data, to directly estimate a blood glucose value ($BG_{model}$). Therefore, $BG_{s\_error}$ will indirectly be calculated as $BG_{model} - CG_{cal}$.

Also, in addition to estimating error in CGM-reported blood glucose, the modeling may be performed to estimate the error in the CGM-reported rate-of-change (ROC) of the blood glucose (e.g., the first derivative of the raw data over time), assuming sufficient numbers of reference blood glucose values collected closely in time are available to enable calculation of a reference rate-of-change. Hence, the "ROC" error can be estimated as $[ROC_{ref} - ROC_{CGM}]$.

Sensor Detection Mode Operation

Methods for collection and calculation of blood analyte level during detection mode operation of the sensor system are discussed with reference to FIGS. 5B and 5F. Specifically, an exemplary embodiment of a method 522 of operating the implanted sensor 200 with the local receiver apparatus 400 and the parent platform 600 and/or the receiver and processor apparatus 450 for collection and calculation of detection mode $BA_{cal}$ data, as well as an exemplary method 529 of data processing and output during detection mode operation, are now described in detail.

It will be appreciated that the method 522 is substantially similar during sensor detection mode operation as during sensor training mode operation, and thus much of the method described supra for determination of $BA_{cal}$ data during the sensor training mode operation is applicable to determination of $BA_{cal}$ data during sensor detection mode operation. Notably, whereas output of $BA_{cal}$ data (i.e., output of the blood analyte level) is optional in the sensor training mode operation, such output is generally a primary function (non-optional) of the sensor system during the detection mode operation, so as to maintain the user and/or caregiver informed as to blood analyte level, and implement any relevant indication or alert regimes. In some instances (such as e.g., when the receiver is out of range of the implanted sensor), blood analyte data (and/or other internal data) can be continuously collected at the sensor during detection mode operation without (immediate) output of $BA_{cal}$ data.

Additionally, one or more of the data processing steps during the detection mode deviate from or supplement those in the training mode operation (e.g., method 529 of FIG. 5C). Specifically, the data processing step of the detection mode operation further includes (at least) application of the stored sensor operational model on the implanted sensor analyte data ($BA_{cal}$ data).

As discussed supra, FIG. 5F is a logical flow diagram illustrating one exemplary implementation of the sensor data processing and output methodology 561 for the local receiver 400 and the parent platform 600 (or the receiver and processor apparatus 450) during sensor detection mode operation according to the method 522 of FIG. 5B. As depicted in FIG. 5F, the method 561 in one embodiment includes first receiving the wireless data transmissions from the (implanted) sensor 200 per step 563. Next, per step 565, the received wireless signals are processed, and the processed data stored (step 567). Exemplary implementations of sensor data receipt and processing, including demodulation/unscrambling, for the receivers 400, 450 are described in U.S. patent application Ser. No. 15/368,436 previously incorporated herein.

Next, calculated blood analyte level ($BA_{cal}$) is determined per step 569. The $BA_{cal}$ data are then processed via application of the stored sensor operational model on (i) the $BA_{cal}$ data, and (ii) data from the one or more identified parameters correlated with $BA_{s\_error}$ (such as e.g., temperature data, motion data, orientation data, pulse rate data, other blood analyte concentration data, manually entered user data, etc.), thereby generating $BA_{cal}$ data corrected for $BA_{s\_error}$ (i.e., systemic error from unmodeled user-specific variables) per step 571. In one implementation (implanted blood glucose sensor), once a new blood glucose sample is recorded by the system, it will compute all the model parameters selected and defined in the model parameters identification process using the new BG sample data (and any number of past samples needed). Once the model parameters are computed, the machine-learning model generated via the user-specific model generation process is applied to predict the $BG_{s\_error}$. Similarly, $CG_{cal}$ (the "calibrated" CGM BG data) is computed by applying the known calibration transform to the raw CGM data, and the predicted $BG_{s\_error}$ is subtracted from $CG_{cal}$ to provide a closer approximation of $BG_{ref}$ (albeit still containing effects due to random noise).

Optionally, one or more random noise signal filters can be applied to the corrected $BA_{cal}$ reading to additionally correct for error due to random noise (i.e., "e") per step 553 (see discussion of random noise supra).

Other parameters of interest if any (such as real-time trend and/or rate of change) are calculated based on the corrected $BA_{cal}$ data per step 573. Optionally, the calculated values from steps 571, 573, 575 are then converted per step 577 to a prescribed output format (e.g., a graphic rendering of a numeric value, a graphic display of a trend arrow, a sequence of haptic vibrations, etc.) consistent with the selected/configured output modality. The converted values or indications can then be output to the user in the appropriate modality/modalities per step 579, such as via the GUI.

It will be appreciated that the analyte sensor system may operate in detection mode simultaneously with its operation in sensor training or sensor re-training modes. That is, if a suitable model has already been made available to the sensor system (e.g. by previous training or by factory programming), then model-based error correction can be applied and error-corrected $BA_{cal}$ reported by the system even while the steps are being carried out to develop a new sensor operational model (training or re-training). After the new sensor model has achieved a sufficient state of readiness, then the system may abandon (or modify) the previous model in favor of a new model.

Sensor System Re-training Determination

As depicted in step 512 of FIG. 5, in one exemplary embodiment, the method of operating the sensor system 500 includes optional "re-training" of the sensor system. The aforementioned sensor "re-training" substantially comprises a subsequent operation of the sensor system in the sensor training mode after an initial training mode operation. As such, sensor re-training may occur for example: (i) after implantation, and after an initial in vivo training operation; (ii) after implantation, and after an initial explanted training operation conducted before the sensor 200 is implanted; (iii) after explant, and subsequent re-implantation of the same or similar sensor 200 in the same individual.

Notably, such re-training can be used, inter alia, to compensate for short-term or long-term changes or variations in sensor response or subject physiology; i.e., how the sensor responds to prevailing in vivo and sensor operational conditions it finds itself in at any given point during its implanted lifetime. For example, one or more of the detector pairs of the sensor 200 may become less sensitive or more sensitive or fail over time, and/or the host's physiological responses (including FBR or other such factors) may vary as a function of time. Ancillary sensors on the sensor 200 (e.g., pressure, temperature, etc.) may also fail or their response characteristics may change, thereby necessitating their re-evaluation or removal from the algorithmic modeling process.

Moreover, the coupling or interface of the sensor 200 and the host's tissue may change, including due to mechanical events such as a physical impact, strenuous exercise or activity, etc., such that the sensor detector pairs must be "re-acclimated" to the new physical coupling after movement of the sensor 200 within its implantation pocket within the host's tissue. Yet further, new and previously un-modeled (within that individual) physiological or non-physiological error sources may arise over time, or other previously modeled sources (i.e., accounted for in the model developed after initial training) may wane over time. New algorithms may also be developed, and it may be desired to retro-fit them into an already implanted device.

As can be appreciated, any number of the above factors or others, may dictate a re-training of the sensor while in vivo. Generally speaking, many if not all of the above sources of possible variation in signal will manifest themselves in varying degree in the $BA_{s\_error}$ value ultimately identified using the applied operational model, and hence the magnitude and/or rate of change (ROC), and/or number of data outliers (e.g., stability), can be used as a determinant or passive/post hoc indicator of change of one or more sensor operational or physiological processes. However, the present disclosure also contemplates proactive or advance determination of the change of one or more sensor operational or physiological processes.

FIG. 5G is a logical flow diagram illustrating one exemplary implementation of a method 544 of determining the need for re-training of the sensor 200. This methodology can be implemented by the implanted sensor apparatus 200 (i.e., by logic operative thereon), by the local receiver 400 and the parent platform 600, the receiver and processor apparatus 450, or combinations of the foregoing (depending on how the logic is distributed within these devices), during detection mode operation according to the method 500 of FIG. 5.

As depicted in FIG. 5G, while the sensor system is operated in the detection mode (per methods 522 of FIG. 5A and 559 of FIG. 5F), it can be determined whether one or more criteria for re-training have been met, with any single criterion triggering re-training in the illustrated embodiment.

In the exemplary method 544, it is first determined whether $BA_{s\_error}$ is greater than a pre-determined threshold at decision block 546; i.e., the magnitude of $BA_{s\_error}$ averaged over a period of time is greater than a pre-determined threshold value for $BA_{s\_error}$. In another variant, it can additionally or alternatively be determined whether the $BA_{s\_error}$ outlier data include a number of outliers that are greater than an outlier threshold (or threshold percentage of the data; e.g., >20 percent are outliers). For example, a pre-determined threshold for a daily average $BA_{s\_error}$ is ±15% of respective $BA_{cal}$ values and/or a pre-determined $BA_{s\_error}$ outlier data threshold is 30% of respective $BA_{cal}$ values. In both variants, if the determined $BA_{s\_error}$ and/or $BA_{s\_error}$ outlier data are greater than the respective pre-determined threshold(s), a repeated operation of the sensor system in the training mode can be initiated (step 554). In some examples, a notification is sent to the user to confirm or request initiation of a subsequent sensor training mode.

Alternatively, per method 544, if $BA_{s\_error}$ and/or $BA_{s\_error}$ outlier data are less than the respective pre-determined threshold(s), other re-training criteria can be determined.

Per decision block 548, it is next determined if a time elapsed since initiation of the detection mode is greater than a pre-determined threshold (e.g., a duration of time for operating the sensor system in the sensor detection mode and hence without training). In one specific example, a pre-determined threshold for a time period for detection mode operation is one week. Thus, if the sensor system has been operating in the detection mode for a duration of time greater than the per-determined threshold, a repeated operation of the sensor system in the sensor training mode is initiated (step 554), so as to keep the error correction capability of the system "fresh" in light of any potential physical or physiological changes in the operation of the sensor 200.

Alternatively, if a time elapsed since the initiation of the detection mode operation is less than the pre-determined threshold, other sensor re-training criteria can be evaluated.

In the method 544, it is further determined whether a sensor "re-training event" has been detected per decision block 550. If such an event is detected, a repeated operation of the sensor system in the sensor training mode is initiated (step 554). Alternatively, if no re-training event is detected, other sensor re-training criteria can be evaluated.

Exemplary re-training events can include one or more of: (i) notification (e.g., via wireless message to/from the sensor apparatus from/to the external receiver) or internal determination that the sensor system has been recalibrated, (ii) detection of an occurrence of an unusually high temperature (e.g., detection of a temperature greater or less than a pre-determined high/low temperature threshold, respectively, and/or detection of the high/low temperature for a duration of time greater than a pre-determined threshold); (iii) detection of a physical impact to the user (e.g., detection of a pressure and/or acceleration value greater than a pre-determined threshold; (iv) detection of an occurrence of an unusually high or low pulse rate (e.g., detection of a pulse rate greater/less than a pre-determined high/low pulse rate threshold respectively, and/or detection the high/low pulse rate for a duration of time greater than a pre-determined threshold); (v) detection of a change in electrical impedance among sensor electrodes; (vi) detection of an increase in variance in the outputs among redundant or duplicative detectors, either located in the same sensor housing or in separate sensors; (vii) detection of change/drift in moving average of the direct sensor measurements or derived sensor measurements, e.g. average daily pO2, average weekly pO2, average daily concentration of glucose, change in daily correlation among different Cg channels when multiple detectors/pairs are available, daily correlation among different O2 channels, daily correlation between Cg and O2 channel, etc.

In some implementations, the re-training events can be selected by the sensor system based on the identified parameters which are correlated to $BA_{s\_error}$ for the specific user. For example, if temperature is correlated to $BA_{s\_error}$ while pulse rate is uncorrelated, sensor re-training events can include the occurrence of the foregoing temperature events, while the aforementioned pulse rate events are excluded from the set of events that initiate sensor retraining.

Per decision block 552, it is next determined whether a command or selection for sensor re-training has been received. Specifically, a user, a medical professional, and/or a caretaker can input a request for re-training of the sensor system, such as based on known user information, or merely as a "soft re-boot" (e.g., to attempt to clear prospectively anomalous behavior by the sensor 200). For example, if a user undergoes a significant lifestyle change (e.g., change in diet or exercise regimen), a change in disease presentation, a physiological change (e.g., onset of a transient illness or diagnosis of a secondary disease, significant weight gain or weight loss, etc.), a change in medication, goes on a vacation or other deviation from normal routine, such changes may warrant retraining to ensure that the generated model is still applicable and optimized. In another example, a user may sense a feeling of being "off" or a sensation of malaise, and may selectively initiate sensor retraining as desired. If a selection for sensor re-training is received, a repeated operation of the sensor system in the training mode is initiated (step 554). Alternatively, if no selection for sensor re-training is received (in addition to a "NO" for each of the other criteria of decision blocks 546-550) operation of the sensor system in the detection mode is continued according to the methods 552 and 559.

It will be appreciated by those skilled in the art given this disclosure that the exemplary method 544 is just one possible method for determining if sensor re-training criteria are met. In alternate implementations, the method can include more or fewer decision blocks, and/or the decision blocks can be executed in a different sequence. Other logical constructs may also be used, such as e.g., a "coincidence" requirement where two or three criteria must simultaneously be met in order to trigger sensor re-training. Moreover, a hierarchy of evaluation may be determined and leveraged; i.e., the order and frequency with which the various criteria are evaluated may be adjusted, such as where a most likely re-training factor/threshold to be exceeded is evaluated first at a first frequency, and other less-likely factors/thresholds evaluated at a reduced frequency.

Figure 7:
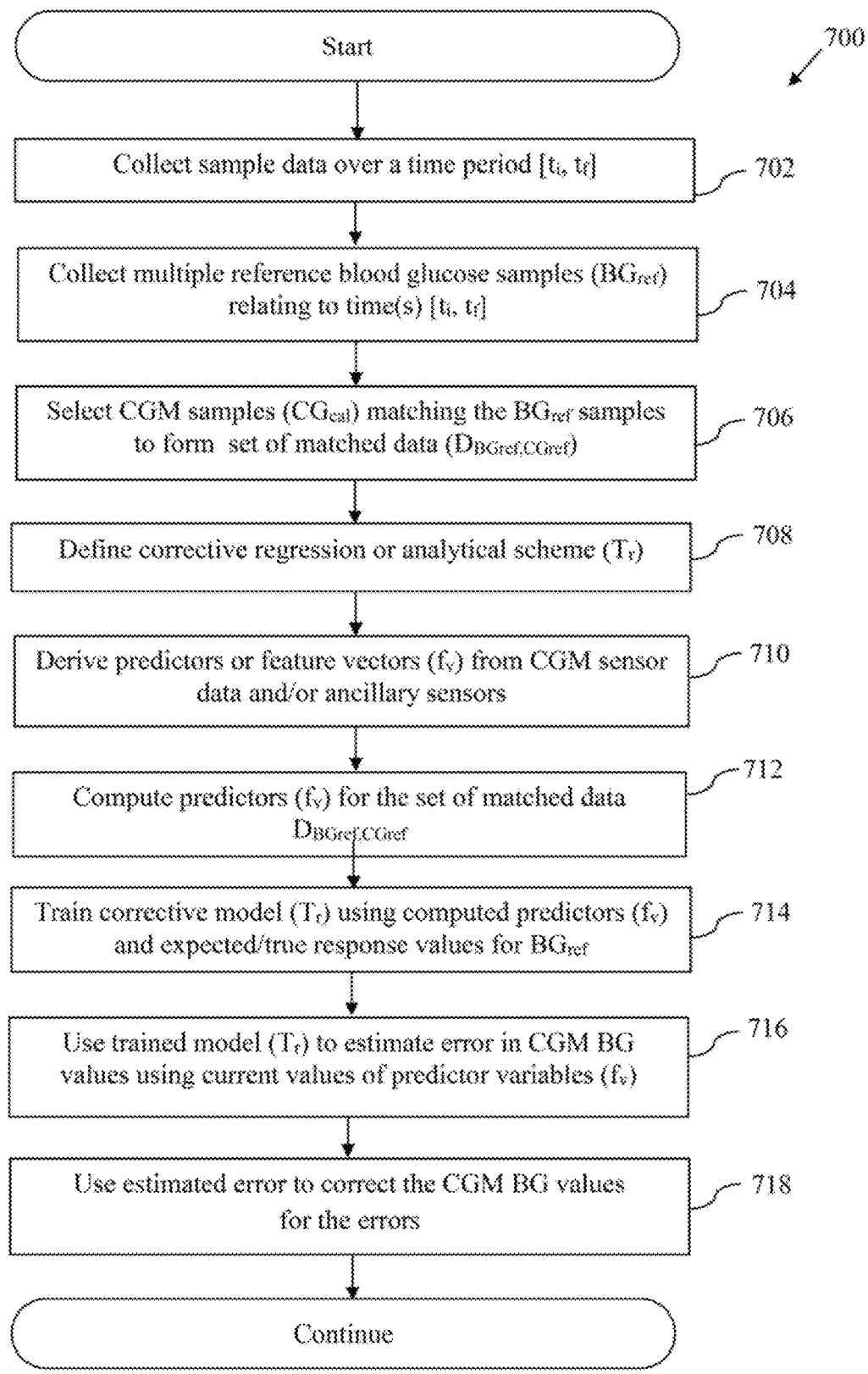
FIG. 7 is a logical flow diagram illustrating one exemplary implementation of the generalized method of operating the implantable sensor system for blood analyte measurement according to FIG. 5, in the context of an implantable oxygen-based blood glucose sensor having a plurality of detector pairs.

FIG. 7 illustrates one particular implementation of the foregoing methodology of correcting for systematic error ($BA_{s\_error}$=Blood Glucose sensor error or $BG_{s\_error}$) in the reported blood analyte level value(s) of FIGS. 5-5F, in the context of an implantable oxygen-based blood continuous glucose monitor (CGM) having multiple detectors/pairs, for purposes of illustration. As shown in FIG. 7, the method 700 includes first collecting sample data from the CGM over a time period $[t_i, t_f]$ per step 702. Multiple reference blood glucose samples ($BG_{ref}$) relating to the same time(s) $[t_i, t_f]$ are also collected per step 704.

Next, CGM-generated samples ($CG_{cal}$) matching the $BG_{ref}$ samples based on a specified criterion (e.g., time and/or CGM measurements rate-of-change) are selected to form a set of matched data ($D_{BGref,CGref}$) per step 706.

A corrective regression or analytical scheme ($T_r$) (e.g. Decision Tree, Random Forest, linear regression, etc.) is next defined per step 708, and one or more predictors or feature vectors ($f_v$) are derived from CGM sensor data and/or ancillary sensors (e.g., fingerstick meters, thermistors, accelerometers, etc.) per step 710.

Predictor variables ($f_v$) for the set of matched data $D_{BGref,CGref}$ are then computed per step 712. These vectors are used within the regression or other analytical model framework to predict respective systematic errors. The corrective regression model ($T_r$) is then "trained" using the computed predictors ($f_v$) and the expected/true response values for blood glucose ($BG_{ref}$) per step 714.

The trained regression model ($T_r$) is then used in step 716 to estimate (in real-time) the error in CGM-reported blood glucose values by processing (then) current new values of the predictor variables ($f_v$) and the estimated error is used in real-time to correct the CGM-reported blood glucose for the effect of such errors (step 718).

Exhibit I hereto contains exemplary computer code implementing one or more aspects of the foregoing methodologies.

Population-Based Sensor Detection Models

In some embodiments, the foregoing training mode operation of the sensor system can be carried out in an experimental or analytical setting on a population (such as e.g., a statistically significant group of test subjects) to build multiple "user-type" sensor operational models, which can inter alia, be later applied to other users with similar characteristics to determine $BA_{s\_error}$. In one such embodiment, user characteristics of the test subject(s) are identified, and each of the test subjects is implanted with a sensor (e.g., pursuant to their normal implantation schedule or needs), and the sensor operated in the training mode (discussed supra). A sensor operational model is then generated for each test subject (whether via onboard processing logic of the implanted sensor, off-board processing via the receiver 400, 450, the parent platform 600, or cloud-based entity such as a server maintained by a health care administrator or even the manufacturer of the sensor, or combinations of the foregoing), and the sensor operational model correlated to the user characteristics, in order to generate one or more population-based operational models or "user-type" operational models.

After such model development, characteristics of other users (i.e., non-test subject users, such as new patients) can be identified, and a specific population-based operational model can be implemented based on the identified characteristics within the implanted sensor system, without the need for operation of the implanted sensor in the training mode (or rather a confirmatory training process). For example, it may be found that persons of a certain gender, age, race or ethnicity, physiologic profile—which may include the presence or absence of certain genetic markers, blood constituents (e.g., proteins, antibodies, antigens, etc.), BMI, or other parameter, exhibit certain types of systematic or other error sources relative to the BG measurement, with a high degree of statistical confidence. This correlation can be used in picking an operational model for a user falling within such class prior to or in place of user-specific operational models.

Moreover, the efficacy or accuracy of such population-based correlations can be assessed based on in vivo data obtained from that user. For example, the implanted sensor can be used to gather data from that particular individual (e.g., according to the methods of FIGS. 5-7 above) and development of a user-specific model, which can then be compared to the population-based model to identify variations therebetween. If the user-specific sensor models developed for numerous individual users show significant statistical divergence or variation from the relevant population-based model(s) selected for that user, then the strength of the statistical correlation or confidence in the population-based models is necessarily low, and their structure (e.g., in terms of errors modeled) and/or selection criteria may need further refinement. In a simple example, assessments of the divergence of the error corrections or corrected BG values produced by the user-specific sensor model could be utilized to de-select a population-based sensor model for a specific user.

Hence, in one approach ("evaluation mode"), the user-specific (training mode derived) sensor operational model can be run in parallel with the pre-designated population-based model on the same in vivo user data to generate corrected BG level outputs for each; these can then be compared to e.g., an external calibration data source or other "gold standard" for the actual BG level in that user at that time, to assess model performance.

Likewise, the sensor system may be programmed to utilize the population-based model (thereby ostensibly obviating training) until one or more indicia of divergence are seen; e.g., where the population model begins to diverge significantly in magnitude, or at a rate greater than a prescribed value, based on periodic external calibration. At such point, the system (e.g., sensor 200) may automatically invoke implementation of "training" via the methodologies described above, and replacement or augmentation of the population-based sensor model with the indigenously developed user-specific model, for subsequent operation within that particular user.

In some examples, the group of test subjects are a selected group of volunteers. In other examples, the group of test subjects can be existing users from which data are collected for generation of population-based models.

Figure 8:
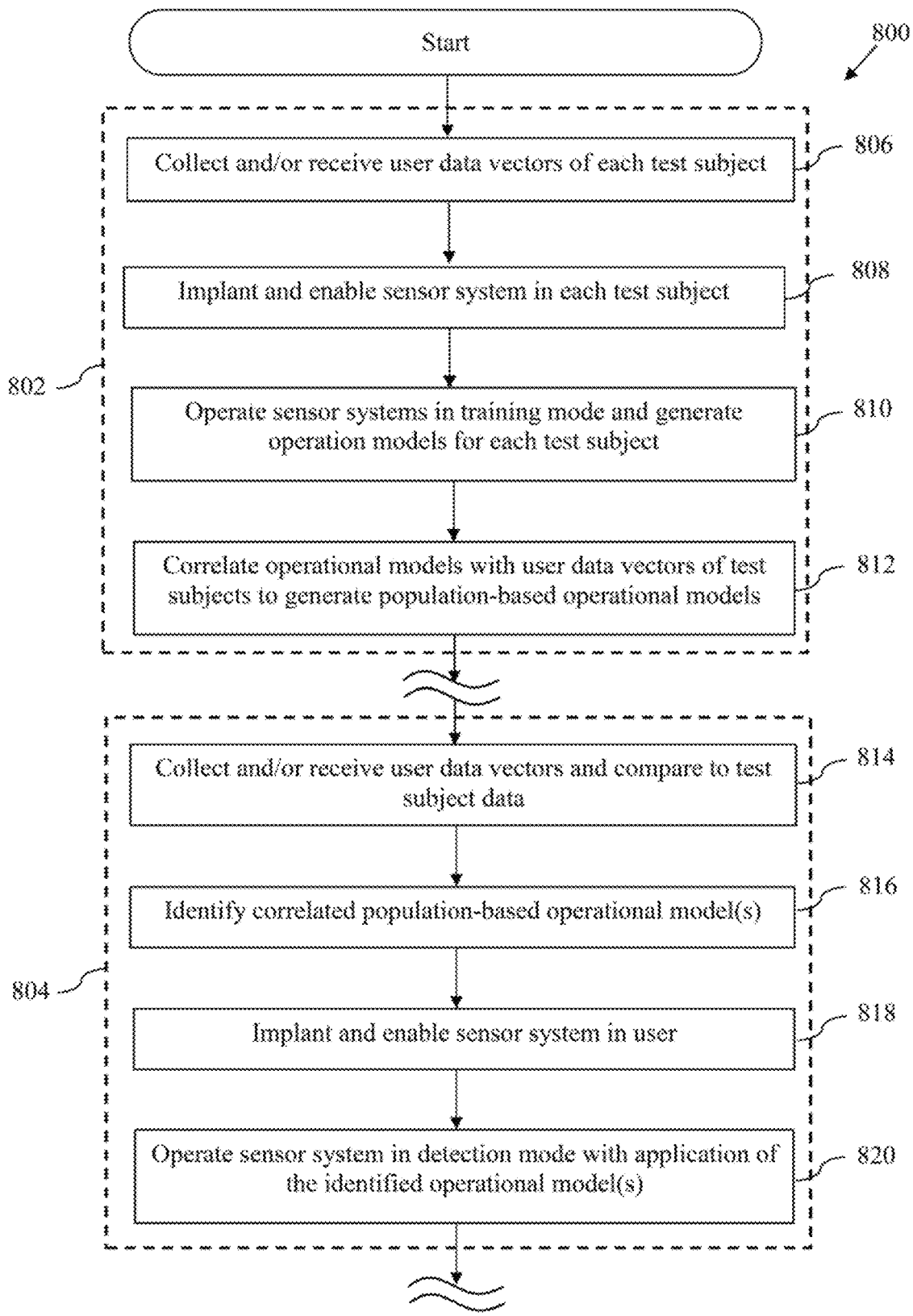
FIG. 8 is a logical flow diagram illustrating another exemplary embodiment of a population-based method of operating the implantable sensor system for blood analyte measurement according to the present disclosure.
Figure 9:
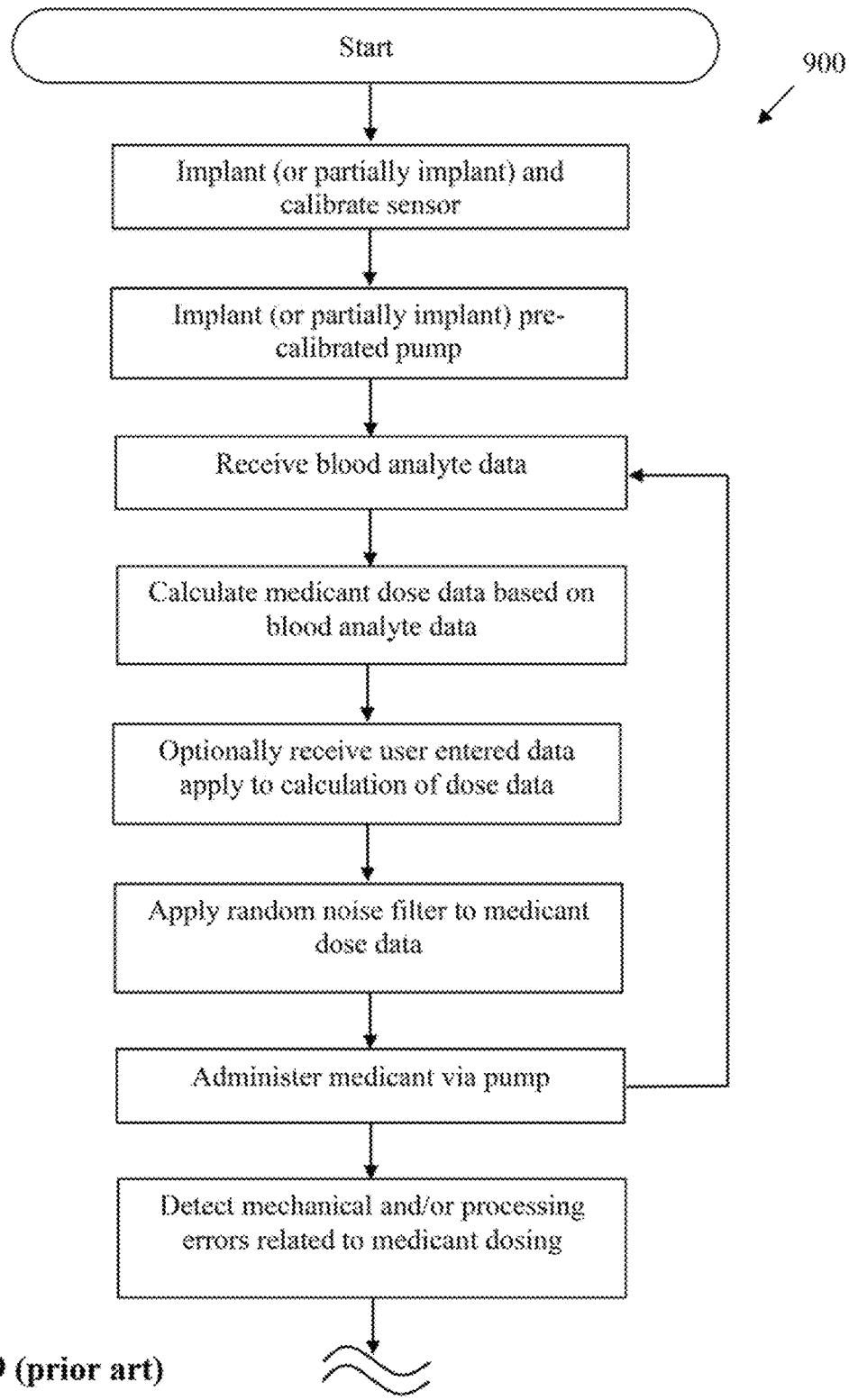
FIG. 9 is a logical flow diagram illustrating a typical generalized prior art methodology for operation of a conventional partially or fully implantable pump system.

One exemplary implementation of a method 800 for generation and application of population-based sensor operational models is shown and described in a logical flow diagram depicted in FIG. 8. The method 800 generally (ii) includes an analytical or experimental phase 802 for generation of the population-based sensor operational model(s), and (ii) a utilization phase 804 for application one of the population-based sensor operational models during normal (or trial) use of the sensor system.

As illustrated in FIG. 8, the analytical or experimental phase 802 begins with collecting (e.g., derived from measurable information) or receiving (e.g., manually input test subject information) a series of user data vectors such as e.g., gender, height, weight, diet, exercise regimen, disease presentation, medications, blood pressure, active pulse rate, resting pulse rate, average body temperature, geographic region of residence, etc. from each member in a group of test subjects (step 806). In some examples, the selected user data vectors are combined into an input vector and/or organized into a matrix of user data vectors.

Per step 808, each of the test subjects is implanted with a sensor 200. After the sensor is implanted and enabled, the sensor system is operated in a training mode (such as e.g., the sensor training mode operation shown in FIGS. 5-5C, discussed supra) in order to generate a sensor operational model for each test subject (step 810). After download of the model data from the sensor system (e.g., via wireless transmission from the implanted sensor 200, or the receiver 400, 450), the various sensor operational models are then correlated with the respective previously collected and/or received user data vectors to identify user characteristics that are associated with each operational model, thereby generating a set of population-based sensor operational models (step 812). Such correlation may be statistical in nature (e.g., according to mean error, standard deviation/variance, and/or other statistical criteria as determined by algorithmic analysis by a computerized system), or even heuristic (e.g., by a human utilizing inductive reasoning or other cognitive tools to identify patterns in both the models and the data sets).

Subsequently, the experimentally determined population-based sensor operational models can be utilized for operation of an implanted sensor system with non-test subject users (phase 804, discussed supra). Specifically, in the exemplary method 800, user data vectors are collected and/or received from a user (i.e., a non-test subject user, such as a new patient), and then compared to the test subject data vectors per step 814 that are correlated with the particular population-based model(s). It will be appreciated that the series of user data vectors for the non-test subject user are substantially similar to those collected and/or received from the test subjects during the experimental phase 802 such that a "best" match comparison can be performed. Further, in some examples, the selected user data vectors may be combined into an input vector and/or organized into a matrix of user data vectors in a substantially similar manner as is carried out for the test subject user data vectors in order to carry out the comparison.

Per step 816, a correlated population-based sensor operational model is identified based at least on the input vectors for the user. The user is implanted with the sensor and the sensor system is enabled per step 818. The sensor system is then operated in the detection mode (such as e.g., the training mode operation shown in FIGS. 5A-5C, discussed supra) utilizing the population-based operational model to correct for $BA_{s\_error}$ (step 820). Thus, in this embodiment, the sensor system is operated in the detection mode (with application of the experimentally determined population-based operational model) directly after implantation without prior or initial operation in a training mode.

Although not specifically shown in method 800 of FIG. 8, in alternate embodiments, the method can further include determining if one or more re-training criteria are met (substantially similar to method 544 shown in FIG. 5G). In this embodiment, the population-based sensor operational model can be updated or replaced as necessary or as desired by the user. Sensor re-training criteria can include those determined from population characteristics (e.g. retraining at time intervals found to provide optimum performance in the population) or other thresholds and variables specific to the individual user, as described supra.

Exemplary Implantable Delivery Devices

Referring now to FIGS. 10A-10F, various exemplary embodiments of implantable solute or medicant delivery device (e.g., pump) apparatus useful with various aspects of the present disclosure are shown and described.

Figure 10A:
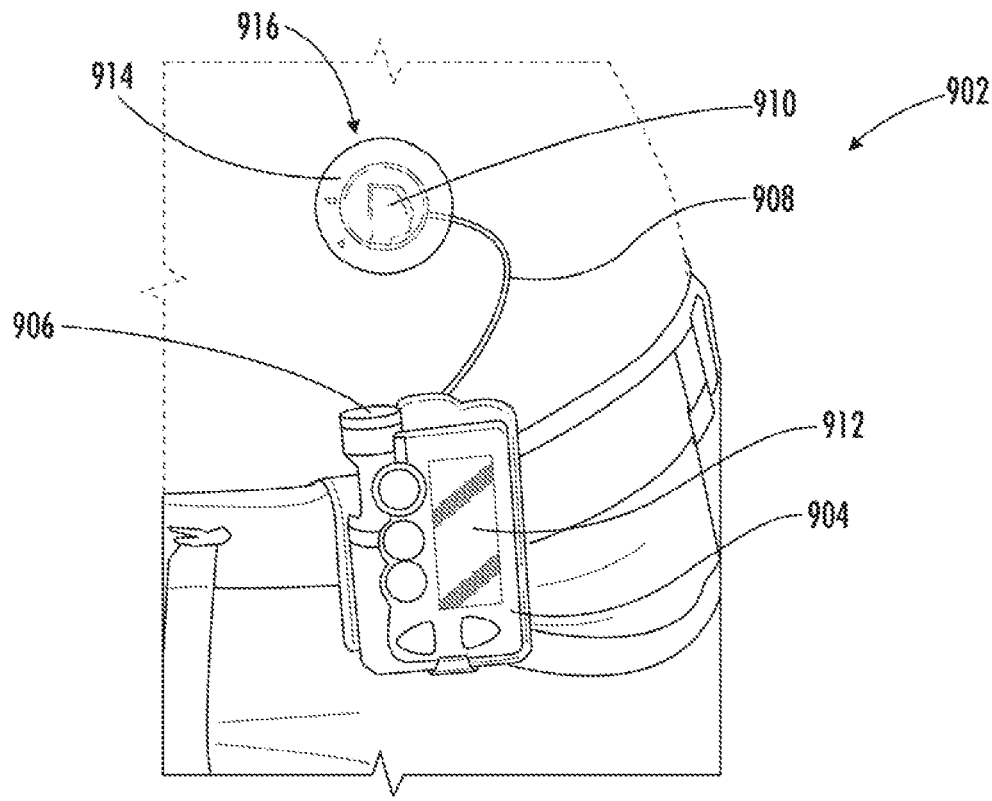
FIG. 10A is a front elevation view of a human torso showing a first exemplary prior art transcutaneous (partially implanted) pump apparatus worn by the user.

As shown in FIG. 10A, one exemplary partially implantable pump system comprises a tethered transcutaneous pump system 902, such as that described in U.S. Pat. Nos. 7,819,843 and 7,267,665, previously incorporated herein. The pump system 902 includes a controller 904, a port 906, a catheter 908, and an insertion set 910. The controller 904 houses a receiver, a medicant reservoir, various sensors (e.g., one or more reservoir sensors, flow meters, etc.), one or more pump actuators, a power source (i.e., battery), and a processing apparatus. A user interface 912 is disposed at an outer surface of the controller. In some embodiments, the pump can include additional sensors, such as an accelerometer, a temperature sensor, heart rate monitor, pressure sensor, etc. disposed at either of the controller or the insertion set 910.

The controller 904 is coupled via its port 906 to one end of the catheter 908 such that the catheter is fluidly coupled to the reservoir housed within the controller. An opposing end of the catheter 908 is fluidly coupled to the insertion set 910. The insertion set includes an adhesive portion 914 which is adherable to the user's skin proximate to (i.e., surrounding) an insertion site 916, as well as a cannula for transcutaneous insertion under the user's skin at the insertion site.

Figure 10B:
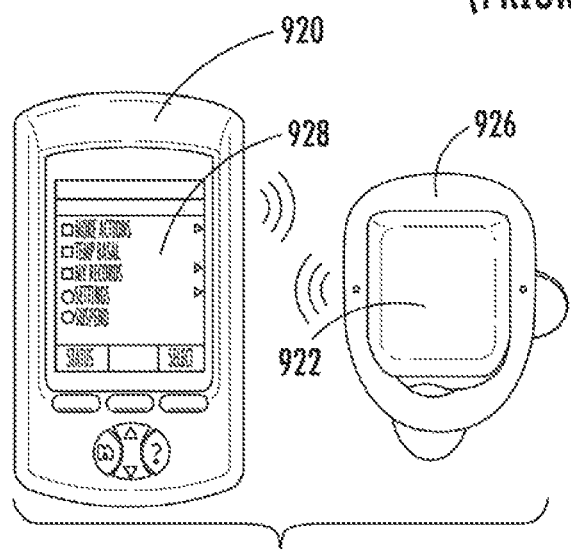
FIGS. 10B and 10C are front elevation and composite views, respectively, of another prior art transcutaneous (partially implanted) pump apparatus and associated receiver, and as worn by the user.
Figure 10C:
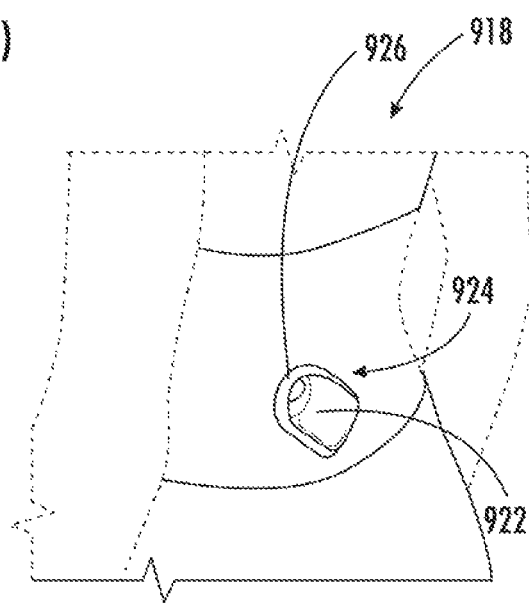

FIGS. 10B and 10C depict another exemplary partially implantable pump system, which comprises a patch transcutaneous pump system 918, such as that described in U.S. Pat. No. 6,960,192, previously incorporated herein. The pump system 918 includes a controller 920 in wireless communication with the adherable pump housing 922. The adherable pump housing 922 contains a receiver, a medicant reservoir, various sensors (e.g., one or more reservoir sensors, flow meters, etc.), one or more pump actuators, a power source (i.e., battery); the housing is attachable to the user's skin at an insertion site 924 via an adhesive portion 926. Within the adherable pump housing 922, the reservoir is directly fluidly coupled to a cannula for transcutaneous insertion under the user's skin at the insertion site 924. In some embodiments, the pump can include additional sensors, such as an accelerometer, a temperature sensor, heart rate monitor, pressure sensor, etc. disposed at the adherable housing. The controller 920 includes a processor apparatus, one or more data communication interfaces and/or receivers, and a user interface 928 disposed at an outer surface of the controller.

Figure 10D:
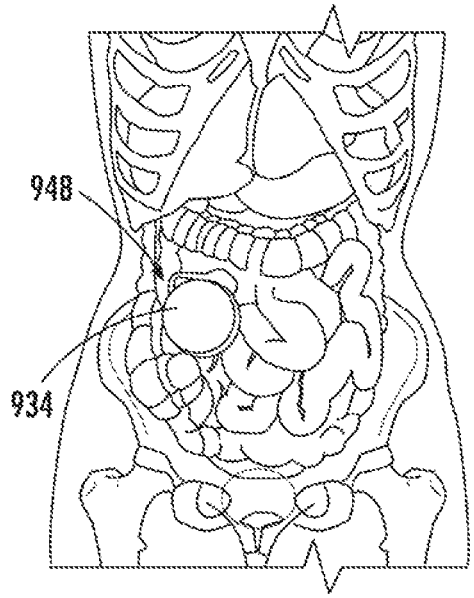
FIGS. 10D and 10E are front and side elevation views, respectively, of one example of a prior art fully implantable pump apparatus and associated remote unit, as implanted in a user.
Figure 10E:
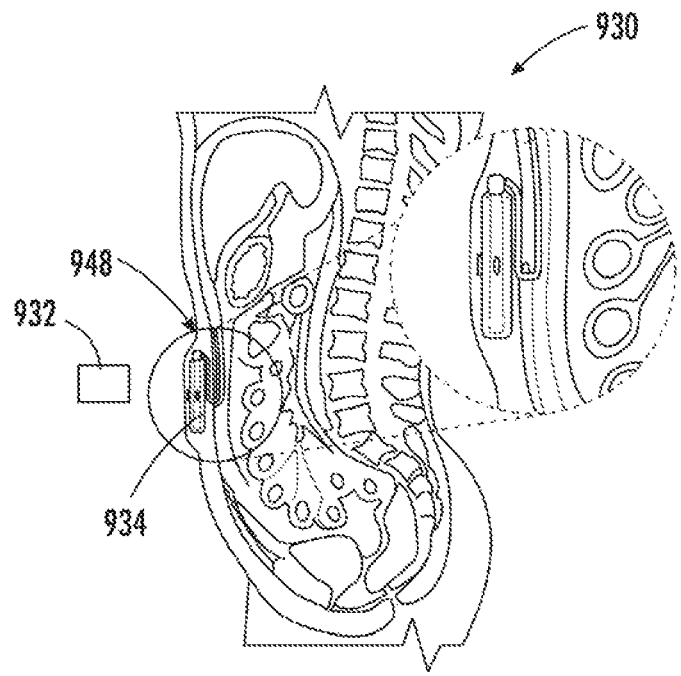
Figure 10F:
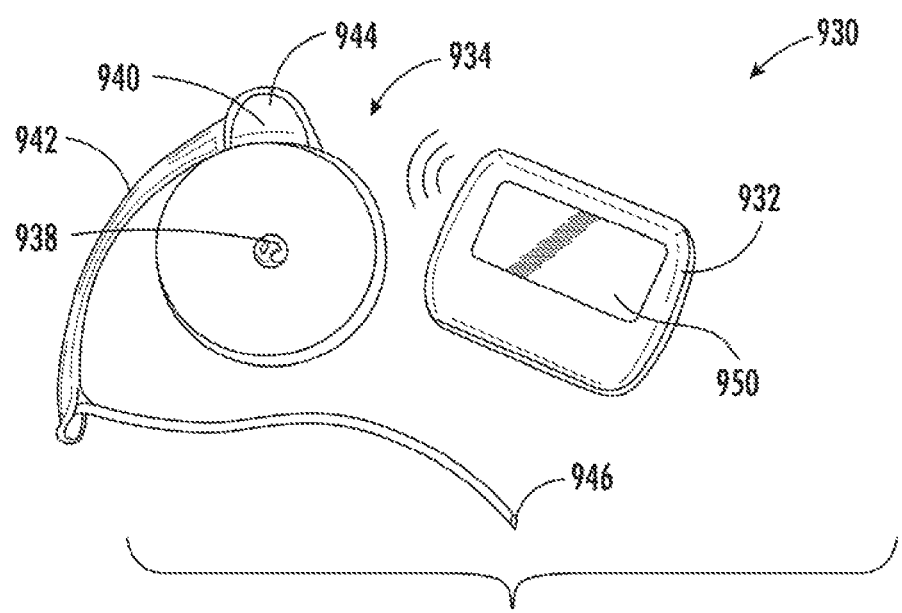
FIG. 10F is a front elevation view of the exemplary fully implantable pump apparatus and associated remote unit of FIGS. 10D and 10E, showing the pump in a non-implanted state.

FIGS. 10D-10F illustrate one exemplary fully implantable pump system 930, such as that described in U.S. Pat. Nos. 4,871,351 and 6,974,437, previously incorporated herein. The pump system 930 includes a (non-implantable) controller 932 in wireless communication with an implantable pump 934. The implanted pump 934 includes a biocompatible housing 936 which contains a receiver, a medicant reservoir, various sensors (e.g., one or more reservoir sensors, flow meters, etc.), and one or more pump actuators, a power source (i.e., battery). A reservoir refill port 938 is disposed on an outer surface of the housing and is configured to receive a needle (which is inserted through the user's skin after implantation of the implantable pump) for filling of the medicant reservoir. The implanted pump 934 further includes a catheter attachment site 940 which fluidly couples a catheter 942 to the reservoir. A catheter rinse port 944 is disposed within the catheter attachment site 940 and is configured to receive a needle (which is inserted through the user's skin after implantation of the implantable pump) for flushing of the catheter to remove partial occlusions due to e.g., precipitation of medicant after implantation. A free open end 946 of the catheter is configured to release medicant into the user's body proximate to an implantation site 948. As can been seen in FIGS. 10D and 10E, in the present example, the implantation site is within the intraperitoneal cavity of the user. In some embodiments, the pump can include additional sensors, such as an accelerometer, a temperature sensor, heart rate monitor, pressure sensor, etc. The controller 932 includes a processor apparatus, one or more data communication interfaces and/or receivers, and a user interface 950 disposed at an outer surface of the controller.

Figure 10G:
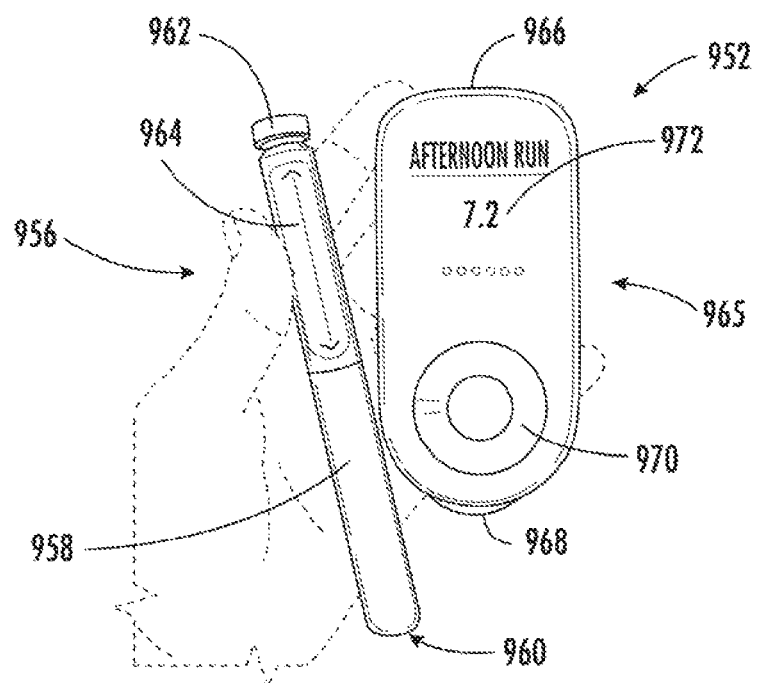
FIG. 10G is a perspective view of a first exemplary prior art non-implantable pump apparatus.
Figure 10H:
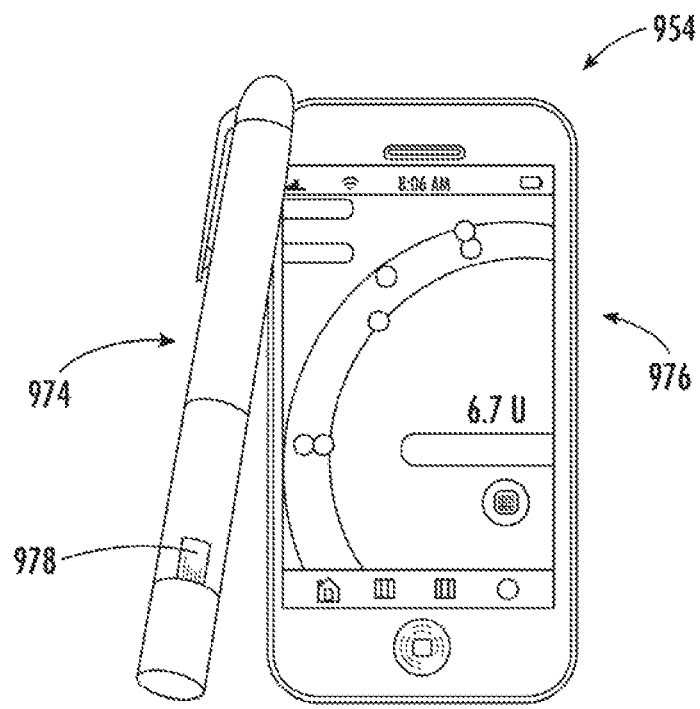
FIG. 10H is a perspective view of a second exemplary prior art non-implantable pump apparatus.

FIGS. 10G and 10H illustrate exemplary non-implantable pump systems 952, 954, similar to those described in U.S. Patent Publication Nos. 2016/0012205 and 2017/0068799, previously incorporated herein. Specifically, non-implantable pump system 952 (shown in FIG. 10G) includes a computerized injection tool 956 (i.e., a "smart" pen) having a housing 958. Although specifically not shown, the housing 958, in one embodiment, contains a medicant reservoir, processor(s), wireless receiver/transmitter, power source, sensor(s), and a dispensing mechanism (for subcutaneous injection of medicant). The dispensing mechanism is disposed at an injection tip 960, while an actuation mechanism (to receive user input) 962 is disposed at an opposing end of the injection tool 956. The injection tool 956 further includes a digital user interface 964 for display of information (e.g., time and current dosage units) and notifications to the user. Additionally, the digital user interface may receive input from the user.

The injection tool 956 is in wireless data communication with a controller 965 for e.g., display of current and historical blood analyte data and calculation of dosage data. The controller 965 includes a housing 966 with contains a finger-sticking blood analyte detection mechanism (not shown) having an external port 968 disposed at an outer surface of the housing. The housing additionally contains a receiver/transmitter, power source, processor(s), and sensor(s) (not shown). A user input mechanism 970 and digital user interface 972 are disposed on an outer surface of the housing. In some examples, the controller automatically determines/sets a volume of medicant to be delivered via the user-initiated injection operation. Additionally or alternatively, the controller may calculate and provide dosage data to the user (e.g., via the digital user interface of the controller), and the dose data can be manually input by the user (e.g., via the digital user interface of the injection tool).

The non-implantable pump system 954 (shown in FIG. 10H includes many of the features described above with respect to the non-implantable pump system 952. Differently, a computerized injection tool 974 (i.e., a "smart" pen) is in data communication with a user's mobile device 976 for e.g., display of current and historical blood analyte data and calculation of dosage data. Further, the injection tool 974 includes a manual (e.g., dial-type) dosage controller which enables a user to set a number of medicant units delivered via the injection.

Although only five exemplary configurations or types of partially implantable, fully implantable, and non-implantable pumps are shown, it is appreciated that the methods and apparatus described herein may be used with other types of medicant or solute delivery devices or mechanisms (pumps, non-pump delivery, manual, or otherwise), whether fully implantable, partly implantable, or non-implantable, having similar or different features.

For example, a delivery pump might include additional reservoirs for delivery of one or more other substances or medicants (e.g., other glucose-regulating medicants such as glucagon, pain-controlling medicants, spasticity-controlling medicants, blood pressure-modulating medicants, antibiotic or antifungal medicants, and medicants belonging to the general classes of peptide and small molecule substances, etc.), a mechanism that regulates medicant absorption (e.g., a localized heating device, an ultrasonic energy delivery device, an electric (iontophoretic) current delivery device, etc.), or yet other features, the foregoing being merely illustrative of the broader concepts.

Sensor and Delivery System Architectures—

As described elsewhere herein, exemplary embodiments of the present disclosure utilize machine learning algorithms to, inter alia, compensate for systemic errors, whether well modeled, or unmodeled, affecting medicant delivery apparatus, such as a partially implanted, fully implanted, or non-implanted pump apparatus (or even non-pump delivery mechanisms), where the delivered medicant is intended to affect the state of a measurable physiologic parameter (e.g., blood analyte level), and where the algorithm utilizes measurement data regarding the physiologic parameter determined from an implanted sensor apparatus and/or other measurement means. Notably, such algorithms may be implemented in computerized logic (software, firmware, or even hardware) that is resident in any number of different locations within the system, including: (i) within the implanted delivery (e.g., pump) apparatus itself; (ii) "off-board" the delivery apparatus, such as in an external receiver apparatus (examples of which are described below, as well as those receiver apparatus discussed with reference above with reference to the sensor system); (iii) off-board, in a data-connected "cloud" entity; (iv) off-board in a data-connected sensor apparatus; and/or (v) combinations of the foregoing (e.g., in a distributed computing architecture). Accordingly, the following embodiments are merely examples of such types of delivery system architectures, and the various aspects of the present disclosure are in no way limited thereto.

Figure 11A:
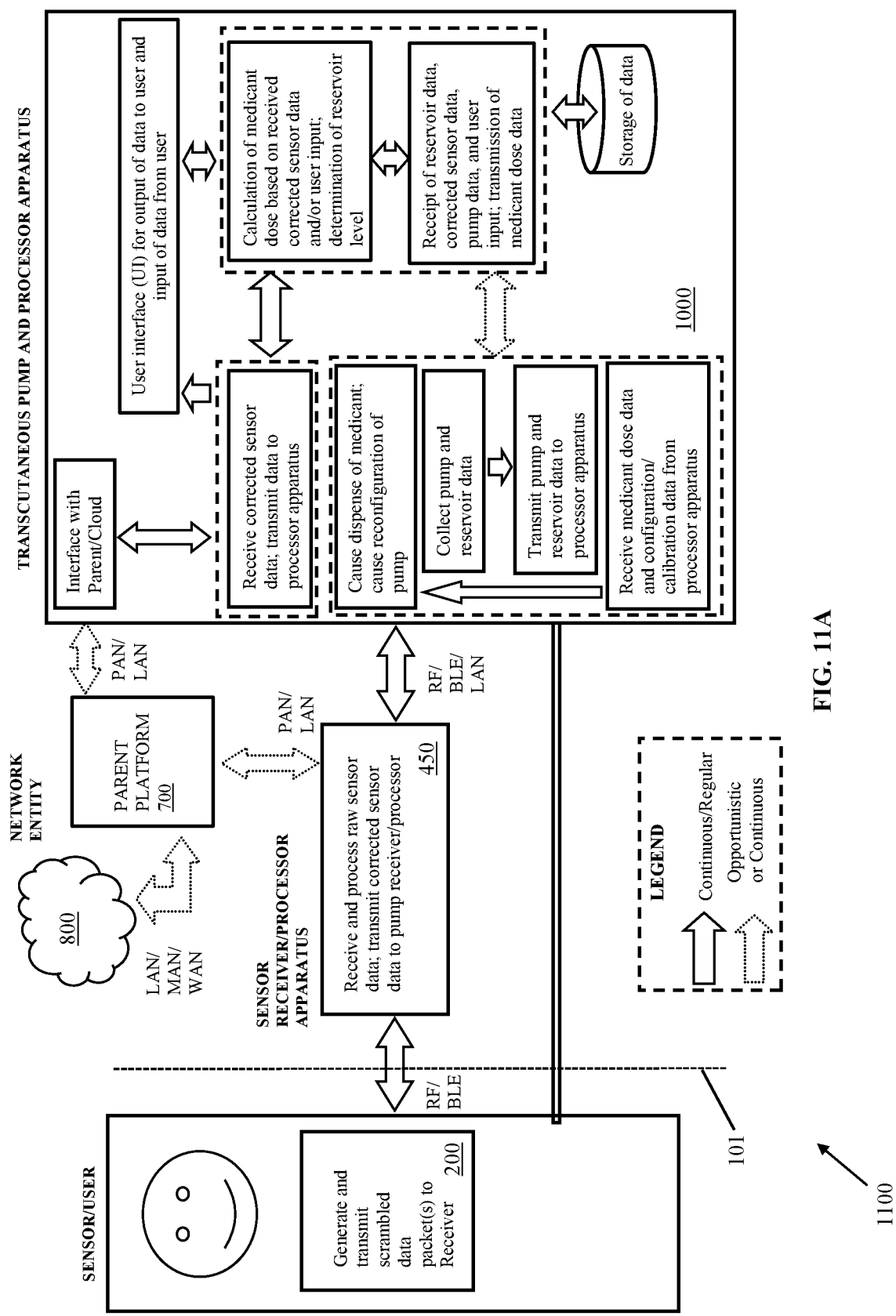
FIG. 11A is a logical block diagram illustrating one embodiment of a system architecture for, inter alia, monitoring blood analyte levels within a user and controlling a delivery device, useful with various aspects of the present disclosure.

Referring now to FIG. 11A, one embodiment of a system architecture for, inter alia, monitoring blood analyte levels and automatically administering medicant within a user, useful with the machine learning-based methods and apparatus of present disclosure, is described in detail. As depicted in FIG. 11A, the system architecture 1100 comprises a sensor apparatus 200 (e.g., that of FIGS. 2-2C discussed above, or yet other types of sensor devices) associated with a user via subcutaneous implantation, a sensor receiver/processor apparatus 450 in continuous data communication with the sensor apparatus 200, a transcutaneous pump and processor apparatus 1000 in continuous data communication with the sensor receiver/processor apparatus 450 and associated with the user via transcutaneous implantation of at least a portion of the apparatus (e.g., transcutaneous insertion of an insertion set or a cannula through the tissue boundary 101), and a network entity 800.

The foregoing pump system also includes in some exemplary embodiments a wireless radio frequency (RF) transceiver; see discussion of FIGS. 12A-12F below. The transceiver may be configured to receive (e.g., from an external receiver 450, or directly from the implanted sensor 200), modulated RF signals. In one variant, the RF transceiver comprises a PAN device (e.g., Bluetooth/BLE, Zigbee (IEEE 802.15.4) or Z-wave device), although it may also be configured for other protocols such as IEEE 802.11. Moreover, in some embodiments, the transceiver can also communicate wirelessly with e.g., a properly equipped consumer electronic device such as a smartphone or tablet computer, as well as network entities (e.g., WLAN AP or the BT master node). The pump apparatus may also be configured to transmit signals to (whether in conjunction with the aforementioned external receiver, or in the alternative, a partially or fully implanted or in vivo receiving device, such as the foregoing sensor apparatus 200 described supra), an embedded "logging" device, or other device.

It is also appreciated that other forms of wireless communication may be used for such applications, including for example inductive (electromagnetic induction) based systems, those based on capacitance or electric fields, or even optical (e.g., infrared) systems where a sufficiently clear path of transmission and reception exists, such as two devices in immediately adjacent disposition, or ultrasonic systems where the two devices are sufficiently close and connected by sound-conductive media such as body tissues or fluids, or a purposely implanted component. Hence, the following embodiments are merely illustrative.

The sensor apparatus 200 communicates (via e.g., narrowband RF such as at 433 MHz, or via PAN such as BLE, 802.15.4 or Z-Wave) with the receiver/processor apparatus 450 via a wireless interface (described in detail supra) through the user's tissue boundary 101. In the system architecture 1100, the pump apparatus and pump receiver/processor apparatus 1000 comprise an integrated device (such as e.g., the exemplary pump system shown in FIG. 10A), and thus a wireless interface of the integrated device is used primarily for communication via narrowband, RF, PAN (e.g., BLE), WLAN, or other communication modality with the sensor receiver/processor 450 for receipt of blood analyte data.

Each of the sensor receiver/processor apparatus 450 and the pump and processor apparatus 1000 may also, if desired, opportunistically or continuously communicate with one or more network entities 800 (such as for cloud data storage, analysis, convenience of access at other locations/synchronization with other user platforms, etc.) via a parent platform 700 of the type previously described herein (e.g., via a PAN or LAN connection to the parent device 700, the latter which interfaces with a LAN/WLAN, WAN, MAN, or other communication modality, or directly with the network entities via the aforementioned protocols.

Figure 11B:
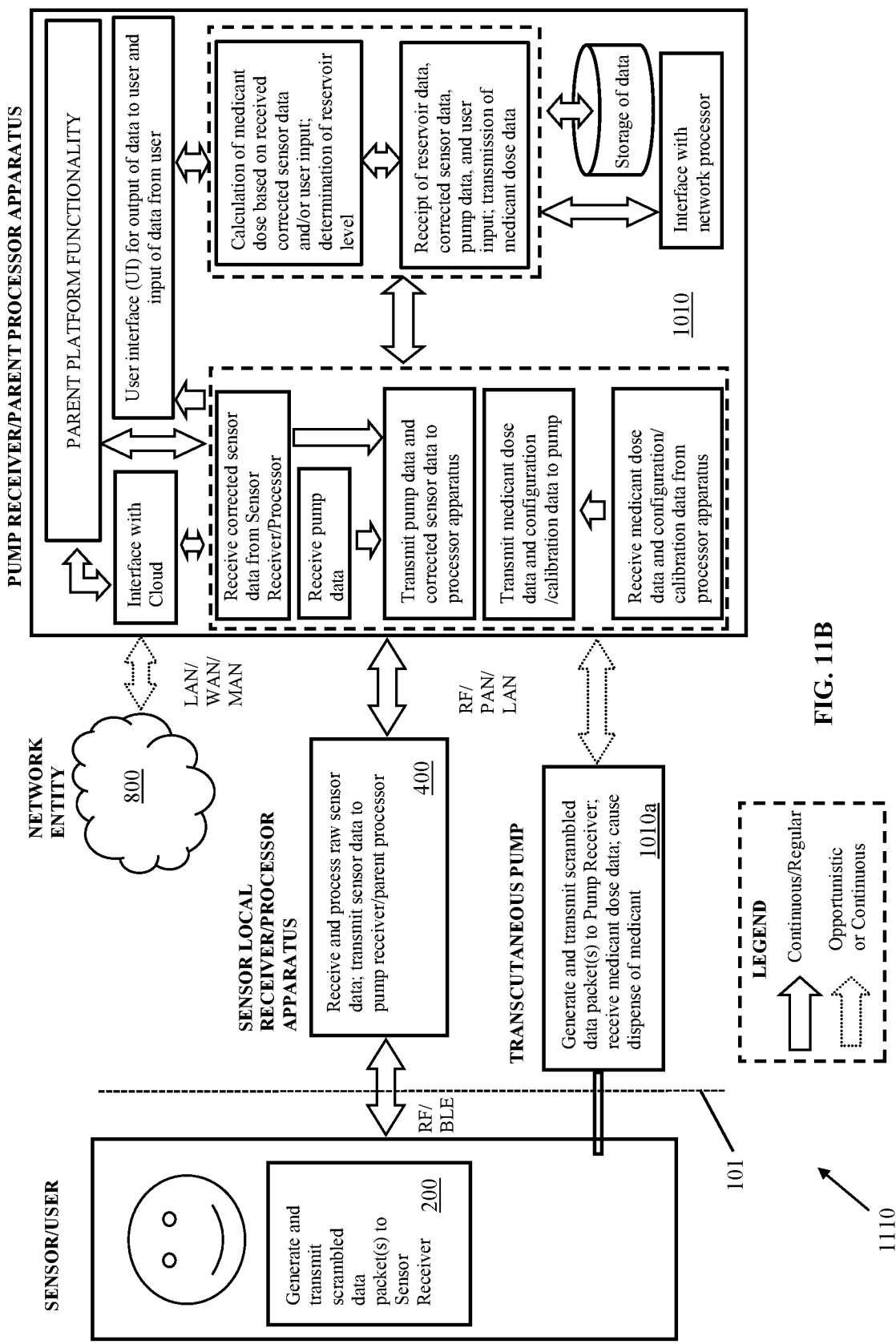
FIG. 11B is a logical block diagram illustrating a second embodiment of a system architecture for, inter alia, monitoring blood analyte levels within a user and controlling a delivery device, useful with various aspects of the present disclosure.

As shown in FIG. 11B, another exemplary system architecture 1110 comprises a sensor apparatus 200 (e.g., that of FIG. 2 discussed above, or yet other types of sensor devices) associated with a user via subcutaneous implantation, a sensor receiver/processor apparatus 450 in continuous data communication with the sensor apparatus 200, a transcutaneous pump apparatus 1010a associated with the user via transcutaneous implantation of at least a portion of the pump apparatus (e.g., transcutaneous insertion of a cannula), a pump receiver/processor apparatus 1010 in continuous data communication with the sensor receiver/processor apparatus 450 and in continuous or opportunistic data communication with the pump apparatus 1010a, and a network entity 800. In an alternate embodiment, the pump apparatus 1010a may additionally be in continuous or opportunistic data communication with the sensor receiver/processor apparatus 450.

In the exemplary system architecture shown in FIG. 11B, the transcutaneous pump apparatus 1010a is a lower profile and/or adherable local pump apparatus attached directly to the user's skin (such as e.g., the exemplary pump shown in FIG. 10B), as compared to the pump apparatus 1000 shown in FIG. 11A. In some examples, the transcutaneous pump apparatus 1010a can include a user alert mechanism and/or minimal user interface (UI) such as, e.g., a substantially flat and flexible LED (e.g., graphene-based), AMOLED, or OTFT (organic thin-film transistor) display device, haptic mechanism (e.g., a vibration mechanism), auditory mechanism (e.g., speakers), and/or other user-signaling capabilities and mechanisms (e.g., indicator lights).

As indicated in FIG. 11B, the sensor apparatus 200 communicates (via e.g., narrowband RF or BLE) with the receiver/processor apparatus 450 via a wireless interface (described in detail supra) through the user's tissue boundary 101. In the system architecture 1110, the pump apparatus 1010a and the receiver/processor apparatus 1010 comprises a non-integrated device, and thus a wireless interface of the integrated device is used for (i) continuous communication via RF, PAN, WLAN, or other communication modality with the sensor receiver/processor 450 for receipt of blood analyte data, and (ii) continuous or opportunistic communication via RF, PAN, WLAN, or other communication modality with the transcutaneous pump apparatus 1010a for transmission of medicant dose data and receipt of pump data (e.g., data related to reservoir levels, pump firing, pump stroke volume, etc.).

Each of the receiver/processor apparatus 450 and the pump apparatus and the receiver/processor apparatus 1010 may also, if desired, opportunistically or continuously communicate with one or more network entities 800 via a LAN/WLAN, WAN, MAN, or other, such as for cloud data storage, analysis, convenience of access at other locations/synchronization with other user platforms, etc.

The illustrated embodiment of the pump receiver and processor apparatus 1010 of FIG. 11B also includes the functionality of the previously described parent platform 700 in an integrated fashion, such that the receiver/processor apparatus 1010 can perform all necessary signal processing indigenously, and communicate directly with any cloud entities (thereby obviating a separate apparatus).

Alternatively, the pump apparatus 1010a and the pump receiver/processor apparatus 1010 can be used in combination with a local receiver apparatus 400 and parent platform 700, discussed supra, for receipt of blood analyte data. For example, the pump apparatus 1010a and/or the pump receiver/processor apparatus 1010 can be in data communication with one or more of the local receiver apparatus or the parent platform for receipt of blood analyte data.

It will be appreciated that the system configuration shown in FIG. 11B is substantially similar to a system configuration for a non-implanted pump system, such as those described supra with reference to FIGS. 10E and 10F. For example, the pump apparatus 1010a can be configured for transient injection (via a user initiated medicant delivery operation) rather than partial implantation. In such an example, the pump apparatus and/or the pump/parent processor apparatus can be configured to alert the user when the delivery operation should be carried out. Further, the pump apparatus may receive dosage data (e.g., number of units, volume, etc.) from the pump/parent processor apparatus or the pump/parent processor apparatus can display dosage data which is then manually input into the pump apparatus by the user. To that end, such an example differs from the system shown in FIG. 11B, as, unlike the transcutaneous pump, the non-implantable pump apparatus is configured to receive signal-based and/or manual input from the user (i.e., actuation input and/or dosage data input).

Figure 11C:
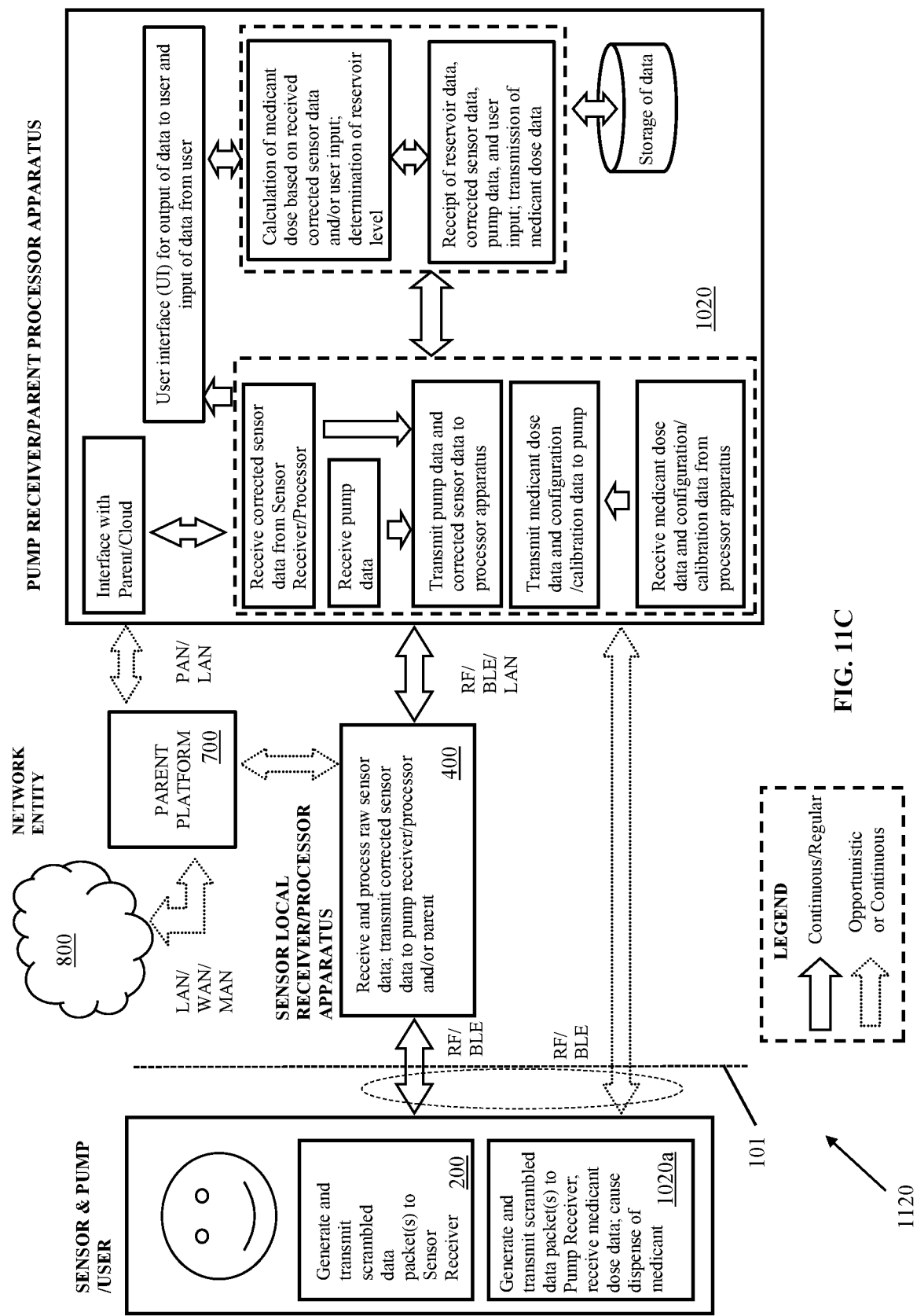
FIG. 11C is a logical block diagram illustrating a third embodiment of a system architecture for, inter alia, monitoring blood analyte levels within a user and controlling a delivery device, useful with various aspects of the present disclosure.

Turning now to FIG. 11C, yet another exemplary system architecture 1120 comprises a sensor apparatus 200 (e.g., that of FIG. 2 discussed above, or yet other types of sensor devices) associated with a user via subcutaneous implantation, a sensor receiver/processor apparatus 450 in continuous data communication with the sensor apparatus 200, a fully implanted pump apparatus 1020a associated with the user via subcutaneous implantation, a pump receiver/processor apparatus 1020 in continuous data communication with the sensor receiver/processor apparatus 450 and in continuous or opportunistic data communication with the fully implanted pump apparatus 1020*a*, and a network entity 800.

In the exemplary system architecture shown in FIG. 11C, the fully implanted pump apparatus 1020*a* is a subcutaneous pump apparatus implanted beneath the user's skin (such as e.g., the exemplary pump shown in FIGS. 10C and 10D). In some examples, the fully implanted pump apparatus 1020*a* can include a user alert mechanism such as e.g., a haptic mechanism (e.g., a vibration mechanism), an auditory mechanism (e.g., speakers), and/or other subcutaneous user-signaling capabilities and mechanisms (e.g., indicator lights).

Similar to the architectures shown in FIGS. 11A and 11B, the sensor apparatus 200 communicates (via e.g., narrowband RF or PAN such as BLE) with the local receiver/processor apparatus 400 via a wireless interface (described in detail supra) through the user's tissue boundary 101. In the system architecture 1120, the pump apparatus and receiver/processor apparatus 1020 comprises a non-integrated device, and thus a wireless interface of the sensor apparatus 200 is used for (i) continuous communication via RF, PAN, LAN, or other communication modality with the sensor local receiver/processor 400 for receipt of blood analyte data, and (ii) continuous or opportunistic communication with the fully implanted pump apparatus 1020*a* for transmission of medicant dose data and receipt of pump data (e.g., data related to reservoir levels, pump firing, pump stroke volume, etc.).

Each of the local receiver/processor apparatus 400 and the pump receiver/processor apparatus 1020 may also, if desired, opportunistically or continuously communicate with one or more network entities 800 via the parent platform 700, such as for cloud data storage, analysis, convenience of access at other locations/synchronization with other user platforms, etc.

In yet another exemplary system architecture 1130 (shown in FIG. 11D), the system architecture comprises a sensor apparatus 200 (e.g., that of FIG. 2 discussed above, or yet other types of sensor devices) associated with a user via subcutaneous implantation, a transcutaneous pump apparatus 1030*a* associated with the user via transcutaneous implantation, an integrated sensor and pump receiver/parent processor apparatus 1030 in continuous data communication with the sensor apparatus 200 and in continuous or opportunistic data communication with the pump apparatus 1030*a*, and a network entity 800.

Figure 11D:
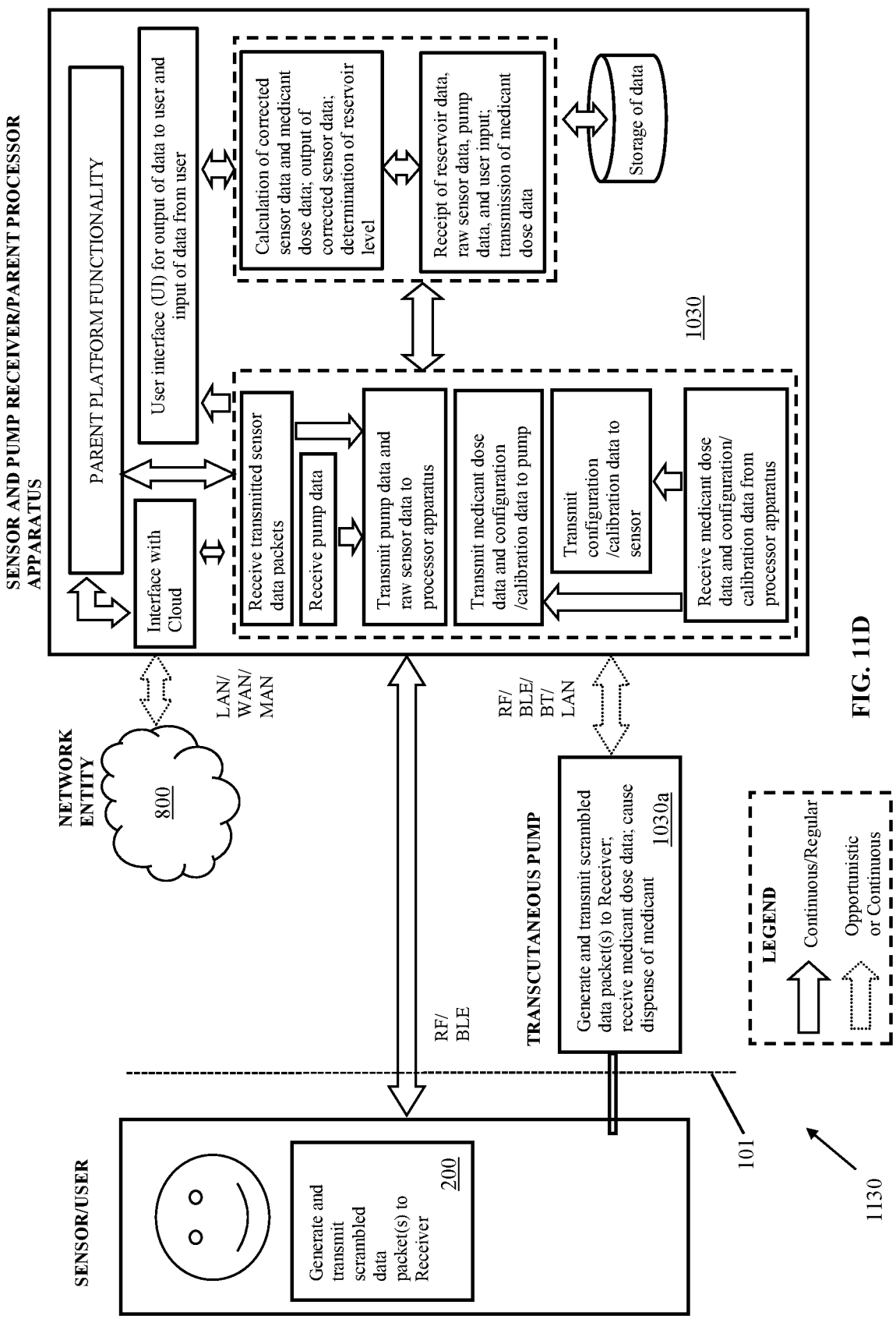
FIG. 11D is a logical block diagram illustrating a fourth embodiment of a system architecture for, inter alia, monitoring blood analyte levels within a user and controlling a delivery device, useful with various aspects of the present disclosure.

In the exemplary system architecture shown in FIG. 11D, the implanted pump apparatus 1030*a* is a low-profile transcutaneous local pump apparatus (such as e.g., the exemplary pump system shown in FIG. 10B), as compared to the pump apparatus 1000 shown in FIG. 11A. In some examples, the transcutaneous pump apparatus 1030*a* can include a user alert mechanism and/or minimal user interface (UI) such as those previously described herein.

Similar to the architectures shown in FIGS. 11A-11C, the sensor apparatus 200 in the architecture 1130 of FIG. 11D communicates (via e.g., narrowband RF or PAN) with the receiver/parent processor apparatus 1030 directly via a wireless interface (described in detail supra) through the user's tissue boundary 101. In the system architecture 1130, the pump apparatus 1030*a* and the sensor and pump receiver/parent processor apparatus 1030 comprises non-integrated pump and controller devices (in contrast with the integrated pump/controller device 1000 of FIG. 11A); however the receiver/processor apparatus is an integrated controlling device for each of the implanted sensor and the partially implanted pump. Thus, one or more wireless interfaces of the integrated receiver/processor apparatus 1130 is/are used for (i) continuous communication with the sensor 200 for receipt of blood analyte data, and (ii) continuous or opportunistic communication with the transcutaneous implanted pump apparatus 1030*a* for transmission of medicant dose data and receipt of pump data (e.g., data related to reservoir levels, pump firing, pump stroke volume, etc.).

The sensor and pump receiver/processor apparatus 1030 may also, if desired, opportunistically or continuously communicate with one or more network entities 800 via a LAN/WLAN, WAN. MAN, or other communication modality, such as for cloud data storage, analysis, convenience of access at other locations/synchronization with other user platforms, etc.

It will be appreciated that the integrated sensor and pump receiver/parent processor apparatus 1030 can alternatively be used in combination with a non-implantable pump apparatus, such as those described supra with reference to FIGS. 10E and 10F. For example, the pump apparatus 1030*a* can be configured for transient injection (via a user initiated medicant delivery operation) rather than partial implantation.

Figure 11E:
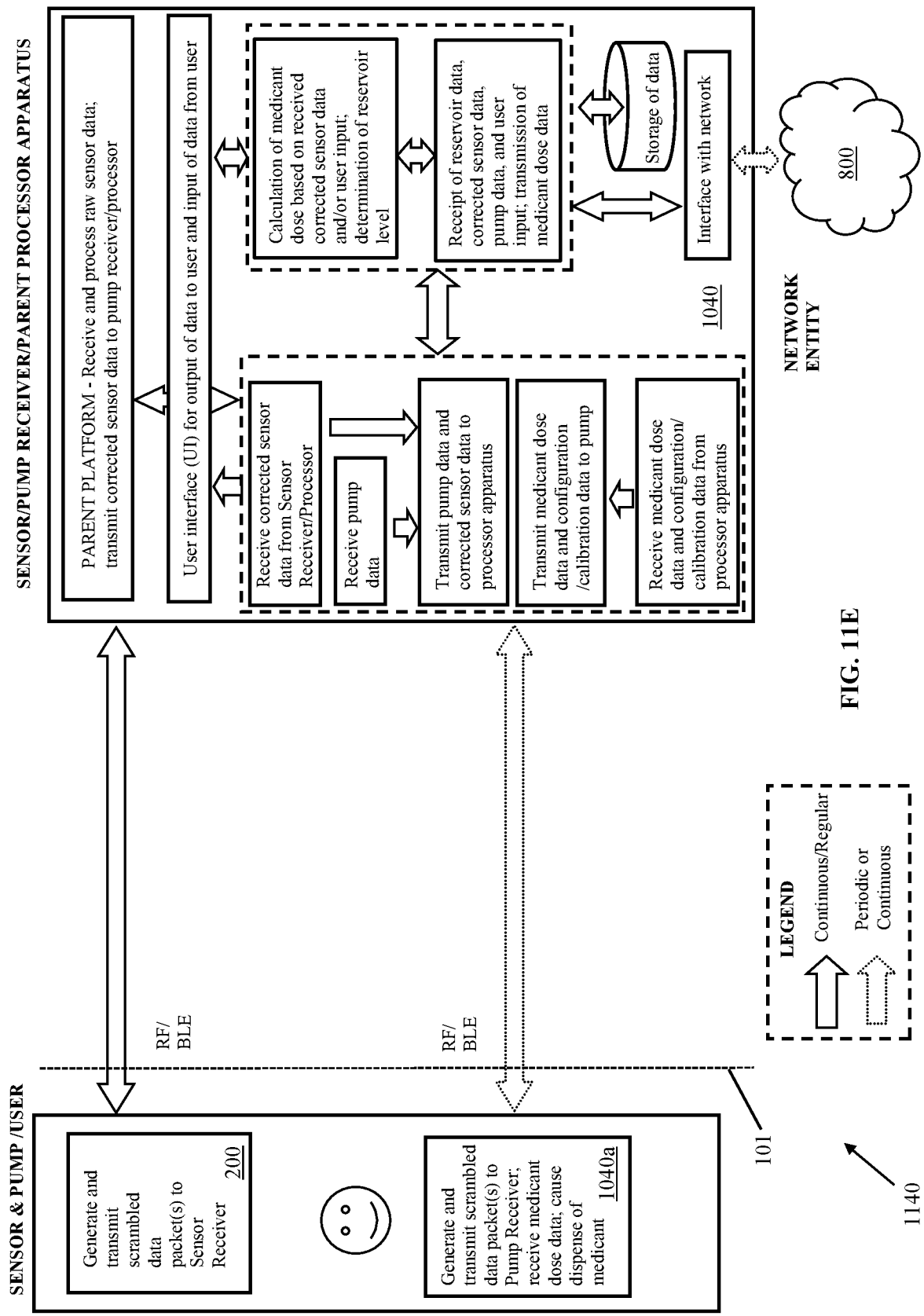
FIG. 11E is a logical block diagram illustrating a fifth embodiment of a system architecture for, inter alia, monitoring blood analyte levels within a user and controlling a delivery device, useful with various aspects of the present disclosure.

It will be further appreciated that the integrated sensor and pump receiver/parent processor apparatus 1030 can alternatively be used in combination with a fully implanted pump apparatus, such as for example the apparatus 1020*a*, discussed supra. See, e.g., FIG. 11E, which illustrates a system architecture 1140 wherein an integrated receiver/parent platform processor 1140 is utilized in conjunction with an implanted sensor 200 and fully implanted pump apparatus 1040. In this embodiment, separate wireless interfaces are utilized by the sensor 200 and the implanted pump 1040*a*; these may be homogenous or heterogeneous interfaces (e.g., the receiver/parent processor 1040 may utilize a single interface making use of a single protocol that is compatible with both the sensor and pump wireless interfaces, or alternatively use one or more interfaces that have different protocols for the respective sensor and pump protocols).

Figure 11F:
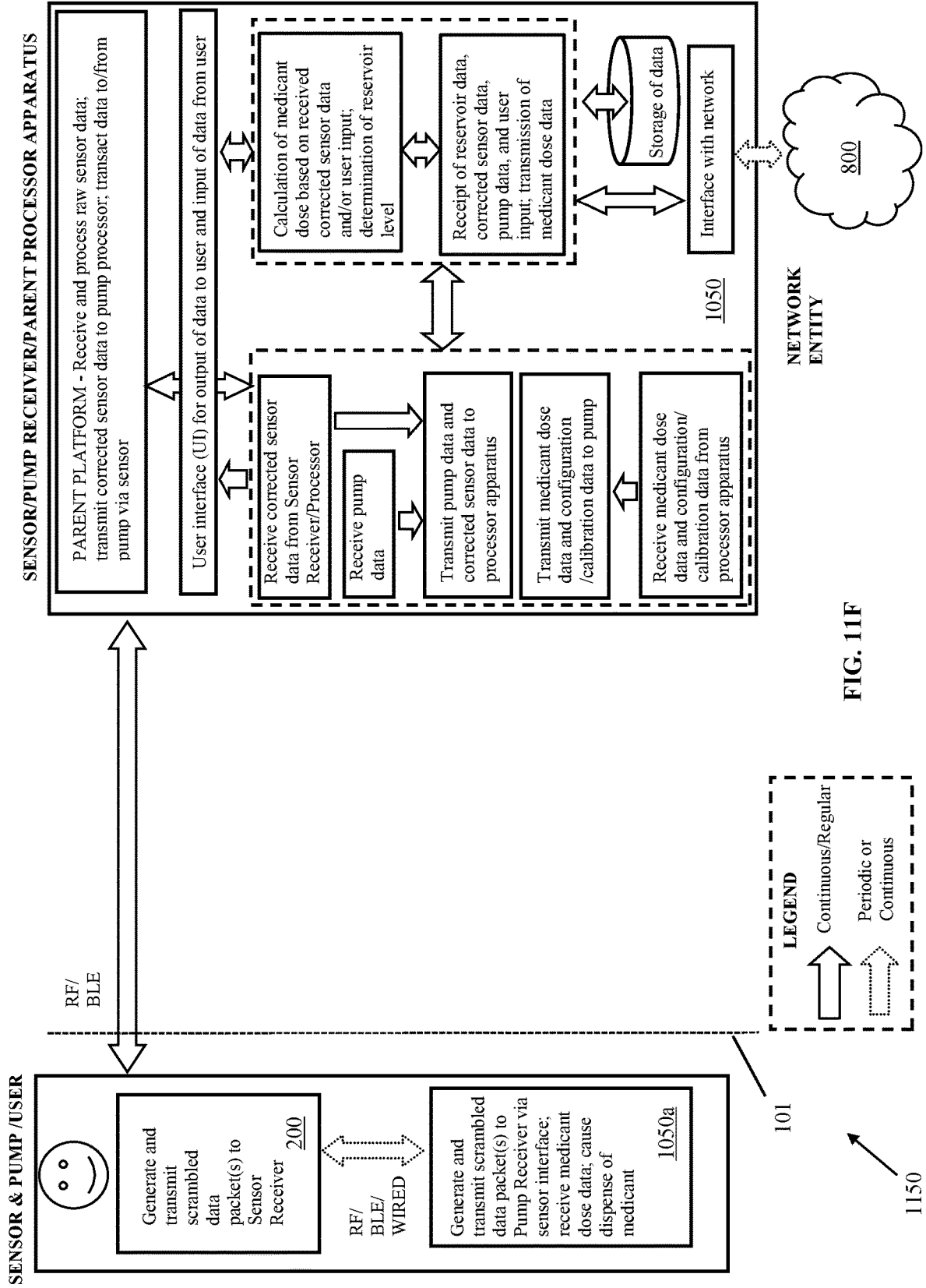
FIG. 11F is a logical block diagram illustrating a sixth embodiment of a system architecture for, inter alia, monitoring blood analyte levels within a user and controlling a delivery device, useful with various aspects of the present disclosure.

Alternatively, in the architecture 1150 of FIG. 11F, the implanted pump 1050*a* and sensor 200 may be integrated at least with respect to their (external) communication modality, such that a single wireless interface is used to communicate with an external receiver (such as for example an integrated sensor/pump/parent processor 1050 as shown). In one variant, the interface comprises a PAN (e.g., BLE or 802.15.4) interface, such the receiver/processor apparatus 1050 merely need be within a certain range of the user. Alternatively, a local receiver arrangement of the type previously described (not shown) may be used such that at least some data connectivity (and hence ability to monitor the sensor and/or pump) is always maintained, even when the parent platform 700 or network entity access point is not with wireless communication range of the user.

In one implementation, the sensor 200 and pump 1050*a* are located at somewhat physically disparate locations, in recognition that an optimal or even suitable site for sensing e.g., blood analyte level (such as for example proximate to abdominal fascia) may differ from an optimal or acceptable site for delivery of the medicant (e.g., insulin) by the pump 1050*a*. Accordingly, in this implementation, the sensor 200 and pump 1050*a* communicate via a wireless interface suitable to transmit data in vivo (i.e., through the tissue and other physiological structures interposed between the sensor 200 and the pump 1050*a*). For example, in one variant, the aforementioned BLE interface is used, which has demonstrated acceptable propagation through tissue at suitable range even with very low radiated RF power. Alternatively, ultrasonic or other transmission modalities may be used so long as sufficient data communication between the components 200, 1050a is established.

In another implementation, the sensor 200 and pump 1050a are co-located within a common structure, such that an internal wired interface (e.g., I²C, USB, PCIe, or other data bus protocol) may be used to transfer data between the components 200, 1050a. In yet another implementation, the sensor 200 and pump 1050a are contained in separate, spaced-apart housings, and are connected via a wired interface, which may optionally include a connector element to allow replacement of one of the sensor 200 or pump 1050a without necessitating replacement or substantial disturbance of the other of the sensor 200 or pump 1050a; see e.g., Renard et al., "Closed loop insulin delivery using implanted insulin pumps and sensors in type 1 diabetic patients" Diab Res Clin Pract. 2006; 74: S173-S177, which is herein incorporated by reference in its entirety.

It will be additionally appreciated that the architectures shown in FIGS. 11-11F are in no way exclusive of one another, and in fact may be used together (such as at different times and/or via different use cases), such as in the examples described above. Myriad other permutations of use cases involving one or more of the various described components 200, 400, 450, 700, 800, 1000, 1010, 1010a, 1020, 1020a, 1030, 1030a, 1040, 1040a, 1050, and 1050a are envisaged by the present disclosure. Exemplary system architectures and communication pathways of system components are also shown and described in U.S. patent application Ser. No. 15/368,436, previously incorporated herein.

Delivery Apparatus and Receiver/Processor Apparatus—

Referring now to FIGS. 12A-12F, various embodiments of the delivery (e.g., pump) apparatus and pump receiver/processor apparatus shown and disclosed with reference to FIGS. 11A-11F herein are described in detail.

Figure 12A:
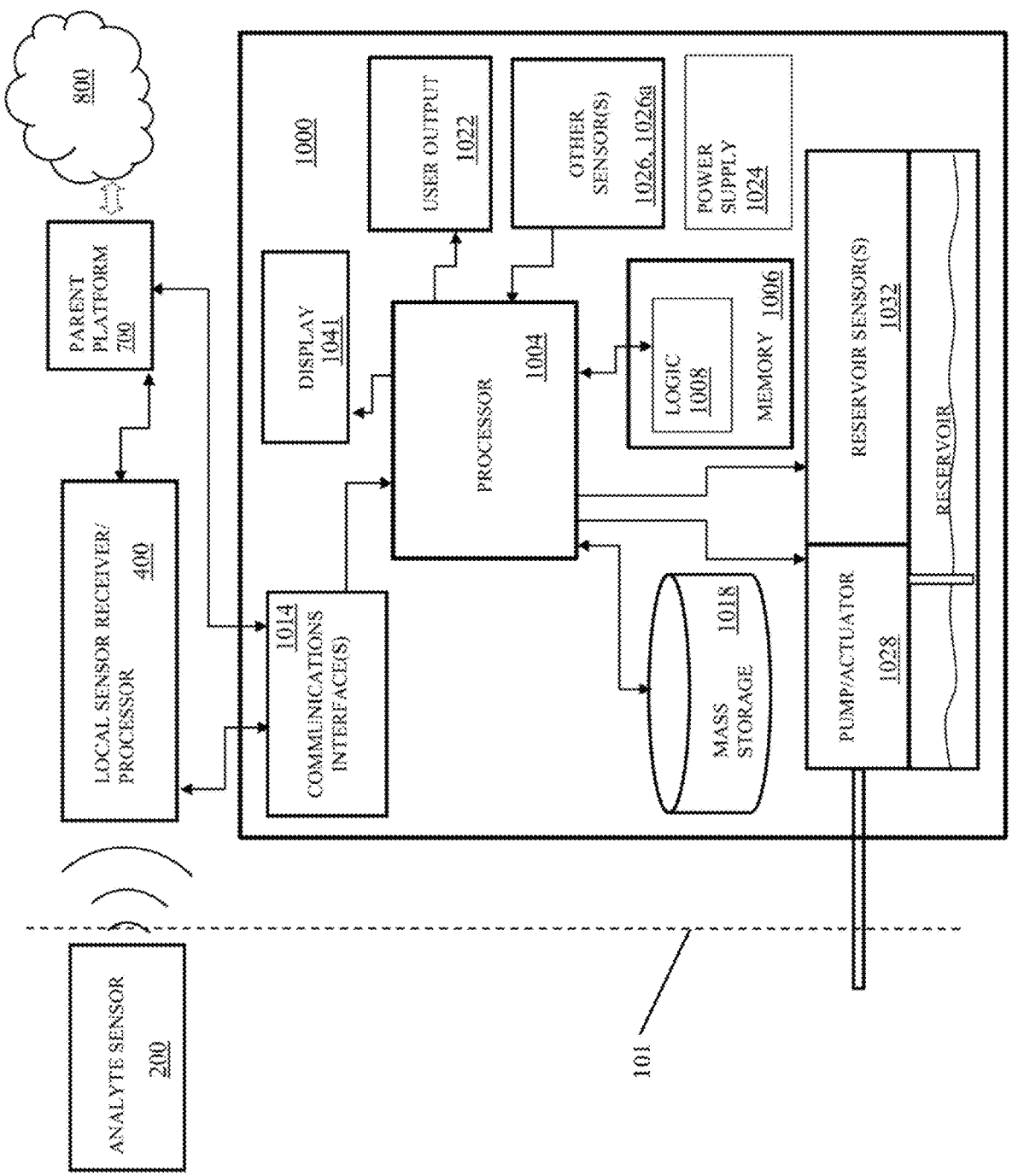
FIG. 12A is a functional block diagram illustrating a first exemplary embodiment of, inter alia, an integrated transcutaneous pump and external pump processor apparatus according to the present disclosure.

As can be seen in FIG. 12A, an exemplary embodiment of the pump and processor apparatus 1000 used in combination with an implantable sensor apparatus 200 (depicted in FIG. 4 and discussed supra) and a local sensor receiver/processor apparatus 400 (depicted in FIG. 4B and discussed supra), is shown. Accordingly, the components shown in FIG. 12A generally correspond to the system architecture shown in FIG. 11A, which includes integrated pump and receiver/processor apparatus.

As indicated, the pump and processor apparatus 1000 includes a processor 1004 (e.g., digital RISC, CISC, and/or DSP device), and/or a microcontroller (not shown), memory 1006, software/firmware 1008 operative to execute on the processor 1004 and stored in e.g., a program memory portion of the processor 1004 (not shown), or the memory 1006, a mass storage device 1018 (e.g., NAND or NOR flash, SSD, etc. to store received raw or preprocessed data, post-processed data, or other data of interest), a communications (e.g., wireless) interface 1014 for communication with one or more of the local sensor receiver/processor and the parent platform 700 (if desired), a power supply 1024 (e.g., NiMH or Lithium ion battery, or other), a graphical display device 1041, one or more pump actuators (and associated sensors) 1028, and one or more reservoir sensors 1032 for sending medicant reservoir level or other parameters associated with the medicant repository.

The pump and processor apparatus 1000 can optionally include one or more output device(s) 1022 (i.e., other types of user outputs in addition to the graphical display device 1040) for communication of the desired data (e.g., reservoir level, medicant dispense notification(s), battery "low" alerts, etc.) in addition to the display 1041. As described in greater detail herein the output device(s) may include for example visual, audible, and/or tactile (e.g., haptic) modalities or mechanisms, which can be used alone or in concert depending on user context, desired functionality, and receiver and processor apparatus configuration.

Further, the apparatus 1000 can optionally include one or more sensors, such as internal sensors 1026a (configured for subcutaneous implantation with a cannula) or external sensors 1026 (disposed at a wearable pump and processor housing). For example, the one or more internal sensors 1026a may be any of a temperature sensor, an accelerometer, a pressure sensor, a pulse meter, a conductivity meter, pH (i.e., hydronium ion concentration), electric field sensor, and/or other (non-target) analyte-detection sensors (e.g., other blood analytes). The one or more external sensors 1026 may be e.g., a temperature sensor, an accelerometer, a pulse meter, a blood pressure sensor, and/or other types of sensors. In one example, the external sensors can be used in place of or in confirmatory or complementary fashion with one or more internal sensors (or the one or more internal sensors 232 of the sensor apparatus 200).

In one specific implementation, the external sensors can be calibrated to the internal sensors (such as e.g., during "training mode" operation of the pump and sensor system), In such an implementation, subsequent "other sensor" data (i.e., data collected from sensors other than the target blood analyte sensor) can be collected from the external sensors during operation of the pump and sensor system in the "detection mode" (of the sensor) and "auto-dispense mode" (of the pump). Further, the internal sensors can be turned off or put into a sleep state, thereby e.g., decreasing power usage and/or processing requirements of the implanted components of the cannula and/or the implanted sensor.

Figure 12B:
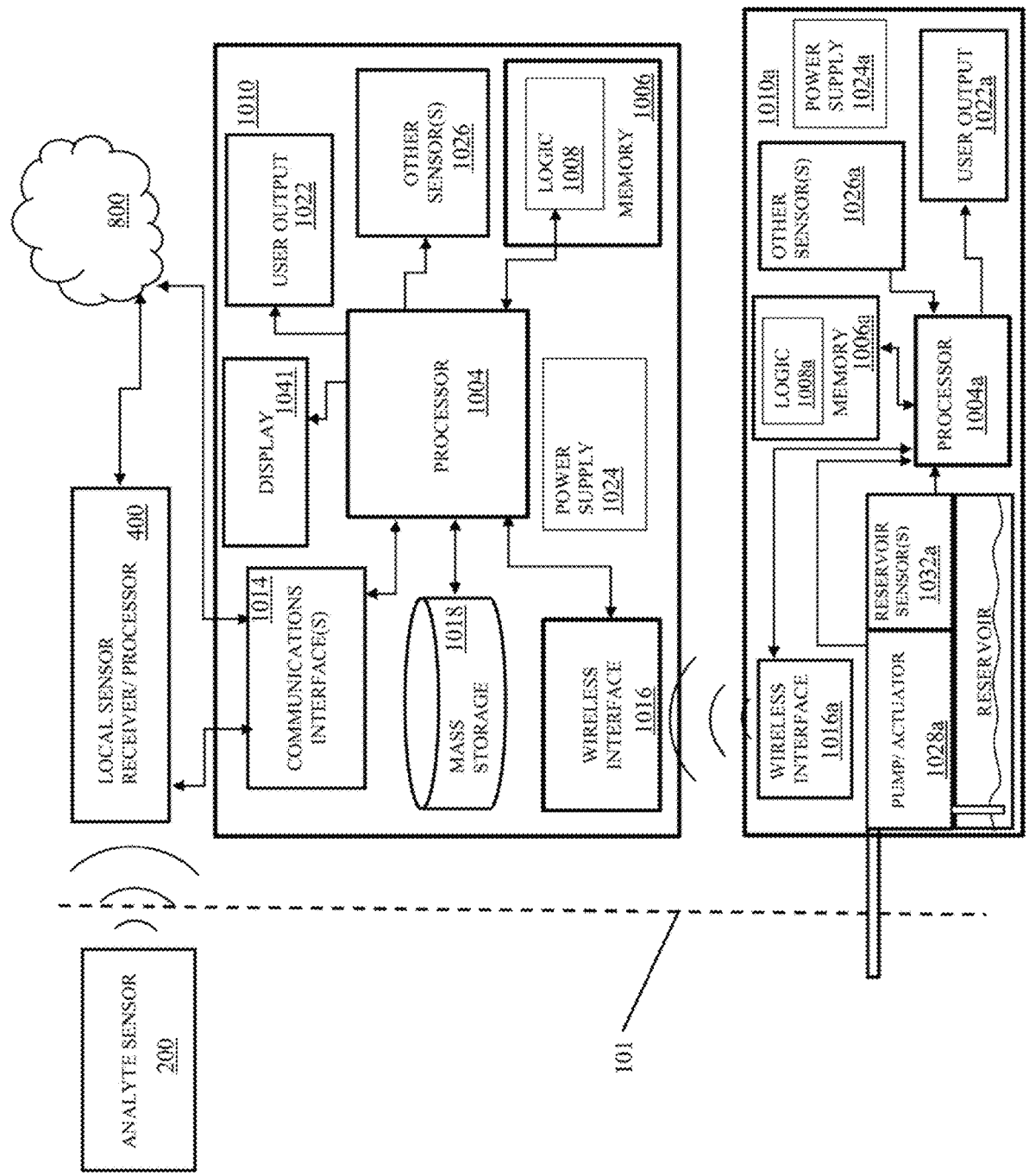
FIG. 12B is a functional block diagram illustrating a second exemplary embodiment of, inter alia, a transcutaneous pump apparatus and external processor apparatus according to the present disclosure.

FIG. 12B depicts a functional block diagram of one embodiment of the pump receiver/processor apparatus 1010 in wireless communication with one embodiment of the partially implanted (e.g., transcutaneous) pump 1010a. The pump receiver/processor apparatus 1010 and the transcutaneous pump 1010a are used in combination with an implantable sensor apparatus 200 (depicted in FIG. 4 and discussed supra) and a local sensor receiver/processor apparatus 400. Accordingly, the components shown in FIG. 12B generally correspond to the system architecture shown in FIG. 11B, which includes a localized transcutaneous pump (e.g., a patch pump) and a separate receiver and parent processor device (e.g., a dedicated receiver/processor, or a user's cell phone, etc.) along with the local sensor receiver 400.

As shown in FIG. 12B, the pump receiver/parent processor apparatus 1010 includes a configuration similar to that of the device 1000 of FIG. 12A; i.e., a processor 1004 (e.g., digital RISC, CISC, and/or DSP device), and/or a microcontroller (not shown), memory 1006, software/firmware 1008 operative to execute on the processor 1004 and stored in e.g., a program memory portion of the processor 1004 (not shown), or the memory 1006, a mass storage device 1018 (e.g., NAND or NOR flash, SSD, etc. to store received raw or preprocessed data, post-processed data, or other data of interest), a communications (e.g., wireless) interface 1014 for communication with the sensor receiver/processor 450 and/or the network entity 800 (if desired), a power supply 1024 (e.g., NiMH or lithium ion battery, or other as described below), and a graphical display device 1041. The pump receiver/parent processor apparatus 1010 further includes a wireless interface 1016 (e.g., narrowband, PAN such as Bluetooth, or other, described below) for data communication with the pump apparatus 1010a.

The pump receiver/parent processor apparatus 1010 can optionally include one or more output device(s) 1022 (i.e., other types of user outputs in addition to the graphical display device 1041) for communication of the desired data (e.g., reservoir level, medicant dispense notification(s), battery "low" alerts, etc.) in addition to the display 1040. As described elsewhere herein, the output device(s) may include for example visual, audible, and/or tactile (e.g., haptic) modalities or mechanisms, which can be used alone or in concert depending on user context, desired functionality, and receiver/processor apparatus configuration. Further, the apparatus 1010 can optionally include one or more external sensors 1026, such as those described above with reference to FIG. 12A.

The pump apparatus 1010*a* includes a processor 1004*a* (e.g., digital RISC, CISC, and/or DSP device), and/or a microcontroller (not shown), memory 1006*a*, software/firmware 1008*a* operative to execute on the processor 1004*a* and stored in e.g., a program memory portion of the processor 1004*a* (not shown), or the memory 1006*a*, a mass storage device 1018*a* (e.g., NAND or NOR flash, SSD, etc. to store received raw or preprocessed data, post-processed data, or other data of interest), a power supply 1024*a* (e.g., NiMH or lithium ion battery, or other), one or more pump actuators (and associated sensors) 1028*a*, one or more reservoir sensors 1032*a*, and a wireless interface 1016*a* (e.g., narrowband, PAN such as Bluetooth, or other, described below) for data communication with the pump receiver/parent processor apparatus 1010.

The pump apparatus 1010*a* can optionally include one or more output device(s) 1022*a* for communication of the desired data (e.g., reservoir level, medicant dispense notification(s), battery "low" alerts, etc.), for example visual, audible, and/or tactile (e.g., haptic) modalities or mechanisms, which can be used alone or in concert depending on user context, desired functionality, and receiver/processor apparatus configuration. Further, the pump apparatus 1010*a* can optionally include one or more internal sensors 1026*a* and/or external sensors 1026, such as those described above with reference to FIG. 12A.

In the embodiment shown in FIG. 12B, the components of the pump apparatus 1010*a* are substantially minimized to the maximum degree practicable in order to reduce a required size of the pump apparatus housing for attachment to the user's skin. Accordingly, it is recognized that one or more components or functions shown for the pump 1010*a* may be disposed on the receiver/parent 1010 if desired, such as display functions or the like. Notably, in the exemplary implementation of FIG. 12B, the pump apparatus 1010*a* lacks a full graphical display device (such as the graphical display device 1041 of the pump receiver/parent processor 1010). Exclusion of the foregoing graphical display allows for overall reduced dimensions of the pump apparatus 1010*a* making it suitably sized for wear on the user's skin and partial (e.g., transcutaneous) implantation. The data from the pump apparatus 1010*a* is displayed at the graphical display device 1040 of the pump receiver/processor 1010. In some embodiments, the pump apparatus 1010*a* can include a reduced or limited graphical display (i.e., small graphical display) as one of the output device(s) 1022*a*. For example, a surface of the housing of an adherable patch pump can include a small LCD, or even a capacitive touch screen for sending alerts and/or other information to the user as well as receiving input from the user.

It will be appreciated that configurations of the pump receiver/processor apparatus 1010 and the partially implanted pump 1010*a* shown in FIG. 12B are substantially similar to configurations for a non-implanted pump (i.e., a computerized injection tool) and its associated controller, such as those described supra with reference to FIGS. 10E and 10F.

Figure 12C:
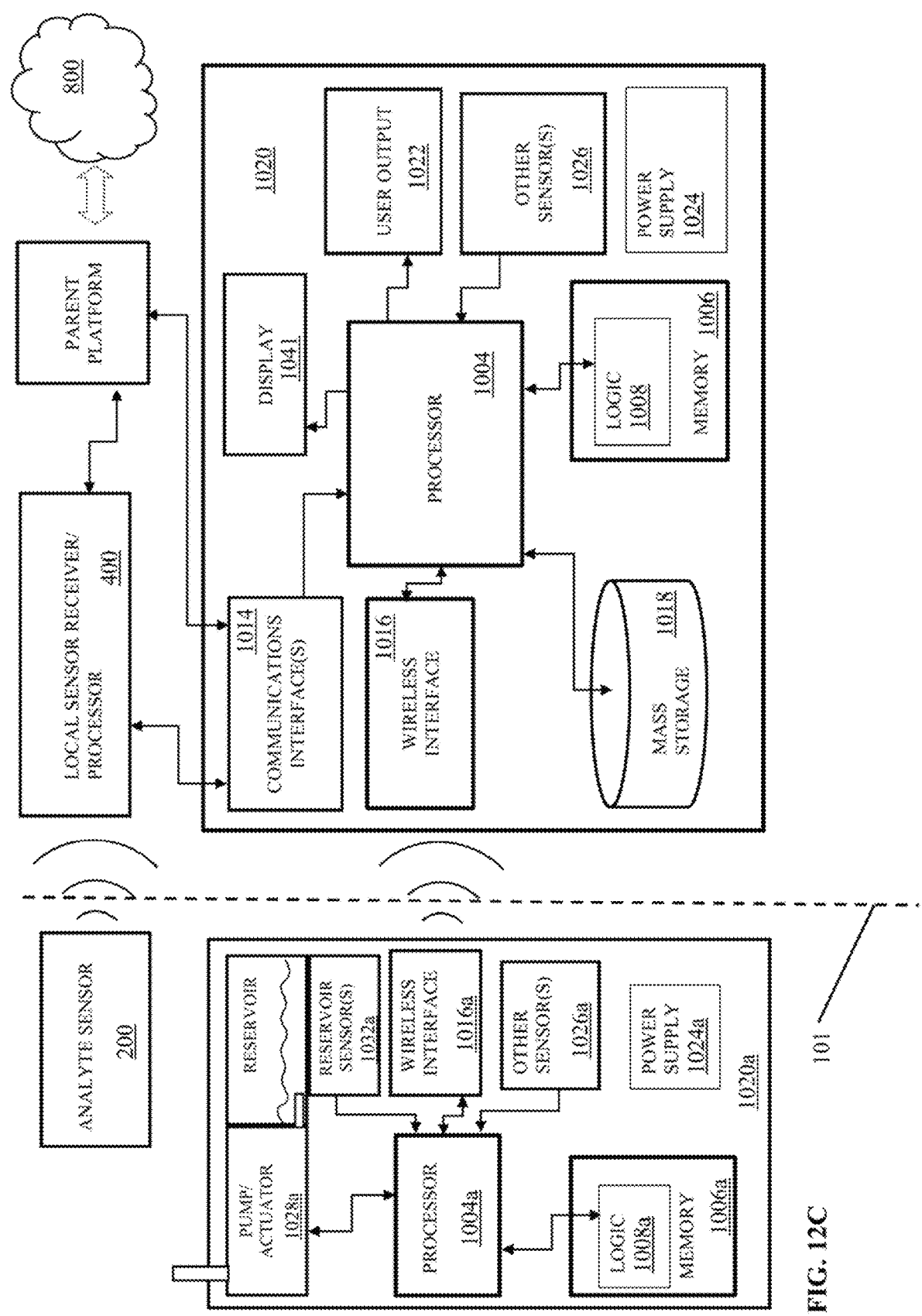
FIG. 12C is a functional block diagram illustrating an exemplary embodiment of, inter alia, an implanted pump apparatus and external pump processor apparatus, according to the present disclosure.

Turning now to FIG. 12C, a functional block diagram of one embodiment of the pump receiver/processor apparatus 1020 in wireless communication with one embodiment of the fully implanted (e.g., subcutaneous, intraperitoneal) pump 1020*a* is illustrated. The pump receiver/processor apparatus 1020 and the subcutaneous pump 1020*a* are used in combination with an implantable sensor apparatus 200 (depicted in FIG. 4 and discussed supra) and a local sensor receiver/processor apparatus 400 (depicted in FIG. 4B and discussed supra), as well as a parent platform 700. Accordingly, the components shown in FIG. 12C generally correspond to the system architecture shown in FIG. 11C, which includes a fully implanted pump and a separate pump receiver and processor device (e.g., a dedicated receiver/processor, a user's cell phone, etc.).

Similar to the pump receiver/processor apparatus 1010 (shown in FIG. 12B), the pump receiver/processor apparatus 1020 of the illustrated embodiment of FIG. 12C includes a processor 1004, and/or a microcontroller (not shown), memory 1006, software/firmware 1008 operative to execute on the processor 1004, a memory 1006, a mass storage device 1018, a communications (e.g., wireless) interface 1014, a power supply 1024, and a graphical display device 1041. The pump receiver/processor apparatus 1020 further includes a wireless interface 1016 (e.g., narrowband, PAN such as Bluetooth LE, or other) for data communication with the pump apparatus 1010*a*; however in contrast to the receiver/processor apparatus 1010, the wireless interface of receiver/processor apparatus 1020 is configured for data communication with the fully implanted pump 1020*a* across the interposed tissue (boundary) 101.

The pump receiver/processor apparatus 1020 can optionally include one or more output device(s) 1022 for communication of the desired data (e.g., reservoir level, medicant dispense notification(s), battery "low" alerts, etc.) in addition to the display 1041, and may include for example visual, audible, and/or tactile (e.g., haptic) modalities or mechanisms, which can be used alone or in concert depending on user context, desired functionality, and receiver/processor apparatus configuration. As with prior embodiments, the apparatus 1020 can optionally include one or more external sensors 1026 as described above.

The fully implanted pump apparatus 1020*a* includes a processor 1004*a* and/or a microcontroller (not shown), memory 1006*a*, software/firmware 1008*a* operative to execute on the processor 1004*a*, a mass storage device, a power supply 1024*a* (e.g., NiMH or lithium ion battery, or other as described below), one or more pumps with actuators (and associated sensors) 1028*a*, one or more reservoir sensors 1032*a*, and a wireless interface 1016*a* (e.g., narrowband, or PAN such as BLE or 802.15.4 or Z-Wave) for data communication with the pump receiver/processor apparatus 1010 across the interposed tissue (boundary) 101. The pump apparatus 1020*a* can optionally include one or more output device(s) 1022*a* for communication of the desired data (e.g., reservoir level, medicant dispense notification(s), battery "low" alerts, etc.), for example audible and/or tactile (e.g., haptic) modalities or mechanisms given that the apparatus 1020*a* is implanted, which can be used alone or in concert depending on user context, desired functionality, and receiver/processor apparatus configuration. Further, the pump apparatus 1020*a* can optionally include one or more internal sensors 1026*a*, such as those described above with reference to FIG. 12A.

In the embodiment shown in FIG. 12C, the components of the pump apparatus 1020*a* may be minimized (and miniaturized where possible) as compared to the components of the pump receiver/processor apparatus 1020 in order to reduce a required size of the pump apparatus housing for implantation beneath the user's skin (e.g., implantation in the intraperitoneal cavity). As the pump is configured for full implantation, the pump apparatus 1020*a* lacks any graphical display device.

Figure 12D:
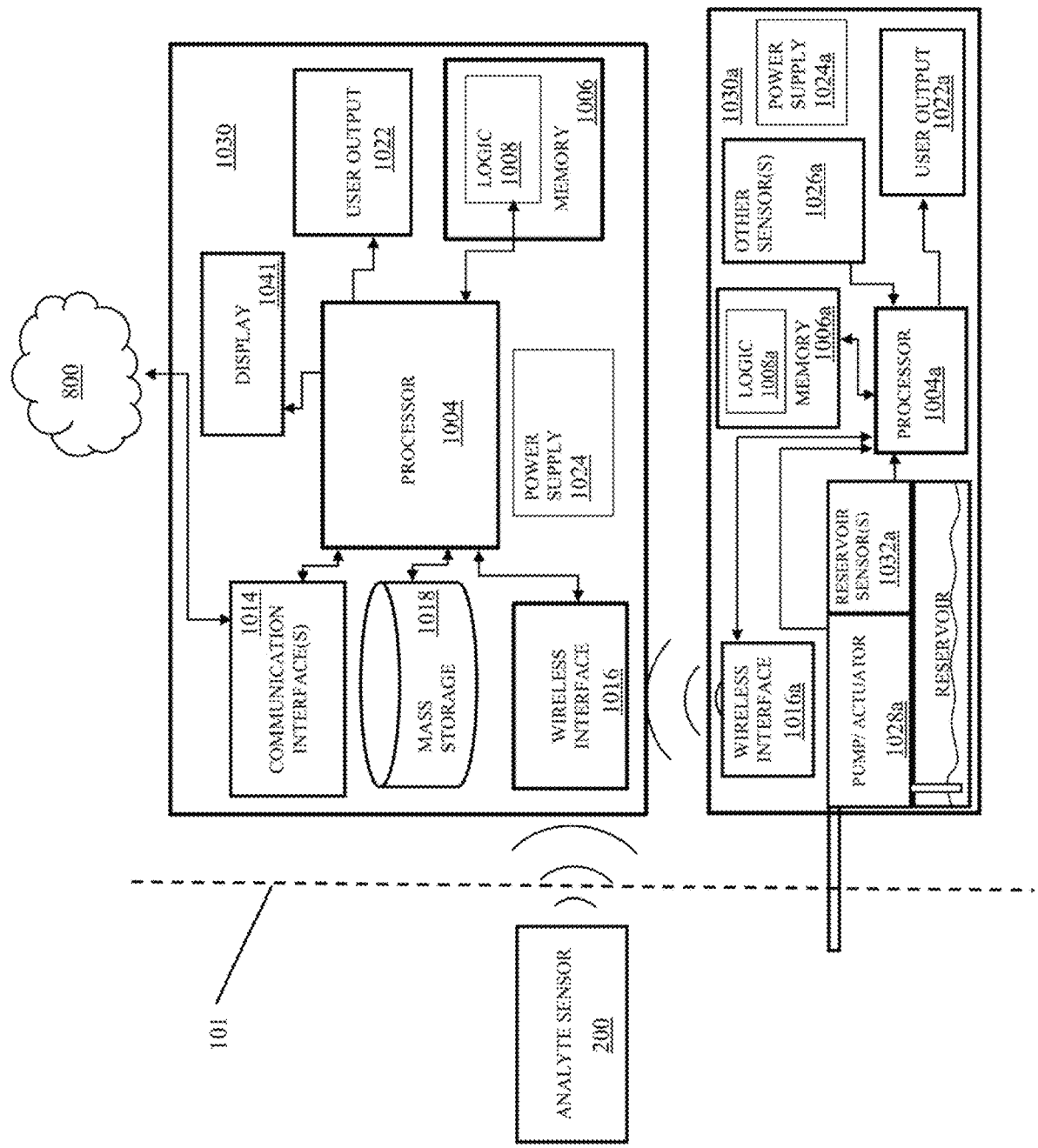
FIG. 12D is a functional block diagram illustrating a third exemplary embodiment of, inter alia, a transcutaneous pump apparatus and external sensor receiver and pump processor apparatus according to the present disclosure.
Figure 12E:
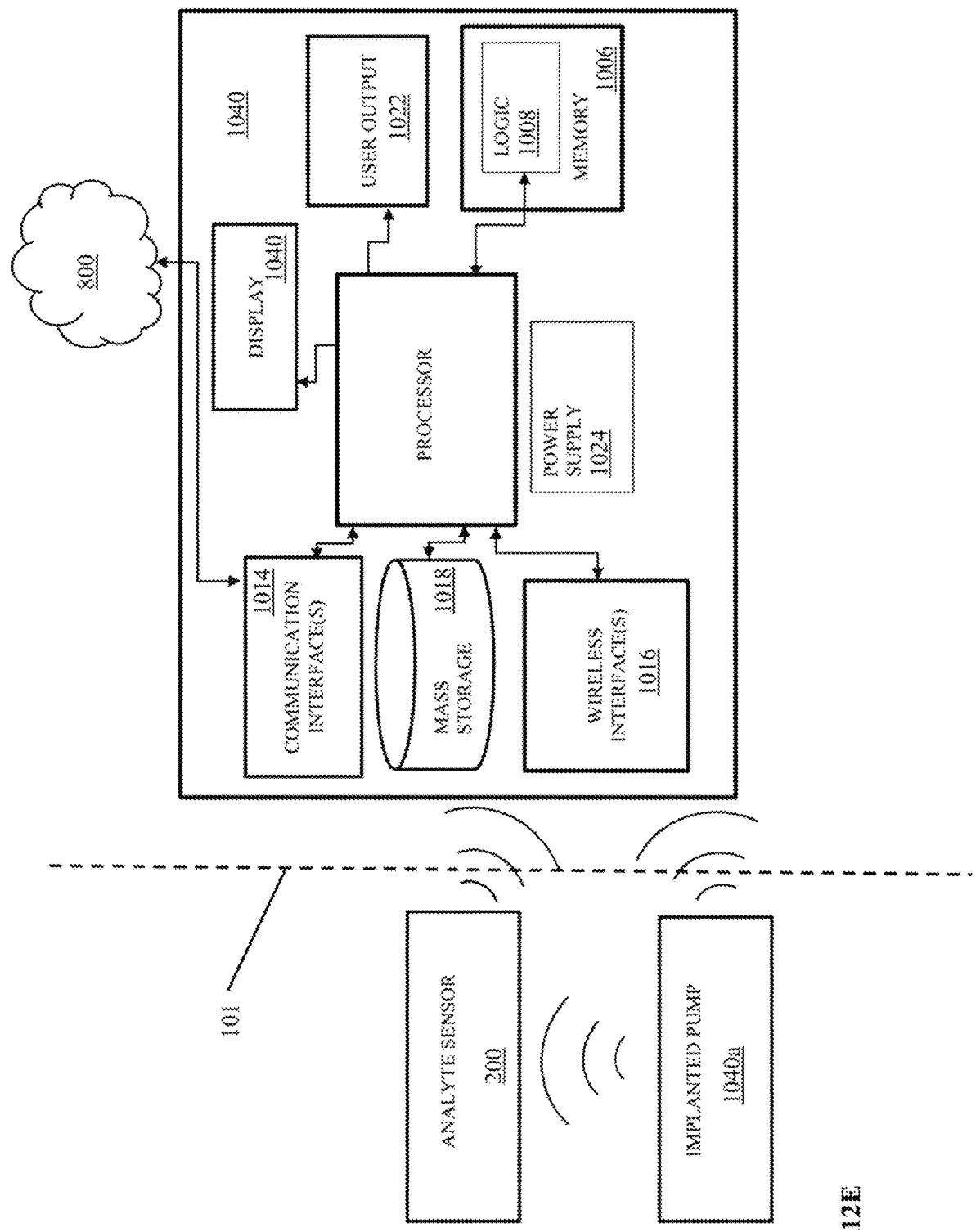
FIG. 12E is a functional block diagram illustrating an exemplary embodiment of, inter alia, an implanted pump apparatus and external sensor receiver and pump processor apparatus, according to the present disclosure.

FIGS. 12D and 12E illustrate functional block diagrams of exemplary embodiments of receiver/processor apparatus 1030 and 1040 which each comprise a receiving and processing device configured for data communication with the both of the sensor 200 and an implanted (partially or fully) pump apparatus. For example, the pump receiver/processor apparatus 1030 and the transcutaneous pump 1030*a* are used in combination with an implantable sensor apparatus 200 (depicted in FIG. 4 and discussed supra), and generally correspond to the system architectures shown in FIGS. 11D and 11E, which each include a partially or fully implanted pump (respectively) and a separate receiver and parent processor device (e.g., a dedicated receiver/parent processor, a user's cell phone, etc.) configured for data communication with an implanted sensor and the partially or fully implanted pump. It will be appreciated that configurations of the pump receiver/processor apparatus 1030 and the partially implanted pump 1030*a* shown in FIG. 12D are substantially similar to configurations for a non-implanted pump (i.e., a computerized injection tool such as those described supra with reference to FIGS. 10E and 10F) and an associated integrated controller.

In the exemplary context of Bluetooth or BLE, the individual devices may comprise "slaves" to the master interface 1016 (FIG. 12E), such that a common protocol can be used for both, thereby simplifying the construction of the external receiver/processor 1040.

Figure 12F:
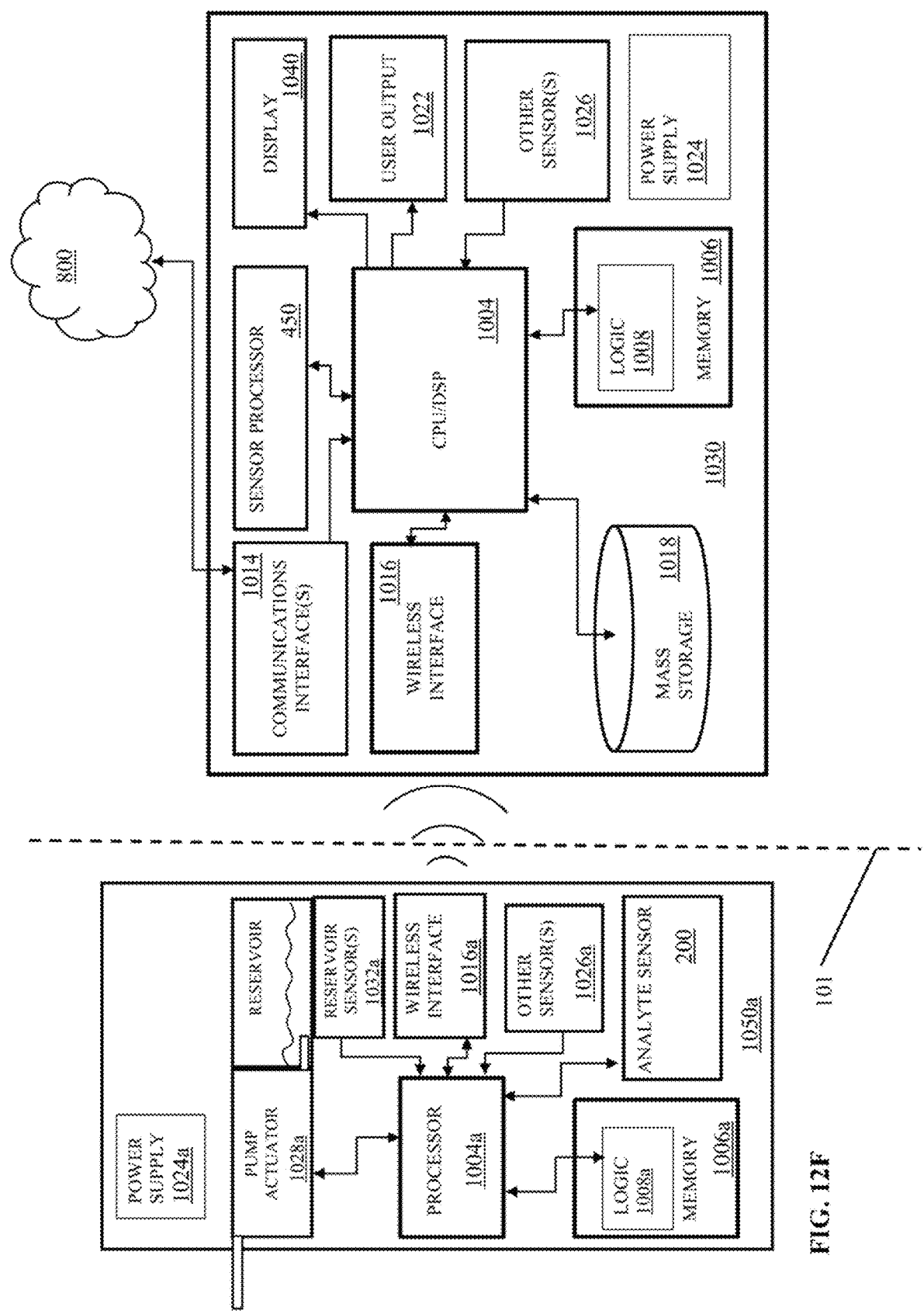
FIG. 12F is a functional block diagram illustrating an exemplary embodiment of, inter alia, an integrated implanted sensor and pump apparatus, and external sensor receiver and pump processor apparatus, according to the present disclosure.

It is also appreciated that despite using two discrete wireless interfaces (i.e., one for the sensor 200 and one for the implanted pump 1030*a*/1040*a*), the implanted devices may also intercommunicate with one another internally within the patient via e.g., RF wireless or other wireless technology (e.g., acoustic/ultrasonic, inductive, or even IR where interposed tissue thickness is very low). For instance, FIG. 12F shows yet another embodiment of the system, wherein the fully implanted pump 1050*a* and analyte sensor 200 are at least logically integrated (and hence corresponding generally to the architecture 1150 of FIG. 11F). The sensor 200 and implanted pump 1050*a* are at minimum in data communication with one another via either wireless (e.g., BLE or other PAN, or narrowband RF such as 433 MHz), or wired interface where the proximity of the devices is such that a wired interface may be supported internally within the patient. The two devices 200, 1050*a* may also be physically integrated into a common implant/housing if desired, assuming that delivery of the medicant can be made in sufficient proximity to the analyte sensing site, as previously described. Notably, under any of the foregoing scenarios, the system of FIG. 12F utilizes a common wireless interface (e.g., RF narrowband, PAN such as BLE, or other) to transmit data across the tissue boundary, thereby advantageously integrating all communications functions to the implanted devices within a single interface. In the foregoing example of Bluetooth, one device may also act as a slave to another, such as where the implanted pump 1050*a* is slave to both the sensor 200 and (master 1) and external device interface 1016 (master 2). Depending on whether Bluetooth mesh networking and/or BLE capability is utilized, additional topologies may be supported. For example, a BLE device can operate in four (4) different device roles, each of which may cause the devices to behave differently. Two of the roles are connection-based; i.e., a peripheral device is an advertiser that is connectable and can operate as a slave as part of a two-way (bidirectional) data connection, and a central device that monitors for advertisers, and can initiate connections operating as a master for those connections. Conversely, the other two device roles are used for unidirectional communications; i.e., a broadcaster (a non-connectable advertiser which, for example, merely broadcasts data from a sensor of the IoT device, or an observer that monitors for advertisements, but cannot initiate connections (e.g., the receiver for the above-referenced broadcaster).

Yet other topologies will be appreciated by those of ordinary skill given the present disclosure. For instance, IEEE 802.15.4 can form various topologies such as star network, cluster tree or mesh. Hence, depending on role, the present disclosure contemplates various functions and/or topologies within a local network (e.g., PAN) for the various wireless components using the 802.15.4 protocol or BLE/mesh networking. This also includes switching of device/component profile or role, such as where a single component (e.g., the wireless interface 1016 of the external receiver/processor) can act as one type of node or role for certain operations, and another type of node or role for other operations.

It will be appreciated that, in the embodiments of FIGS. 12D-12F, the relevant aspects of the above descriptions of the components of the receiver/processor devices 1000, 1010, 1020 (including parent platform functions in certain embodiments) are generally applicable to the sensor and pump receiver/processor devices 1030, 1040. Additionally, the relevant aspects of the above description of the components of the partially implanted pump 1010*a* is generally applicable to the partially implanted pump 1030*a*, while the above description of the components of the fully implanted pump 1020*a* is applicable to the fully implanted pump 1040*a*.

Moreover, as can be appreciated by those of ordinary skill given the present disclosure, any number of different hardware/software/firmware architectures and component arrangements can be utilized for the receiver/(parent) processor apparatus 1000, 1010, 1020, 1030, 1040, 1050, the foregoing being merely illustrative. For instance, a less-capable (processing, sensing, and/or data storage-wise) or "thinner" configuration may be used (e.g., excluding the one or more additional internal sensors), or additional functionality not shown added (e.g., including additional types of other sensors, and/or other components).

Sensor and Pump System Operational Methods—

Figure 13:
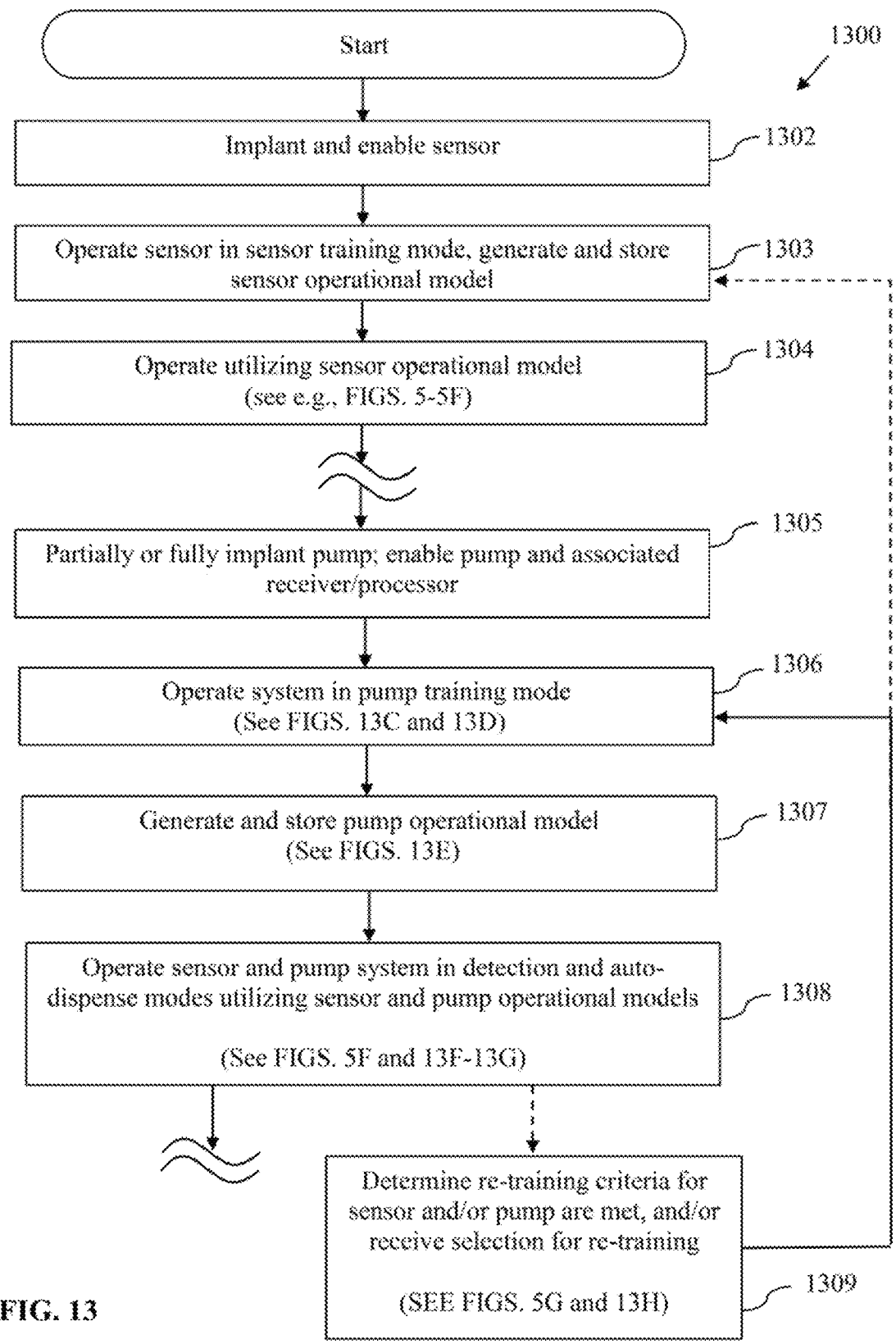
FIG. 13 is a logical flow diagram illustrating one exemplary embodiment of a methodology for operating the analyte sensing and medicant dispensing system of the present disclosure.
Figure 13A:
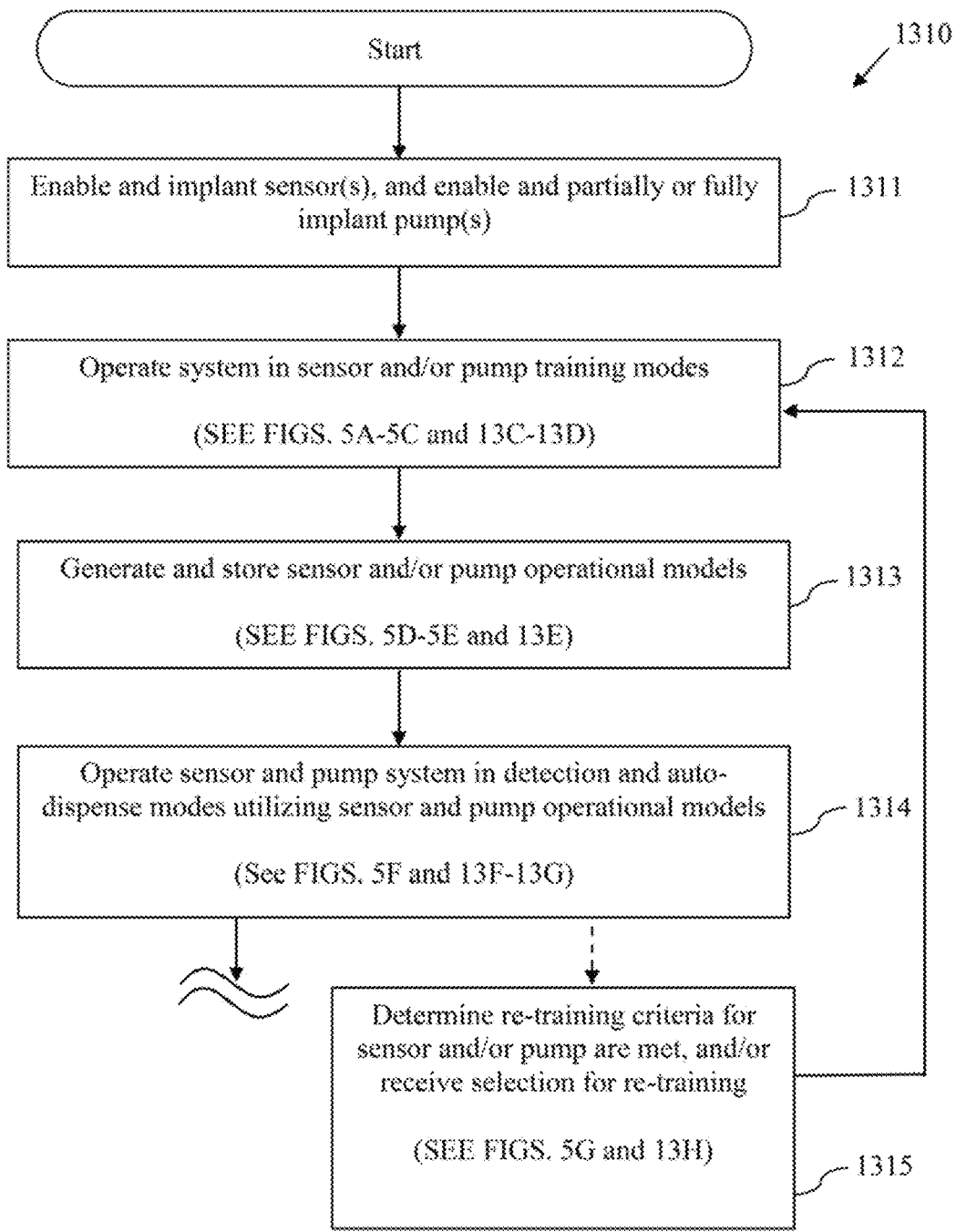
FIG. 13A is a logical flow diagram illustrating a first alternate embodiment of the methodology of FIG. 13.
Figure 13B:
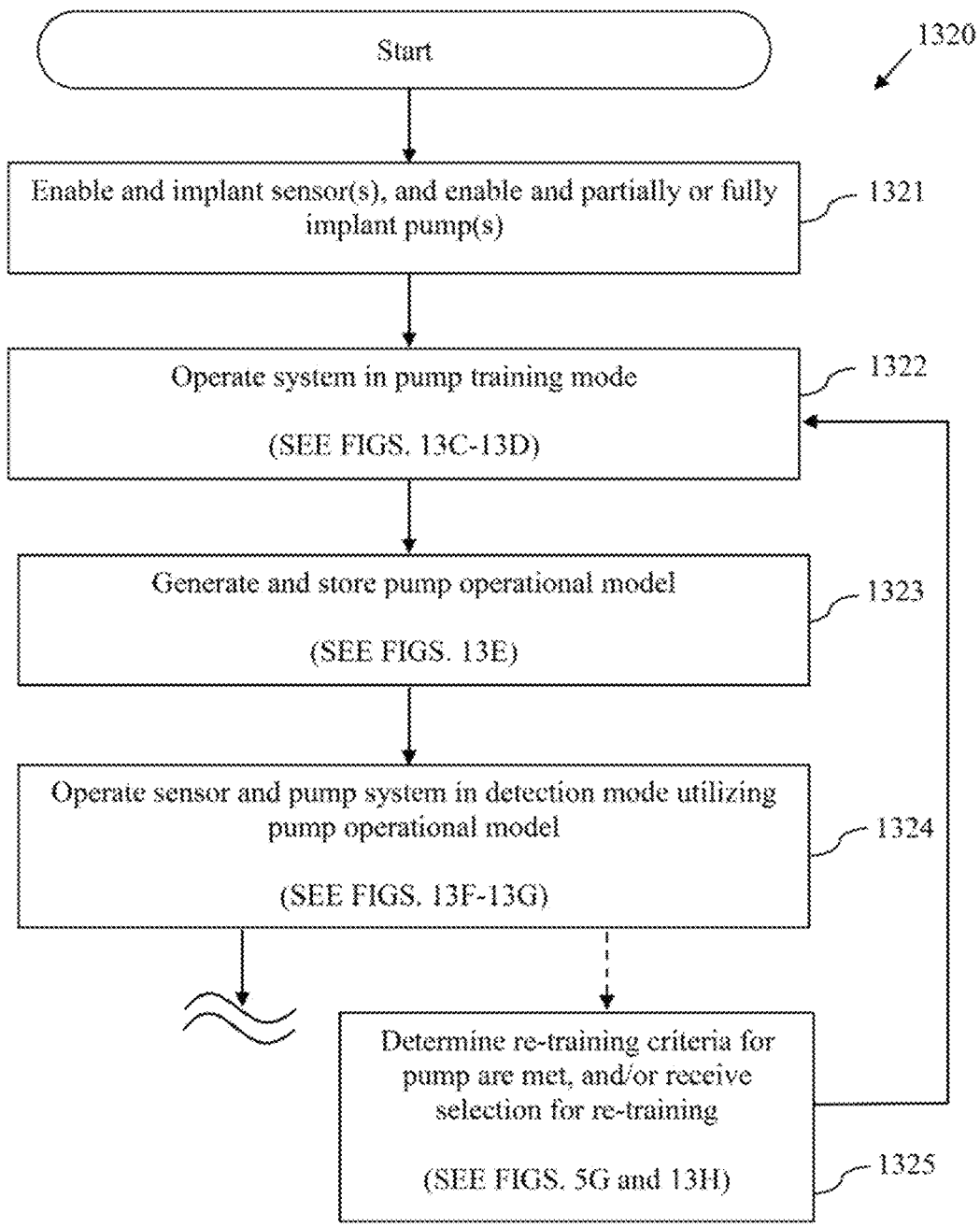
FIG. 13B is a logical flow diagram illustrating a second alternate embodiment of the methodology of FIG. 13.
Figure 13C:
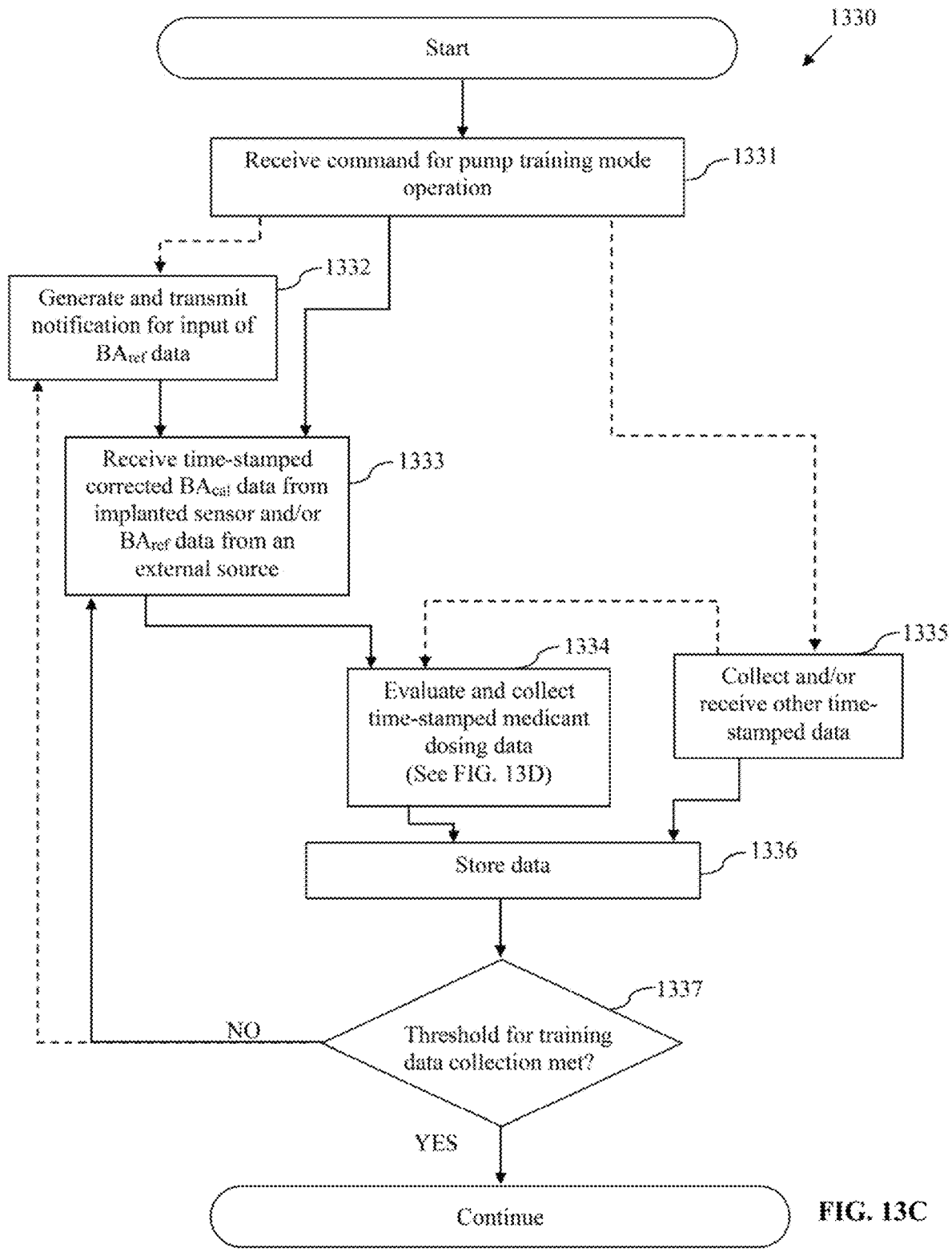
FIG. 13C is a logical flow diagram illustrating one exemplary embodiment of a methodology for operating the analyte sensing and medicant dispensing system of the present disclosure in the pump training mode.
Figure 13D:
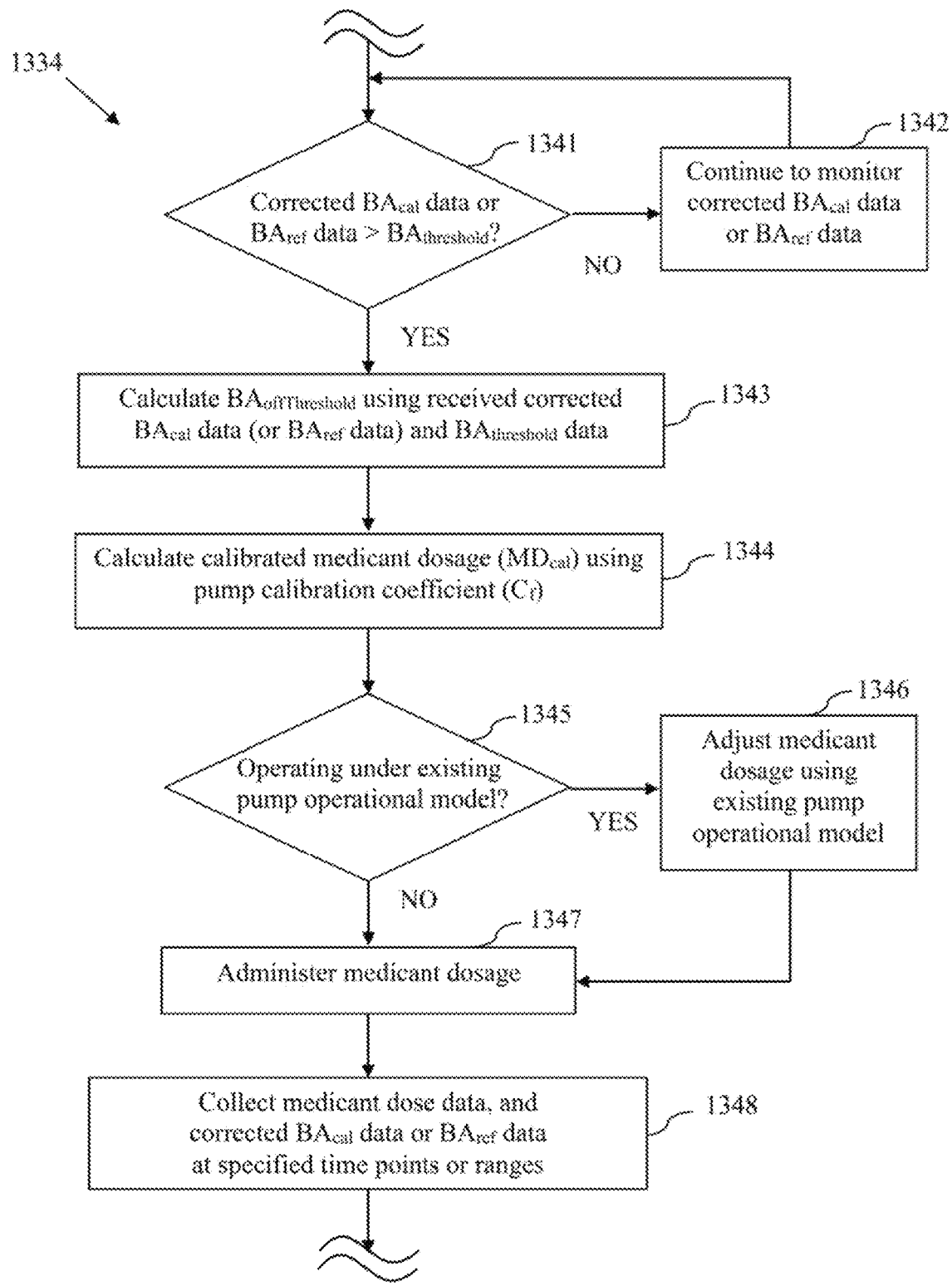
FIG. 13D is a logical flow diagram illustrating one exemplary embodiment of a methodology for evaluation of blood analyte data and calculation of medicant dosing data during pump training mode operation.
Figure 13E:
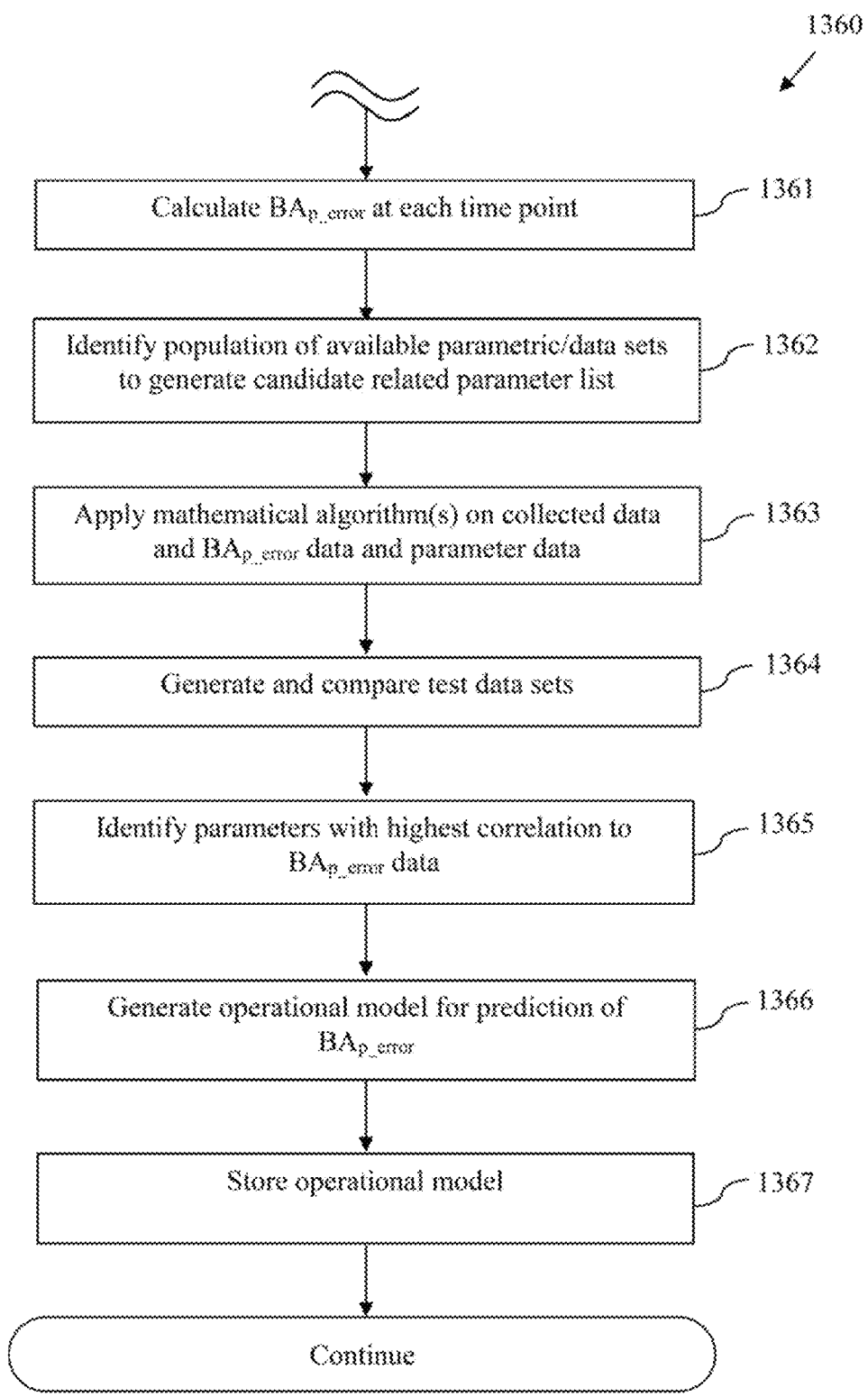
FIG. 13E is a logical flow diagram illustrating one exemplary embodiment of a methodology for data analysis and generation of an operational model (e.g., a user-specific operational model) according to the present disclosure.
Figure 13F:
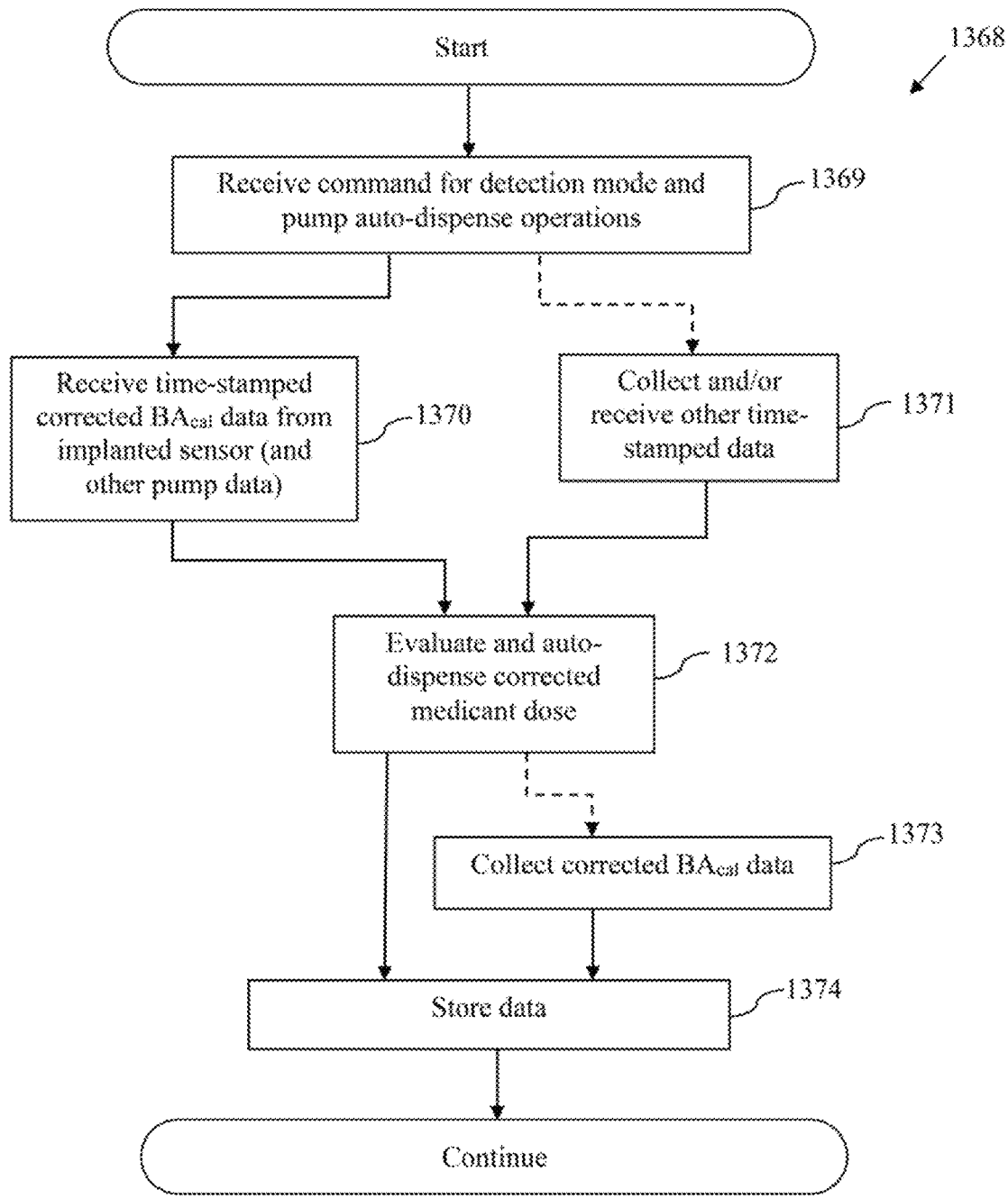
FIG. 13F is a logical flow diagram illustrating one exemplary embodiment of a methodology for operating the analyte sensing and medicant dispensing system of the present disclosure in the auto-dispense mode.
Figure 13G:
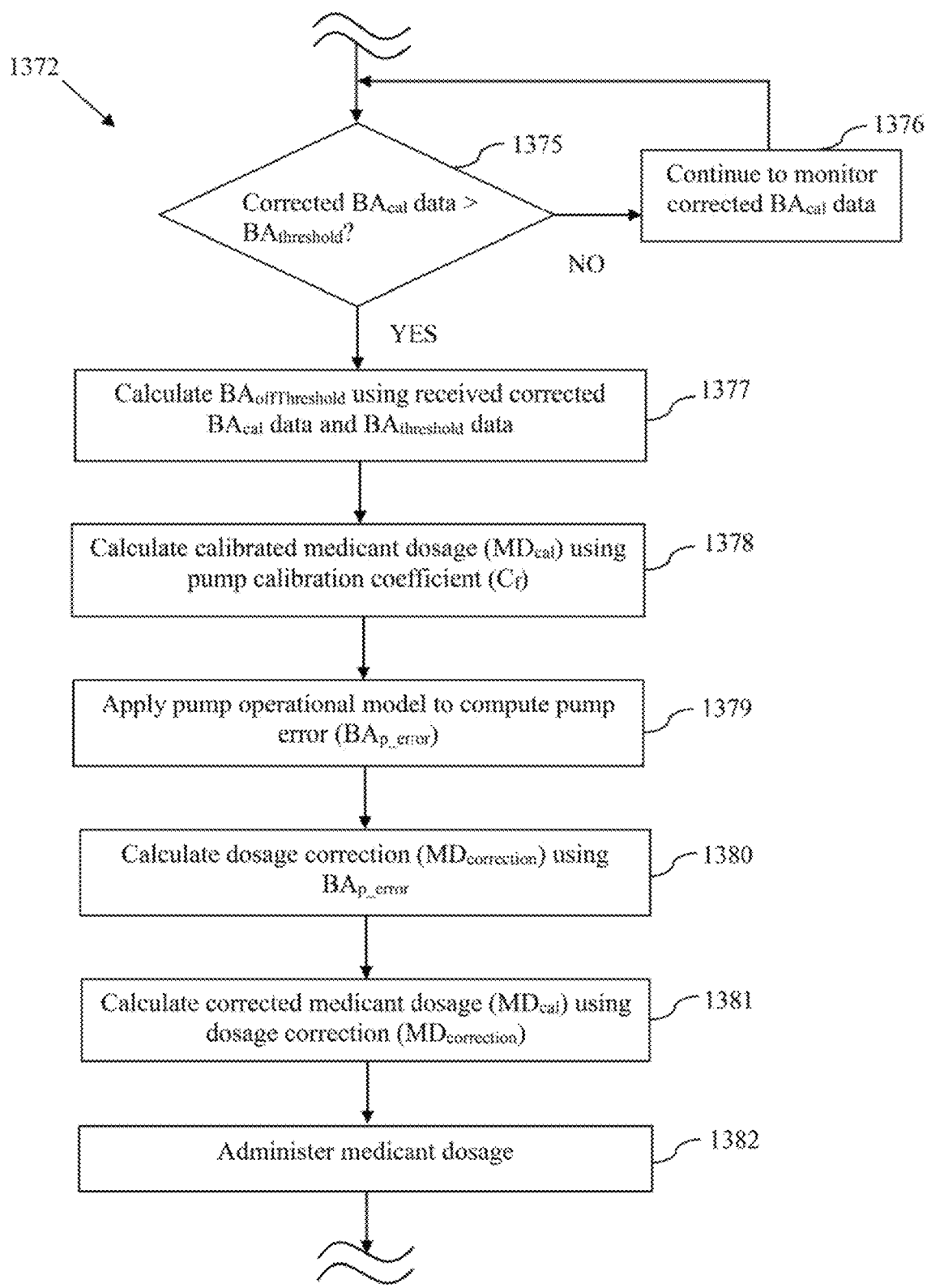
FIG. 13G is a logical flow diagram illustrating one exemplary embodiment of a methodology for evaluation of blood analyte data and calculation of medicant dosing data during auto-dispense mode operation.
Figure 13H:
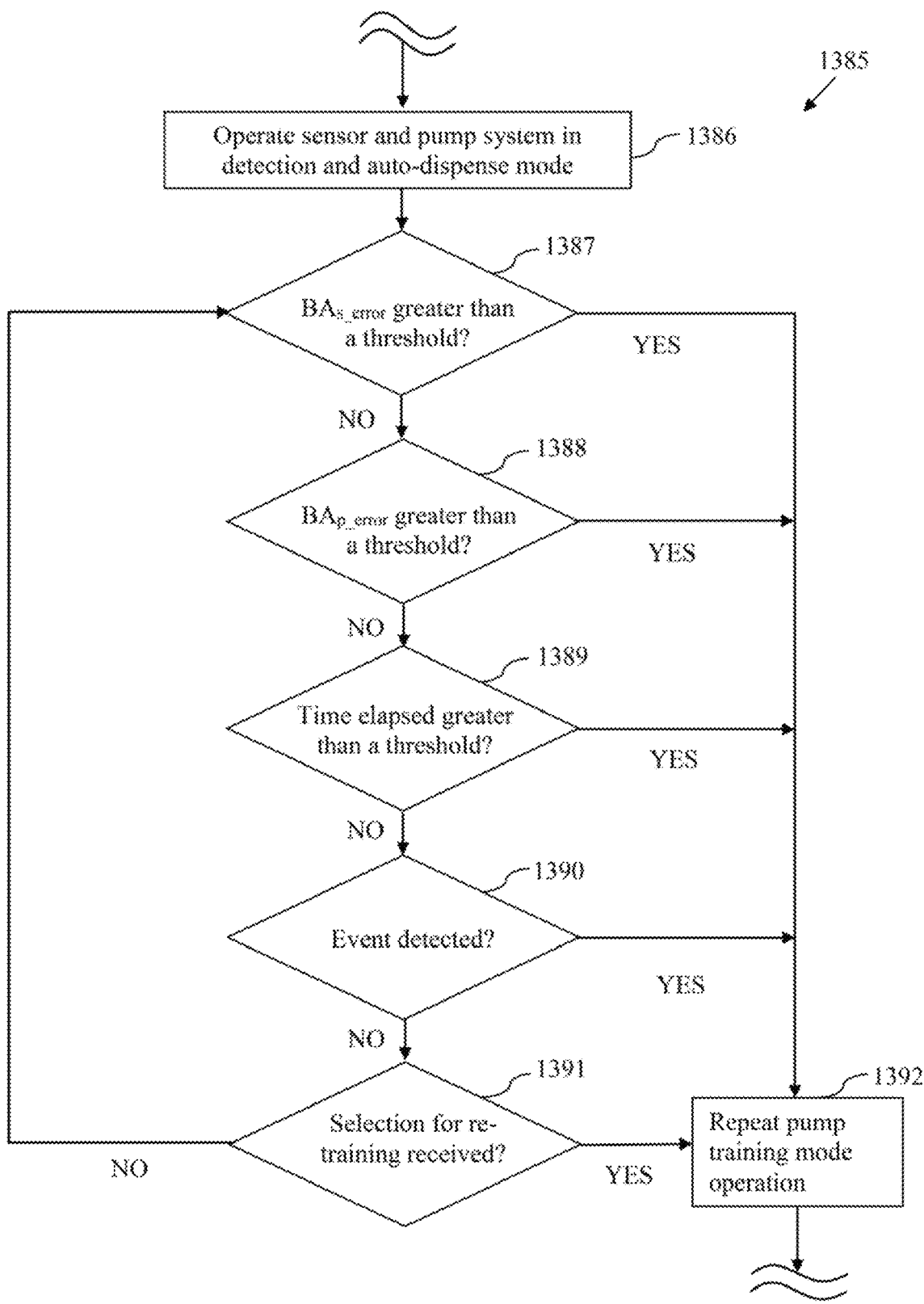
FIG. 13H is a logical flow diagram illustrating one exemplary embodiment of a methodology for determining the need for re-training of a partially or fully implanted pump, according to the present disclosure.
Figure 13I:
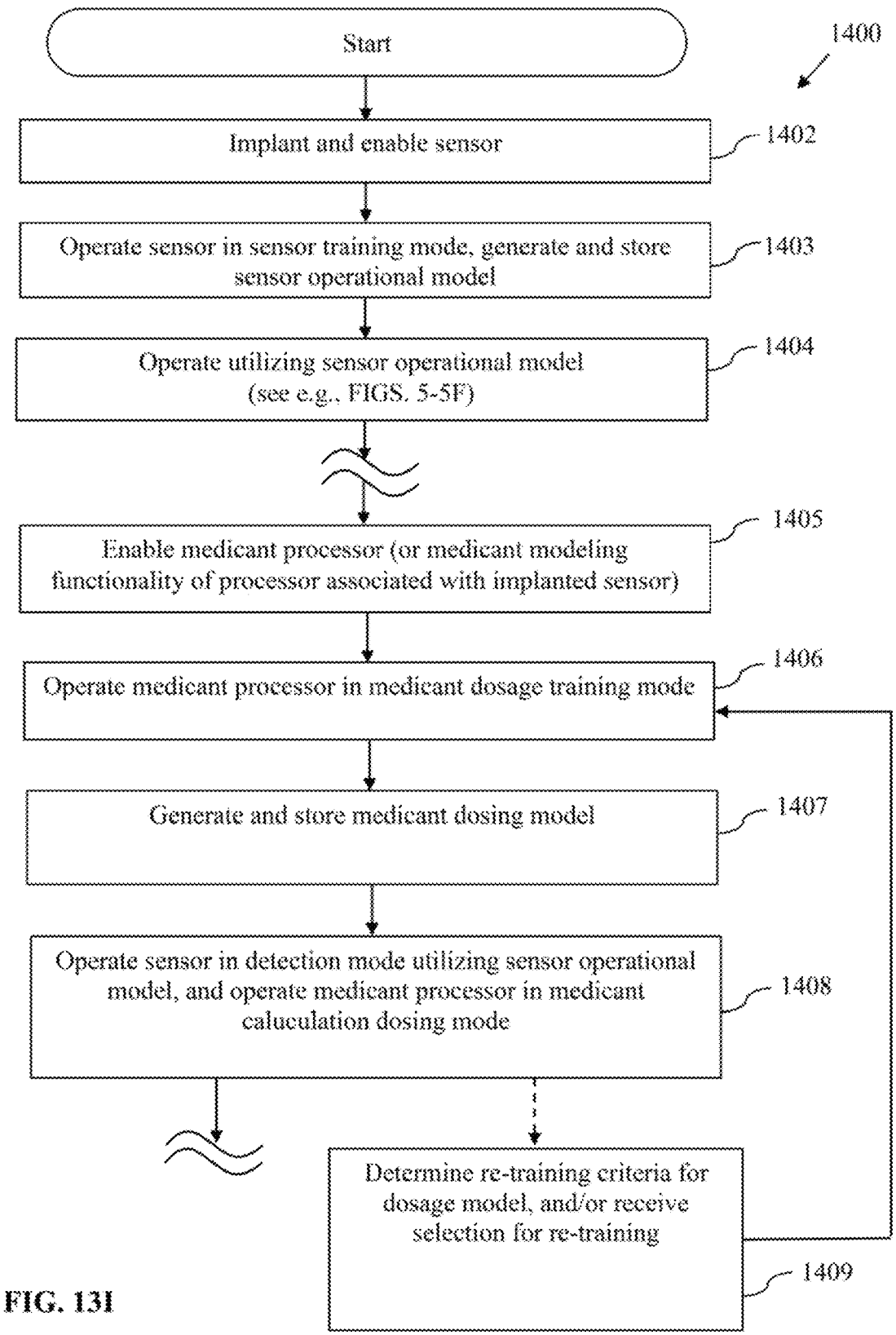
FIG. 13I is a logical flow diagram illustrating one exemplary embodiment of a methodology for operating the analyte sensing and medicant dosage calculation system of the present disclosure.

Referring now to FIGS. 13-13H, exemplary embodiments of the methods of operating the analyte sensing and medicant dispensing system (e.g., a system including an implanted sensor, an implanted (partially or fully) pump, and either of a sensor receiver/(parent) processor in data communication with a pump processor or an integrated sensor and pump receiver/(parent) processor) are described in detail. Additionally, an exemplary embodiment of a method of operating the implanted sensing system with a non-implanted pump (e.g., a computerized injection tool) or other manual/semi-manual medicant delivery mechanism is shown in FIG. 13I.

FIG. 13 is a logical flow diagram depicting a first exemplary embodiment of a generalized method 1300 for operation of the implanted sensor and implanted (partially or fully) pump system according to the present disclosure. The method 1300 substantially includes first implanting and training the sensor, and further utilizing the corrected sensor data for training mode operation of a partially or fully implanted pump.

Specifically, as shown in FIG. 13, the method 1300 includes first: (i) enabling and implanting the sensor 200 (and/or other sensors) per step 1302, (ii) operating the implanted sensor in a sensor training mode, including generating and storing a sensor operational model (step 1303), and (iii) operating the sensor in the detection mode utilizing the sensor operational model, per step 1304. See the method 500 depicted in FIGS. 5-5F and the corresponding descriptions thereof for a detailed description of sensor implantation, training, operational model generation, and detection mode operation.

Further, in the case of the implantable sensor 200 of FIG. 2, the sensor is enabled and implanted in the host via the exemplary procedures described in U.S. patent application Ser. No. 14/982,346 filed Dec. 29, 2015 previously incorporated herein), and tested as part of steps 1302-1304.

Next, per step 1305, the pump apparatus (and associated receiver/processor) is enabled and implanted (or, depending on configuration, implanted and then enabled). In one implementation, the pump and processor apparatus 1000 is powered on, tested, calibrated, user preference or medicant dosing settings entered, reservoir filled, etc., and an insertion set (which is fluidly coupled to a reservoir within a housing of the apparatus via a catheter) is implanted transcutaneously through the skin of a user and attached at the insertion site.

In another implementation, the partially implantable pump apparatus 1010a, 1030a is enabled (e.g., powered on, calibrated, reservoir filled, etc.) and the associated receiver 1010, 1030 is enabled. Subsequently, a cannula of the pump, which is fluidly coupled to a reservoir within a housing of the pump apparatus, is implanted transcutaneously through the skin of a user and attached at the insertion site.

In yet another implementation, the fully implantable pump apparatus 1020a, 1040a is enabled (e.g., powered on, calibrated, reservoir filled, etc.) and surgically implanted within the user subcutaneously and the medicant-dispensing cannula associated therewith directed into a body cavity (e.g., within the intraperitoneal cavity). In one specific example, the fully implantable pump apparatus is a separate device from the sensor (see FIGS. 12C and 12E) that is implanted either in a same (contemporaneous) surgical procedure or in a different (non-contemporaneous) surgical procedure at a distinct implantation site from the sensor. In an alternate example, the fully implantable pump apparatus is integrated with the sensor (see FIG. 12F), and is co-enabled and co-implanted as a single device at a single implantation site.

In one variant, the exemplary embodiment of the partially or fully implantable pump apparatus 1010a-1050a uses a 433 MHz narrowband RF transceiver (such frequency having good signal transmission characteristics through human tissue), or alternatively a PAN (e.g., BLE or Z-Wave or 802.15.4) transceiver, and thereby has a communications range, dependent on transmission power, of at least several feet even through human tissue (for implantable variants). Hence, in one implementation of the method step 1304, the host/user merely needs to keep the corresponding receiver/processor within arm's reach, or somewhere on their body personally. As discussed infra, however, certain embodiments of the disclosure may implement the "machine learning" aspects indigenously on the implanted pump apparatus itself, thereby effectively obviating the need for communication with the corresponding receiver/processor apparatus, at least for functions relating to systemic or other error modeling and correction.

Subsequent to enablement and implantation of the pump apparatus (and enablement of any corresponding receiver/processor for the exemplary pump apparatus 1010a-1050a), the sensor and pump system is operated in an initial "pump training mode" (step 1306, and described below in greater detail with respect to FIGS. 13C and 13D), wherein corrected blood analyte data are received from the sensor 200, and are utilized to calculate medicant dosage for administration from the pump based on an initial dosing calculation algorithm. In one implementation, time-stamped blood analyte data are collected before, during, and/or after medicant delivery, and are analyzed via comparison to an expected outcome or BA target data (e.g., an expected response curve or a table of data corresponding to an expected response curve) to determine pump error data. Additionally, other data are collected and stored (e.g., data from one or more other sensors, time of day, blood analyte level range, etc.).

Figure 14A:
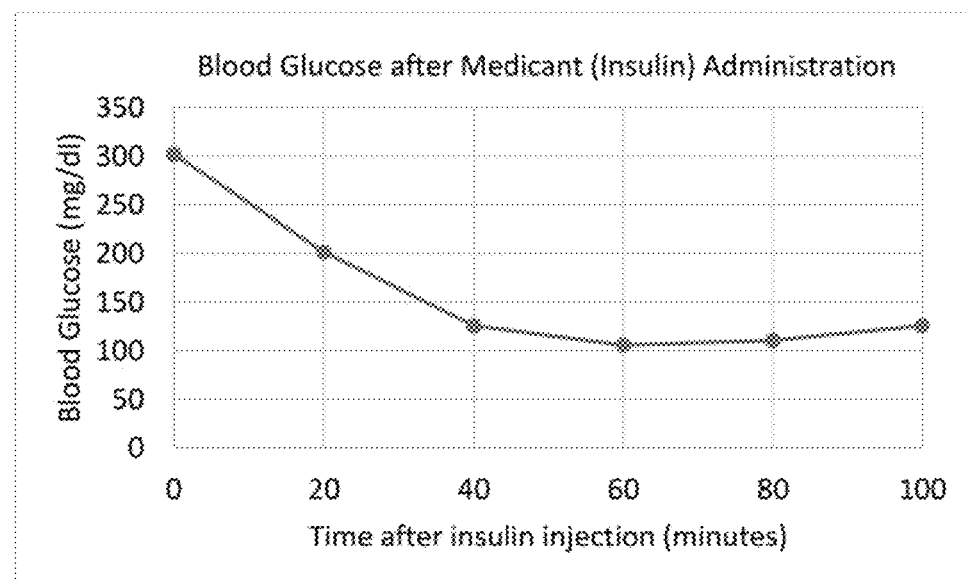
FIGS. 14A and 14B are exemplary embodiments of expected response curves showing expected blood analyte level over time after medicant delivery.
Figure 14B:
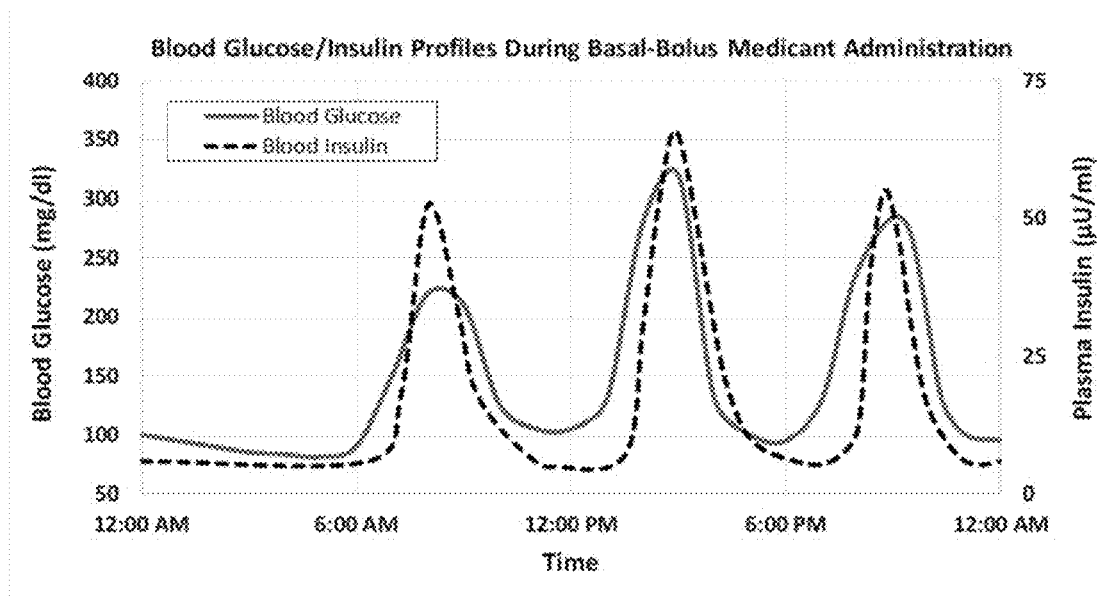

Exemplary BA target data are shown in FIGS. 14A-14C. Specifically, an exemplary expected response curve showing analyte level (e.g., BG level) over time in an individual after delivery of a single dose of medicant (e.g., 4 units of insulin) is shown in FIG. 14A. As can be seen in the curve of FIG. 14A, the data show that after delivery of the specified amount of insulin, a blood analyte level of the user is expected to drop from 300 mg/dl to 100 mg/dl over approximately a 60 minute period, and thereafter the BA level begins to slightly increase. An alternate exemplary expected BA response curve showing analyte level (e.g., BG level) over time in an individual for a multiple delivery profile of medicant (i.e., insulin) is shown in FIG. 14B. The aforementioned multiple delivery is achieved via a combination of basal (i.e., constant infusion) and bolus (i.e., periodic doses) administration of insulin, and thus can be characterized as "basal-bolus" delivery. In the exemplary "basal-bolus" delivery expected response curve of FIG. 14B, basal insulin is infused to maintain a blood medicant level (i.e., plasma insulin level) in the range of approximately 6 to 12 μU/ml, and in response it is expected that the BG level is maintained at approximately 75-110 mg/dl. Additionally, bolus insulin (e.g., 2-8 units, which correspond to a plasma insulin of 300-350 μU/ml) is delivered in close proximity to occurrences of meal ingestion, where BG level can spike to approximately 200-350 mg/dl. Expected response data for bolus delivery show that a blood analyte level of the user is expected to return from the peak (e.g., 200-350 mg/dl) to the basal level (e.g., 75-110 mg/dl) over approximately a 60 min period, and thereafter the BA level begins to slightly increase.

FIG. 14C is a representation of tabular data corresponding to exemplary expected blood glucose response to insulin for various starting glucose levels.

It will be appreciated from the foregoing that various data storage and/or representation schemes can be utilized consistent with the various aspects of the present disclosure, depending on the particular application. For instance, data intended for human cognizance (e.g., a graphical display of response over time) may be represented as a graph, such as that of FIGS. 14A-14B. Tabular data such as that of FIG. 14C may be useful for e.g., data export, such as to a user-maintained database or spreadsheet program or the like.

Moreover, while the curves and data of FIGS. 14A-14C are shown as essentially collections of discrete data points, one or more mathematical functional relationships can be utilized for all or a portion of the expected response modeling. For instance, a portion of the response curve of FIG. 14A may follow an exponential (e) decay function or the like. Such mathematical functional relationships may be useful for, inter alia, interpolating between actual or calculated data points, rather than e.g., simple point-to-point linear modeling between such points.

Data collected and/or received during the training mode operation are then used to generate and store a pump operational model (such as e.g., a user-specific operational model for operation of the particular pump or other delivery device used by that individual) per step 1307, as described below in greater detail with respect to FIGS. 13E-13F.

As an aside, it will be recognized that the term "particular pump" as used above may be either with respect to (i) data representative of the same make/model of pump (i.e., a class of ostensibly identical pumps); or (ii) data representative of one particular pump (e.g., Serial No. XYZ), which while of the aforementioned pump class, may in fact vary from mean/median performance characteristics associated with the class. As in any electromechanical device, individuals of a population will exhibit performance characteristics often according to a normal or Gaussian distribution. Engineering manufacturing tolerances and performance specifications seek to eliminate "data outliers" from the population (such as a pump with an unbalanced or defective internal mechanism); however, small variations may still exist with regard to one or more performance attributes of pumps within an acceptable population (i.e., ones that passed all manufacturing criteria). Hence, the present disclosure may utilize one or both of the foregoing; i.e., class-based data on the population as a whole, and/or device-specific data for the actual device used by the particular patient for whom the modeling is being performed.

Next, at step 1308, after the pump operational model is generated, the sensor and pump system is operated in a detection and auto-dispense mode (i.e., a mode whereby sensor data collected from the user are corrected as needed, and output for use by the pump for calculation of corrected medicant dosing data), based on the sensor operational model and the pump operational model (described in greater detail with respect to FIGS. 5F, 13F, and 13G).

In some embodiments, operation of the sensor and pump system utilizing the initial sensor operational model is continued until explant of the sensor, and operation of the sensor and pump system utilizing the initial pump operational model is continued until explant of the pump (i.e., relocation of a transcutaneous pump to a new insertion site, utilization of a new insertion set for a transcutaneous pump, surgical removal of a fully implanted pump, etc.).

Optionally, per step 1309, the system can determine that one or more criteria for operation of the system in a subsequent training mode (i.e., "re-training") for either of the sensor or the pump are met, and/or the system can receive a selection from a user or a medical professional/caregiver for re-training (described in greater detail with respect to FIG. 5G and 13H). If such a determination or selection is made for pump re-training, the sensor and pump system returns to step 1306 for a repeated operation in the pump training mode.

Turning now to FIG. 13A, a logical flow diagram of a second exemplary embodiment of a generalized method 1310 for operation of the sensor and pump system according to the present disclosure is illustrated. The method 1310 substantially includes implanting the sensor and (partially or fully, as applicable) implanting the pump, and then training the sensor and the pump simultaneously utilizing reference data from an external source for training mode operation of each of the sensor and the pump.

Specifically, as shown in FIG. 13A, the method includes first implanting and enabling each of the sensor and the pump, per step 1311. In one embodiment for implantation, the implantable sensor 200 of FIG. 2 is enabled and implanted in the host (such as via the procedures described in U.S. patent application Ser. No. 14/982,346 filed Dec. 29, 2015, previously incorporated herein), and tested as part of step 1311.

In one variant, before or after subcutaneous implantation of the sensor 200, a partially implantable pump is enabled and an associated cannula is implanted at an insertion site on the user. In another variant, before or after subcutaneous implantation of the sensor, a fully implantable pump is enabled and subcutaneously implanted in a separate surgical procedure at an implantation site within tissues of the user distinct from an implantation site of the sensor. In yet another variant, simultaneous with enablement and implantation of the sensor (i.e., comprising a single surgical procedure), a fully implantable pump is enabled and subcutaneously implanted at an implantation site within tissues of the user distinct from an implantation site of the sensor. In still another variant, an implantable sensor and pump comprise an integrated device and are thereby co-enabled and co-implanted at a single implantation side within the tissues of the user.

It will be appreciated that specific implementations of enablement of the sensor, pump, and associated receiver and/or (parent) processor devices are similar to those discussed above with reference to FIGS. 5 and 13.

Subsequent to enablement and implantation of the sensor and pump apparatus (and enablement of corresponding receiver/processor devices), the sensor and pump system is operated in concurrent initial sensor and pump training modes (step 1312, and described in greater detail with respect to FIGS. 5A-5C and 13C-13D), wherein reference blood analyte data received from an external source is utilized to train the sensor (as shown and described with reference to FIGS. 5-5C), and to calculate medicant dosage for administration from the pump based on an initial dosing calculation algorithm. Time-stamped blood analyte reference data are collected before, during, and/or after medicant delivery and are analyzed via comparison to an expected outcome (e.g., an expected response curve) to determine "pump" error data. Additionally, other data are collected and stored (e.g., data from one or more other sensors, time of day, blood analyte level range, etc.).

Data collected and/or received during the concurrent sensor and pump training mode operation are then used to generate and store a sensor operational model and a pump operational model (such as e.g., user-specific operational models for operation of each of the sensor and the pump) (step 1313, and described in greater detail with respect to FIGS. 5D-5E and 13E-13F).

Next, at step 1314, after the sensor and pump operational models are generated, the sensor and pump system is operated in a detection and auto-dispense mode (i.e., a mode whereby sensor data collected from the user is corrected as needed, and output for use by the pump for calculation of corrected medicant dosing data), based on the sensor operational model and the pump operational model (described in greater detail with respect to FIGS. 5F and 13F-13G).

As above, in some embodiments, operation of the system utilizing the initial sensor operational model is continued until explant of the sensor, and operation of the system utilizing the initial pump operational model is continued until explant of the pump (i.e., relocation of a transcutaneous pump to a new insertion site, utilization of a new insertion set for a transcutaneous pump, surgical removal of a fully implanted pump, etc.). Similar to the method 1300 of FIG. 13, per step 1315, the system can determine that one or more criteria for operation of the system in a subsequent training mode (i.e., "re-training") for either of the sensor or the pump are met. Additionally or alternatively, the sensor and pump system can receive a selection from a user or a medical professional/caregiver for re-training (described below in greater detail with respect to FIGS. 5G and 13H). If such a determination or selection is made for sensor and/or pump re-training, the sensor and pump system returns to step 1312 for a repeated operation in one or more of the sensor training mode or the pump training mode.

A logical flow diagram of a third exemplary embodiment of a generalized method 1320 for operation of the sensor and pump system according to the present disclosure is shown in FIG. 13B. The method 1320 substantially includes implanting the sensor and (partially or fully) implanting the pump, and then training only the pump utilizing reference data from an external source for training mode operation of the pump. In this embodiment, the sensor error is essentially "ignored" in output of sensor data to the pump, and any sensor and/or pump error is corrected via the pump operational model. Such a method may be utilized when, for example, the implanted sensor 200 and the pump are in data communication, and there is minimal or no output of sensor data to the user (or medical professional) from the implanted sensor. In that no external readings are provided to the patient (and hence the patient is not relying on potentially less accurate displayed values for their own behavior modification or treatment), the correction for systemic errors can be applied in one step. Alternatively, if external data are provided as the input (i.e., from a finger-stick or the like), then the sensor output value is moot (i.e., "corrected" as input).

Specifically, as shown in FIG. 13B, the method 1320 includes first implanting and enabling each of the sensor and the pump, per step 1321. In one embodiment for implantation, the implantable sensor 200 of FIG. 2 is enabled and implanted in the host (such as via the procedures described in U.S. patent application Ser. No. 14/982,346 filed Dec. 29, 2015 previously incorporated herein), and tested as part of step 1321.

As above, before or after subcutaneous implantation of the sensor 200, a partially implantable pump is enabled and an associated cannula is implanted at an insertion site on the user. Alternatively, before or after subcutaneous implantation of the sensor, a fully implantable pump is enabled and subcutaneously implanted in a separate surgical procedure at an implantation site within tissues of the user distinct from an implantation site of the sensor. A single surgical procedure may also be used as discussed above (i.e., whether at the same site or two different surgical implant locations).

Moreover, specific implementations of enablement of sensor, pump, and associated receiver and/or processor devices for FIG. 13B are similar to those discussed above with reference to FIGS. 5 and 13/13A.

Subsequent to enablement and implantation of the sensor and pump apparatus (and enablement of corresponding receiver/processor devices), the sensor and pump system is operated in an initial pump training mode (step 1322, and described below in greater detail with respect to FIGS. 13C-13D), wherein reference blood analyte data received from an external source are utilized to calculate medicant dosage for administration from the pump based on an initial dosing calculation algorithm. Additionally, time-stamped (uncorrected) blood analyte data are collected from the sensor 200. Blood analyte reference data are collected before, during, and/or after medicant delivery, and are analyzed via comparison to an expected outcome (e.g., an expected response curve) to determine pump error data. Additionally, other data are collected and stored (e.g., data from one or more other sensors, time of day, blood analyte level range, etc.).

Data collected and/or received during the pump training mode operation are then used to generate and store a pump operational model (such as e.g., a user-specific operational model for operation of the pump) (step 1323, and described below in greater detail with respect to FIG. 13E).

Next, at step 1324, after the pump operational model is generated, the sensor and pump system is operated in an auto-dispense mode (i.e., a mode whereby uncorrected sensor data are collected from the user, and output for use only by the pump for calculation of corrected medicant dosing data), based on the pump operational model.

In some embodiments, operation of the sensor and pump system utilizing the initial pump operational model (only) is continued until explant of the sensor and/or explant of the pump (i.e., relocation of a transcutaneous pump to a new insertion site, utilization of a new insertion set for a transcutaneous pump, surgical removal of a fully implanted pump, etc.). Optionally, per step 1325, the system can determine that re-training criteria are met, or the sensor and pump system can receive a selection from a user or a medical professional/caregiver for re-training as previously described. If such a determination or selection is made for pump re-training, the sensor and pump system returns to step 1322 for a repeated operation in the pump training mode.

It is appreciated that while the generalized methodologies set forth above with respect to FIGS. 13-13B utilize implant of the sensor 200 and implant/partial implant of the pump (as applicable) as preconditions for training of the machine learning algorithms (so as to ostensibly provide the best training environment for that particular sensor, pump, and patient combination), there may be instances where such implantation is not required for sensor and/or pump training. For example, the present disclosure contemplates conditions where the sensor and pump system (or the sensor and pump individually) may be "pre-trained" prior to implantation, such as based on data previously acquired for that same individual (e.g., as part of a prior training session, prior sensor implantation, prior pump implantation, etc.), or even data derived from one or more similarly situated individuals (e.g., family member, similar physiologic characteristics, similar disease expression, etc.). Moreover, training based on pump "class" data (as opposed to that specifically derived from the pump to be implanted) can be used as the basis of modeling, at least for initial training estimates.

In such cases, the sensor and pump to be implanted in the individual may for instance each be pre-programmed with data representative of a prior operational model using wireless or other data communication with the sensor and pump (such as via its 433 MHz or Bluetooth/PAN wireless interface described supra) prior to implantation, such that the model (data) is stored and accessible immediately upon activation of the sensor and pump system in vivo.

It is further appreciated that the training of the sensor and the pump, and/or application of one or more of the derived models may be delayed or "phased in" over time. For instance, in one contemplated scenario, the machine learning logic may be programmed to collect data and generate several operational models (for either or both of the sensor and/or the pump), including further analysis of the models with respect to one another (and/or other criteria or models, such as those based on purely theoretical or certain a priori assumptions). In one example, two or more successive models for the pump are generated via sensor and/or pump data collected after implantation (or partial implantation) of the pump, and evaluated against one another for factors such as inter-model consistency, and/or rates of change of various attributes of the models (i.e., loosely correlated to an operational "shelf life" of the model(s)).

Similarly, different paradigms for generation of the models can be tested against one another, such as where for example a first model accounting for N factors or systemic error sources is compared against a second model accounting for N-x factors or sources, the latter ostensibly requiring less processing overhead and/or other resources. In effect, there may be diminishing returns to increasingly sophisticated modeling approaches, at the cost of additional required sensor inputs, processing, power consumption within the sensor or the pump, etc., especially when the incremental improvement afforded by the models is within a prescribed allowable error band or tolerance of the system (e.g., when the more complex model generates an improvement in measured blood glucose level accuracy of 0.1 mg/dl, but the system display, data storage, or other requisite accuracy is only 1 mg/dl, or when the more complex model generates an improvement in average medicant response but at the expense of increased response variability.)

Similarly, the model iteration rate may be adjusted, such as where the rate at which a model adjusts or operates is controlled in order to, inter alia, enhance stability. Specifically, overly aggressive or rapid model corrections may in fact create an undesirable "feedback loop" of sorts, wherein the model(s) is/are attempting to compensate at a rate faster than the underlying physiological processes can respond. Sensitivity analysis may be used as well, such as where one factor or variable is adjusted to a prescribed degree (e.g., small percentage of the total) in either of an increasing or a decreasing direction, and the underlying physiological (and component) response evaluated to determine the rate and magnitude of response. Hence, the model update rate may be informed by a determined sensitivity in the given patient; a high sensitivity variable within a given patient may require a slower model update rate, so as to give time for the underlying physiological processes to take hold, and such effects to be reflected within the sensed data generated by the system.

Yet further, the present disclosure contemplates use of two or more models for each of the sensor and the pump collectively, whether in parallel or in sequence (or based on context or events, such as may be detected by one or more ancillary sensors of the type described supra; e.g., pressure, temperature, acceleration, conductivity, pH, oxygen level, blood flow, electrical impedance, and others). For example, in one such scenario, the corrections or other output generated through application of a given model to operational data may be averaged or otherwise mathematically or statistically combined, or weighted, with similar outputs or corrections generated from other heterogeneous models, so as to avoid any particular model skewing the correction unduly.

Likewise, certain models may be best-suited to or perform best when in a prescribed context or operational setting, and hence the weighting of that model (or even use or non-use of the model in its entirety) may be algorithmically adjusted based on e.g., sensor data input(s). As a simple illustration, consider a user implanted with a sensor and pump system who is ambulatory (as determined by e.g., accelerometer data resident on the sensor, the pump, or external receiver/processor devices, and/or yet other sensors such as body temperature). Certain systemic error sources may be more applicable or present themselves to a greater degree in an ambulatory vs. non-ambulatory state, and hence models adapted to such error sources would ostensibly perform better in the ambulatory state as compared to others not so adapted. Hence, upon detection of ambulation, the computerized logic may select (or at least more heavily weight) such ambulation-specific models for application to the generated operational model sensor data and/or the generated operational model medicant dosing data.

Delivery Device Training Mode Operation

Turning now to FIG. 13C, a logical flow diagram of an exemplary embodiment of a method 1330 for operation of the system in the delivery device (e.g., pump) training mode (step 1306 of FIG. 13, as well as step 1312 of FIG. 13A and step 1322 of FIG. 13B) is shown and described.

First, at step 1331, a command is received to operate the sensor and pump system in the pump training mode (either concurrently, as in method 1310, or non-concurrently, as in methods 1300 and 1320, with a sensor training mode). In one example, after enablement and implantation of each of the sensor and the pump, the user, a medical professional or caregiver enters a selection for operating the sensor and pump system in the pump training mode via a graphical user interface (GUI) displayed on a display device of the processor or receiver/processor associated with the pump, such as touch-screen icon selection corresponding to a "calibration" or "learning" function or the like, which causes generation and transmission of a (wired or wireless) data command to the implanted pump. In an alternate example, the sensor and pump system can be automatically configured to operate in the pump training mode after (partial or full) implantation of the pump e.g., by performing an automatic "boot-up" procedure, such as based on pre-stored firmware in e.g., ROM; once the pump is enabled and implanted, the sensor and pump system can automatically enter pump training mode operation.

In yet another alternative, the sensor and pump system can be pre-programmed to automatically operate in the pump training mode after implantation each time that it receives (either based on a user input into the processor or receiver/processor or via direct transmission from a device associated with the user and the sensor and pump system) a new reference analyte value, a signal indicating reservoir refilling, a signal indicating cannula flushing, etc.

In any of the above examples, the command to initiate pump training mode operation (via e.g., a received wired or wireless command, or automatic initiation) can be optionally delayed. In some such cases, initiation of the pump training mode can be set to occur after expiration of a delay period (e.g., a day, a week, a month, etc.). Such a delay period can, depending on the desired functionality, be selected by the user or medical professional, or alternatively the delay period can be pre-programmed. Particularly in the case of fully implanted (subcutaneous) pump apparatus, provision of the delay period can allow the tissue surrounding the implanted pump to heal and/or adjust to the presence of the pump prior to collecting "training" data from the implanted pump (e.g., thereby making the physiologic and chemical environment surrounding the implanted pump 1020a, 1040a, 1050a ostensibly more stable, including blood vessel perfusion or FBR in the immediate locality). Note that this delay is to be contrasted with that described previously; i.e., the latter referencing application of the model(s) to operational medicant dosing data.

After the pump training mode is initialized, optionally (when external reference data are utilized for pump training), a notification is generated and transmitted to the GUI requesting input of external blood analyte reference data ($BA_{ref}$) per step 1332. For example, during training mode operation, the sensor and pump system can periodically transmit notifications to a user to enter a manual blood analyte reading such as e.g., a blood glucose level determined via the aforementioned "fingersticking" method and/or laboratory-type analyzers (e.g., YSI analyzers). For example, notifications may be sent to the user hourly, every two hours, every three hours, daily, weekly, or according to other desired notification schedules. Alternatively, the user may obtain and enter manual blood analyte readings spontaneously (i.e. not in response to any notification); in such a case, if the rate of delivery by the user of such reference information exceeds a programmed threshold, then the need for notifications may be obviated.

Thus, either spontaneously or in response to receipt of the notification, the user obtains and inputs $BA_{ref}$ data (such as e.g., entering data via the GUI) which are received by the sensor system per step 1333. The $BA_{ref}$ data either include a time-stamp generated by an external digital blood analyte measurement device or are time-stamped when received by the sensor and pump system. It is noted in passing that in some cases the internal time domains maintained by physically separate devices are not perfectly aligned, and hence a time stamp applied to data transmitted from a device before transmission (e.g., based on collection of the data at actual time t) is different than or misaligned with a time stamp applied by another device to data collected at that same (actual) time t. Hence, the two time stamps indicate different values, even though both actually collected at time t. Accordingly, the present disclosure contemplates using a single, unified time domain (e.g., that of the sensor apparatus 200, the sensor receiver/processor 450, local receiver 400, or pump or pump/receiver processor apparatus), for consistency, such as where all data are time-stamped with values associated with the unified domain.

It will be appreciated that the time-stamping in such implementations, while conducted based on the unified domain, need not be performed by the device maintaining the unified domain (clock). For example, in one variant, the pump processor or receiver/processor periodically transmits clock signals indicative of time in its unified domain (referenced to a known standard or event) to the sensor apparatus, the sensor receiver/processor apparatus, and/or the pump apparatus (when non-integral to the pump processor apparatus), the receiving devices using this data to periodically align their own clock domains as needed. Other schemes for maintaining unified time-stamp data between the various data sets and devices will be appreciated by those of ordinary skill given the present disclosure.

As one alternative, a user can manually enter a time at which the $BA_{ref}$ data were collected. As another alternative, the $BA_{ref}$ data can be digitally uploaded to the sensor system without requiring a user to manually input the $BA_{ref}$ reading and/or the time of data collection. As yet another alternative, the external blood analyte meter can be a component of an external processor apparatus associated with either or both of the implanted sensor and implanted pump, thereby enabling the $BA_{ref}$ data to be automatically stored without requiring a user to manually input the $BA_{ref}$ reading and/or the time of data collection.

It is also appreciated that user notification and/or input may be obviated in favor of direct communication between the sensor and pump system and the source of $BA_{ref}$ data, such as where the sensor and pump system generates and transmits a datagram to an API (application programming interface) of the reference data source, requesting the reference data. Upon receiving the datagram, the reference data source generates and transmits a responsive datagram containing the requested reference data and any other appropriate data such as temporal reference, source ID, CRC or other error correction data, etc. The user may also be given confirmatory capability via the GUI if desired (e.g., notification to the user via GUI display that the source has sent a $BA_{ref}$ value to the sensor and pump system, and requesting assent by the user via the GUI or other input device to enter and utilize the value). Alternatively, the reference data source may initiate the data transmission activity, when e.g., new reference data have been generated and are available for transmission to the implanted sensor and pump system.

In alternative embodiments, at step 1333 the pump processor or receiver/processor receives corrected blood analyte data (corrected $BA_{cal}$) from the implanted sensor operating in a detection mode (subsequent to training mode operation of the sensor, and generation of the sensor operational model based thereon, as shown in method 1300 of FIG. 13). Similar to $BA_{ref}$ data, corrected $BA_{cal}$ data are time-stamped according to one or more of the time stamping methods described supra. Utilization of the corrected $BA_{cal}$ data from the sensor can allow for finer granularity in data collection. For example, corrected $BA_{cal}$ data provide a reference to the pump data which can be collected continuously over a desired time period. For example, corrected $BA_{cal}$ data can be collected and selectively analyzed at seconds, minutes, or hours before, during, and/or after medicant delivery. Thus, $BA_{cal}$ data can enable continuous or near-continuous analysis of the time-course of BA response to various medicant delivery profiles and potentially enable more robust model parameter estimation.

Contemporaneous with the receipt of $BA_{ref}$ data and/or corrected $BA_{cal}$ data, the processing components of the sensor and pump system evaluate BA level, calculate medicant dosage data, dispense medicant, and collect the medicant dosage data as well as other pump data (e.g., stroke volume, reservoir level, duration of time after filling of reservoir, etc.) per step 1334.

Per step 1335, in addition to receiving the corrected $BA_{cal}$ data and/or $BA_{ref}$ data and collecting/calculating the medicant dosing and other pump data, the sensor and pump system can optionally collect and/or receive other data. Optionally, these data are utilized in evaluation and/or calculation of medicant dosing data based on application of a current pump operational model (see FIG. 13D discussed infra). In one exemplary implementation, the system can collect data (hereinafter "$OS_{cal}$" data) received from one or more other sensors (such as from one or more of e.g., internal sensors and external sensors associated with the sensor apparatus and the sensor receiver/processor apparatus, internal and external sensors associated with the pump apparatus and the pump receiver/processor apparatus, and/or other additional sensors associated with the sensor and pump system). For example, the one or more internal sensors 1026a associated with the fully implanted pump 1020a, 1040a, 1050a or a portion of the partially implanted pump 1000, 1010a, 1030a (or similar sensors implanted proximate to the implantation or insertion site) can collect/calculate internal $OS_{cal}$ data such as e.g., (i) internal body temperature in the region of the implanted sensor, (ii) pulse rate/rate-of-change of the user, (iii) motion and/or orientation data, (iv) pressure, (v) pH, (vi) local blood flow/tissue perfusion, (vii) electrical impedance of the sensor/tissue interface, (viii) blood analyte concentration of other non-target analytes (e.g., oxygen), and/or other internal data.

In another example, the one or more external sensors 1026 associated with the pump and processor apparatus 1000 or pump receiver/(parent) processor apparatus 1010, 1020, 1030, 1040, 1050 can collect external $OS_{cal}$ data such as e.g., (i) external body temperature, (ii) pulse rate/rate-of-change of the user, (iii) systolic/diastolic blood pressure values, (iv) motion and/or orientation data, (vi) medicant reservoir temperature, (vii) altitude, (viii) and/or other external environmental data. Moreover, pre-processed "state" or other context data; e.g., as to what activity or state the user is currently engaged in (such as ambulatory, sleeping, exercising, eating, etc., so in effect the computerized modeling logic does not have to deduce or derive this information from raw sensor data alone).

In another example, the $OS_{cal}$ data can include information that the system calculates using stored data, and may comprise, e.g., the length of time that the pump has been in operation, length of time the medicant has been stored in the reservoir, reservoir level, pump actuator stroke volume, other pump actuation data, length of time of implantation at current insertion site, etc.

Alternatively or additionally, the one or more internal sensors 232 associated with the implanted sensor 200 (or similar sensors implanted proximate to the sensor 200) can collect/calculate internal or external $OS_{cal}$ data such as that described above.

Further, in some examples, a user or medical practitioner/caregiver can manually enter other external data such as e.g., body temperature, pulse rate, blood pressure, indicator of exercise, an indicator of intake of medication, an indicator of resting state (e.g., sleep), an indicator of active state (e.g., exercise), an indicator of ingestion of food (e.g., slow-acting carbohydrates, fast-acting carbohydrates, etc.), and/or other manually entered data, such as via a user interface and an application layer program operative to run on the pump and processor apparatus 1000 or receiver/processor apparatus 1010, 1020, 1030, 1040 (depending on how each is configured). It will be appreciated that manually entered data can be used alone or in combination with data collected via the internal sensors and/or the external sensors.

In another implementation, the data can comprise both internal $OS_{cal}$ data and external $OS_{cal}$ data (and/or manually entered external data). In one such variant, the internal sensor data are generated only periodically, such as during several discrete periods during pump training mode operation to ensure signal stability, yet minimize electrical power consumption with the pump apparatus and/or sensor apparatus so as to, inter alia, enhance battery life. The external $OS_{cal}$ data can also be calibrated to the internal $OS_{cal}$ data during the training mode operation, such as where internal temperature is registered (by the internal temperature sensor of the pump or the analyte sensor, or a separately implanted internal sensor) as a first value that is higher than say an externally-sensed temperature produced by a skin temperature sensor on a receiver/processor device (for the sensor and/or pump), thereby requiring application of an offset or calibration factor for data generated by the external sensor to reflect internal body temperature. Thus, in subsequent detection and auto-dispense mode operation of the sensor and pump system, the external sensors can be utilized, and the internal sensors can be turned off, thereby decreasing power and processing demands on the implanted pump or sensor (or the other sensors implanted proximate to the implantation site or insertion site if used).

In yet another variant, both the external $OS_{cal}$ data and the internal $OS_{cal}$ data are collected and utilized by the system during the pump training mode operation and the detection and auto-dispense mode operation to improve accuracy via e.g., collating data from multiple sources. In still other variants, external and internal $OS_{cal}$ data can be dynamically selected for use during detection mode operation based on data analyses carried out during the operational model generation (discussed infra).

In each of the above implementations, the other data (i.e., the $OS_{cal}$ data and/or manually entered data) are time stamped such that they can later be temporally correlated with the corrected $BA_{cal}$ data or $BA_{ref}$ data and the pump data during data processing.

Turning now to FIG. 13D, methods for calculation of medicant dose data (based on an initial or pre-programmed medicant dosing algorithm, and/or a current pump operational model) and collection of pump data during training mode operation of the sensor and pump system are discussed in detail. Specifically, an exemplary embodiment of a method of operating the implanted sensor and pump system for collection and calculation of pump training mode data, as well as an exemplary method of data processing and output during pump training mode operation of the system (corresponding to step 1334 of FIG. 13C) are described in detail infra.

In one exemplary embodiment, the medicant dose calibration coefficients (correction factors, $C_f$) for the pump and/or specific user populations are known a priori and stored in the system. Similarly, the BA level desired by the user and/or prescribed for the user is programmed into the system as $BA_{threshold}$. For example, $BA_{threshold}$ is a BA level that defines a "safety" threshold for the user, and is programmed into the system by the user and/or a medical professional or caregiver. Thus, a $BA_{ref}$ value or a corrected $BA_{cal}$ value that is equal to or below the $BA_{threshold}$ indicates a BA level condition that does not require management via medicant treatment, while a $BA_{ref}$ value or corrected $BA_{cal}$ value that is above the $BA_{threshold}$ is indicative of a BA level condition that is "unsafe" and requires management via medicant treatment.

In an alternative implementation, the desired and/or prescribed BA level for a user ($BA_{threshold}$) can be a range of BA values instead of a single number, where a specific point of the range (center, minima, or maxima, etc.) is used as the $BA_{threshold}$. Further, in another alternative implementation, a $BA_{ref}$ value or a corrected $BA_{cal}$ value that is equal to or above the $BA_{threshold}$ indicates a BA level condition that does not require management via medicant treatment, while a $BA_{ref}$ value or corrected $BA_{cal}$ value that is below the $BA_{threshold}$ is indicative of a BA level condition that is potentially "unsafe" and requires management via medicant treatment. In yet another alternative implementation, "safety threshold" may be defined by upper and lower values of a range, such as $BA_{upper\_threshold}$ and $BA_{lower\_threshold}$. In such an implementation, a $BA_{ref}$ value or a corrected $BA_{cal}$ value that is equal to or above the $BA_{lower\_threshold}$ and equal to or below the $BA_{upper\_threshold}$ indicates a BA level condition that does not require management via medicant treatment, while a $BA_{ref}$ value or corrected $BA_{cal}$ value that is above the $BA_{upper\_threshold}$ or below the $BA_{lower\_threshold}$ is indicative of a BA level condition that is potentially "unsafe" and requires management via medicant treatment.

During the training mode operation, as discussed above and per steps 1332 and 1333, corrected $BA_{cal}$ data and/or $BA_{ref}$ data are received by the system on fixed time intervals (or semi-continuously or continuously), and evaluated by the sensor and pump system as a potential time for medicant delivery. As can be seen in FIG. 13D, following the receipt of $BA_{ref}$ data and/or corrected $BA_{cal}$ data, the processing components of the sensor and pump system determine whether the $BA_{ref}$ data and/or corrected $BA_{cal}$ data are greater than the $BA_{threshold}$ (step 1341). If the current $BA_{ref}$ data and/or corrected $BA_{cal}$ data (i.e., a current blood analyte level of the user) is less than or equal to the $BA_{threshold}$, the system continues to monitor the blood analyte level (step 1342). Alternatively, per step 1343, if the $BA_{ref}$ data and/or corrected $BA_{cal}$ data are greater than the $BA_{threshold}$, the system calculates $BA_{offThreshold}$ data as the difference between the received $BA_{ref}$ data and/or corrected $BA_{cal}$ data and the programmed $BA_{threshold}$ data. The application of the correction factor ($C_f$) coefficient on the $BA_{offThreshold}$ provides the calibrated medicant dosage data ($MD_{cal}$), as shown in step 1344.

It will be appreciated that the pump system can also be programmed to operate in training mode and auto-dispense mode simultaneously. For example, the pump system can continue operation in an auto-dispense mode according to a "first" pump operational model, while undergoing a re-training operation to generate a "second" pump operational model. Thus, per step 1345, it is determined whether the sensor and pump system is operating under a previously trained pump correction model (such as the foregoing "first" pump operational model). If so, the existing pump operational model (which may include utilization of the other time-stamped data shown and described with respect to step 1335 of FIG. 13C) is utilized to correct the medicant dosage, as shown in step 1346. As indicated in step 1347, in either scenario, the medicant dose is then automatically administered to the user by the pump. Per step 1348, after medicant delivery, the sensor and pump system automatically collects (i) the medicant dose data (e.g., volume, rate, time point, etc. of delivered medicant), and (ii) additional (subsequent) corrected $BA_{cal}$ data and/or $BA_{ref}$ data measurements (which have each been timestamped reflective of the time of their generation) for later or concurrent analysis of the blood analyte level response to the delivered medicant (described in detail with reference to FIGS. 13E).

Returning to FIG. 13C, per step 1336 of, the data collected and received at steps 1333-1335 are stored on a storage device associated with the pump apparatus, pump processor or pump receiver/processor apparatus, and/or another storage device in data communication with the pump and sensor system. For example, the pump data can be stored at one or more of the mass storage devices 1018 associated with the pump and processor apparatus 1000 or the pump receiver/processor apparatus 1010, 1020, 1030, 1040, 1050, storage associated with the implantable pump apparatus 1010a, 1020a, 1030a, 1040a, 1050a, or a network ("cloud") storage device accessible via data communication with the network 800. Storage is effected via the software/firmware operative to run on the processing (or receiving and processing) platform and/or on a (separate) pump apparatus.

In another configuration, the collected data are calculated on-board the implantable/partly implantable pump apparatus 1010a, 1020a, 1030a, 1040a, 1050a using its internal computerized logic alone, and the resulting data stored locally onboard. In yet another configuration, data calculation is offloaded to the receiver/processor apparatus 1010, 1020, 1030, 1040, 1050 via the wireless interface of the pump, processed off-board, and the processed data returned to the pump for local storage. In yet another configuration, the data calculation is offloaded to the receiver/processor apparatus 1010, 1020, 1030, 1040, 1050 via the wireless interface of the pump, and the processed data stored external of the pump (i.e., in the receiver/processor or cloud storage), and a wireless datagram sent to the pump apparatus 1010a, 1020a, 1030a, 1040a indicating to the latter that the values have been calculated, and are accessible at prescribed data storage locations, or via API calls.

Alternatively or additionally, the pump data can be stored at the sensor 200, the receiver 400, 450, and/or the parent platform 700. For example, the data can be stored at one or more of the mass storage 420 associated with the receiver 400, 450, the storage 220 associated with the sensor 200, a storage device associated with the parent platform 700 (where used separately).

Receipt, collection, and storage of data are continued until a threshold of stored data or other criterion is met. Specifically, in the embodiment of method 1330, it is determined whether a statistically relevant amount of data has been stored at decision block 1337. In one exemplary implementation, the "training mode" operation of the pump is employed for a pre-determined amount of time (e.g., one hour, one day, one week, two weeks, etc.). In the foregoing implementation, the threshold for data collection is the pre-determined amount of time for the duration of the pump training mode operation; therefore, the determination of whether the threshold for data collection has been met includes determining if a time elapsed since the initiation of the pump training mode is greater than the pre-determined amount of time, such as via a clock function resident on the local receiver logic. This threshold can be made irrespective of actual data collected, or coupled with a prescribed threshold of data collection volume (described infra).

In another implementation, the "training mode" of the pump is implemented until a pre-determined number of data points (i.e., a pre-determined amount of data having corresponding time points) are collected. In this implementation, the threshold for data collection is the pre-determined number of data points; and therefore, the determination of whether the threshold for data collection has been met includes determining if a number of collected data points is greater than the pre-determined number of data points (which may be e.g., on a numerical basis such as an integer number, on an aggregated data size/storage value such as N kb or Mb, on a storage address basis such as a number of row/column addresses in a memory array, or yet other).

It will further be appreciated that other threshold criteria and/or a combination of threshold criteria may be utilized to determine whether the sensor and pump system has collected sufficient "training mode" data for the pump. For instance, the data collection may be controlled based on a subsequent processing of collected data, such as where a prescribed first amount of data are obtained, and subsequent steps of the methodology herein (i.e., model processing/generation) are performed to determine if satisfactory results can be obtained, such as based on statistical criteria. In effect, a trial run on analysis and model generation for the pump may be performed using a given amount of collected data, so as to determine statistical or other sufficiency of the data with respect to generation of a useful model. Depending on the model chosen for application during the operational phase or mode (which may in fact be multiple models applied in series or tandem), certain data sets may or may not be sufficient for model generation and application in terms of their size, diversity, etc. Hence, by performing "look ahead" processing (including in an iterative fashion; i.e., wherein a first data set is collected, evaluated, and second heterogeneous or more expansive data set is subsequently collected and evaluated), the data collection threshold may be dynamically specified, as opposed to a predetermined value which, while conservative, may cause undue delay and utilization of pump (and/or sensor) processing resources (and hence power consumption).

Per the method 1330 of FIG. 13C, if the data collection threshold or criterion has not yet been met at decision block 1337, data collection is continued. Alternatively, if the threshold or criterion is met, the pump training mode operation of the system is completed, and the collected and received data are subsequently analyzed and processed for pump operational model generation as described elsewhere herein.

Although not specifically depicted in FIG. 13C, it will be appreciated that the training mode operation can additionally include a "manual override" or similar function selectable by a user and/or a medical professional. In one example, the manual override function allows the method 1330 to be stopped (algorithmically) prior to meeting the data collection threshold/criterion, and proceed to the pump operational model generation. In another example, the manual override function allows the method 1330 to continue (i.e., allows collection of "training data" to continue) after the data collection threshold/criterion is met, prior to pump operational model generation, so as to permit enrichment of the collected data set, or for other reasons (e.g., to ensure that readings are taken in different ambulatory or other user contexts such that the data are representative in such regards).

Delivery Device Operational Model Generation

Referring now to FIG. 13E, exemplary methodologies for model parameter identification and delivery device (e.g., pump) operational model generation are described in detail.

As shown in FIG. 13E, an exemplary embodiment of a method 1360 for data analysis and generation of a pump operational model (e.g., a user-specific pump operational model) (per step 1361) includes first calculating blood analyte pump error data ($BA_{p\_error}$ data) for each medicant delivery instance. Calculation of the $BA_{p\_error}$ data is based on the received corrected $BA_{cal}$ data or $BA_{ref}$ data and accessed (stored) $BA_{target}$ data, at each corresponding time point (e.g. time points within a time period corresponding to sample range before, at, and after medicant delivery). For example, the $BA_{p\_error}$ data can be calculated as the relative difference (RD) between the expected blood analyte level at a specific time point in medicant treatment ($BA_{target}$ data) and the external analyte reference data ($BA_{ref}$ data) or corrected sensor data (corrected $BA_{cal}$ data), as set forth in Eqn. (8) below:

$$RD = \frac{BA_{target} - BA_{measurement}}{BA_{target}} \quad (8)$$

where blood analyte measurement ($BA_{measurement}$) is either a sensor reading (corrected $BA_{cal}$) or a reference sample ($BA_{ref}$) matched with an expected blood analyte target ($BA_{target}$) due to medicant treatment. For example, an expected blood analyte target can be determined from an expected response curve (see e.g., FIGS. 14A and 14B), or a table of data corresponding to one or more expected response curves (see e.g., FIG. 14C).

Alternatively (or in tandem), the $BA_{p\_error}$ data can be calculated for each time point within each of the medicant delivery instances, where each medicant delivery instance comprises multiple blood analyte measurements (i.e. multiple received corrected $BA_{cal}$ or $BA_{ref}$ data) to generate a set of $BA_{measurement,i}$ values and paired $BA_{target,i}$ data (which may be a set of static values (i.e., all of the same value) or may be a set of different values thus representing a time-varying target profile) collected within a predefined time period, as the mean relative difference (MRD) set forth in Eqn. (9) below:

$$MRD = \frac{1}{2}\sum_{i=1}^{N} \frac{BA_{target,i} - BA_{measurement,i}}{BA_{target,i}} \quad \text{or,} \quad (9)$$

where N is the number of matched pairs of blood analyte measurements ($BA_{measurement,i}$) and their targets ($BA_{target,i}$) for a medicant delivery instance, and where each blood analyte measurement ($BA_{measurement,i}$) could be either an instance of a sensor reading (corrected $BA_{cal}$) or a reference sample ($BA_{ref}$).

Additionally or alternatively, the $BA_{p\_error}$ data can be calculated utilizing one or more other methods (such as e.g., arithmetic difference, standard deviation, mean absolute difference, etc.).

After calculation of $BA_{p\_error}$ data, the method 1360 includes identifying a set of available model parameters, per step 1362. This set may be identified for example based on the available sensors (e.g., sensor 200 and one or more other sensors) and/or data accessible in a given hardware/software environment within which the pump apparatus will be used. For example, the accessible sensor/data set may be as little as (i) data of the blood analyte sensor(s) on the sensor apparatus 200, (ii) data on the pump/actuators and sensors (e.g., activation/de-activation, reservoir sensor(s)), and (iii) time. More fully featured/instrumented applications may include additional sensors and data sources. In the exemplary context of blood glucose measurement (via the sensor 200) and automatic delivery of insulin (or one or more other medicants, such as e.g., glucagon) via the pump, some candidate parameters include: (i) reference background $pO_2$ ($O_2$ partial pressure) measured by the CGM sensor; (ii) electrode(s) current measured by the CGM sensor; (ii) rate-of-change (ROC) of electrode(s) current measured by the CGM sensor; (iv) temperature measured by a temperature sensor (e.g. a thermistor) embedded in the CGM sensor or the insulin pump or separate therefrom; (v) accelerations measured by an accelerometer embedded in or external to the CGM or the insulin pump or separate therefrom; (v) pressure (e.g., via indigenous piezoelectric or other sensor in or external to the CGM or the insulin pump or separate therefrom), (vi) pH measured via a pH meter in or external to the CGM or the insulin pump or separate therefrom, (vii) altitude, and (viii) "state" variable inputs such as user-input data regarding their activities, ambulatory state, items eaten and times, and the like. It will be appreciated that the foregoing list is merely exemplary; other parameters may be used in addition to, or in substitution of, the foregoing.

Next, at step 1363, one or more "machine learning" algorithms are selected/applied on the data corresponding to the related parameters and the $BA_{p\_error}$ data, thereby enabling evaluation of the candidate model parameters (identified in step 1362) for inclusion in the pump operational model. In one embodiment, the candidate parameters are evaluated using analytical techniques structured to identify relative parameter importance. For example, once candidate parameters and a particular machine learning algorithm (including e.g., Decision Tree, Random Forest, etc.) are defined, those parameters demonstrating utility in reducing a specified error measure (e.g. RD, MARD, MAD, outlier prevalence, etc. with respect to the difference between expected BA response ($BA_{target}$ data) and measured BA response (corrected $BA_{cal}$ or $BA_{ref}$ data)) in a pump training data set are selected by means of a "feature selection" technique. For example, when a Random Forest algorithm is trained using the model parameters and reference-derived $BA_{p\_error}$, an "out-of-bag" or other predictor (parameter) importance can be evaluated, such as by permuting the input parameter values. See e.g., *Out-of-Bag Estimation*, L. Brieman, et al, University of California at Berkley (https://www.stat.berkeley.edu/~breiman/OOBestimation.pdf), incorporated herein by reference in its entirety, as one exemplary approach. In such an analysis, the parameters with higher importance metrics tend to better predict the output variable, $BA_{p\_error}$.

In one implementation, a single algorithm is pre-selected (e.g., an experimentally pre-determined algorithm) for utilization in pump model generation prior to implantation of the pump. Differently stated, the pump system can be pre-programmed to utilize a single desired algorithm, such as e.g., an algorithm selected for its particular attributes such as robustness, accuracy, etc., which may be the same or a different algorithm as that for pre-programmed algorithm for generating the sensor operational model. In another implementation, a medical practitioner may select (e.g., prescribe) one of multiple algorithms for use in a specific patient (i.e., user) prior to or after implantation of the pump, ostensibly based on the desirability of that algorithm for utilization within the particular user based on their particular physiologic attributes, disease presentation, lifestyle, pump location (e.g., particularly for fully implanted pumps), etc. For example, in each of the foregoing implementations, the desired algorithm or the prescribed algorithm may be selected based on known algorithm characteristics (e.g., speed, accuracy, required processing power, robustness to errors, etc.), and/or characteristics of the user (e.g., known medications or treatments, known lifestyle characteristics, known disease characteristics, etc.), including based on prior analysis of the algorithms prior to implantation such as via computer analysis on various test or patient-derived data sets.

It will be appreciated that the exemplary decision tree 600 shown in FIG. 6 with respect to sensor modeling is also one possible implementation of machine learning for generation of the pump operational model (which can be, for example, pre-programmed into the sensor and/or pump system for generation of the pump operational model). Further, the foregoing discussion of supervised, unsupervised and reinforcement based learning based on the types of input/output generated by the system with regard to sensor operational model generation is also applicable to generation of the pump operational model.

In yet another implementation, more than one machine learning algorithm (including but not limited to e.g., Decision Tree, Random Forest, Naïve Bayes classification, support vector machines (SVM), Gradient Boosting, and AdaBoost) can be utilized to model the training data during pump operational model generation, and the algorithm that yields the "best" result can be used in the pump operational model. For example, the sensor and pump system can be pre-programmed to analyze the data via e.g., three (3) different machine learning algorithms, thereby generating at least three sets of data (i.e., at least one set of data output from each algorithm). Each of the sets of data can then be compared or otherwise evaluated against performance criteria to identify the best algorithm for generation of the operational model. In the foregoing example, the "best" algorithm may be selected based on a desired characteristic such as e.g., speed, accuracy, required processing power, robustness, and/or other desired features. The initial set of three algorithms in this example may be selected by the aforementioned experimental or other analytical evaluation, based on the particular attributes of the user in which the pump is intended to be implanted. For instance, the data vectors for a given individual (e.g., height/weight, BMI, race/ethnicity, age, stage of disease progression, etc.) can be evaluated to identify a previously determined subset of algorithms which are better suited to those falling within such classes, and their partially or fully implanted pump preprogrammed with that subset of algorithms, in effect pre-filtering the algorithms for that individual so that the best algorithm(s) can be more rapidly converged on during model generation.

Similar to generation of the sensor operational model, in each of the foregoing implementations, the one or more machine learning algorithms may be differentially applied to selected portions of the collected data in order to analyze various parameters which may or may not be correlated with error occurring at the fully or partially implanted pump (i.e., correlated with the $BA_{p\_error}$ data). In a variant where only the $BA_{ref}$ data or corrected $BA_{cal}$ data and pump data are collected from the implanted sensor and pump system during pump training mode operation (i.e., no external data or $OS_{cal}$ data are received/collected), variables or parameters can include time of day (e.g., 6 AM, 7 AM, 8 AM, etc.), range of time of day (e.g., early morning, midday, night, etc.), range of blood analyte concentration (e.g., high range, median range, low range, etc.), age of pump (i.e. length of time the pump has been operating), duration of implantation at current insertion site (for fully or partially implanted pumps), level of medicant reservoir, age of medicant stored in reservoir (i.e., time elapsed since reservoir refill), and/or other determinable parameters that can be extracted from the corrected sensor data and/or pump data.

In another variant where other data (e.g., internal $OS_{cal}$ data, external $OS_{cal}$ data, or other user input data) are received and/or collected in addition to the $BA_{ref}$ data or corrected $BA_{cal}$ data and pump data during pump training mode operation, variables or parameters can additionally include temperature, acceleration, altitude, orientation, pressure, pulse rate, one or more other non-target blood analyte concentrations, intake of medication, intake of food, designated resting period of the user, designated active period the user, and/or other determinable parameters that can be extracted from the other sensor data and/or the user input data such as user state or context data.

Per step 1364, (and as discussed above) test data sets are generated and compared for, inter alia, evaluation purposes. Per step 1365, the evaluation may include identification of one or more parameters having a highest (or statistically significant) correlation to $BA_{p\_error}$. Thus, the final list of one or more parameters is selected based on a predictor importance/relevance to $BA_{p\_error}$ criterion, such as for example based on a pre-defined threshold of predictor importance. Alternatively, a simple criterion to select a prescribed number (e.g., top 'n') of predictors can be employed. It will be appreciated that the parameter identification process may be conducted algorithmically (e.g., by an application computer program or other software) based on provided data sets, heuristically by a human, or combinations thereof. Moreover, if the relevant model parameters are known a priori, such model parameter identification methodology may be completely obviated.

Per step 1366, a pump operational model is then generated for prediction of $BA_{p\_error}$ during normal operation of the implanted pump (i.e., auto-dispense mode operation) based on the one or more selected/identified parameters and the determined relationship with $BA_{p\_error}$. The pump model is stored at one or more of the storage devices discussed supra (step 1367) for subsequent use during operation of the sensor and pump system in the detection and auto-dispense mode (e.g., step 1308 of FIG. 13).

In another implementation, more than one pump operational model is generated and stored. In such implementations, a specific pump operational model can be selected based on the conditions under which the sensor and pump system is operating during detection and auto-dispense modes operation such as e.g., availability of $OS_{cal}$ data and/or optimization of a specific operational model under certain environmental conditions (discussed infra with reference to method 1372 of FIG. 13G).

Delivery Apparatus Auto-Dispense Mode Operation

Methods for collection and calculation of medicant dose data during detection mode and auto-dispense mode operations of the sensor and delivery device (e.g., pump) system are discussed with reference to FIGS. 13F and 13G.

As shown in an exemplary method 1368 of FIG. 13F, at step 1369, the sensor and pump system first receives a command to operate the sensor in the detection mode and the pump in the auto-dispense mode. In one embodiment, during the auto-dispense mode operation, per step 1370, corrected $BA_{cal}$ data are received by the system on fixed time intervals, near-continuously, continuously, or as determined by the user or the sensor system as a potential medicant delivery time. In an alternate embodiment, $BA_{cal}$ data and estimated error (instead of corrected $BA_{cal}$ data) are provided to the pump system processor from the sensor system processor. Contemporaneous with the receipt of the corrected $BA_{cal}$ data (or $BA_{cal}$ data and estimated error), the processing components of the sensor and pump system can optionally collect other pump data (e.g., stroke volume, reservoir level, duration of time after filling of reservoir, etc.). Additionally, per step 1371, $OS_{cal}$ data (such as those discussed supra) which are associated with the one or more parameters identified and/or utilized in the operational model generation (see step 1365 of FIG. 13E) are collected contemporaneously with the corrected $BA_{cal}$ data (and other pump data). Following the receipt of the corrected $BA_{cal}$ data (and any associated $OS_{cal}$ data and other pump data), the processing components of the pump system evaluate BA level, and calculate and auto-dispense the corrected medicant dosage, as shown in step 1372.

Turning now to FIG. 13G, an exemplary method corresponding to step 1372 is shown and described. As discussed supra, in one exemplary embodiment, the medicant dose calibration coefficients (correction factors, $C_f$) for the pump and/or specific user population are known a priori and stored in the system. Similarly, the BA level desired by the user and/or prescribed for the user is programmed into the system as $BA_{threshold}$, or manually entered and/or updated by the user. As discussed supra, $BA_{threshold}$ is a BA level that defines a "safety" threshold for the user, and is programmed into the system by the user and/or a medical professional or caregiver. Thus, a $BA_{ref}$ value or a corrected $BA_{cal}$ value that is equal to or below the $BA_{threshold}$ indicates a BA level condition that does not require management via medicant treatment, while a $BA_{ref}$ value or corrected $BA_{cal}$ value that is above the $BA_{threshold}$ is indicative of a BA level condition that is "unsafe" and requires management via medicant treatment.

In an alternative implementation, the BA level desired and/or prescribed for a user can be a range of BA values instead of a single number, where a specific point within the range (the center, the minima, or the maxima, etc.) is used as the $BA_{threshold}$. Further, in another alternative implementation, a $BA_{ref}$ value or a corrected $BA_{cal}$ value that is equal to or above the $BA_{Threshold}$ indicates a BA level condition that does not require management via medicant treatment, while a $BA_{ref}$ value or corrected $BA_{cal}$ value that is below the $BA_{threshold}$ is indicative of a BA level condition that is "unsafe" and requires management via medicant treatment. In yet another alternative implementation, "safety threshold" may be defined by upper and lower values of a range, such as $BA_{upper\_threshold}$ and $BA_{lower\_threshold}$). In such an implementation, a $BA_{ref}$ value or a corrected $BA_{cal}$ value that is equal to or above the $BA_{lower\_threshold}$ and equal to or below the $BA_{upper\_threshold}$ indicates a BA level condition that does not require management via medicant treatment, while a $BA_{ref}$ value or corrected $BA_{cal}$ value that is above the $BA_{upper\_threshold}$ or below the $BA_{lower\_threshold}$ is indicative of a BA level condition that is "unsafe" and requires management via medicant treatment.

During auto-dispense mode operation, as discussed above and per steps 1370 and 1371, corrected $BA_{cal}$ data (or $BA_{cal}$ data and estimated error) and other data corresponding to the identified relevant parameters are received on fixed time intervals (or semi-continuously or continuously) and evaluated by the sensor and pump system. Specifically, per step 1375, following the receipt of corrected $BA_{cal}$ data (or $BA_{cal}$ data and estimated error) and other relevant parameter data, the processing components of the sensor and pump system determine whether the current $BA_{cal}$ data are greater than the $BA_{threshold}$. In a case where $BA_{cal}$ data and estimated error are provided, the pump system must first determine a corrected $BA_{cal}$. Subsequently, if the corrected $BA_{cal}$ data (i.e., a current blood analyte level of the user) are less than or equal to the $BA_{threshold}$, the system continues to monitor the blood analyte level (step 1376). Alternatively, per step 1377, if the corrected $BA_{cal}$ data are greater than the $BA_{threshold}$, the system calculates $BA_{offThreshold}$ data as the difference between the received corrected $BA_{cal}$ data and the programmed $BA_{threshold}$ data.

As shown in step 1378, application of the correction factor ($C_f$) coefficient on the $BA_{offThreshold}$ data yields the uncorrected medicant dosage data ($MD_{cal}$). For the medicant dose adjustment process, relevant parameters (as identified in method 1360) are applied to the trained pump operational model to determine $BA_{p\_error}$, as shown in step 1379. Next, per step 1380, the application of the pump calibration coefficient ($C_f$) on the $BA_{p\_error}$ data provides the medicant dosage correction ($MD_{correction}$). The arithmetic operation (e.g., difference, percentage reduction, etc.) between the uncorrected medicant dosage ($MD_{cal}$) and medicant dosage correction ($MD_{correction}$) provides the corrected medicant dosage, as shown in step 1381, which is utilized (in step 1382) to auto-dispense the corrected medicant dose to the user via the pump.

In an alternate embodiment, the sensor and pump system may include multiple operational models trained and stored during the pump training mode operation. In one implementation, the $BA_{p\_error}$ is predicted from multiple operational models, and an aggregate $BA_{p\_error}$ (e.g., weighted mean, etc.) is computed for medicant dosage correction ($MD_{conection}$). In alternate implementation, the sensor and pump system may select one operational model (out of the multiple stored operational models) for use in computing $BA_{p\_error}$ and medicant dosage correction $MD_{correction}$). In one variant, a specific operational model may be selected based on availability of related parameter data included in the operational model (such as e.g., temperature, altitude, pressure data, etc.). If one or more of the related parameter data utilized within an operational model is not available (due to e.g., a broken or powered down sensor), an alternate operational model can be selected for use. In another variant, a specific operational model may be selectively employed based on the collected data indicating a specific condition which an operational model is "best" suited for. For example, it may be determined during the operational model generation that a first operational model is optimal for temperature below a specific threshold temperature, while a second operational model is optimal for temperatures above the threshold temperature. It will be appreciated that myriad other schemes for utilization of multiple operational models and/or selection of a specific operational model may be determined during operational model generation.

Returning now to FIG. 13F, optionally, one or more corrected $BA_{cal}$ data measurements (timestamped) are received after medicant delivery, as shown in step 1373. Accordingly, information comprising pre-delivery corrected $BA_{cal}$ data, medicant dosing data, and the post-delivery corrected $BA_{cal}$ data can be timestamped and stored, as indicated in step 1374.

Sensor System Re-Training Determination

As depicted in FIGS. 13-13B (see e.g., step 1325 of FIG. 13B), exemplary embodiments of the methods of operating the sensor and pump system includes optional "re-training" of the pump. The aforementioned pump "re-training" comprises a subsequent operation of the sensor and pump system in the pump training mode after an initial training mode operation. As such, pump re-training may occur for example: (i) after implantation, and after an initial in vivo training operation; (ii) after implantation, and after an initial explanted training operation conducted before the pump is implanted; (iii) after explant, and subsequent re-implantation of the same or similar pump in the same individual.

Notably, such re-training can be used, inter alia, to compensate for short-term or long-term changes or variations in pump operation or subject physiology; i.e., how the pump responds to prevailing in vivo and pump operational conditions it finds itself in at any given point during its implanted period or lifetime. For example, one or more mechanical components of the pump/actuator may be subject to normal wear and tear over time. Moreover, the host's physiological responses (including FBR or other such factors) may vary as a function of time in a fully implanted pump, and/or tissues at a new insertion site of a partially implanted pump may have different absorption kinetics over a previous insertion site, thereby necessitating re-evaluation. Further, new and previously un-modeled (within that individual) physiological or non-physiological error sources may arise over time (including, e.g., levels of medicant-specific antibodies), or other previously modeled sources (i.e., accounted for in the model developed after initial training) may wane over time. New algorithms may also be developed, and it may be desired to retro-fit them into a partially or fully implanted pump device.

As can be appreciated, any number of the above factors (or others) may dictate a re-training of the sensor while in vivo. Generally speaking, many if not all of the above sources of possible variation in signal will manifest themselves in varying degree in the $BA_{p\_error}$ value ultimately identified using the applied operational model, and hence a change in the average $BA_{p\_error}$ value calculated over a given time period can be used as a determinant or passive/post hoc indicator of change of one or more sensor operational or physiological processes. Similarly, a change in the average sensor error data ($BA_{s\_error}$ value) can be used as a determinant or passive/post hoc indicator of change of one or more sensor operational or physiological processes. However, the present disclosure also contemplates proactive or advance determination of the change of one or more sensor and/or pump operational or physiological processes.

FIG. 13H is a logical flow diagram illustrating one exemplary implementation of a method 1385 of determining the need for re-training of the partially or fully implanted pump. This methodology can be implemented by the pump and processor apparatus 1000, the implanted pump apparatus 1010a, 1020a, 1030a, 1040a, 1050a, the receiver/processor apparatus 1010, 1020, 1030, 1040, the sensor 200, the sensor receiver/processor 450, local receiver 400, or combinations of the foregoing (depending on how the logic is distributed within these devices), during detection and auto-dispense mode operation of the sensor and pump system according to the generalized methods 1300, 1310 and 1320 of FIGS. 13-13B.

As depicted in FIG. 13H, while the sensor and pump system is operated in the detection and auto-dispense modes per step 1386 (i.e., per sensor methods 522 of FIG. 5A, 559 of FIG. 5F, and pump methods 1368 of FIG. 13F, 1372 of FIG. 13G), it can be determined whether one or more criteria for re-training have been met, with any single or prescribed coincident number of criterion triggering re-training in the illustrated embodiment.

In the exemplary method 1385, it is first determined whether sensor error ($BA_{s\_error}$) is greater than a pre-determined threshold at decision block 1387; i.e., the magnitude of $BA_{s\_error}$ averaged over a period of time is greater than a pre-determined threshold value for $BA_{s\_error}$. In another variant, it can additionally or alternatively be determined whether the $BA_{s\_error}$ outlier data include a number of outliers that are greater than an outlier threshold (or threshold percentage of the data; e.g., >20 percent are outliers). In both variants, if the determined $BA_{s\_error}$ and/or $BA_{s\_error}$ outlier data are greater than the respective pre-determined threshold(s), a repeated operation of the sensor and pump system (either consecutively (e.g., sensor training mode, then pump training mode) or concurrently) in the training mode can be initiated (step 1392). In some examples, a notification is sent to the user to confirm or request initiation of a subsequent sensor and/or pump training modes.

Alternatively, per the method 1385, if $BA_{s\_error}$ and/or $BA_{s\_error}$ outlier data are less than the respective pre-determined threshold(s), other re-training criteria can be determined.

Next, per decision block 1388 it is determined whether pump error ($BA_{p\_error}$) is greater than a pre-determined threshold at decision block 1388; i.e., the magnitude of $BA_{p\_error}$ averaged over a period of time is greater than a pre-determined threshold value for $BA_{p\_error}$. In another variant, it can additionally or alternatively be determined whether the $BA_{p\_error}$ outlier data include a number of outliers that are greater than an outlier threshold (or threshold percentage of the data; e.g., >20 percent are outliers). In both variants, if the determined $BA_{p\_error}$ and/or $BA_{p\_error}$ outlier data are greater than the respective pre-determined threshold(s), a repeated operation of the pump system in the training mode can be initiated (step 1392). In some examples, a notification is sent to the user to confirm or request initiation of a subsequent pump training mode.

Alternatively, per the method 1385, if $BA_{p\_error}$ and/or $BA_{p\_error}$ outlier data are less than the respective pre-determined threshold(s), other re-training criteria can be determined.

Per decision block 1389, it is next determined if a time elapsed since initiation of the detection and/or auto-dispense modes is greater than a pre-determined threshold (e.g., a duration of time for operating the sensor and pump system in the detection and auto-dispense mode and hence without training). In one specific example, a pre-determined threshold for a time period for detection and auto-dispense modes operation is three (3) days. Thus, if the sensor system has been operating in the auto-dispense mode for a duration of time greater than the per-determined threshold, a repeated operation of the pump system in the pump training mode is initiated (step 1392), so as to keep the error correction capability of the system "fresh" in light of any potential physical or physiological changes in the operation of the pump.

Alternatively, if a time elapsed since the initiation of the detection and auto-dispense mode operation is less than the pre-determined threshold, other pump re-training criteria can be evaluated.

In the method 1385, it is further determined whether a pump "re-training event" has been detected per decision block 1390. If such an event is detected, a repeated operation of the sensor and pump system in the pump training mode is initiated (step 1392).

Exemplary re-training events can include one or more of: (i) recalibration of the pump; (ii) relocation of a transcutaneous pump to a new insertion site; (iii) flushing of a catheter; (iv) refilling of a medicant reservoir; (v) detection of an occurrence of an unusually high temperature (e.g., detection of a temperature greater or less than a pre-determined high/low temperature threshold, respectively, and/or detection of the high/low temperature for a duration of time greater than a pre-determined threshold); (vi) detection of a physical impact to the user (e.g., detection of a pressure and/or acceleration value greater than a pre-determined threshold); (vii) detection of an occurrence of an unusually high or low pulse rate (e.g., detection of a pulse rate greater/less than a pre-determined high/low pulse rate threshold respectively, and/or detection the high/low pulse rate for a duration of time greater than a pre-determined threshold), (viii) detection of an occurrence of an unusually high or low backpressure associated with the system medicant delivery, etc.

In some implementations, the re-training events can be selected by the sensor and pump system based on the identified parameters which are correlated to $BA_{p\_error}$ for the specific user. For example, if temperature is correlated to $BA_{p\_error}$ while pulse rate is uncorrelated, pump re-training events can include the occurrence of the foregoing temperature events, while the aforementioned pulse rate events are excluded from the set of events that initiate pump retraining.

Alternatively, if no re-training event is detected, other pump re-training criteria can be evaluated.

Per decision block 1391 of the method 1385, it is next determined whether a command or selection for pump re-training has been received. Specifically, a user, a medical professional, and/or a caretaker can input a request for re-training of the pump within the sensor and pump system, such as based on known user information, or merely as a "soft re-boot" (e.g., to attempt to clear prospectively anomalous behavior by the pump). For example, if a user undergoes a significant lifestyle change (e.g., change in diet or exercise regimen), a change in disease presentation, a physiological change (e.g., onset of a transient illness or diagnosis of a secondary disease, significant weight gain or weight loss, etc.), a change in medication, goes on a vacation or other deviation from normal routine, such changes may warrant retraining to ensure that the generated model is still applicable and optimized. In another example, a user may sense a feeling of being "off" or a sensation of malaise, and may selectively initiate pump retraining as desired. If a selection for pump re-training is received, a repeated operation of the sensor system in the training mode is initiated (step 1392). Alternatively, if no selection for pump re-training is received (in addition to a "NO" for each of the other criteria of decision blocks 1387-1391), operation of the sensor and pump system in the detection and auto-dispense mode is continued.

It will be appreciated by those skilled in the art given this disclosure that the exemplary method 1385 is just one possible method for determining if pump re-training criteria are met. In alternate implementations, the method can include more or fewer decision blocks, and/or the decision blocks can be executed in a different sequence. Other logical constructs may also be used, such as e.g., a "coincidence" requirement where two or three criteria must simultaneously be met in order to trigger pump re-training. Moreover, a hierarchy of evaluation may be determined and leveraged; i.e., the order and frequency with which the various criteria are evaluated may be adjusted, such as where a most likely re-training factor/threshold to be exceeded is evaluated first at a first frequency, and other less-likely factors/thresholds evaluated at a reduced frequency.

Exhibit II hereto contains exemplary computer code implementing one or more aspects of the foregoing methodologies.

Method for Implanted Sensor and Non-Implanted Pump Medicant Delivery Mechanisms

As discussed supra, the present disclosure further contemplates that the apparatus and methods discussed herein are applicable to non-implantable medicant delivery mechanism, such as, inter alia, non-implantable pumps (such as those shown in FIGS. 10E-10F) and other manual or semi-manual medicant delivery mechanisms.

FIG. 13I is a logical flow diagram depicting an exemplary embodiment of a generalized method 1400 for operation of the implanted sensor system and an associated medicant processor and dosage output apparatus according to the present disclosure. The method 1400 substantially includes first implanting and training the sensor, and further utilizing the corrected sensor data for training mode operation of the medicant processor during manual or semi-manual delivery of medicant.

Specifically, as shown in FIG. 13I, the method 1400 includes first: (i) enabling and implanting the sensor 200 (and/or other sensors) per step 1402, (ii) operating the implanted sensor in a sensor training mode, including generating and storing a sensor operational model (step 1403), and (iii) operating the sensor in the detection mode utilizing the sensor operational model, per step 1404. See the method 500 depicted in FIGS. 5-5F and the corresponding descriptions thereof for a detailed description of sensor implantation, training, operational model generation, and detection mode operation.

Further, in the case of the implantable sensor 200 of FIG. 2, the sensor is enabled and implanted in the host via the exemplary procedures described in U.S. patent application Ser. No. 14/982,346 filed Dec. 29, 2015 previously incorporated herein), and tested as part of steps 1402-1404.

Next, per step 1405, the medicant processor is enabled. In one implementation, the medicant processor is a processing apparatus in data communication with the receiver/processor associated with the implanted sensor. In another implementation, the receiver/processor associated with the implanted sensor is an integrated device having additional functionality for modeling medicant dosage data and output of a recommended dosage to the user and/or a semi-manual non-implantable delivery device (e.g., a computerized insulin pen).

Subsequent to enablement and implantation of the sensor apparatus and enablement of the medicant processor (or enablement of medicant modeling functionality of the receiver/processor associated with implanted sensor), the sensor system is operated in an initial "medicant dosing training mode" (step 1406), wherein corrected blood analyte data are received from the sensor 200, and are utilized to calculate medicant dosage for manual or semi-manual administration by the user based on an initial dosing calculation algorithm. In one implementation, time-stamped blood analyte data are collected before, during, and/or after medicant delivery, and are analyzed via comparison to an expected outcome (e.g., an expected response curve) to determine dosing error data, due e.g., unmodeled error(s) associated with patient (user) physiology, lifestyle, disease characteristics, environment, etc. and/or mechanical components of a delivery device (if utilized in medicant delivery). Additionally, other data are collected and stored (e.g., data from one or more other sensors, time of day, blood analyte level range, etc.).

In one implementation, where the medicant is manually administered (such as via e.g., oral, subcutaneous, transcutaneous, nasal, ocular, suppository mechanisms), the medicant processor includes a user interface for receiving user entered data associated with medicant delivery (amount of medicant delivered and a time of delivery). In another implementation, medicant is delivered semi-manually (such as via, e.g., a computerized injection tool, computerized dropper device, or computerized spray device). In such an implementation, the computerized semi-manual delivery device can include a transmitter for automatically transmitting administered dosage data to the medicant processor, thereby obviating the need for user entered data.

It will be appreciated that the medicant dosing training mode methods include many similar features to the pump training mode methods shown in FIGS. 13C-13D.

Data collected and/or received during the medicant dosage training mode operation are then used to generate and store a medicant dosing operational model (such as e.g., a user-specific operational model for intake of the specific medicant and/or operation of the particular delivery device used by that individual for medicant delivery) per step 1407.

Similar to use of a "particular pump", it will be recognized that the term "particular delivery device" as used above may be either with respect to (i) data representative of the same make/model of device (i.e., a class of ostensibly identical devices); or (ii) data representative of one particular device (e.g., Serial No. XYZ), which while of the aforementioned device class, may in fact vary from mean/median performance characteristics associated with the class. As in any electromechanical device, individuals of a population will exhibit performance characteristics often according to a normal or Gaussian distribution. Engineering manufacturing tolerances and performance specifications seek to eliminate "data outliers" from the population (such as a delivery device with an unbalanced or defective internal mechanism); however, small variations may still exist with regard to one or more performance attributes of delivery devices within an acceptable population (i.e., ones that passed all manufacturing criteria). Hence, the present disclosure may utilize one or both of the foregoing; i.e., class-based data on the population as a whole, and/or device-specific data for the actual device used by the particular patient for whom the modeling is being performed.

It will be appreciated that a method for generation of the medicant dosing operational model includes many similar features to the pump operation model generation method shown in FIG. 13E.

Next, at step 1408, after the medicant dosing model is generated, the sensor system is operated in a detection mode and the medicant processor is operated in dosage output mode (i.e., a mode whereby sensor data collected from the user are corrected as needed, and output for use by the medicant processor for calculation of corrected medicant dosing data) based on the sensor operational model and the medicant dosing model. In one implementation, the medicant processor includes a user interface for signaling/alerting a user as to timing and/or a recommended amount of medicant to be delivered. In another implementation, utilizing a semi-manual delivery device, the medicant processor can automatically communicate the dosage data to the computerized delivery device. Thus, the user can be provided with just a notification for a timing of medicant delivery, while the amount of medicant delivered is controlled by the medicant processor and the computerized delivery device.

It will be appreciated that methods for operation of the sensor system and manual or semi-manual medicant delivery according to the medicant dosing operational model include many similar features to the methods for operation of the sensor and pump system in the detection and auto-dispense modes shown in FIGS. 13F-13G.

In some embodiments, operation of the sensor system utilizing the initial sensor operational model and the initial medicant dosing model is continued until explant of the sensor or discontinued use of a delivery device and/or medicant.

Optionally, per step 1409, the system can determine that one or more criteria for operation of the system in a subsequent training mode (i.e., "re-training") for either of the sensor or the medicant dosing model are met, and/or the system can receive a selection from a user or a medical professional/caregiver for re-training. If such a determination or selection is made for re-training, the sensor system returns to step 1406 for a repeated operation in the medicant dosage training mode.

It will additionally be appreciated that a method for determination of retraining the sensor system and generation of a new medicant dosing model include many similar features to the re-training determination method for operation of the sensor and pump system shown in FIG. 13H.

Population-Based Sensor and Delivery System Detection and Auto Dispense Models

Similar to the sensor training mode operation, the foregoing pump training mode operation of the sensor and pump system can be carried out in an experimental or analytical setting on a population (such as e.g., a statistically significant group of test subjects) to build multiple "user-type" pump operational models, which can inter alia, be later applied to other users with similar characteristics to determine BA$_{p\_error}$. In one such embodiment, user characteristics of the test subject(s) are identified, and each of the test subjects is implanted with a sensor (e.g., pursuant to their normal implantation schedule or needs) and a partially or fully implantable pump, and the sensor and pump system is operated in the pump training mode (discussed supra). A pump operational model is then generated for each test subject, and the pump operational model correlated to the user characteristics, in order to generate one or more population-based operational models or "user-type" operational models related to the pump. It will be appreciated that many of the features discussed above with respect to the generation of population-based operational models or "user-type" operational models related to the sensor are applicable to the sensor and pump system.

It will be recognized that while certain embodiments of the present disclosure are described in terms of a specific sequence of steps of a method, these descriptions are only illustrative of the broader methods described herein, and may be modified as required by the particular application. Certain steps may be rendered unnecessary or optional under certain circumstances. Additionally, certain steps or functionality may be added to the disclosed embodiments, or the order of performance of two or more steps permuted. All such variations are considered to be encompassed within the disclosure and claimed herein.

While the above detailed description has shown, described, and pointed out novel features as applied to various embodiments, it will be understood that various omissions, substitutions, and changes in the form and details of the device or process illustrated may be made by those skilled in the art without departing from principles described herein. The foregoing description is of the best mode presently contemplated. This description is in no way meant to be limiting, but rather should be taken as illustrative of the general principles described herein. The scope of the disclosure should be determined with reference to the claims.

EXHIBIT I
Exemplary Computer Code for Senor
©2017 GlySens, Inc. All rights reserved

```
%% Function performing feature (modeling parameters) selection
% Apply calibration to sensor measurements and return
% calculated Cg subject to systematic errors and modeling parameters
[Cg_preprocessed_cal, featureSet1, featureSet2, featureSet3]
    = computeCgUsingCalCoeffs(sensorRawIworks_cal,
    O2_Calibration_coeffs, Cg_cal_coeffs);
feature_composite = [featureSet1, featureSet2, featureSet3];
Cg_error = BloodGlucoseReference.samples –
    Cg_preprocessed_cal;
numOfFeatures = size(feature_composite,2); % number of modeling parameters
% linear correlation between parameters and the BG error
correlationIndex = zeros(numOfFeatures,1);
for i = 1 : numOfFeatures
    correlationBwFeatureAndError = corrcoef(Cg_error,
    feature_composite(:,i));
        correlationIndex(i,1) =
    abs(correlationBwFeatureAndError(1,2));
end
importantFeatureIndices = find(correlationIndex > 0.4); % Selected features
if(length(importantFeatureIndices) < 5)
    [~, idxs] = sort(correlationIndex, 'descend');
    importantFeatureIndices = idxs(1:5);
end
```

EXHIBIT II
Exemplary Computer Code for Medicant Delivery Device
©2017 GlySens, Inc. All rights reserved

```
%% Function performing feature (modeling parameters) selection for pump error
% Calculate pump error (subject to systematic errors) by subtracting measured Cg from targeted Cg
pumpError = targetCg – BGref;
% Generate matrix of model's candidate parameters (features). Columns are different parameters measured; Rows are different medicant delivery instances
featureComposite = [Temperature, DoseRate, TimeOfDay, sensorData];
numOfFeatures = size(featureComposite,2); % number of modeling parameters
% Correlate each parameter with the pump error
correlationIndex = zeros(numOfFeatures,1);
for i = 1 : numOfFeatures
    correlationBwFeatureAndError = corrcoef(pumpError,
    featureComposite(:,i));
        correlationIndex(i,1) =
    abs(correlationBwFeatureAndError(1,2));
end
importantFeatureIndices = find(correlationIndex > 0.4); % Selected features
if(length(importantFeatureIndices) < 5)
    [~, idxs] = sort(correlationIndex, 'descend');
    importantFeatureIndices = idxs(1:5);
end
```

What is claimed is:

1. A medicant dosing apparatus for use with a medicant delivery device, the medicant dosing apparatus comprising:
    a data interface for data communication with a physiologic parameter sensor apparatus and the medicant delivery device;
    data processing apparatus, the data processing apparatus in data communication with the data interface; and
    a storage apparatus in data communication with the data processing apparatus, the storage apparatus comprising a computer program which is configured to, when executed by the data processing apparatus, cause the medicant dosing apparatus to:
        (i) cause operation of the medicant delivery device in a training mode;
        (ii) based at least in part on the operation of the medicant delivery device in the training mode, cause generation of an error correction operational model, the generation of the error correction operational model comprising a dynamic determination of an identity of one or more of a plurality of candidate parameters that relate to physiologic data measurable by the physiologic parameter sensor apparatus, the dynamic determination based at least on a machine learning algorithm; and
        (iii) subsequent to generation of the error correction operational model, cause operation of the medicant delivery device in an operational mode, the operational mode comprising:
            receipt of physiologic parameter signal data generated by the physiologic parameter sensor apparatus; and
            utilization of the physiologic parameter signal data and the error correction operational model so as to generate a prediction of one or more error sources associated with medicant delivery, and to correct or compensate for the predicted one or more error sources.

2. The medicant dosing apparatus of claim 1, wherein the medicant dosing apparatus is disposed on or within the medicant delivery device and integrated therewith.

3. The medicant dosing apparatus of claim 1, wherein the operational mode comprises an auto-dispense mode within which the medicant delivery device operates autonomously to deliver medicant.

4. The medicant dosing apparatus of claim 1, wherein the determined one or more of the plurality of candidate parameters comprise one or more of values relating to (i) oxygen partial pressure measured by the physiologic parameter sensor apparatus, (ii) oxygen concentration measured by the physiologic parameter sensor apparatus, (iii) current measured by at least one electrode of the physiologic parameter sensor apparatus, (iv) a rate of change associated with the current.

5. The medicant dosing apparatus of claim 1, wherein the dynamic determination is further based at least on relative importance of each of the plurality of candidate parameters, the relative importance determined based at least on the machine learning algorithm.

6. The medicant dosing apparatus of claim 1, wherein the physiologic parameter sensor apparatus comprises a fully implantable blood glucose sensor that utilizes a glucose-modulated enzymatic matrix to detect oxygen concentration.

7. The medicant dosing apparatus of claim 6, wherein the medicant dosing apparatus is disposed on or within a receiver apparatus disposed external to a user within whom the physiologic parameter sensor apparatus is implanted.

8. The medicant dosing apparatus of claim 1, wherein the medicant dosing apparatus is disposed on or within the physiologic parameter sensor apparatus and functionally integrated therewith.

9. The medicant dosing apparatus of claim 8, wherein:
the medicant delivery device comprises an implantable insulin pump; and
the medicant dosing apparatus is disposed on or within a receiver apparatus disposed external to a user within whom the medicant delivery device is implanted.

10. The medicant dosing apparatus of claim 1, wherein the operation of the medicant delivery device in the training mode comprises:
receipt of initial physiologic parameter reference data prior to medicant delivery by the medicant delivery device;
determination that a current physiologic parameter value from the initial physiologic parameter reference data is outside of a predetermined range;
calculation of medicant dosage data based on an initial dosage model;
actuation of the medicant delivery device to effect medicant delivery; and
receipt of subsequent physiologic parameter reference data after the medicant delivery.

11. The medicant dosing apparatus of claim 10, wherein the initial physiologic parameter reference data and the subsequent physiologic parameter reference data comprises data received from a non-implanted physiologic parameter measurement device.

12. The medicant dosing apparatus of claim 10, wherein the initial physiologic parameter reference data and the subsequent physiologic parameter reference data comprises data received from the physiologic parameter sensor apparatus.

13. The medicant dosing apparatus of claim 10, wherein the operation of the medicant delivery device in the training mode further comprises:

access of expected physiologic parameter response data;
calculation of error data at corresponding time points for at least the subsequent physiologic parameter reference data and the expected physiologic parameter response data; and
generation of the operational model based at least on application of the machine learning algorithm on the calculated error data.

14. The medicant dosing apparatus of claim 13, wherein the operation of the medicant delivery device in the training mode further comprises:
receipt of other parameter signal data from one or more other internal or external sensors; and
generation of the operational model based at least on application of the machine learning algorithm on the calculated error data and the other parameter signal data.

15. The medicant dosing apparatus of claim 13, wherein the operation of the medicant delivery device in the training mode further comprises:
receipt of other parameter signal data associated with one or more of (i) the initial physiologic parameter reference data, (ii) the medicant dosage data, or (iii) the subsequent physiologic parameter reference data; and
generation of the operational model based at least on application of the machine learning algorithm on the calculated error data and the other parameter signal data.

16. A medicant dosing apparatus for use with a medicant delivery device, the medicant dosing apparatus comprising:
a data interface in communication with the medicant delivery device and a sensor apparatus;
processing apparatus in data communication with the data interface; and
a storage apparatus in data communication with the processing apparatus, the storage apparatus comprising instructions configured to, when executed by the processing apparatus, cause the medicant dosing apparatus to:
(i) receive data relating to operation of the medicant delivery device in a training mode;
(ii) cause generation of an error correction operational model based at least in part on the received data;
(iii) cause receipt of sensor data generated by the sensor apparatus;
(iv) utilize the sensor data and the error correction operation model to estimate one or more unmodeled errors associated with delivery of the medicant, and produce at least one compensation for the estimated one or more unmodeled errors.

17. The medicant dosing apparatus of claim 16, wherein the generation of the error correction operational model comprises an application of one or more machine learning algorithms with respect to the data relating to operation of the medicant delivery device.

18. The medicant dosing apparatus of claim 16, wherein the at least one compensation for one or more errors associated with the delivery comprises compensation for one or more physiological error sources particular to a human being to which the medicant is to be delivered.

19. The medicant dosing apparatus of claim 18, wherein the one or more errors vary as a function of at least time.

20. The medicant dosing apparatus of claim 16, wherein the sensor apparatus comprises a blood analyte sensor apparatus, and wherein the instructions are further configured to, when executed by the processing apparatus, cause the medicant dosing apparatus to:

(i) cause operation of the blood analyte sensor apparatus in an initial sensor training mode;
(ii) based at least in part on the operating of the blood analyte sensor apparatus in the initial sensor training mode, cause generation of a sensor error correction operational model, and
(iii) subsequent to the generation of the sensor error correction operation model, cause operation of the blood analyte sensing apparatus in a detection mode to generate corrected blood analyte data, the operation in the detection mode including application of the sensor error correction operation model on at least a portion of current blood analyte data.

21. The medicant dosing apparatus of claim 20, wherein the instructions are further configured to, when executed by the processing apparatus, cause the medicant dosing apparatus to:
subsequent to the generation of the error correction operation model, cause operation of the medicant delivery device in an auto-dispense mode, the auto-dispense mode including application of the error correction operation model on at least a portion of current blood analyte signal data.

22. A medicant dosing apparatus for use with a medicant delivery device and a sensor apparatus, the medicant dosing apparatus comprising:
a data interface in communication with the medicant delivery device and the sensor apparatus;
processing apparatus in data communication with the data interface; and
a storage apparatus in data communication with the processing apparatus, the storage apparatus comprising at least one computer program having a plurality of instructions configured to, when executed by the processing apparatus, cause the medicant dosing apparatus to at least:
(i) generate data relating to an error correction operational model, the generation of the data based at least in part on operation of the medicant delivery device in a medicant delivery device training mode;
(ii) cause operation of the sensor apparatus in a sensor training mode, the sensor training mode comprising (a) an identification of model parameter data acquirable by the sensor apparatus, (b) an evaluation of at least a portion of the identified model parameter data, and (c) a selection of at least one model parameter based at least on the evaluation meeting at least one prescribed criterion;
(iii) based at least in part on the operation of the sensor apparatus in the sensor training mode, cause generation of a sensor error correction operational model; and
(iv) cause application of the error correction operational model to at least a portion of current sensor signal data, the application of the error correction operational model enabling predictive correction of one or more sensor errors associated with the selected at least one model parameter.

23. The medicant dosing apparatus of claim 22, wherein the plurality of instructions are further configured to, when executed by the processing apparatus, cause the medicant dosing apparatus to at least, based on a determination that one or more criteria for sensor re-training are met, initiate a repeat of the operation of the sensor apparatus in the sensor training mode.

24. A medicant dosing apparatus for use with a medicant delivery device, the medicant dosing apparatus comprising:
a data interface for data communication with a physiologic parameter sensor and the medicant delivery device;
data processing apparatus, the data processing apparatus in data communication with the data interface; and
a storage apparatus in data communication with the data processing apparatus, the storage apparatus comprising at least one computer program which is configured to, when executed by the data processing apparatus, cause the medicant dosing apparatus to:
collect first data generated by the physiologic parameter sensor when in a sensor training mode;
based at least on the collected data, cause generation of a sensor operational model, the sensor operational model based at least on modeling one or more unmodeled first errors associated with a blood analyte measurement process used by the physiologic parameter sensor;
compensate for at least a portion of the one or more unmodeled first errors during non-sensor training mode operation of the physiologic parameter sensor for collection of blood analyte data;
collect second data generated by the medicant delivery device when in a medicant delivery device training mode;
generate a medicant delivery device operational model, the medicant delivery device model based at least on modeling one or more unmodeled second errors associated with a medicant dosing calculation process used by the medicant delivery device; and
correct or compensate for the one or more unmodeled second errors during non-sensor training mode operation of the medicant delivery device for calculation of at least medicant dosage data.

25. The medicant dosing apparatus of claim 24, wherein:
the compensation for at least a portion of the one or more unmodeled first errors during non-sensor training mode operation of the physiologic parameter sensor for collection of blood analyte data comprises generated of corrected blood analyte data; and
the sensor training mode operation precedes the medicant delivery device training mode operation.

26. The medicant dosing apparatus of claim 24, wherein at least one of the modeling one or more unmodeled first errors or modeling one or more unmodeled second errors comprises modeling using a machine learning algorithm selected from a group consisting of: (i) Decision Tree, (ii) Random Forest, and (iii) Nave Bayes classification.

27. The medicant dosing apparatus of claim 24, wherein at least one of the modeling one or more unmodeled first errors or modeling one or more unmodeled second errors comprises modeling using a machine learning algorithm selected from a group consisting of: (i) support vector machines (SVM), (ii) Gradient Boosting, and (iii) AdaBoost.

28. The medicant dosing apparatus of claim 24, wherein the at least one computer program is further configured to, when executed, cause selection of a plurality of parameters from a plurality of candidate parameters, data values associated with the selected plurality of parameters to be used in at least one of (i) the generation of the sensor operational model, or (ii) the generation of the medicant delivery device operational model.

29. The medicant dosing apparatus of claim 28, wherein the selection of the plurality of parameters comprises evaluation of the plurality of parameters to identify relative parameter importance.

30. The medicant dosing apparatus of claim 29, wherein the evaluation of the plurality of parameters to identify relative parameter importance comprises evaluation of one or more of the plurality of candidate parameters based on at least one machine learning algorithm and respective ones of reduction of a specified error measure associated with the one or more candidate parameters.

31. A medicant dosing apparatus for use with a medicant delivery device, the medicant dosing apparatus comprising:
- a data interface for data communication with a physiologic parameter sensor apparatus and the medicant delivery device;
- data processing apparatus, the data processing apparatus in data communication with the data interface; and
- a storage apparatus in data communication with the data processing apparatus, the storage apparatus comprising a computer program which is configured to, when executed by the data processing apparatus, cause the medicant dosing apparatus to:
  - (i) cause operation of the medicant delivery device in a medicant delivery device training mode;
  - (ii) based at least in part on the operation of the medicant delivery device in the training mode, cause generation of a medicant delivery device error correction operational model, the generation of the medicant delivery device error correction operational model comprising a dynamic determination of which of a plurality of candidate parameters that relate to physiologic data measurable by the physiologic parameter sensor apparatus should be used, the dynamic determination based at least on a machine learning algorithm selected from the group consisting of: (a) Decision Tree, (b) Random Forest, (c) Naïve Bayes classification, (d) support vector machines (SVM), (e) Gradient Boosting, and (f) AdaBoost; and
  - (iii) subsequent to generation of the medicant delivery device error correction operational model, cause operation of the medicant delivery device in an operational mode, the operational mode comprising:
    - receipt of physiologic parameter signal data generated by the physiologic parameter sensor apparatus; and
    - utilization of the physiologic parameter signal data and the medicant delivery device error correction operational model so as to generate a prediction of one or more error sources associated with the medicant delivery device, and to correct or compensate for the predicted one or more error sources.

* * * * *